United States Patent
Sigurdsson

(10) Patent No.: US 12,398,201 B2
(45) Date of Patent: Aug. 26, 2025

(54) TAU SINGLE DOMAIN ANTIBODIES

(71) Applicant: NEW YORK UNIVERSITY, New York, NY (US)

(72) Inventor: Einar M. Sigurdsson, Scarsdale, NY (US)

(73) Assignee: NEW YORK UNIVERSITY, New York, NY (US)

( * ) Notice: Subject to any disclaimer, the term of this patent is extended or adjusted under 35 U.S.C. 154(b) by 925 days.

(21) Appl. No.: 16/969,835

(22) PCT Filed: Feb. 19, 2019

(86) PCT No.: PCT/US2019/018571
§ 371 (c)(1),
(2) Date: Aug. 13, 2020

(87) PCT Pub. No.: WO2019/161384
PCT Pub. Date: Aug. 22, 2019

(65) Prior Publication Data
US 2023/0203139 A1 Jun. 29, 2023

Related U.S. Application Data

(60) Provisional application No. 62/672,949, filed on May 17, 2018, provisional application No. 62/632,261, filed on Feb. 19, 2018.

(51) Int. Cl.
*C07K 16/18* (2006.01)
*A61P 25/28* (2006.01)
*C12N 15/86* (2006.01)

(52) U.S. Cl.
CPC .............. *C07K 16/18* (2013.01); *A61P 25/28* (2018.01); *C12N 15/86* (2013.01); *C07K 2317/22* (2013.01); *C07K 2317/24* (2013.01); *C07K 2317/31* (2013.01); *C07K 2317/565* (2013.01); *C07K 2317/622* (2013.01)

(58) Field of Classification Search
CPC ............... C07K 16/18; C07K 2317/22; C07K 2317/24; C07K 2317/31; C07K 2317/565; C07K 2317/622; A61P 25/28; C12N 15/86
See application file for complete search history.

(56) References Cited

U.S. PATENT DOCUMENTS

| | | | |
|---|---|---|---|
| 8,940,272 B2 | 1/2015 | Nitsch et al. | |
| 2014/0234214 A1 | 8/2014 | Griswold-Prenner et al. | |
| 2015/0196663 A1* | 7/2015 | Shusta | C07K 16/28 435/254.11 |
| 2015/0266947 A1* | 9/2015 | Sierks | C07K 16/005 435/6.12 |
| 2016/0251420 A1 | 9/2016 | Hayashi et al. | |
| 2017/0355756 A1* | 12/2017 | Julien | A61P 25/00 |

FOREIGN PATENT DOCUMENTS

| | | | |
|---|---|---|---|
| WO | WO2008068048 | * | 6/2008 |
| WO | 2016/079597 A1 | | 5/2016 |
| WO | 2017/096397 A1 | | 6/2017 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
International Search Report and Written Opinion for corresponding Application No. PCT/2019/018571 (mailed Jul. 22, 2019).

* cited by examiner

*Primary Examiner* — Olga N Chernyshev
(74) *Attorney, Agent, or Firm* — Troutman Pepper Locke LLP (Rochester)

(57) ABSTRACT

The present disclosure is directed to single domain antibodies that bind to tau and the use of these antibodies for the treatment and diagnosis of tauopathies. The present disclosure is also directed to polynucleotides encoding the tau single domain antibodies, therapeutic vectors comprising these polynucleotides and methods of administering these therapeutic vectors for the treatment of tauopathies.

34 Claims, 12 Drawing Sheets
Specification includes a Sequence Listing.

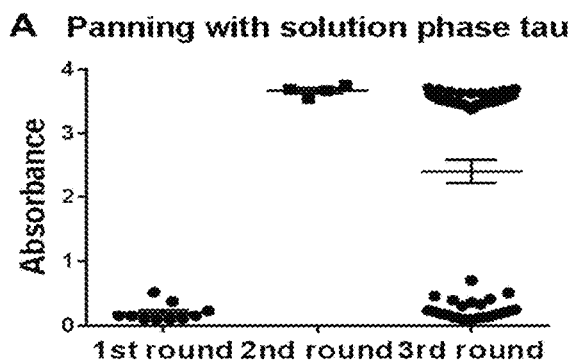
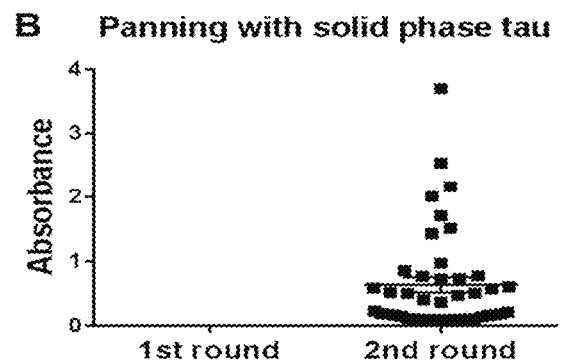
FIG. 2A
FIG. 2B
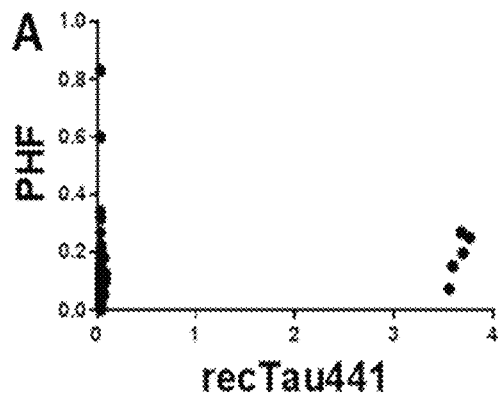
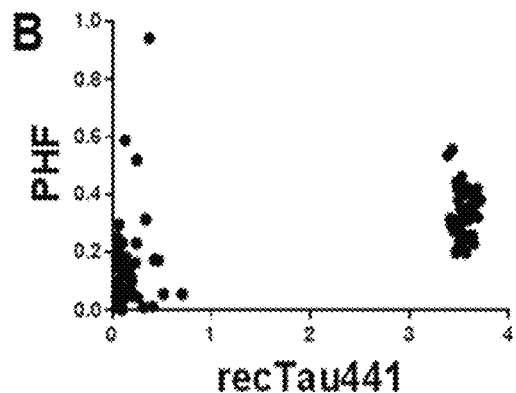
FIG. 3A
FIG. 3B
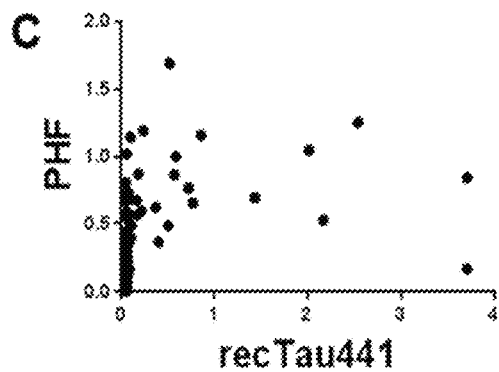
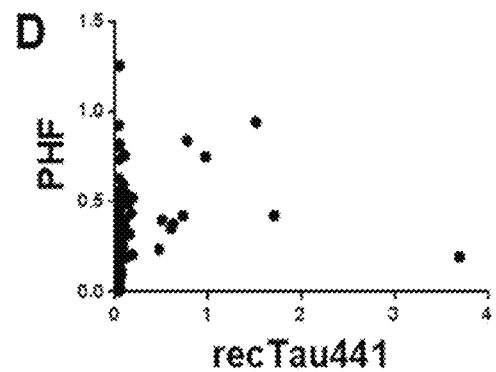
FIG. 3C
FIG. 3D

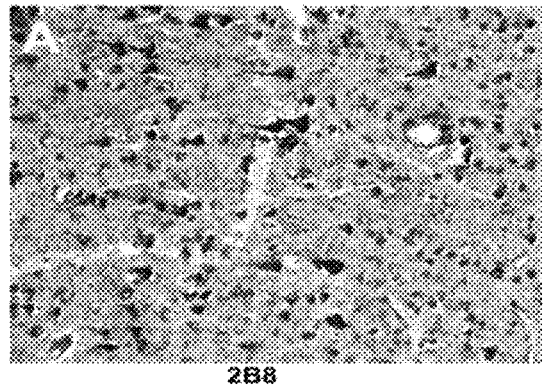
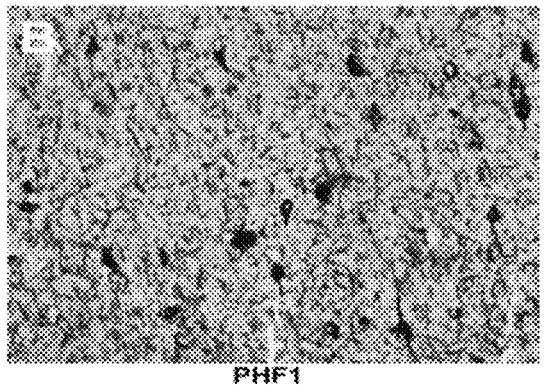
FIG. 4A  FIG. 4B
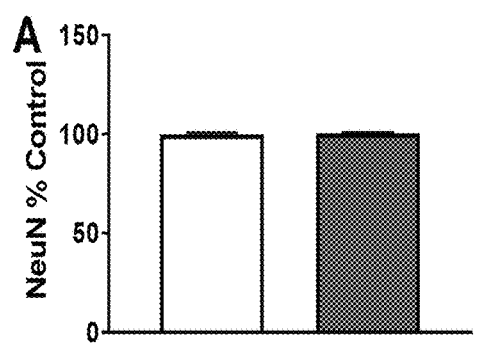
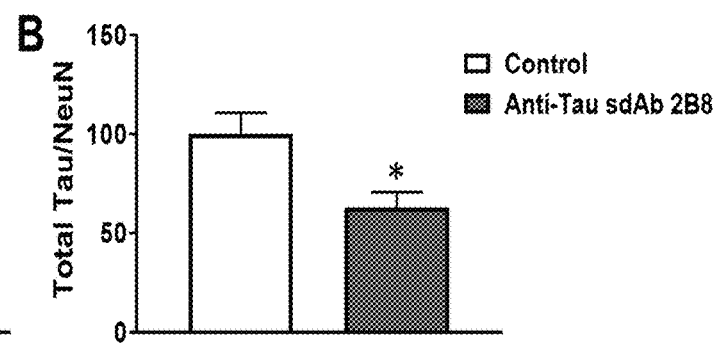
FIG. 5A  FIG. 5B

| SEQ ID NO: | sdAb Name | Sequence (positions 80-150) |
|---|---|---|
| 133 | T-sR2-2C5 | AKNTMYLQMNSLKPEDTAVYYCAARSSLLEEFWLGSRRGYDYWGQGTQVTVSSTSGPGGQHHHHHHGAEQKLISEEDLS |
| 147 | T-sR2-1G12 | G...V............................NAG.SLLRNWRTNE.A............................ |
| 119 | T-sR2-2F8 | ...V.............................NAG.SLLRNWRTNE.A............................ |
| 132 | T-sR2-1F8 | V...V............................LALGFFTNYYVRESS.R........................... |
| 138 | T-sR2-2H5 | ....V........N....................NLFQWRLNDNGNQYGS~........................... |
| 151 | T-sR2-1H12 | ....V.........................GR.SRG.SGS.YLRSSYP~............................. |
| 126 | T-sR2-2G8 | G.AV.........Q....L...............RPTARWDLFREKYDFR~........................... |
| 130 | T-sR2-2G9 | ....V..............I..............AQGGFMKPRANWYNS~.........L.................. |
| 140 | T-sR2-1G5 | .S.L..............................DPRWRLPFP.YGMD~..K......................... |
| 124 | T-sR2-1E9 | ....V.............................TLRAWALTFATSYA~............................. |
| 128 | T-sR2-1F5 | ....V............S................SRFGINYYTARQY.~............................ |
| 149 | T-sR2-2E8 | .T.VV........S...G................S.RR.LGGPFAYD~....L........................ |
| 141 | T-sR2-2D8 | .K.V........DN....................NVE.RRGIGF.RKTYS~........................... |
| 116 | T-sR2-2A11 | ....L........D....................K.GRHPHFSMDYPDL~............................ |
| 137 | T-sR2-2C9 | ....V........I....................KV.GPRIIPQLR.E~~~........................... |
| 143 | T-sR2-1C7 | ....V........I....................KYPTITWYGRHDY.~~~~.......................... |
| 148 | T-sR2-2E7 | .K.V..............................N.VPYRWGSSWYAG.~~~~........................ |
| 127 | T-sR2-1B7 | ....V........H....I...............V.DRRSSYLGPRFD~~~~~......................... |
| 146 | T-sR2-1C10 | .E.V..............................N.DIRPRIISFFKD~~~~~........................ |
| 134 | T-sR2-2H4 | ....V.............................TGRAWSTLATTYV~~~~~~........................ |
| 121 | T-sR2-2B7 | ....V........I....I...............AKQI.IRPDAYV~~~~~~~........................ |
| 136 | T-sR2-1G1 | ....A........T....................GPRIAVWRYEYN~~~~~~~......................... |
| 139 | T-sR2-1C6 | ....V.............................G.RAVL.GTYD~~~~~~~~~........................ |
| 129 | T-sR2-2C1 | ....V........G.S..................GPRAVL.GTYD~~~~~~~~~....L................... |
| 152 | T-sR2-2E9 | ....V........K.S..................RVYGRVWSRPYD~~~~~~~~......................... |
| 125 | T-sR2-1D3 | .MV..........K.S..................RVYGRVWSRPYD~~~~~~~~........................ |
| 125 | T-sR2-2B11 | .MV...........S...................NFKYRYGLGPRD~~~~~~~~.......................L |
| 122 | T-sR2-2G7 | ....L.............................GRFMGSYD~~~~~~~~~~......................... |
| 150 | T-sR2-1D9 | ....V........D....................NVKKHFGIRYD~~~~~~~~......................... |
| 118 | T-sR2-2B4 | ....V.............................F.NVHLVFTNRD~~~~~~~........................ |
| 145 | T-sR2-2H8 | .K.L..............................N.DTHFSTRN~~~~~~~~~~......................L |
| 123 | T-sR2-1B2 | ....V.............................N.YFRWGTR~~~~~~~~~~~~...................... |
| 135 | T-sR2-1C5 | ....V..........N.T................N.YFRWGTR~~~~~~~~~~~~...................... |
| 115 | T-sR2-1D10 | ....V..........N.T................N.NRRGWN~~~~~~~~~~~~~...................... |
| 142 | T-sR2-2H7 | G.................G................NVQRFITT~~~~~~~~~~~~~....L................. |
| 120 | T-sR2-1A8 | ....V.............G................NVQRFITT~~~~~~~~~~~~~.....L................ |
| 131 | T-sR2-1B8 | ....V........M....................KLTRL.NT~~~~~~~~~~~~~~...................... |
| 144 | T-sR2-2E6 | .K.L..............................N.NYLIRS~~~~~~~~~~~~~~...................... |
| 117 | T-sR2-1E4 | | |

CDR3

| SEQ ID NO: | sdAb Name | 90 TLYLQMNSLKSEDTAMYYCGK | 100 VDEIRPTVSAS | 110 | 120 ~~~~~~~~YDLWGQGTL | 130 VTVSSTSGPGGQHHHHHHGAEQKLISEEDLS | 140 | 150 | 160 |
|---|---|---|---|---|---|---|---|---|---|
| 189 | T-bR3-1A8 | ................... | ........... | | ~~~~~~~~........ | .............................. | | | |
| 189 | T-bR3-1A10 | ................... | ........... | | ~~~~~~~~........ | .............................. | | | |
| 189 | T-bR3-1B1 | ................... | ........... | | ~~~~~~~~........ | .............................. | | | |
| 189 | T-bR3-1B5 | ................... | ........... | | ~~~~~~~~........ | .............................. | | | |
| 189 | T-bR3-1B9 | ................... | ........... | | ~~~~~~~~........ | .............................. | | | |
| 189 | T-bR3-1B12 | ................... | ........... | | ~~~~~~~~........ | .............................. | | | |
| 189 | T-bR3-1C1 | ................... | ........... | | ~~~~~~~~........ | .............................. | | | |
| 189 | T-bR3-1C2 | ................... | ........... | | ~~~~~~~~........ | .............................. | | | |
| 189 | T-bR3-1C3 | ................... | ........... | | ~~~~~~~~........ | .............................. | | | |
| 189 | T-bR3-1C4 | ................... | ........... | | ~~~~~~~~........ | .............................. | | | |
| 189 | T-bR3-1C5 | ................... | ........... | | ~~~~~~~~........ | .............................. | | | |
| 189 | T-bR3-1C6 | ................... | ........... | | ~~~~~~~~........ | .............................. | | | |
| 189 | T-bR3-1C9 | ................... | ........... | | ~~~~~~~~........ | .............................. | | | |
| 189 | T-bR3-1C10 | ................... | ........... | | ~~~~~~~~........ | .............................. | | | |
| 189 | T-bR3-1C12 | ................... | ........... | | ~~~~~~~~........ | .............................. | | | |
| 189 | T-bR3-1D1 | ................... | ........... | | ~~~~~~~~........ | .............................. | | | |
| 189 | T-bR3-1D5 | ................... | ........... | | ~~~~~~~~........ | .............................. | | | |
| 189 | T-bR3-1D6 | ................... | ........... | | ~~~~~~~~........ | .............................. | | | |
| 189 | T-bR3-1D7 | ................... | ........... | | ~~~~~~~~........ | .............................. | | | |
| 189 | T-bR3-1D8 | ................... | ........... | | ~~~~~~~~........ | .............................. | | | |
| 189 | T-bR3-1D10 | ................... | ........... | | ~~~~~~~~........ | .............................. | | | |
| 189 | T-bR3-1D11 | ................... | ........... | | ~~~~~~~~........ | .............................. | | | |
| 189 | T-bR3-1E2 | ................... | ........... | | ~~~~~~~~........ | .............................. | | | |
| 189 | T-bR3-1E4 | ................... | ........... | | ~~~~~~~~........ | .............................. | | | |
| 192 | T-bR3-1A9 | AA................. | IP........N | AT.GQSCDLWDHPQV | PVRYRGR~~~~~ | ..Q........................... | | | |
| 192 | T-bR3-1B3 | AA................. | IP........N | AT.GQSCDLWDHPQV | PVRYRGR~~~~~ | ..Q........................... | | | |
| 192 | T-bR3-1B10 | AA................. | IP........N | AT.GQSCDLWDHPQV | PVRYRGR~~~~~ | ..Q........................... | | | |
| 192 | T-bR3-1C7 | AA................. | IP........N | AT.GQSCDLWDHPQV | PVRYRGR~~~~~ | ..Q........................... | | | |
| 192 | T-bR3-1E12 | AA................. | IP........N | AT.GQSCDLWDHPQV | PVRYRGR~~~~~ | ..Q........................... | | | |
| 191 | T-bR3-1F8 | AA................. | IP........N | AT.GQSCDLWDHPQV | PVRYRGR~~~~~ | ..Q........................... | | | |
| 192 | T-bR3-1H11 | AA................. | IP........N | AT.GQSCDLWDHPQV | PVRYRGR~~~~~ | ..Q........................... | | | |
| 198 | T-bR3-1B8 | ...I............... | .....D.... | V.H.A.LDYYCSGYGCYAS. | ........... | .............................. | | | |
| 198 | T-bR3-1D12 | ...I............... | .....D.... | V.H.A.LDYYCSGYGCYAS. | ........... | .............................. | | | |
| 194 | T-bR3-1F10 | .V................. | .P........V | NAWSPVGHD~~~~~~ | ........~Y | ..Q........................... | | | |
| 194 | T-bR3-1G5 | .V................. | .P........V | NAWSPVGHD~~~~~~ | ........~Y | ..Q........................... | | | |
| 199 | T-bR3-1E1 | VS................. | .P........V | NAGRYVPGAIVTN.. | ........~Y | ..Q........................... | | | |
| 200 | T-bR3-1B11 | .V...I............. | .P........V | NARRYYSLARYDYN. | ........~Y | ..Q........................... | | | |
| 195 | T-bR3-1F12 | .V................. | .P........T | AAARGG.WYST~~~~ | ........~Y | ..Q........................... | | | |
| 197 | T-bR3-1C8 | .V.V.N.P........... | .P........V | AARRSG.YE~~~~~~ | ........~Y | ..Q........................... | | | |
| 190 | T-bR3-1A11 | ...E...TP.......... | ........V | AVSRYYTAGA.DTKT | ........~Y | ............................. | | | |
| 193 | T-bR3-1B2 | .V..D..PD.......... | ........V | ADVNYGSPDYID... | ........~Y | ..Q........................... | | | |
| 201 | T-bR3-1E11 | .V.R..D.RI......... | ........V | YAEGLLL.ST~~~~~ | ........... | .............................. | | | |
| 196 | T-bR3-1G3 | .F................. | .P........V | NARLWLNN~~~~~~~ | ........~Y | ..Q........................... | | | |

CDR3

TAU SINGLE DOMAIN ANTIBODIES

This application is a national stage application under 35 U.S.C. § 371 of PCT Application No. PCT/US2019/018571, filed Feb. 19, 2019, which claims the benefit of U.S. Provisional Patent Application Ser. Nos. 62/632,261 filed Feb. 19, 2018, and 62/672,949 filed May 17, 2018, which are hereby incorporated by reference in their entirety.

This invention was made with government support under R21 AG058282 awarded by the National Institutes of Health. The government has certain rights in the invention.

FIELD OF THE INVENTION

The present invention is directed to antibodies for the treatment and diagnosis of conditions involving pathological tau.

BACKGROUND OF THE INVENTION

Immunotherapies targeting various protein aggregates such as amyloid-β (Aβ), tau and α-synuclein are in different stages of clinical development, and collectively are the most common approach by the pharmaceutical industry to tackle diseases characterized by such depositions (Golde T. E. "Open Questions for Alzheimer's Disease Immunotherapy," Alzheimers Res Ther 6:3 (2014); Valera et al., "Immunotherapy for Neurodegenerative Diseases: Focus on Alpha-Synucleinopathies," Pharmacol Ther 138:311-322 (2013); Pedersen et al. "Tau Immunotherapy for Alzheimer's Disease," Trends Mol Med 21:394-402 (2015)). The majority of these approaches involve whole antibodies and much less attention has been paid to antibody fragments which have certain advantages and their therapeutic and diagnostic potential should be explored further.

The present invention is directed to overcoming these and other deficiencies in the art.

SUMMARY OF THE INVENTION

A first aspect of the present disclosure is directed to an antibody or fragment thereof comprising a heavy chain variable region. The heavy chain variable region comprises a complementarity-determining region 1 (H-CDR1) comprising an amino acid sequence of any one of SEQ ID NOs: 1-38, 202, 206, 210, 214 or a modified amino acid sequence of any one of SEQ ID NOs: 1-38, 202, 206, 210 and 214 said modified sequence containing 1, 2, or 3 amino acid residue modifications as compared to any one of SEQ ID NOs: 1-38, 202, 206, 210 and 214; a complementarity-determining region 2 (H-CDR2) comprising an amino acid sequence of any one of SEQ ID NOs: 39-76, 203, 207, 211, 215 or a modified amino acid sequence of any one of SEQ ID NOs: 39-76, 203, 207, 211, and 215 said modified sequence containing 1, 2, or 3 amino acid residue modifications as compared to any one of SEQ ID NOs: 39-76, 203, 207, 211, and 215; and a complementarity-determining region 3 (H-CDR3) comprising an amino acid sequence of any one of SEQ ID NOs: 77-114, 204, 208, 212, 216 or a modified amino acid sequence of any one of SEQ ID NOs: 77-114, 204, 208, 212, and 216 said modified sequence containing 1, 2, or 3 amino acid residue modifications as compared to any one of SEQ ID NOs: 77-114, 204, 208, 212 and 216.

Another aspect of the present disclosure is directed to an antibody or fragment thereof comprising a heavy chain variable region. The heavy chain variable region comprises a complementarity-determining region 1 (H-CDR1) comprising an amino acid sequence of any one of SEQ ID NOs: 153-164, 307, or a modified amino acid sequence of any one of SEQ ID NOs: 153-164 and 307, said modified sequence containing 1, 2, or 3 amino acid residue modifications as compared to any one of SEQ ID NOs: 153-164 and 307; a complementarity-determining region 2 (H-CDR2) comprising an amino acid sequence of any one of SEQ ID NOs: 165-176, 308, or a modified amino acid sequence of any one of SEQ ID NOs: 165-176 and 308, said modified sequence containing 1, 2, or 3 amino acid residue modifications as compared to any one of SEQ ID NOs: 165-176 and 308; and a complementarity-determining region 3 (H-CDR3) comprising an amino acid sequence of any one of SEQ ID NOs: 177-188, 309 or a modified amino acid sequence of any one of SEQ ID NOs: 177-188 and 309, said modified sequence containing 1, 2, or 3 amino acid residue modifications as compared to any one of SEQ ID NOs: 177-188 and 309.

Another aspect of the present disclosure is directed to a method of inhibiting onset of one or more symptoms of a condition involving pathological tau protein in a subject. This method involves administering to the subject a pharmaceutical composition comprising one or more antibodies or binding fragments thereof as described herein, or polynucleotides encoding the one or more antibodies or binding fragments thereof as described herein, in an amount effective to inhibit onset of one or more symptoms of the condition involving pathological tau protein in the subject.

Another aspect of the present disclosure is directed to a method of treating a condition involving pathological tau protein in a subject. This method involves administering to the subject a pharmaceutical composition comprising one or more antibodies or binding fragments thereof as described herein, or polynucleotides encoding the one or more antibodies or binding fragments thereof as described herein, in an amount effective to treat the condition involving pathological tau protein in the subject.

Another aspect of the present disclosure is directed to a method of diagnosing Alzheimer's disease or a tauopathy in a subject. This method involves detecting, in the subject, the presence of accumulated tau protein or peptide using the antibody or binding fragment as described herein, and diagnosing Alzheimer's disease or a tauopathy based on the detection of the accumulated tau protein or peptide in the subject.

Another aspect of the present disclosure is directed to a method of monitoring the progression of Alzheimer's disease or a tauopathy in a subject. This method involves detecting, in the subject, the presence of accumulated tau protein or peptide using the antibody or binding fragment thereof as described herein, repeating the detecting step periodically; and monitoring the progression of Alzheimer's disease or the tauopathy in the subject as a result of the repeated detecting.

Another aspect of the present disclosure is directed to a diagnostic kit. The diagnostic kit contains any one or more antibodies or binding fragments thereof as described herein, and a detectable label.

BRIEF DESCRIPTION OF THE DRAWINGS

FIGS. 2A-2B shows enrichment of tau sdAbs by phage display library panning against biotinylated-tau solution phase (FIG. 2A) and solid phase (FIG. 2B).

FIGS. 3A-3D show the binding profiles of tau sdAbs to recTau441 and paired helical filaments (PHF). FIG. 3A-B show the binding profile of tau sdAbs enriched by solution phase tau binding (round 2 enriched antibodies shown in FIG. 3A and round 3 enriched antibodies shown in FIG. 3B). FIGS. 3C-3D show the binding profile of tau sdAbs enriched by solid phase tau binding (round 2 enriched antibodies shown in FIG. 3C and round 3 enriched antibodies shown in FIG. 3D).

FIGS. 4A-4B show anti-tau sdAb binding tau pathology in human tauopathy brains. FIG. 4A is human tauopathy brain section reacted with tau sdAb 2B8. FIG. 4B is an adjacent human tauopathy brain section reacted with PHF1 antibody for comparison.

FIGS. 5A-5B show that tau sdAb clears tau from primary neurons derived from Tg JNPL3 tauopathy pups (Day 0) (FIG. 5B) without overt signs of toxicity (FIG. 5A).

FIG. 9, far left), and an antibody against early endosomes (EEA1; FIG. 9 top panel, second image from left) or late endosomes/lysosomes (Rab; FIG. 9, bottom panel, second image from left). Merged images and their magnification (as per white boxes; FIG. 9, top/bottom panel right images) revealed that sdAb1 enters the brain following i.v. injection and is taken up into neurons into the endosomal-lysosomal system. sdAb1: 2B8

FIG. 10, far left images), and an antibody against hyperphosphorylated tau epitope (PHF1; FIG. 10, top panel, second image from left) or a conformational tau epitope (MC1; FIG. 10, bottom panel, second image from left). Merged images and their magnification (as per white boxes; FIG. 10, top/bottom panel right images) revealed that sdAb1 enters the brain following i.v. injection and is taken up into neurons, where it binds to pathological tau protein in the endosomal-lysosomal system as per FIG. 9 sdAb1: 2B8

Figure 11:
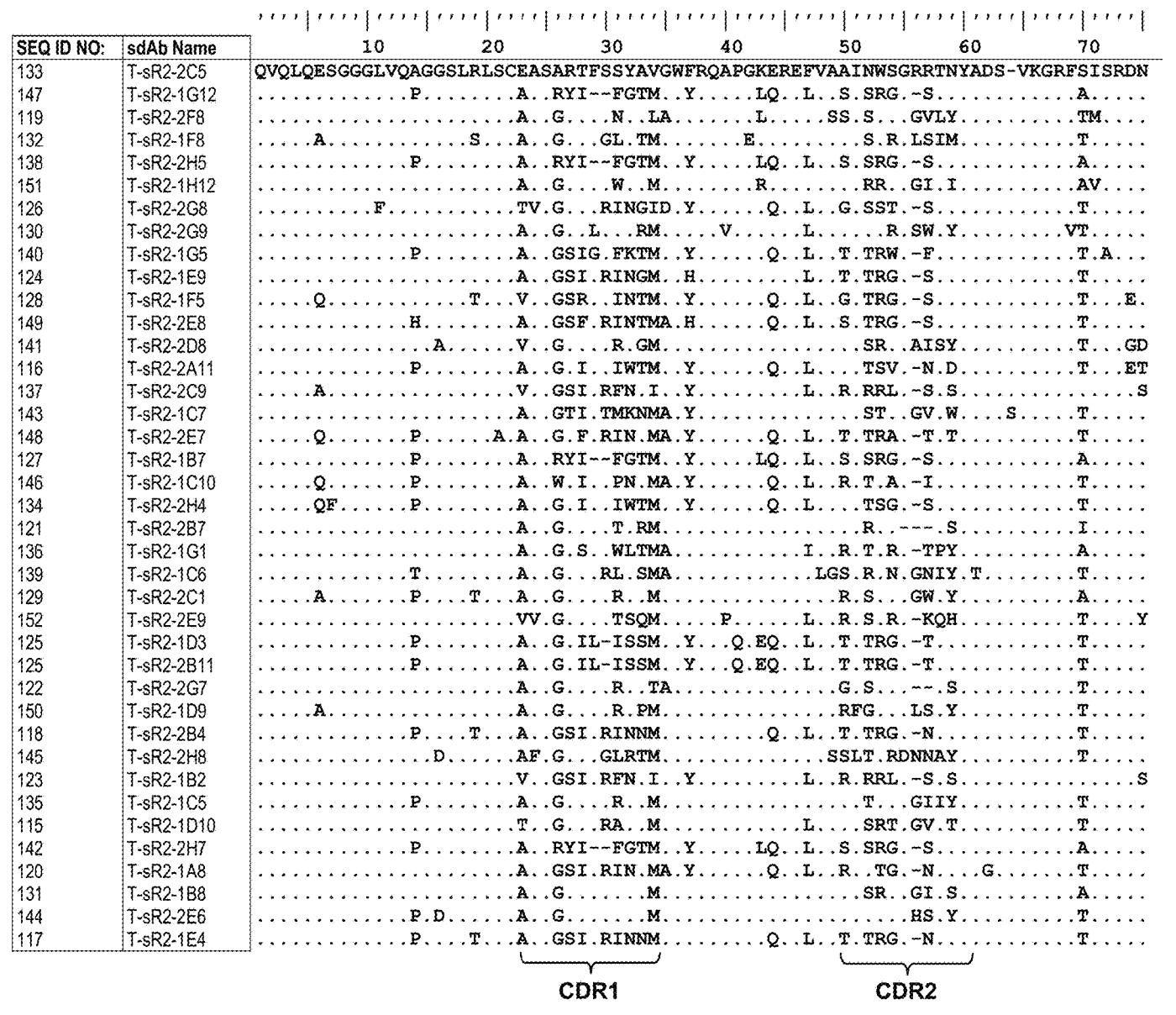

FIG. 11 is a sequence alignment of the anti-tau sdAbs selected via solid-phase panning. The three complementarity determining regions (CDRs) are shown. Sequence identifiers for each of the sdAbs is indicated in the figure. Omitted from each sequence in the Sequence Listing is the portion containing the histidine tag.

Figure 12:
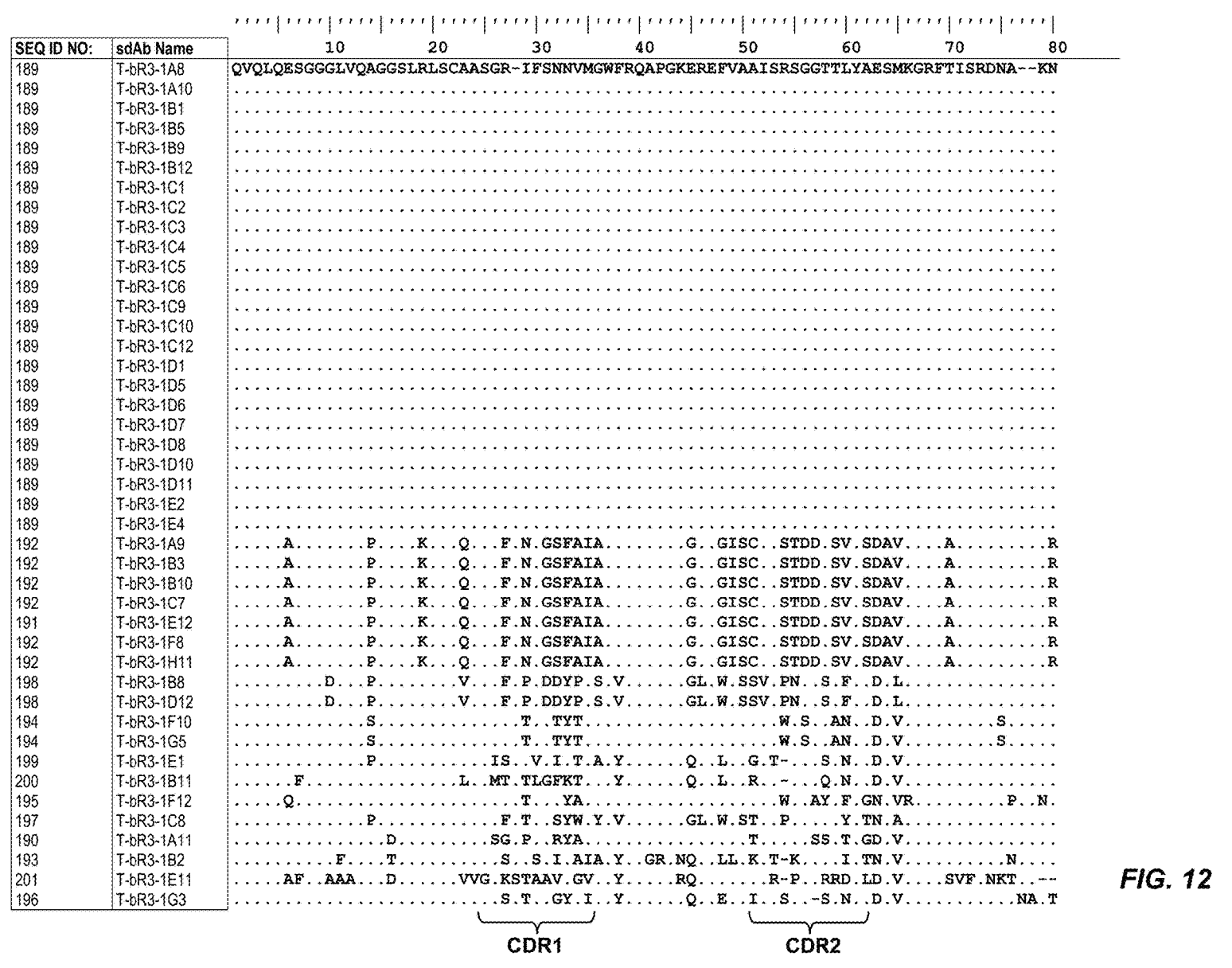

FIG. 12 is a sequence alignment of the anti-tau sdAb selected via solution-phase panning. The three complementarity determining regions (CDRs) are shown. Sequence identifiers for each of the sdAbs is indicated in the figure. Omitted from each sequence in the Sequence Listing is the portion containing the histidine tag.

DETAILED DESCRIPTION OF THE INVENTION

Figure 1A:
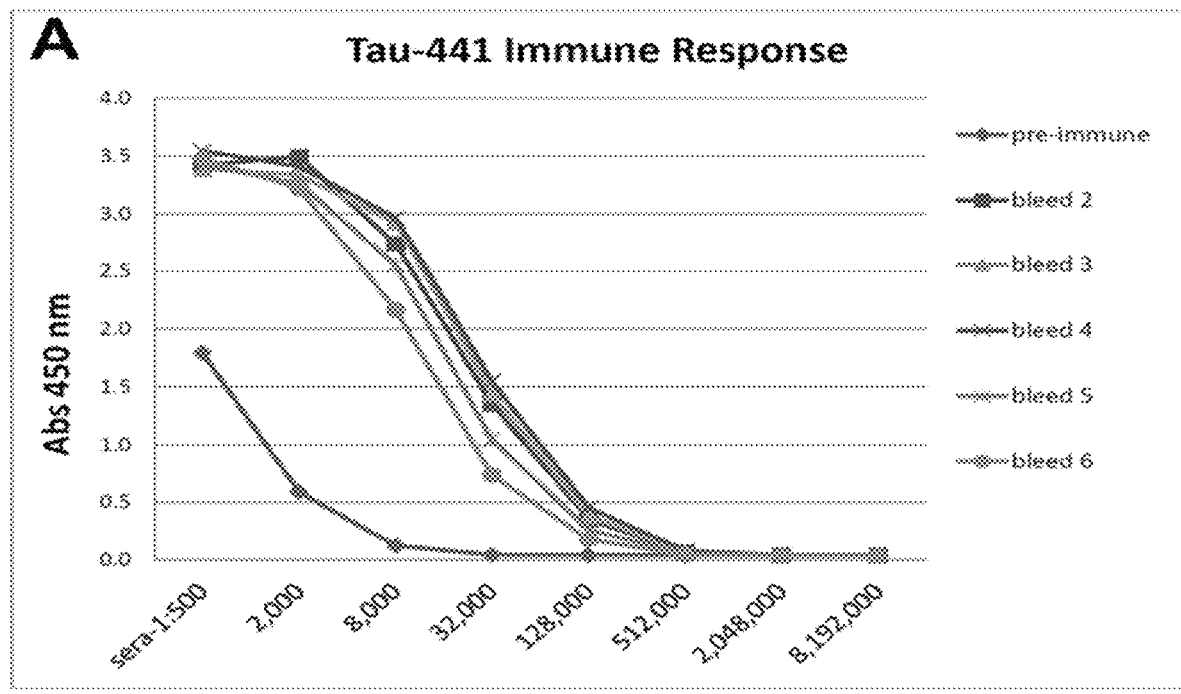
FIG. 1A shows the tau single domain antibody (sdAb) titer generated in llama following 1-5 immunizations with recombinant tau441.

A first aspect of the present invention is directed to an antibody or binding fragment thereof that binds tau protein. In particular, the antibody or binding fragment as disclosed herein binds to human tau protein. In one embodiment, the antibody or binding fragment thereof of the present disclosure binds to pathological aggregated forms of tau protein, such as tangles, paired helical filaments, and tau oligomers that are associated with the development and progression of a tauopathy or associated condition. In another embodiment, the antibody or binding fragment thereof of the present disclosure binds to the non-pathological forms of tau.

In one embodiment, the antibodies described herein are single domain antibodies. The unique binding property or antigen binding specificity of a given antibody is determined by its complementarity determining regions (CDR) typically found in the light and heavy chain variable regions of an immunoglobulin. Single domain antibodies are antibodies whose CDRs are part of a single domain polypeptide. Examples include, but are not limited to, heavy chain variable domain antibodies (including three CDRs) and light chain variable domain antibodies (containing three CDRs). Single domain antibodies can be derived from heavy chains and light chains of conventional 4-chain antibodies, antibodies naturally devoid of light chains, engineered antibodies and single domain scaffolds other than those derived from antibodies. In one embodiment, the single domain antibody of the present invention is a heavy chain single domain antibody, i.e., a $V_HH$ or nanobody. In one embodiment, the heavy chain single domain antibodies described herein are derived from naturally occurring heavy chain antibodies devoid of light chains.

Single domain antibodies are about 10-times smaller than conventional heavy chain and light chain containing IgG molecules. They are single polypeptides that are very stable, as they are resistant to extreme pH and temperature conditions. Moreover, unlike conventional antibodies, single domain antibodies are resistant to the action of proteases. In vitro expression of $V_HHs$ produces high yield, properly folded functional $V_HHs$. Given their small size, $V_HHs$ are capable of recognizing unique epitopes of an antigen that cannot be bound by traditional full sized antibodies. As such, the anti-tau single domain antibodies described herein bind unique epitopes of tau and/or bind epitopes more efficiently than conventional tau antibodies.

The single domain antibodies as described herein can be derived from antibodies raised in Camelidae species, for example in camel, dromedary, llama, vicuna, alpaca and guanaco. Single domain antibodies produced by other species are also within the scope of the invention. For example, single domain antibodies as disclosed herein may be derived from antibodies produced in any species including, but not limited to mouse, human, camel, llama, goat, rabbit, bovine, and cartilaginous fish.

In another embodiment, the antibody as described herein is an antibody fragment. In one embodiment, an antibody fragment is a single-chain polypeptide comprising one CDR as described herein. In another embodiment, the antibody fragment is a single-chain polypeptide comprising two CDRs as described herein. In another embodiment, the antibody fragment is a single-chain polypeptide containing all three CDRs of the heavy chain variable regions as described herein. An antibody fragment as referred to herein may be devoid of one or more framework regions (FR1, FR2, FR3, or FR4) or any portion thereof of the heavy chain variable region.

In one embodiment, the antibody as described herein comprises a $V_H$ domain coupled to one or more heavy chain constant regions ($C_H$). Mammalian heavy chain immunoglobulins typically have three or four constant region domains. Accordingly, the heavy chain variable regions described herein may be coupled to one heavy chain constant region, two heavy chain constant regions, three heavy chain constant regions, or four heavy chain constant regions.

In one embodiment, the antibody as described herein comprises a $V_H$ domain coupled to an Fc region, i.e., the antibody is an Fc-fusion antibody. The Fc region can be composed of the second and third constant domain regions (as it is for IgG, IgA, and IgD antibody isotypes), or composed of the second, third, and fourth constant domain regions (as it is for IgM and IgE antibody isotypes). In one embodiment, the Fc domain is derived from a human immunoglobulin. In one embodiment, the Fc domain is derived from human IgG1 including the $C_H2$ and $C_H3$ regions.

The Fc-region or domain of the fusion polypeptides described herein may impart non-antigen binding functions to the polypeptide, termed "effector functions", such as complement binding, antibody-dependent cell cytotoxicity (ADCC), and other functions mediated through the binding of subregions of this dimeric structure with immune cell surface receptors, Fc-receptors. Certain natural and synthetic variants of the Fc-region polypeptide sequences with altered effector functions that are suitable for use in the fusion polypeptides described herein include the subclass variants; e.g. IgGi, IgG2i, IgG3i, IgG24; and mutant polypeptides as described in e.g. U.S. Pat. No. 5,624,821 to Winter, U.S. Pat. No. 6,528,624 to Idusogie, U.S. Pat. No. 7,183,387 to Presta, and U.S. Pat. No. 7,317,091 to Lazar et al., which are hereby incorporated by reference in their entirety.

In another embodiment, the antibody or fragment thereof comprises two or more variable domain regions coupled together. For example, in one embodiment, the antibody as described herein comprises two, or three, or more heavy chain variable regions linked together in tandem. In another embodiment, the heavy chain variable region is fused together with a light chain variable region to form a single-chain variable domain antibody (scFv) or a single-chain variable domain with an Fc portion (i.e., a scFv-Fc, e.g., a minibody). In another embodiment, two or more single-chain antibodies are linked together either in tandem (i.e., tandem scFvs), or such that they dimerize to form diabodies or triabodies. In another embodiment, the antibody is a tetrabody single chain variable fragment. In another embodiment, the antibody is a "linear antibody", which is an antibody comprising a pair of tandem Fd segments ($V_H$—$C_H1$-$V_H$-$C_H1$) that form a pair of antigen binding regions (see Zapata et al. *Protein Eng.* 8(10):1057-1062 (1995), which is hereby incorporated by reference in its entirety).

In another embodiment, the antibody of the disclosure is a conventional immunoglobulin (Ig) molecule comprising four polypeptide chains, i.e., two heavy chains and two light chains linked by disulfide bonds. In accordance with this embodiment, the single-domain antibodies as described herein are coupled to constant domain regions and further coupled to Ig light chains to create a four chain conventional antibody.

Antibody and antibody fragments disclosed herein can be mono-valent, bi-valent, or tri-valent with regard to binding domains, and the binding domains may be mono-specific, bi-specific, or tri-specific in binding specificity by design.

In one embodiment, the antibody or fragment thereof is isolated. As used herein, the term "isolated" refers to an antibody which has been separated from a component of its natural environment. In some embodiments, an antibody is purified to greater than 95% or 99% purity as determined by, for example, electrophoretic separation (e.g., SDS-PAGE, isoelectric focusing (IEF), capillary electrophoresis) or chromatographic separation (e.g., gel filtration, ion exchange or reverse phase HPLC). Methods for assessing antibody purity are known in the art (see e.g., Flatman et al., *J. Chromatogr. B* 848:79-87 (2007), which is hereby incorporated by reference in its entirety), and are suitable for assessing the purity of the antibodies described herein.

In one embodiment, the antibody or binding fragment thereof described herein is a chimeric antibody. A chimeric antibody is an antibody where one portion of the amino acid sequence of each of the heavy chains is homologous to corresponding sequences in an antibody derived from a particular species or belonging to a particular class, while the remaining segment of each chain is homologous to corresponding sequences in another species or class. Typically, the variable region mimics the variable region of an antibody derived from one species of mammals, while the constant portions are homologous to sequences of antibodies derived from another. For example, the variable region can be any one of the heavy chain variable regions disclosed herein derived from a camelid antibody coupled to one or more constant regions derived from a human immunoglobulin. Methods of making chimeric antibodies are well known in the art, see e.g., U.S. Pat. No. 4,816,567; and Morrison et al., "Chimeric human antibody molecules: mouse antigen-binding domains with human constant region domains" *Proc. Natl. Acad. Sci. USA* 81:6851-6855 (1984), which are hereby incorporated by reference in their entirety).

In another embodiment, the antibody or binding fragment thereof is a CDR-grafted antibody. A "CDR-grafted antibody" is an antibody which comprises variable region sequences of one species, where one or more of the CDR regions are replaced with CDR regions of another species. For example, in one embodiment the CDR grafted antibody comprises human or humanized heavy chain variable regions, where one or more of the CDRs within these regions is replaced with one or more CDRs disclosed herein that are derived from camelid heavy chain antibodies.

In another embodiment, the antibody or binding fragment thereof is a humanized antibody. A humanized antibody is an antibody or a variant, derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody in accordance with the present disclosure comprises, for example, substantially all of at least one variable domains (Fv) in which all or substantially all of the CDR regions correspond to those of a non-human immunoglobulin (i.e., the donor camelid antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," *Frontiers in Bioscience* 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones: Introduction to Gene Technology" (1987); Carter et al., *Proc. Natl. Acad. Sci. USA,* 89:4285 (1992); and Presta et al., *J. Immunol.,* 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain FR sequences known in the art can be used as heavy chain "acceptor" framework sequences (or simply, "acceptor" sequences) to humanize a non-human antibody using techniques known in the art (see e.g., Sims et al., *J. Immunol.,* 151:2296 (1993); Chothia et al., *J. Mol. Biol.,* 196:901 (1987), which are hereby incorporated by reference in their entirety). In one embodiment, human heavy chain acceptor sequences are selected from the framework sequences listed in publically available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the heavy chain variable domain. The humanized antibody may further comprise the CH1, hinge, CH2, CH3, and CH4 regions of a human heavy chain. In another embodiment, the humanized antibody comprises only a humanized heavy chain. Humanized antibodies and binding fragments thereof as described herein may be selected from any class of immunoglobulins, including IgM, IgG, IgD, IgA and IgE, and any isotype, including without limitation IgG1, IgG2, IgG3 and IgG4. The humanized antibody or binding fragment thereof may comprise sequences from more than one class or isotype, and particular constant domains may be selected to optimize desired effector functions using techniques well-known in the art.

The antibodies and binding fragments thereof described herein can be humanized antibodies (fully or partially humanized) as described supra. Alternatively, the antibodies and binding fragments thereof can be animal antibodies such as, but not limited to, a bird (for example, a duck or a goose), a shark, a whale, or a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.). In one embodiment, the antibodies and binding fragments thereof as described herein are derived from camelid antibodies.

Methods of antibody production, in particular, monoclonal antibody production, may be carried out using the methods described herein and those well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest (e.g., full length tau as set forth in the Examples herein) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," Eur J Immunol 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment, monoclonal antibodies can be isolated from antibody phage libraries generated using the techniques described herein or known in the art, see e.g., McCafferty et al., "Phage Antibodies: Filamentous Phage Displaying Antibody Variable Domains," Nature 348:552-554 (1990), which is hereby incorporated by reference in its entirety. Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., BioTechnology 10:779-783 (1992), which is hereby incorporated by reference in its entirety), as well as combinatorial infection and in vivo recombination as a strategy for constructing very large phage libraries (Waterhouse et al., Nuc. Acids. Res. 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the heavy chain constant domains of a camelid monoclonal antibody can be substituted for those regions of a human antibody to generate a chimeric antibody. Alternatively, the heavy chain constant domains of a camelid monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In one embodiment of the present disclosure, the antibody or binding fragment thereof as disclosed herein comprises a heavy chain variable region (HCVR) having a H-CDR1 with an amino acid sequence selected from SEQ ID NOs: 1-38, 202, 206, 210, 214 or a modified amino acid sequence thereof containing 1, 2, 3, 4, 5, 6, 7, 8, 9, or 10 amino acid residue modifications as compared to SEQ ID NOs: 1-38, 202, 206, 210, and 214 that maintain or enhance binding specificity of the H-CDR1. In one embodiment, the amino acid sequence of the H-CDR1 contains no more than 1, 2, or 3 amino acid modifications as compared to SEQ ID NOs: 1-38, 202, 206, 210, and 214 respectively. The HCVR further comprises a H-CDR2 with an amino acid sequence selected from any one of SEQ ID NOs: 39-76, 203, 207, 211, 215, or a modified amino acid sequence thereof containing 1, 2, 3, 4, 5, 6 or 7, amino acid residue modifications as compared to SEQ ID NOs: 39-76, 203, 207, 211, and 215 that maintain or enhance binding specificity of the H-CDR2. In one embodiment, the amino acid sequence of the H-CDR2 contains no more than 1, 2, or 3, amino acid modifications as compared to SEQ ID NOs: 39-76, 203, 207, 211, and 215 respectively. The HCVR of the antibody or binding fragment thereof comprises a H-CDR3 with an amino acid sequence selected from any one of SEQ ID NOs: 77-114, 204, 208, 212, 216 or a modified amino acid sequence thereof containing 1, 2, 3, 4, 5, 6 or 7 amino acid residue modifications as compared to SEQ ID NOs: 77-114, 204, 208, 212, and 216 that maintain or enhance binding specificity of the H-CDR3. In one embodiment, the amino acid sequence of the H-CDR3 contains no more than 1, 2, or 3 amino acid modifications as compared to SEQ ID NOs: 77-114, 204, 208, 212, and 216 respectively. The amino acid sequences of SEQ ID NOs: 1-114, 202-204, 206-208, 210-212, and 214-216 are provided in Table 1 below.

TABLE 1

Tau Single Domain Antibody Complementarity Determining Regions

| Antibody ID | descr | sequence | SEQ ID NO: | descr | sequence | SEQ ID NO: | descr | sequence | SEQ ID NO: |
|---|---|---|---|---|---|---|---|---|---|
| 03-T-sR2-1D10 | CDR1 | TASGRTFRAYAM | 1 | CDR2 | AISRTGGVTTY | 39 | CDR3 | AYFRWGTRY | 77 |
| 04-T-sR2-2A11 | CDR1 | AASGRIFSIWTM | 2 | CDR2 | AITSVGNTDY | 40 | CDR3 | VESRRGIGFLRKTYSY | 78 |

TABLE 1-continued

Tau Single Domain Antibody Complementarity Determining Regions

| Antibody ID | descr | sequence | SEQ ID NO: | descr | sequence | SEQ ID NO: | descr | sequence | SEQ ID NO: |
|---|---|---|---|---|---|---|---|---|---|
| 11-T-sR2-1E4 | CDR1 | AASGSIFRINNM | 3 | CDR2 | TITRGGNTNY | 41 | CDR3 | ANYLIRSY | 79 |
| 12-T-sR2-2B4 | CDR1 | AASGSIFRINNM | 4 | CDR2 | TITRGGNTNY | 42 | CDR3 | VKKHFGIRYDY | 80 |
| 13-T-sR2-2F8 | CDR1 | AASGRTFSNYAL | 5 | CDR2 | SISWSGGVLYY | 43 | CDR3 | ANAGLSLLRNWRTNEYAY | 81 |
| 18-T-sR2-1A8 | CDR1 | AASGSIFRINAM | 6 | CDR2 | RINTGGNTNY | 44 | CDR3 | VQRFITTY | 82 |
| 20-T-sR2-2B7 | CDR1 | AASGRTFSTYRM | 7 | CDR2 | AIRWSTSY | 45 | CDR3 | TGRAWSTLATTYVY | 83 |
| 21-T-sR2-2G7 | CDR1 | AASGRTFSRYAT | 8 | CDR2 | GISWSGTSY | 46 | CDR3 | NFKYRYGLGPRDY | 84 |
| 26-T-sR2-1B2 | CDR1 | VASGSIFRFNAI | 9 | CDR2 | RIRRLGSTSY | 47 | CDR3 | ADTHFSTRNY | 85 |
| 27-T-sR2-1E9 | CDR1 | AASGSIFRINGM | 10 | CDR2 | TITRGGSTNY | 48 | CDR3 | ADPRWRLPFPGYGMDY | 86 |
| 28-T-sR2-2B11; 82-T-sR2-1D3 | CDR1 | AASGRILISSM | 11 | CDR2 | TITRGGTTNY | 49 | CDR3 | RVYGRVWSRPYDY | 87 |
| 29-T-sR2-2G8 | CDR1 | TVSGRTFRINGI | 12 | CDR2 | GISSTGSTNY | 50 | CDR3 | ASRGLSGSWYLRSSYPY | 88 |
| 34-T-sR2-1B7 | CDR1 | AASRYIFGTM | 13 | CDR2 | SISRGGSTNY | 51 | CDR3 | AVPYRWGSSWYAGRY | 89 |
| 35-T-sR2-1F5 | CDR1 | VASGSRFSINTM | 14 | CDR2 | GITRGGSTNY | 52 | CDR3 | ATLRAWALTFATSYAY | 90 |
| 36-T-sR2-2C1 | CDR1 | AASGRTFSRYAM | 15 | CDR2 | RISWSGGWTYY | 53 | CDR3 | AGSRAVLFGTYDY | 91 |
| 37-T-sR2-2G9 | CDR1 | AASGRTLSSYRM | 16 | CDR2 | AINWRGSWTYY | 54 | CDR3 | RPTARWDLFREKYDFR | 92 |
| 42-T-sR2-1B8 | CDR1 | AASGRTFSSYAM | 17 | CDR2 | AISRSGGITSY | 55 | CDR3 | VQRFITTY | 93 |
| 43-T-sR2-1F8 | CDR1 | AASGRTFGLYTM | 18 | CDR2 | AISWRGLSIMY | 56 | CDR3 | ANAGLSLLRNWRTNEYAY | 94 |
| 44-T-sR2-2C5 | CDR1 | EASARTFSSYAV | 19 | CDR2 | AINWSGRRTNY | 57 | CDR3 | ARSLLEFWLGSRRGYDY | 95 |
| 45-T-sR2-2H4 | CDR1 | AASGRIFSIWTM | 20 | CDR2 | AITSGGSTNY | 58 | CDR3 | ADIRPRIISFFKDY | 96 |
| 50-T-sR2-1C5 | CDR1 | AASGRTFSRYAM | 21 | CDR2 | AITWSGGHYY | 59 | CDR3 | AYFRWGTRY | 97 |
| 51-T-sR2-1G1 | CDR1 | AASGRSFSWLTM | 22 | CDR2 | RITWRGTPYY | 60 | CDR3 | AAKQILIRPDAYVY | 98 |
| 52-T-sR2-2C9 | CDR1 | VASGSIFRFNAI | 23 | CDR2 | RIRRLGSTSY | 61 | CDR3 | AGRHPHFSMDYPDL | 99 |
| 53-T-sR2-2H5 | CDR1 | AASRYIFGTM | 24 | CDR2 | SISRGGSTNY | 62 | CDR3 | LALGFFTNYYVRESSYRY | 100 |
| 58-T-sR2-1C6 | CDR1 | AASGRTFRLYSM | 25 | CDR2 | SIRWNGGNIYY | 63 | CDR3 | AGPRIAVWRYEYNY | 101 |
| 59-T-sR2-1G5 | CDR1 | AASGSIGSFKTM | 26 | CDR2 | TITRWGFTNY | 64 | CDR3 | AAQGGFMKPRANWYNS | 102 |
| 60-T-sR2-2D8 | CDR1 | VASGRTFSRYGM | 27 | CDR2 | AISRSGAISYY | 65 | CDR3 | ASSRRLLGGPFAYDY | 103 |
| 61-T-sR2-2H7 | CDR1 | AASRYIFGTM | 28 | CDR2 | SISRGGSTNY | 66 | CDR3 | ANRRGWNY | 104 |
| 66-T-sR2-1C7 | CDR1 | AASGTIFTMKNM | 29 | CDR2 | AISTSGGVTWY | 67 | CDR3 | VRSGPRIIPQLRREY | 105 |
| 68-T-sR2-2E6 | CDR1 | AASGRTFSSYAM | 30 | CDR2 | AINWSGHSTYY | 68 | CDR3 | LTRLLNTY | 106 |
| 69-T-sR2-2H8 | CDR1 | AFSGRTFGLRTM | 31 | CDR2 | SLTWRDNNAYY | 69 | CDR3 | VHLVFTNRDY | 107 |
| 74-T-sR2-1C10 | CDR1 | AASWRIFSPNAM | 32 | CDR2 | RITWAGITNY | 70 | CDR3 | ADRRSSYLGPRFDY | 108 |
| 75-T-sR2-1G12 | CDR1 | AASRYIFGTM | 33 | CDR2 | SISRGGSTNY | 71 | CDR3 | ARSLLEFWLGSRRGYDY | 109 |
| 76-T-sR2-2E7 | CDR1 | AASGRFFRINAM | 34 | CDR2 | TITRAGTTTY | 72 | CDR3 | KYPTITWYGRHDYR | 110 |
| 84-T-sR2-2E8 | CDR1 | AASGSFFRINTM | 35 | CDR2 | SITRGGSTNY | 73 | CDR3 | ASRFGINYYTARQYGY | 111 |
| 90-T-sR2-1D9 | CDR1 | AASGRTFSRYPM | 36 | CDR2 | RFGWSGLSTYY | 74 | CDR3 | AGRFMGSYDY | 112 |
| 91-T-sR2-1H12 | CDR1 | AASGRTFSWYAM | 37 | CDR2 | AIRRSGGITIY | 75 | CDR3 | ANLFQWRLNDNGNQYGS | 113 |
| 92-T-sR2-2E9 | CDR1 | VVSGRTFSTSQM | 38 | CDR2 | RISWRGKQHY | 76 | CDR3 | AGPRAVLFGTYDY | 114 |

TABLE 1-continued

Tau Single Domain Antibody Complementarity Determining Regions

| Antibody ID | descr | sequence | SEQ ID NO: | descr | sequence | SEQ ID NO: | descr | sequence | SEQ ID NO: |
|---|---|---|---|---|---|---|---|---|---|
| T-sR2-2B8 | CDR1 | VSGRTFSTSQ | 202 | CDR2 | ARISWRGKQH | 203 | CDR3 | AADRRRTYLGQQHD | 204 |
| T-sR2-2F12 | CDR1 | ASGSIFRING | 206 | CDR2 | ATITRGGSIS | 207 | CDR3 | AKYRRPLFYSGSNYREGDFAS | 208 |
| T-sR2-2B3 | CDR1 | ASGRTFGSYT | 210 | CDR2 | AAISRSGGSTY | 211 | CDR3 | NVRGRPFILSKPFDS | 212 |
| T-sR2-2C4 | CDR1 | ASGRTFSNYA | 214 | CDR2 | AAITRNGGITY | 215 | CDR3 | NIKARRGSFFNPVNN | 216 |

Suitable amino acid modifications to the heavy chain CDR sequences of the anti-tau antibodies disclosed herein include, for example, conservative substitutions or functionally equivalent amino acid residue substitutions that result in variant CDR sequences having similar or enhanced binding characteristics to those of the CDR sequences disclosed herein. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences and the light chain CDR sequences as disclosed herein. Non-conservative substitutions involve substituting one or more amino acid residues of the CDR with one or more amino acid residues from a different class of amino acids to improve or enhance the binding properties of CDR.

The amino acid sequences of the heavy chain variable region CDRs of the anti-tau antibodies described herein may further comprise one or more internal neutral amino acid insertions or deletions that do not alter tau protein binding. In one embodiment, the H-CDR3 having an amino acid sequence of any one of SEQ ID NOs: 77-114, 204, 208, 212, and 216 further contains one or more internal neutral amino acid insertions or deletions that do not alter tau binding.

In one embodiment, the antibody or binding fragment thereof has a heavy chain variable region with a H-CDR1 having the amino acid sequence of SEQ ID NO: 1, or a modified amino acid sequence thereof containing 1, 2, 3, or more amino acid residue modifications as compared to SEQ ID NO: 1; a H-CDR2 having the amino acid sequence of SEQ ID NO: 39, or a modified amino acid sequence thereof containing 1, 2, 3, or more amino acid residue modifications as compared to SEQ ID NO: 39; and a H-CDR3 comprising the amino acid sequence of SEQ ID NO: 77, or a modified amino acid sequence thereof, said modified amino acid sequence containing 1, 2, 3, or more amino acid modifications as compared to SEQ ID NO: 77.

An exemplary single domain antibody having this heavy chain variable region is referred to herein as the 03-T-sR2-1D10 antibody. The 03-T-sR2-1D10 antibody comprises a $V_H$ chain amino acid sequence of SEQ ID NO: 115 as shown below.

SEQ ID NO: 115
QVQLQESGGGLVQAGGSLRLSCTASGRTFRAYAMGWFRQAPGKERELVA
AISRTGGVTTYADSVKGRFTISRDNAKNTVYLQMNNLKTEDTAVYYCNA
YFRWGTRYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 115

In one embodiment, the antibody or binding fragment thereof of the present disclosure comprises a humanized variant of the heavy chain variable region of SEQ ID NO: 115, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 115), or a combination of these approaches. The humanized framework regions are designed to be similar in length and sequence to the parental framework sequences of SEQ ID NO: 115. In one embodiment, the humanized framework regions share 50%, 55%, 60%, 65%, 70%, 75%, 80%, 85%, 90%, 95% or more sequence identity to the framework regions of SEQ ID NO: 115. In another embodiment, the humanized framework regions are 60%, 65%, 70%, 75%, 80%, 85%, 90%, 95% or more similar in length to the framework regions of SEQ ID NO: 115. Humanized variants of the heavy chain variable region of SEQ ID NO: 115 share at least 50%, at least 55%, at least 60%, at least 65%, at least 70%, at least 75%, at least 80%, at least 85%, at least 90%, at least 95% sequence identity along the entire length of SEQ ID 115.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 115. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 2, or a modified amino acid sequence thereof containing 1, 2, 3, or more amino acid residue modifications as compared to SEQ ID NO: 2; a H-CDR2 having the amino acid sequence of SEQ ID NO: 40, or a modified amino acid sequence thereof containing 1, 2, 3, or more amino acid residue modifications as compared to SEQ ID NO: 40; and a H-CDR3 comprising the amino acid sequence of SEQ ID NO: 78, or a modified amino acid sequence thereof, said modified amino acid sequence containing 1, 2, 3, or more amino acid modifications as compared to SEQ ID NO: 78.

Exemplary single domain antibodies having this heavy chain variable region are referred to herein as the 04-T-sR2-2A11 antibody and the 04-T-sR2-2A11 antibody. These antibodies comprise a $V_H$ chain amino acid sequence of SEQ ID NO: 116 as shown below.

SEQ ID NO: 116
QVQLQESGGGLVQPGGSLRLSCAASGRIFSIWTMGWYRQAPGKQRELVA
AITSVGNTDYADSVKGRFTISRETAKKTVYLQMNSLKPEDTAVYYCNVE
SRRGIGFLRKTYSYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 116.

In one embodiment, the antibody or binding fragment thereof of the present disclosure comprises a humanized variant of the heavy chain variable region of SEQ ID NO: 116, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 116), or a combination of these approaches. The humanized framework regions are designed to be similar in length and sequence to the parental framework sequences of SEQ ID NO: 116. In one embodiment, the humanized framework regions share 50%, 55%, 60%, 65%, 70%, 75%, 80%, 85%, 90%, 95% or more sequence identity to the framework regions of SEQ ID NO: 116. In another embodiment, the humanized framework regions are 60%, 65%, 70%, 75%, 80%, 85%, 90%, 95% or more similar in length to the framework regions of SEQ ID NO: 116. Humanized variants of the heavy chain variable region of SEQ ID NO: 116 share at least 50%, at least 55%, at least 60%, at least 65%, at least 70%, at least 75%, at least 80%, at least 85%, at least 90%, at least 95% sequence identity along the entire length of SEQ ID 116.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 116. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 3, or a modified amino acid sequence thereof containing 1, 2, 3, or more amino acid residue modifications as compared to SEQ ID NO: 3; a H-CDR2 having the amino acid sequence of SEQ ID NO: 41, or a modified amino acid sequence thereof containing 1, 2, 3, or more amino acid residue modifications as compared to SEQ ID NO: 41; and a H-CDR3 comprising the amino acid sequence of SEQ ID NO: 79, or a modified amino acid sequence thereof, said modified amino acid sequence containing 1, 2, 3, or more amino acid modifications as compared to SEQ ID NO: 79.

An exemplary single domain antibody having this heavy chain variable region is referred to herein as the 11-T-sR2-1E4 antibody. The 11-T-sR2-1E4 antibody comprises a $V_H$ chain amino acid sequence of SEQ ID NO: 117 as shown below.

SEQ ID NO: 117
QVQLQESGGGLVQPGGSLTLSCAASGSIFRINNMGWFRQAPGKQRELVA
TITRGGNTNYADSVKGRFTISRDNAKKTLYLQMNSLKPEDTAVYYCNAN
YLIRSYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 117.

In one embodiment, the antibody or binding fragment thereof of the present disclosure comprises a humanized variant of the heavy chain variable region of SEQ ID NO: 117, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 117), or a combination of these approaches. The humanized framework regions are designed to be similar in length and sequence to the parental framework sequences of SEQ ID NO: 117. In one embodiment, the humanized framework regions share 50%, 55%, 60%, 65%, 70%, 75%, 80%, 85%, 90%, 95% or more sequence identity to the framework regions of SEQ ID NO: 117. In another embodiment, the humanized framework regions are 60%, 65%, 70%, 75%, 80%, 85%, 90%, 95% or more similar in length to the framework regions of SEQ ID NO: 117. Humanized variants of the heavy chain variable region of SEQ ID NO: 117 share at least 50%, at least 55%, at least 60%, at least 65%, at least 70%, at least 75%, at least 80%, at least 85%, at least 90%, at least 95% sequence identity along the entire length of SEQ ID 117.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 117. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 4, or a modified amino acid sequence thereof containing 1, 2, 3, or more amino acid residue modifications as compared to SEQ ID NO: 4; a H-CDR2 having the amino acid sequence of SEQ ID NO: 42, or a modified amino acid sequence thereof containing 1, 2, 3, or more amino acid residue modifications as compared to SEQ ID NO: 42; and a H-CDR3 comprising the amino acid sequence of SEQ ID NO: 80, or a modified amino acid sequence thereof, said modified amino acid sequence containing 1, 2, 3, or more amino acid modifications as compared to SEQ ID NO: 80.

An exemplary single domain antibody having this heavy chain variable region is referred to herein as the 12-T-sR2-2B4 antibody. The 12-T-sR2-2B4 antibody comprises a V$_H$ chain amino acid sequence of SEQ ID NO: 118 as shown below.

SEQ ID NO: 118
QVQLQESGGGLVQPGGSLTLSCAASGSIFRINNMGWFRQAPGKQRELVA
TITRGGNTNYADSVKGRFTISRDNAKNTVYLQMDSLKPEDTAVYYCNVK
KHFGIRYDYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 118.

In one embodiment, the antibody or binding fragment thereof of the present disclosure comprises a humanized variant of the heavy chain variable region of SEQ ID NO: 118, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 118), or a combination of these approaches. The humanized framework regions are designed to be similar in length and sequence to the parental framework sequences of SEQ ID NO: 118. In one embodiment, the humanized framework regions share 50%, 55%, 60%, 65%, 70%, 75%, 80%, 85%, 90%, 95% or more sequence identity to the framework regions of SEQ ID NO: 118. In another embodiment, the humanized framework regions are 60%, 65%, 70%, 75%, 80%, 85%, 90%, 95% or more similar in length to the framework regions of SEQ ID NO: 118. Humanized variants of the heavy chain variable region of SEQ ID NO: 118 share at least 50%, at least 55%, at least 60%, at least 65%, at least 70%, at least 75%, at least 80%, at least 85%, at least 90%, at least 95% sequence identity along the entire length of SEQ ID 118.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 118. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 5, or a modified amino acid sequence thereof containing 1, 2, 3, or more amino acid residue modifications as compared to SEQ ID NO: 5; a H-CDR2 having the amino acid sequence of SEQ ID NO: 43, or a modified amino acid sequence thereof containing 1, 2, 3, or more amino acid residue modifications as compared to SEQ ID NO: 43; and a H-CDR3 comprising the amino acid sequence of SEQ ID NO: 81, or a modified amino acid sequence thereof, said modified amino acid sequence containing 1, 2, 3, or more amino acid modifications as compared to SEQ ID NO: 81.

An exemplary single domain antibody having this heavy chain variable region is referred to herein as the 13-T-sR2-2F8 antibody. The 13-T-sR2-2F8 antibody comprises a V$_H$ chain amino acid sequence of SEQ ID NO: 119 as shown below.

SEQ ID NO: 119
QVQLQESGGGLVQAGGSLRLSCAASGRTFSNYALAWFRQAPGLEREFVS
SISWSGGVLYYADSVKGRFTMSRDNGKNTVYLQMNSLKPEDTAVYYCAA
NAGLSLLRNWRTNEYAYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 119.

In one embodiment, the antibody or binding fragment thereof of the present disclosure comprises a humanized variant of the heavy chain variable region of SEQ ID NO: 119, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 119), or a combination of these approaches. The humanized framework regions are designed to be similar in length and sequence to the parental framework sequences of SEQ ID NO: 119. In one embodiment, the humanized framework regions share 50%, 55%, 60%, 65%, 70%, 75%, 80%, 85%, 90%, 95% or more sequence identity to the framework regions of SEQ ID NO: 119. In another embodiment, the humanized framework regions are 60%, 65%, 70%, 75%, 80%, 85%, 90%, 95% or more similar in length to the framework regions of SEQ ID NO: 119. Humanized variants of the heavy chain variable region of SEQ ID NO: 119 share at least 50%, at least 55%, at least 60%, at least 65%, at least 70%, at least 75%, at least 80%, at least 85%, at least 90%, at least 95% sequence identity along the entire length of SEQ ID 119.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 119. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 6, or a modified amino acid sequence thereof containing 1, 2, 3, or more amino acid residue modifications as compared to SEQ ID NO: 6; a H-CDR2 having the amino acid sequence of SEQ ID NO: 44, or a modified amino acid sequence thereof containing 1, 2, 3, or more amino acid residue modifications as compared to SEQ ID NO: 44; and a H-CDR3 comprising the amino acid sequence of SEQ ID NO: 82, or a modified amino acid sequence thereof, said modified amino acid sequence containing 1, 2, 3, or more amino acid modifications as compared to SEQ ID NO: 82.

An exemplary single domain antibody having this heavy chain variable region is referred to herein as the 18-T-sR2-1A8 antibody. The 18-T-sR2-1A8 antibody comprises a $V_H$ chain amino acid sequence of SEQ ID NO: 120 as shown below.

```
                                        SEQ ID NO: 120
QVQLQESGGGLVQAGGSLRLSCAASGSIFRINAMAWYRQAPGKQRELVA
RINTGGNTNYAGSVKGRFTISRDNGKNTVYLQMNSLKPEDTGVYYCNVQ
RFITTYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 120.

In one embodiment, the antibody or binding fragment thereof of the present disclosure comprises a humanized variant of the heavy chain variable region of SEQ ID NO: 120 where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 120), or a combination of these approaches. The humanized framework regions are designed to be similar in length and sequence to the parental framework sequences of SEQ ID NO: 120. In one embodiment, the humanized framework regions share 50%, 55%, 60%, 65%, 70%, 75%, 80%, 85%, 90%, 95% or more sequence identity to the framework regions of SEQ ID NO: 120. In another embodiment, the humanized framework regions are 60%, 65%, 70%, 75%, 80%, 85%, 90%, 95% or more similar in length to the framework regions of SEQ ID NO: 120. Humanized variants of the heavy chain variable region of SEQ ID NO: 120 share at least 50%, at least 55%, at least 60%, at least 65%, at least 70%, at least 75%, at least 80%, at least 85%, at least 90%, at least 95% sequence identity along the entire length of SEQ ID 120.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 120. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 7, or a modified amino acid sequence thereof containing 1, 2, 3, or more amino acid residue modifications as compared to SEQ ID NO: 7; a H-CDR2 having the amino acid sequence of SEQ ID NO: 45, or a modified amino acid sequence thereof containing 1, 2, 3, or more amino acid residue modifications as compared to SEQ ID NO: 45; and a H-CDR3 comprising the amino acid sequence of SEQ ID NO: 83, or a modified amino acid sequence thereof, said modified amino acid sequence containing 1, 2, 3, or more amino acid modifications as compared to SEQ ID NO: 83.

An exemplary single domain antibody having this heavy chain variable region is referred to herein as the 20-T-sR2-2B7 antibody. The 20-T-sR2-2B7 antibody comprises a $V_H$ chain amino acid sequence of SEQ ID NO: 121 as shown below.

```
                                        SEQ ID NO: 121
QVQLQESGGGLVQAGGSLRLSCAASGRTFSTYRMGWFRQAPGKEREFVA
AIRWSTSYADSVKGRFIISRDNAKNTVYLQMNSLKPEDTAVYYCATGRA
WSTLATTYVYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 121.

In one embodiment, the antibody or binding fragment thereof of the present disclosure comprises a humanized variant of the heavy chain variable region of SEQ ID NO: 121, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 121), or a combination of these approaches. The humanized framework regions are designed to be similar in length and sequence to the parental framework sequences of SEQ ID NO: 121. In one embodiment, the humanized framework regions share 50%, 55%, 60%, 65%, 70%, 75%, 80%, 85%, 90%, 95% or more sequence identity to the framework regions of SEQ ID NO: 121. In another embodiment, the humanized framework regions are 60%, 65%, 70%, 75%, 80%, 85%, 90%, 95% or more similar in length to the framework regions of SEQ ID NO: 121. Humanized variants of the heavy chain variable region of SEQ ID NO: 121 share at least 50%, at least 55%, at least 60%, at least 65%, at least 70%, at least 75%, at least 80%, at least 85%, at least 90%, at least 95% sequence identity along the entire length of SEQ ID 121.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 121. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 8, or a modified amino acid sequence thereof containing 1, 2, 3, or more amino acid residue modifications as compared to SEQ ID NO: 8; a H-CDR2 having the amino acid sequence of SEQ ID NO: 46, or a modified amino acid sequence thereof containing 1, 2, 3, or more amino acid residue modifications as compared to SEQ ID NO: 46; and a H-CDR3 comprising the amino acid sequence of SEQ ID NO: 84, or a modified amino acid sequence thereof, said modified amino acid sequence containing 1, 2, 3, or more amino acid modifications as compared to SEQ ID NO: 84.

An exemplary single domain antibody having this heavy chain variable region is referred to herein as the 21-T-sR2-2G7 antibody. This antibody comprises a $V_H$ chain amino acid sequence of SEQ ID NO: 122 as shown below.

```
                                          SEQ ID NO: 122
QVQLQESGGGLVQAGGSLRLSCAASGRTFSRYATAWFRQAPGKEREFVA
GISWSGTSYADSVKGRFTISRDNAKNTLYLQMNSLKSEDTAVYYCANFK
YRYGLGPRDYWGQGTLVTSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 122.

In one embodiment, the antibody or binding fragment thereof of the present disclosure comprises a humanized variant of the heavy chain variable region of SEQ ID NO: 122, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 122), or a combination of these approaches. The humanized framework regions are designed to be similar in length and sequence to the parental framework sequences of SEQ ID NO: 122. In one embodiment, the humanized framework regions share 50%, 55%, 60%, 65%, 70%, 75%, 80%, 85%, 90%, 95% or more sequence identity to the framework regions of SEQ ID NO: 122. In another embodiment, the humanized framework regions are 60%, 65%, 70%, 75%, 80%, 85%, 90%, 95% or more similar in length to the framework regions of SEQ ID NO: 122. Humanized variants of the heavy chain variable region of SEQ ID NO: 122 share at least 50%, at least 55%, at least 60%, at least 65%, at least 70%, at least 75%, at least 80%, at least 85%, at least 90%, at least 95% sequence identity along the entire length of SEQ ID NO: 122, respectively.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 122. In accordance with this aspect of the disclosure, a competitive binding assay, such as Bio-Layer Interferometry (BLI) can be utilized to identify an antibody or binding portion thereof that competes for binding to tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 9, or a modified amino acid sequence thereof containing 1, 2, 3, or more amino acid residue modifications as compared to SEQ ID NO: 9; a H-CDR2 having the amino acid sequence of SEQ ID NO: 47, or a modified amino acid sequence thereof containing 1, 2, 3, or more amino acid residue modifications as compared to SEQ ID NO: 47; and a H-CDR3 comprising the amino acid sequence of SEQ ID NO: 85, or a modified amino acid sequence thereof, said modified amino acid sequence containing 1, 2, 3, or more amino acid modifications as compared to SEQ ID NO: 85.

An exemplary single domain antibody having this heavy chain variable region is referred to herein as the 26-T-sR2-1B2 antibody. The 26-T-sR2-1B2 antibody comprises a $V_H$ chain amino acid sequence of SEQ ID NO: 123 as shown below.

```
                                          SEQ ID NO: 123
QVQLQESGGGLVQAGGSLRLSCVASGSIFRFNAIGWYRQAPGKERELVA
RIRRLGSTSYADSVKGRFSISRDSAKNTVYLQMNSLKPEDTAVYYCNAD
THFSTRNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 123.

In one embodiment, the antibody or binding fragment thereof of the present disclosure comprises a humanized variant of the heavy chain variable region of SEQ ID NO: 123, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 123), or a combination of these approaches. The humanized framework regions are designed to be similar in length and sequence to the parental framework sequences of SEQ ID NO: 123. In one embodiment, the humanized framework regions share 50%, 55%, 60%, 65%, 70%, 75%, 80%, 85%, 90%, 95% or more sequence identity to the framework regions of SEQ ID NO: 123. In another embodiment, the humanized framework regions are 60%, 65%, 70%, 75%, 80%, 85%, 90%, 95% or more similar in length to the framework regions of SEQ ID NO: 123. Humanized variants of the heavy chain variable region of SEQ ID NO: 123 share at least 50%, at least 55%, at least 60%, at least 65%, at least 70%, at least 75%, at least 80%, at least 85%, at least 90%, at least 95% sequence identity along the entire length of SEQ ID 123.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 123. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 10, or a modified amino acid sequence thereof containing 1, 2, 3, or more amino acid residue modifications as compared to SEQ ID NO: 10; a H-CDR2 having the amino acid sequence of SEQ ID NO: 48, or a modified amino acid sequence thereof containing 1, 2, 3, or more amino acid residue modifications as compared to SEQ ID NO: 48; and a H-CDR3 comprising the amino acid sequence of SEQ ID NO: 86, or a modified amino acid sequence thereof, said modified amino acid sequence containing 1, 2, 3, or more amino acid modifications as compared to SEQ ID NO: 86.

An exemplary single domain antibody having this heavy chain variable region is referred to herein as the 27-T-sR2-1E9 antibody. The 27-T-sR2-1E9 antibody comprises a $V_H$ chain amino acid sequence of SEQ ID NO: 124 as shown below.

SEQ ID NO: 124
QVQLQESGGGLVQAGGSLRLSCAASGSIFRINGMGWHRQAPGKERELVA
TITRGGSTNYADSVKGRFTISRDNAKNTVYLQMNSLKPEDTAVYYCAAD
PRWRLPFPGYGMDYWGKGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 124.

In one embodiment, the antibody or binding fragment thereof of the present disclosure comprises a humanized variant of the heavy chain variable region of SEQ ID NO: 124, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 124), or a combination of these approaches. The humanized framework regions are designed to be similar in length and sequence to the parental framework sequences of SEQ ID NO: 124. In one embodiment, the humanized framework regions share 50%, 55%, 60%, 65%, 70%, 75%, 80%, 85%, 90%, 95% or more sequence identity to the framework regions of SEQ ID NO: 124. In another embodiment, the humanized framework regions are 60%, 65%, 70%, 75%, 80%, 85%, 90%, 95% or more similar in length to the framework regions of SEQ ID NO: 124. Humanized variants of the heavy chain variable region of SEQ ID NO: 124 share at least 50%, at least 55%, at least 60%, at least 65%, at least 70%, at least 75%, at least 80%, at least 85%, at least 90%, at least 95% sequence identity along the entire length of SEQ ID 124.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 124. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 11, or a modified amino acid sequence thereof containing 1, 2, 3, or more amino acid residue modifications as compared to SEQ ID NO: 11; a H-CDR2 having the amino acid sequence of SEQ ID NO: 49, or a modified amino acid sequence thereof containing 1, 2, 3, or more amino acid residue modifications as compared to SEQ ID NO: 49; and a H-CDR3 comprising the amino acid sequence of SEQ ID NO: 87, or a modified amino acid sequence thereof, said modified amino acid sequence containing 1, 2, 3, or more amino acid modifications as compared to SEQ ID NO: 87.

Exemplary single domain antibodies having this heavy chain variable region are the 28-T-sR2-2B11 and 82-T-sR2-1D3 antibodies. The 28-T-sR2-2B11 and 82-T-sR2-1D3 antibodies comprise a $V_H$ chain amino acid sequence of SEQ ID NO: 125 as shown below.

SEQ ID NO: 125
QVQLQESGGGLVQPGGSLRLSCAASGRILISSMGWYRQAQGEQRELVAT
ITRGGTTNYADSVKGRFTISRDNAKNMVYLQMNKLKSEDTAVYYCARVY
GRVWSRPYDYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 125.

In one embodiment, the antibody or binding fragment thereof of the present disclosure comprises a humanized variant of the heavy chain variable region of SEQ ID NO: 125, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 125), or a combination of these approaches. The humanized framework regions are designed to be similar in length and sequence to the parental framework sequences of SEQ ID NO: 125. In one embodiment, the humanized framework regions share 50%, 55%, 60%, 65%, 70%, 75%, 80%, 85%, 90%, 95% or more sequence identity to the framework regions of SEQ ID NO: 125. In another embodiment, the humanized framework regions are 60%, 65%, 70%, 75%, 80%, 85%, 90%, 95% or more similar in length to the framework regions of SEQ ID NO: 125. Humanized variants of the heavy chain variable region of SEQ ID NO: 125 share at least 50%, at least 55%, at least 60%, at least 65%, at least 70%, at least 75%, at least 80%, at least 85%, at least 90%, at least 95% sequence identity along the entire length of SEQ ID 125.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 125. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 12, or a modified amino acid sequence thereof containing 1, 2, 3, or more amino acid residue modifications as compared to SEQ ID NO: 12; a H-CDR2 having the amino acid sequence of SEQ ID NO: 50, or a modified amino acid sequence thereof containing 1, 2, 3, or more amino acid residue modifications as compared to SEQ ID NO: 50; and a H-CDR3 comprising the amino acid sequence of SEQ ID NO: 88, or a modified amino acid sequence thereof, said modified amino acid sequence containing 1, 2, 3, or more amino acid modifications as compared to SEQ ID NO: 88.

An exemplary single domain antibody having this heavy chain variable region is referred to herein as the 29-T-sR2-2G8 antibody. The 29-T-sR2-2G8 antibody comprises a $V_H$ chain amino acid sequence of SEQ ID NO: 126 as shown below.

```
                                          SEQ ID NO: 126
QVQLQESGGGFVQAGGSLRLSCTVSGRTFRINGIDWYRQAPGKQRELVA
GISSTGSTNYADSVKGRFTISRDNAGNAVYLQMNNLKPEDTGRYYCAAS
RGLSGSWYLRSSYPYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 126.

In one embodiment, the antibody or binding fragment thereof of the present disclosure comprises a humanized variant of the heavy chain variable region of SEQ ID NO: 126, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 126), or a combination of these approaches. The humanized framework regions are designed to be similar in length and sequence to the parental framework sequences of SEQ ID NO: 126. In one embodiment, the humanized framework regions share 50%, 55%, 60%, 65%, 70%, 75%, 80%, 85%, 90%, 95% or more sequence identity to the framework regions of SEQ ID NO: 126. In another embodiment, the humanized framework regions are 60%, 65%, 70%, 75%, 80%, 85%, 90%, 95% or more similar in length to the framework regions of SEQ ID NO: 126. Humanized variants of the heavy chain variable region of SEQ ID NO: 126 share at least 50%, at least 55%, at least 60%, at least 65%, at least 70%, at least 75%, at least 80%, at least 85%, at least 90%, at least 95% sequence identity along the entire length of SEQ ID 126.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 126. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 13, or a modified amino acid sequence thereof containing 1, 2, 3, or more amino acid residue modifications as compared to SEQ ID NO: 13; a H-CDR2 having the amino acid sequence of SEQ ID NO: 51, or a modified amino acid sequence thereof containing 1, 2, 3, or more amino acid residue modifications as compared to SEQ ID NO: 51; and a H-CDR3 comprising the amino acid sequence of SEQ ID NO: 89, or a modified amino acid sequence thereof, said modified amino acid sequence containing 1, 2, 3, or more amino acid modifications as compared to SEQ ID NO: 89.

An exemplary single domain antibody having this heavy chain variable region is referred to herein as the 34-T-sR2-1B7 antibody. The 34-T-sR2-1B7 antibody comprises a $V_H$ chain amino acid sequence of SEQ ID NO: 127 as shown below.

```
                                          SEQ ID NO: 127
QVQLQESGGGLVQPGGSLRLSCAASRYIFGTMGWYRQAPGLQRELVASI
SRGGSTNYADSVKGRFAISRDNAKKTVYLQMNSLKPEDTAVYYCNAVPY
RWGSSWYAGRYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 127.

In one embodiment, the antibody or binding fragment thereof of the present disclosure comprises a humanized variant of the heavy chain variable region of SEQ ID NO: 127, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 127), or a combination of these approaches. The humanized framework regions are designed to be similar in length and sequence to the parental framework sequences of SEQ ID NO: 127. In one embodiment, the humanized framework regions share 50%, 55%, 60%, 65%, 70%, 75%, 80%, 85%, 90%, 95% or more sequence identity to the framework regions of SEQ ID NO: 127. In another embodiment, the humanized framework regions are 60%, 65%, 70%, 75%, 80%, 85%, 90%, 95% or more similar in length to the framework regions of SEQ ID NO: 127. Humanized variants of the heavy chain variable region of SEQ ID NO: 127 share at least 50%, at least 55%, at least 60%, at least 65%, at least 70%, at least 75%, at least 80%, at least 85%, at least 90%, at least 95% sequence identity along the entire length of SEQ ID 127.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 127. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 14, or a modified amino acid sequence thereof containing 1, 2, 3, or more amino acid residue modifications as compared to SEQ ID NO: 14; a H-CDR2 having the amino acid sequence of SEQ ID NO: 52, or a modified amino acid sequence thereof containing 1, 2, 3, or more amino acid residue modifications as compared to SEQ ID NO: 52; and a H-CDR3 comprising the amino acid sequence of SEQ ID NO: 90 or a modified amino acid sequence thereof, said modified amino acid sequence containing 1, 2, 3, or more amino acid modifications as compared to SEQ ID NO: 90.

An exemplary single domain antibody having this heavy chain variable region is referred to herein as the 35-T-sR2-1F5 antibody. The 35-T-sR2-1F5 antibody comprises a $V_H$ chain amino acid sequence of SEQ ID NO: 128 as shown below.

```
                                              SEQ ID NO: 128
QVQLQQSGGGLVQAGGSLTLSCVASGSRFSINTMGWYRQAPGKQRELVA
GITRGGSTNYADSVKGRFTISRENAKNTVYLQMNSLKPEDTAVYYCAAT
LRAWALTFATSYAYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 128.

In one embodiment, the antibody or binding fragment thereof of the present disclosure comprises a humanized variant of the heavy chain variable region of SEQ ID NO: 128, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 128), or a combination of these approaches. The humanized framework regions are designed to be similar in length and sequence to the parental framework sequences of SEQ ID NO: 128. In one embodiment, the humanized framework regions share 50%, 55%, 60%, 65%, 70%, 75%, 80%, 85%, 90%, 95% or more sequence identity to the framework regions of SEQ ID NO: 128. In another embodiment, the humanized framework regions are 60%, 65%, 70%, 75%, 80%, 85%, 90%, 95% or more similar in length to the framework regions of SEQ ID NO: 128. Humanized variants of the heavy chain variable region of SEQ ID NO: 128 share at least 50%, at least 55%, at least 60%, at least 65%, at least 70%, at least 75%, at least 80%, at least 85%, at least 90%, at least 95% sequence identity along the entire length of SEQ ID 128.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 128. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 15, or a modified amino acid sequence thereof containing 1, 2, 3, or more amino acid residue modifications as compared to SEQ ID NO: 15; a H-CDR2 having the amino acid sequence of SEQ ID NO: 53, or a modified amino acid sequence thereof containing 1, 2, 3, or more amino acid residue modifications as compared to SEQ ID NO: 53; and a H-CDR3 comprising the amino acid sequence of SEQ ID NO: 91, or a modified amino acid sequence thereof, said modified amino acid sequence containing 1, 2, 3, or more amino acid modifications as compared to SEQ ID NO: 91.

An exemplary single domain antibody having this heavy chain variable region is referred to herein as the 36-T-sR2-2C1 antibody. The 36-T-sR2-2C1 antibody comprises a $V_H$ chain amino acid sequence of SEQ ID NO: 129 as shown below.

```
                                              SEQ ID NO: 129
QVQLQASGGGLVQPGGSLTLSCAASGRTFSRYAMGWFRQAPGKEREFVA
RISWSGGWTYYADSVKGRFAISRDNAKNTVYLQMNSLKPEDTAVYYCAA
GSRAVLFGTYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 129.

In one embodiment, the antibody or binding fragment thereof of the present disclosure comprises a humanized variant of the heavy chain variable region of SEQ ID NO: 129, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 129), or a combination of these approaches. The humanized framework regions are designed to be similar in length and sequence to the parental framework sequences of SEQ ID NO: 129. In one embodiment, the humanized framework regions share 50%, 55%, 60%, 65%, 70%, 75%, 80%, 85%, 90%, 95% or more sequence identity to the framework regions of SEQ ID NO: 129. In another embodiment, the humanized framework regions are 60%, 65%, 70%, 75%, 80%, 85%, 90%, 95% or more similar in length to the framework regions of SEQ ID NO: 129. Humanized variants of the heavy chain variable region of SEQ ID NO: 129 share at least 50%, at least 55%, at least 60%, at least 65%, at least 70%, at least 75%, at least 80%, at least 85%, at least 90%, at least 95% sequence identity along the entire length of SEQ ID 129.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 129. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 16, or a modified amino acid sequence thereof containing 1, 2, 3, or more amino acid residue modifications as compared to SEQ ID NO: 16; a H-CDR2 having the amino acid sequence of SEQ ID NO: 54, or a modified amino acid sequence thereof containing 1, 2, 3, or more amino acid residue modifications as compared to SEQ ID NO: 54; and a H-CDR3 comprising the amino acid sequence of SEQ ID NO: 92, or a modified amino acid sequence thereof, said modified amino acid sequence containing 1, 2, 3, or more amino acid modifications as compared to SEQ ID NO: 92.

An exemplary single domain antibody having this heavy chain variable region is referred to herein as the 37-T-sR2-2G9 antibody. The 37-T-sR2-2G9 antibody comprises a $V_H$ chain amino acid sequence of SEQ ID NO: 130 as shown below.

```
                                         SEQ ID NO: 130
QVQLQESGGGLVQAGGSLRLSCAASGRTLSSYRMGWFRQVPGKERELVA
AINWRGSWTYYADSVKGRVTISRDNAKNTVYLQMNSLQPEDTALYYCAR
PTARWDLFREKYDFRGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 130.

In one embodiment, the antibody or binding fragment thereof of the present disclosure comprises a humanized variant of the heavy chain variable region of SEQ ID NO: 130, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 130), or a combination of these approaches. The humanized framework regions are designed to be similar in length and sequence to the parental framework sequences of SEQ ID NO: 130. In one embodiment, the humanized framework regions share 50%, 55%, 60%, 65%, 70%, 75%, 80%, 85%, 90%, 95% or more sequence identity to the framework regions of SEQ ID NO: 130. In another embodiment, the humanized framework regions are 60%, 65%, 70%, 75%, 80%, 85%, 90%, 95% or more similar in length to the framework regions of SEQ ID NO: 130. Humanized variants of the heavy chain variable region of SEQ ID NO: 130 share at least 50%, at least 55%, at least 60%, at least 65%, at least 70%, at least 75%, at least 80%, at least 85%, at least 90%, at least 95% sequence identity along the entire length of SEQ ID 130.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 130. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 17, or a modified amino acid sequence thereof containing 1, 2, 3, or more amino acid residue modifications as compared to SEQ ID NO: 17; a H-CDR2 having the amino acid sequence of SEQ ID NO: 55, or a modified amino acid sequence thereof containing 1, 2, 3, or more amino acid residue modifications as compared to SEQ ID NO: 55; and a H-CDR3 comprising the amino acid sequence of SEQ ID NO: 93, or a modified amino acid sequence thereof, said modified amino acid sequence containing 1, 2, 3, or more amino acid modifications as compared to SEQ ID NO: 93.

An exemplary single domain antibody having this heavy chain variable region is referred to herein as the 42-T-sR2-1B8 antibody. The 42-T-sR2-1B8 antibody comprises a $V_H$ chain amino acid sequence of SEQ ID NO: 131 as shown below.

```
                                         SEQ ID NO: 131
QVQLQESGGGLVQAGGSLRLSCAASGRTFSSYAMGWFRQAPGKEREFVA
AISRSGGITSYADSVKGRFAISRDNAKNTVYLQMNSLKPEDTGVYYCNV
QRFITTYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 131.

In one embodiment, the antibody or binding fragment thereof of the present disclosure comprises a humanized variant of the heavy chain variable region of SEQ ID NO: 131, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 131), or a combination of these approaches. The humanized framework regions are designed to be similar in length and sequence to the parental framework sequences of SEQ ID NO: 131. In one embodiment, the humanized framework regions share 50%, 55%, 60%, 65%, 70%, 75%, 80%, 85%, 90%, 95% or more sequence identity to the framework regions of SEQ ID NO: 131. In another embodiment, the humanized framework regions are 60%, 65%, 70%, 75%, 80%, 85%, 90%, 95% or more similar in length to the framework regions of SEQ ID NO: 131. Humanized variants of the heavy chain variable region of SEQ ID NO: 131 share at least 50%, at least 55%, at least 60%, at least 65%, at least 70%, at least 75%, at least 80%, at least 85%, at least 90%, at least 95% sequence identity along the entire length of SEQ ID 131.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 131. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 18, or a modified amino acid sequence thereof containing 1, 2, 3, or more amino acid residue modifications as compared to SEQ ID NO: 18; a H-CDR2 having the amino acid sequence of SEQ ID NO: 56, or a modified amino acid sequence thereof containing 1, 2, 3, or more amino acid residue modifications as compared to SEQ ID NO: 56; and a H-CDR3 comprising the amino acid sequence of SEQ ID NO: 94, or a modified amino acid sequence thereof, said modified amino acid sequence containing 1, 2, 3, or more amino acid modifications as compared to SEQ ID NO: 94.

An exemplary single domain antibody having this heavy chain variable region is referred to herein as the 43-T-sR2-1F8 antibody. The 43-T-sR2-1F8 antibody comprises a $V_H$ chain amino acid sequence of SEQ ID NO: 132 as shown below.

```
                                        SEQ ID NO: 132
QVQLQASGGGLVQAGGSLSLSCAASGRTFGLYTMGWFRQAPEKEREFVA
AISWRGLSIMYADSVKGRFTISRDNVKNTVYLQMNSLKPEDTAVYYCAA
NAGLSLLRNWRTNEYAYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 132.

In one embodiment, the antibody or binding fragment thereof of the present disclosure comprises a humanized variant of the heavy chain variable region of SEQ ID NO: 132, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 132), or a combination of these approaches. The humanized framework regions are designed to be similar in length and sequence to the parental framework sequences of SEQ ID NO: 132. In one embodiment, the humanized framework regions share 50%, 55%, 60%, 65%, 70%, 75%, 80%, 85%, 90%, 95% or more sequence identity to the framework regions of SEQ ID NO: 132. In another embodiment, the humanized framework regions are 60%, 65%, 70%, 75%, 80%, 85%, 90%, 95% or more similar in length to the framework regions of SEQ ID NO: 132. Humanized variants of the heavy chain variable region of SEQ ID NO: 132 share at least 50%, at least 55%, at least 60%, at least 65%, at least 70%, at least 75%, at least 80%, at least 85%, at least 90%, at least 95% sequence identity along the entire length of SEQ ID 132.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 132. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 19, or a modified amino acid sequence thereof containing 1, 2, 3, or more amino acid residue modifications as compared to SEQ ID NO: 19; a H-CDR2 having the amino acid sequence of SEQ ID NO: 57, or a modified amino acid sequence thereof containing 1, 2, 3, or more amino acid residue modifications as compared to SEQ ID NO: 57; and a H-CDR3 comprising the amino acid sequence of SEQ ID NO: 95, or a modified amino acid sequence thereof, said modified amino acid sequence containing 1, 2, 3, or more amino acid modifications as compared to SEQ ID NO: 95.

An exemplary single domain antibody having this heavy chain variable region is referred to herein as the 44-T-sR2-2C5 antibody. The 44-T-sR2-2C5 antibody comprises a $V_H$ chain amino acid sequence of SEQ ID NO: 133 as shown below.

```
                                        SEQ ID NO: 133
QVQLQESGGGLVQAGGSLRLSCEASARTFSSYAVGWFRQAPGKEREFVA
AINWSGRRTNYADSVKGRFSISRDNAKNTMYLQMNSLKPEDTAVYYCAA
RSSLLEFWLGSRRGYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 133.

In one embodiment, the antibody or binding fragment thereof of the present disclosure comprises a humanized variant of the heavy chain variable region of SEQ ID NO: 133, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 133), or a combination of these approaches. The humanized framework regions are designed to be similar in length and sequence to the parental framework sequences of SEQ ID NO: 133. In one embodiment, the humanized framework regions share 50%, 55%, 60%, 65%, 70%, 75%, 80%, 85%, 90%, 95% or more sequence identity to the framework regions of SEQ ID NO: 133. In another embodiment, the humanized framework regions are 60%, 65%, 70%, 75%, 80%, 85%, 90%, 95% or more similar in length to the framework regions of SEQ ID NO: 133. Humanized variants of the heavy chain variable region of SEQ ID NO: 133 share at least 50%, at least 55%, at least 60%, at least 65%, at least 70%, at least 75%, at least 80%, at least 85%, at least 90%, at least 95% sequence identity along the entire length of SEQ ID 133.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 133. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 20, or a modified amino acid sequence thereof containing 1, 2, 3, or more amino acid residue modifications as compared to SEQ ID NO: 20; a H-CDR2 having the amino acid sequence of SEQ ID NO: 58, or a modified amino acid sequence thereof containing 1, 2, 3, or more amino acid residue modifications as compared to SEQ ID NO: 58; and a H-CDR3 comprising the amino acid sequence of SEQ ID NO: 96, or a modified amino acid sequence thereof, said modified amino acid sequence containing 1, 2, 3, or more amino acid modifications as compared to SEQ ID NO: 96.

An exemplary single domain antibody having this heavy chain variable region is referred to herein as the 45-T-sR2-2H4 antibody. The 45-T-sR2-2H4 antibody comprises a $V_H$ chain amino acid sequence of SEQ ID NO: 134 as shown below.

```
                                        SEQ ID NO: 134
QVQLQQFGGGLVQPGGSLRLSCAASGRIFSIWTMGWYRQAPGKQRELVA
AITSGGSTNYADSVKGRFTISRDNAENTVYLQMNSLKPEDTAVYYCNAD
IRPRIISFFKDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 134.

In one embodiment, the antibody or binding fragment thereof of the present disclosure comprises a humanized variant of the heavy chain variable region of SEQ ID NO: 134, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 134), or a combination of these approaches. The humanized framework regions are designed to be similar in length and sequence to the parental framework sequences of SEQ ID NO: 134. In one embodiment, the humanized framework regions share 50%, 55%, 60%, 65%, 70%, 75%, 80%, 85%, 90%, 95% or more sequence identity to the framework regions of SEQ ID NO: 134. In another embodiment, the humanized framework regions are 60%, 65%, 70%, 75%, 80%, 85%, 90%, 95% or more similar in length to the framework regions of SEQ ID NO: 134. Humanized variants of the heavy chain variable region of SEQ ID NO: 134 share at least 50%, at least 55%, at least 60%, at least 65%, at least 70%, at least 75%, at least 80%, at least 85%, at least 90%, at least 95% sequence identity along the entire length of SEQ ID 134.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 134. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 21, or a modified amino acid sequence thereof containing 1, 2, 3, or more amino acid residue modifications as compared to SEQ ID NO: 21; a H-CDR2 having the amino acid sequence of SEQ ID NO: 59, or a modified amino acid sequence thereof containing 1, 2, 3, or more amino acid residue modifications as compared to SEQ ID NO: 59; and a H-CDR3 comprising the amino acid sequence of SEQ ID NO: 97, or a modified amino acid sequence thereof, said modified amino acid sequence containing 1, 2, 3, or more amino acid modifications as compared to SEQ ID NO: 97.

An exemplary single domain antibody having this heavy chain variable region is referred to herein as the 50-T-sR2-1C5 antibody. The 50-T-sR2-1C5 antibody comprises a $V_H$ chain amino acid sequence of SEQ ID NO: 135 as shown below.

```
                                        SEQ ID NO: 135
QVQLQESGGGLVQPGGSLRLSCAASGRTFSRYAMGWFRQAPGKEREFVA
AITWSGGIIYYADSVKGRFTISRDNAKNTVYLQMNNLKTEDTAVYYCNA
YFRWGTRYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 135.

In one embodiment, the antibody or binding fragment thereof of the present disclosure comprises a humanized variant of the heavy chain variable region of SEQ ID NO: 135, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 135), or a combination of these approaches. The humanized framework regions are designed to be similar in length and sequence to the parental framework sequences of SEQ ID NO: 135. In one embodiment, the humanized framework regions share 50%, 55%, 60%, 65%, 70%, 75%, 80%, 85%, 90%, 95% or more sequence identity to the framework regions of SEQ ID NO: 135. In another embodiment, the humanized framework regions are 60%, 65%, 70%, 75%, 80%, 85%, 90%, 95% or more similar in length to the framework regions of SEQ ID NO: 135. Humanized variants of the heavy chain variable region of SEQ ID NO: 135 share at least 50%, at least 55%, at least 60%, at least 65%, at least 70%, at least 75%, at least 80%, at least 85%, at least 90%, at least 95% sequence identity along the entire length of SEQ ID 135.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 135. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 22, or a modified amino acid sequence thereof containing 1, 2, 3, or more amino acid residue modifications as compared to SEQ ID NO: 22; a H-CDR2 having the amino acid sequence of SEQ ID NO: 60, or a modified amino acid sequence thereof containing 1, 2, 3, or more amino acid residue modifications as compared to SEQ ID NO: 60; and a H-CDR3 comprising the amino acid sequence of SEQ ID NO: 98, or a modified amino acid sequence thereof, said modified amino acid sequence containing 1, 2, 3, or more amino acid modifications as compared to SEQ ID NO: 98.

An exemplary single domain antibody having this heavy chain variable region is referred to herein as the 51-T-sR2-1G1 antibody. The 51-T-sR2-1G1 antibody comprises a $V_H$ chain amino acid sequence of SEQ ID NO: 136 as shown below.

```
                                         SEQ ID NO: 136
QVQLQESGGGLVQAGGSLRLSCAASGRSFSWLTMAWFRQAPGKEREIVA
RITWRGTPYYADSVKGRFAISRDNAKNTVYLQMNSLKPEDTAIYYCAAA
KQILIRPDAYVYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 136.

In one embodiment, the antibody or binding fragment thereof of the present disclosure comprises a humanized variant of the heavy chain variable region of SEQ ID NO: 136, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 136), or a combination of these approaches. The humanized framework regions are designed to be similar in length and sequence to the parental framework sequences of SEQ ID NO: 136. In one embodiment, the humanized framework regions share 50%, 55%, 60%, 65%, 70%, 75%, 80%, 85%, 90%, 95% or more sequence identity to the framework regions of SEQ ID NO: 136. In another embodiment, the humanized framework regions are 60%, 65%, 70%, 75%, 80%, 85%, 90%, 95% or more similar in length to the framework regions of SEQ ID NO: 136. Humanized variants of the heavy chain variable region of SEQ ID NO: 136 share at least 50%, at least 55%, at least 60%, at least 65%, at least 70%, at least 75%, at least 80%, at least 85%, at least 90%, at least 95% sequence identity along the entire length of SEQ ID 136.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 136. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 23, or a modified amino acid sequence thereof containing 1, 2, 3, or more amino acid residue modifications as compared to SEQ ID NO: 23; a H-CDR2 having the amino acid sequence of SEQ ID NO: 61, or a modified amino acid sequence thereof containing 1, 2, 3, or more amino acid residue modifications as compared to SEQ ID NO: 61; and a H-CDR3 comprising the amino acid sequence of SEQ ID NO: 99, or a modified amino acid sequence thereof, said modified amino acid sequence containing 1, 2, 3, or more amino acid modifications as compared to SEQ ID NO: 99.

An exemplary single domain antibody having this heavy chain variable region is referred to herein as the 52-T-sR2-2C9 antibody. The 52-T-sR2-2C9 antibody comprises a $V_H$ chain amino acid sequence of SEQ ID NO: 137 as shown below.

```
                                         SEQ ID NO: 137
QVQLQASGGGLVQAGGSLRLSCVASGSIFRFNAIGWYRQAPGKERELVA
RIRRLGSTSYADSVKGRFSISRDSAKNTVYLQMDNLKPEDTAVYYCKAG
RHPHFSMDYPDLGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 137.

In one embodiment, the antibody or binding fragment thereof of the present disclosure comprises a humanized variant of the heavy chain variable region of SEQ ID NO: 137, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 137), or a combination of these approaches. The humanized framework regions are designed to be similar in length and sequence to the parental framework sequences of SEQ ID NO: 137. In one embodiment, the humanized framework regions share 50%, 55%, 60%, 65%, 70%, 75%, 80%, 85%, 90%, 95% or more sequence identity to the framework regions of SEQ ID NO: 137. In another embodiment, the humanized framework regions are 60%, 65%, 70%, 75%, 80%, 85%, 90%, 95% or more similar in length to the framework regions of SEQ ID NO: 137. Humanized variants of the heavy chain variable region of SEQ ID NO: 137 share at least 50%, at least 55%, at least 60%, at least 65%, at least 70%, at least 75%, at least 80%, at least 85%, at least 90%, at least 95% sequence identity along the entire length of SEQ ID 137.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 137. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 24, or a modified amino acid sequence thereof containing 1, 2, 3, or more amino acid residue modifications as compared to SEQ ID NO: 24; a H-CDR2 having the amino acid sequence of SEQ ID NO: 62, or a modified amino acid sequence thereof containing 1, 2, 3, or more amino acid residue modifications as compared to SEQ ID NO: 62; and a H-CDR3 comprising the amino acid sequence of SEQ ID NO: 100, or a modified amino acid sequence thereof, said modified amino acid sequence containing 1, 2, 3, or more amino acid modifications as compared to SEQ ID NO: 100.

An exemplary single domain antibody having this heavy chain variable region is referred to herein as the 53-T-sR2-2H5 antibody. The 53-T-sR2-2H5 antibody comprises a $V_H$ chain amino acid sequence of SEQ ID NO: 138 as shown below.

```
                                              SEQ ID NO: 138
QVQLQESGGGLVQPGGSLRLSCAASRYIFGTMGWYRQAPGLQRELVASI
SRGGSTNYADSVKGRFAISRDNAKNTVYLQMNNLKPEDTAVYYCALALG
FFTNYYVRESSYRYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 138.

In one embodiment, the antibody or binding fragment thereof of the present disclosure comprises a humanized variant of the heavy chain variable region of SEQ ID NO: 138, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 138), or a combination of these approaches. The humanized framework regions are designed to be similar in length and sequence to the parental framework sequences of SEQ ID NO: 138. In one embodiment, the humanized framework regions share 50%, 55%, 60%, 65%, 70%, 75%, 80%, 85%, 90%, 95% or more sequence identity to the framework regions of SEQ ID NO: 138. In another embodiment, the humanized framework regions are 60%, 65%, 70%, 75%, 80%, 85%, 90%, 95% or more similar in length to the framework regions of SEQ ID NO: 138. Humanized variants of the heavy chain variable region of SEQ ID NO: 138 share at least 50%, at least 55%, at least 60%, at least 65%, at least 70%, at least 75%, at least 80%, at least 85%, at least 90%, at least 95% sequence identity along the entire length of SEQ ID 138.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 138. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 25, or a modified amino acid sequence thereof containing 1, 2, 3, or more amino acid residue modifications as compared to SEQ ID NO: 25; a H-CDR2 having the amino acid sequence of SEQ ID NO: 63, or a modified amino acid sequence thereof containing 1, 2, 3, or more amino acid residue modifications as compared to SEQ ID NO: 63; and a H-CDR3 comprising the amino acid sequence of SEQ ID NO: 101, or a modified amino acid sequence thereof, said modified amino acid sequence containing 1, 2, 3, or more amino acid modifications as compared to SEQ ID NO: 101.

An exemplary single domain antibody having this heavy chain variable region is referred to herein as the 58-T-sR2-1C6 antibody. The 58-T-sR2-1C6 antibody comprises a $V_H$ chain amino acid sequence of SEQ ID NO: 139 as shown below.

```
                                              SEQ ID NO: 139
QVQLQESGGGLVQTGGSLRLSCAASGRTFRLYSMAWFRQAPGKEREFLG
SIRWNGGNIYYTDSVKGRFTISRDNAKNTAYLQMNSLTPEDTAVYYCAA
GPRIAVWRYEYNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 139.

In one embodiment, the antibody or binding fragment thereof of the present disclosure comprises a humanized variant of the heavy chain variable region of SEQ ID NO: 139, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 139), or a combination of these approaches. The humanized framework regions are designed to be similar in length and sequence to the parental framework sequences of SEQ ID NO: 139. In one embodiment, the humanized framework regions share 50%, 55%, 60%, 65%, 70%, 75%, 80%, 85%, 90%, 95% or more sequence identity to the framework regions of SEQ ID NO: 139. In another embodiment, the humanized framework regions are 60%, 65%, 70%, 75%, 80%, 85%, 90%, 95% or more similar in length to the framework regions of SEQ ID NO: 139. Humanized variants of the heavy chain variable region of SEQ ID NO: 139 share at least 50%, at least 55%, at least 60%, at least 65%, at least 70%, at least 75%, at least 80%, at least 85%, at least 90%, at least 95% sequence identity along the entire length of SEQ ID 139.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 139. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 26, or a modified amino acid sequence thereof containing 1, 2, 3, or more amino acid residue modifications as compared to SEQ ID NO: 26; a H-CDR2 having the amino acid sequence of SEQ ID NO: 64, or a modified amino acid sequence thereof containing 1, 2, 3, or more amino acid residue modifications as compared to SEQ ID NO: 64; and a H-CDR3 comprising the amino acid sequence of SEQ ID NO: 102, or a modified amino acid sequence thereof, said modified amino acid sequence containing 1, 2, 3, or more amino acid modifications as compared to SEQ ID NO: 102.

An exemplary single domain antibody having this heavy chain variable region is referred to herein as the 59-T-sR2-1G5 antibody. The 59-T-sR2-1G5 antibody comprises a $V_H$ chain amino acid sequence of SEQ ID NO: 140 as shown below.

```
                                           SEQ ID NO: 140
QVQLQESGGGLVQPGGSLRLSCAASGSIGSFKTMGWYRQAPGKQRELVA
TITRWGFTNYADSVKGRFTIARDNAKSTLYLQMNSLKPEDTAIYYCAAA
QGGFMKPRANWYNSWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 140.

In one embodiment, the antibody or binding fragment thereof of the present disclosure comprises a humanized variant of the heavy chain variable region of SEQ ID NO: 140, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 140), or a combination of these approaches. The humanized framework regions are designed to be similar in length and sequence to the parental framework sequences of SEQ ID NO: 140. In one embodiment, the humanized framework regions share 50%, 55%, 60%, 65%, 70%, 75%, 80%, 85%, 90%, 95% or more sequence identity to the framework regions of SEQ ID NO: 140. In another embodiment, the humanized framework regions are 60%, 65%, 70%, 75%, 80%, 85%, 90%, 95% or more similar in length to the framework regions of SEQ ID NO: 140. Humanized variants of the heavy chain variable region of SEQ ID NO: 140 share at least 50%, at least 55%, at least 60%, at least 65%, at least 70%, at least 75%, at least 80%, at least 85%, at least 90%, at least 95% sequence identity along the entire length of SEQ ID 140.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 140. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 27, or a modified amino acid sequence thereof containing 1, 2, 3, or more amino acid residue modifications as compared to SEQ ID NO: 27; a H-CDR2 having the amino acid sequence of SEQ ID NO: 65, or a modified amino acid sequence thereof containing 1, 2, 3, or more amino acid residue modifications as compared to SEQ ID NO: 65; and a H-CDR3 comprising the amino acid sequence of SEQ ID NO: 103, or a modified amino acid sequence thereof, said modified amino acid sequence containing 1, 2, 3, or more amino acid modifications as compared to SEQ ID NO: 103.

An exemplary single domain antibody having this heavy chain variable region is referred to herein as the 60-T-sR2-2D8 antibody. The 60-T-sR2-2D8 antibody comprises a $V_H$ chain amino acid sequence of SEQ ID NO: 141 as shown below.

```
                                           SEQ ID NO: 141
QVQLQESGGGLVQAGASLRLSCVASGRTFSRYGMGWFRQAPGKEREFVA
AISRSGAISYYADSVKGRFTISRGDATNTVVLQMSSLKPGDTAVYYCAA
SSRRLLGGPFAYDYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 141.

In one embodiment, the antibody or binding fragment thereof of the present disclosure comprises a humanized variant of the heavy chain variable region of SEQ ID NO: 141, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 141), or a combination of these approaches. The humanized framework regions are designed to be similar in length and sequence to the parental framework sequences of SEQ ID NO: 141. In one embodiment, the humanized framework regions share 50%, 55%, 60%, 65%, 70%, 75%, 80%, 85%, 90%, 95% or more sequence identity to the framework regions of SEQ ID NO: 141. In another embodiment, the humanized framework regions are 60%, 65%, 70%, 75%, 80%, 85%, 90%, 95% or more similar in length to the framework regions of SEQ ID NO: 141. Humanized variants of the heavy chain variable region of SEQ ID NO: 141 share at least 50%, at least 55%, at least 60%, at least 65%, at least 70%, at least 75%, at least 80%, at least 85%, at least 90%, at least 95% sequence identity along the entire length of SEQ ID 141.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 141. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 28, or a modified amino acid sequence thereof containing 1, 2, 3, or more amino acid residue modifications as compared to SEQ ID NO: 28; a H-CDR2 having the amino acid sequence of SEQ ID NO: 66, or a modified amino acid sequence thereof containing 1, 2, 3, or more amino acid residue modifications as compared to SEQ ID NO: 66; and a H-CDR3 comprising the amino acid sequence of SEQ ID NO: 104, or a modified amino acid sequence thereof, said modified amino acid sequence containing 1, 2, 3, or more amino acid modifications as compared to SEQ ID NO: 104.

An exemplary single domain antibody having this heavy chain variable region is referred to herein as the 61-T-sR2-2H7 antibody. The 61-T-sR2-2H7 antibody comprises a $V_H$ chain amino acid sequence of SEQ ID NO: 142 as shown below.

```
                                          SEQ ID NO: 142
QVQLQESGGGLVQPGGSLRLSCAASRYIFGTMGWYRQAPGLQRELVASI
SRGGSTNYADSVKGRFAISRDNAKNTVYLQMNSLKPEDTAVYYCNANRR
GWNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 142.

In one embodiment, the antibody or binding fragment thereof of the present disclosure comprises a humanized variant of the heavy chain variable region of SEQ ID NO: 142, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 142), or a combination of these approaches. The humanized framework regions are designed to be similar in length and sequence to the parental framework sequences of SEQ ID NO: 142. In one embodiment, the humanized framework regions share 50%, 55%, 60%, 65%, 70%, 75%, 80%, 85%, 90%, 95% or more sequence identity to the framework regions of SEQ ID NO: 142. In another embodiment, the humanized framework regions are 60%, 65%, 70%, 75%, 80%, 85%, 90%, 95% or more similar in length to the framework regions of SEQ ID NO: 142. Humanized variants of the heavy chain variable region of SEQ ID NO: 142 share at least 50%, at least 55%, at least 60%, at least 65%, at least 70%, at least 75%, at least 80%, at least 85%, at least 90%, at least 95% sequence identity along the entire length of SEQ ID 142.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 142. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 29, or a modified amino acid sequence thereof containing 1, 2, 3, or more amino acid residue modifications as compared to SEQ ID NO: 29; a H-CDR2 having the amino acid sequence of SEQ ID NO: 67, or a modified amino acid sequence thereof containing 1, 2, 3, or more amino acid residue modifications as compared to SEQ ID NO: 67; and a H-CDR3 comprising the amino acid sequence of SEQ ID NO: 105, or a modified amino acid sequence thereof, said modified amino acid sequence containing 1, 2, 3, or more amino acid modifications as compared to SEQ ID NO: 105.

An exemplary single domain antibody having this heavy chain variable region is referred to herein as the 66-T-sR2-1C7 antibody. The 66-T-sR2-1C7 antibody comprises a $V_H$ chain amino acid sequence of SEQ ID NO: 143 as shown below.

```
                                          SEQ ID NO: 143
QVQLQESGGGLVQAGGSLRLSCAASGTIFTMKNMAWYRQAPGKEREFVA
AISTSGGVTWYADSSVKGRFTISRDNAKNTLYLQMDSLKPEDTAVYYCK
VRSGPRIIPQLRREYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 143.

In one embodiment, the antibody or binding fragment thereof of the present disclosure comprises a humanized variant of the heavy chain variable region of SEQ ID NO: 143, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 143), or a combination of these approaches. The humanized framework regions are designed to be similar in length and sequence to the parental framework sequences of SEQ ID NO: 143. In one embodiment, the humanized framework regions share 50%, 55%, 60%, 65%, 70%, 75%, 80%, 85%, 90%, 95% or more sequence identity to the framework regions of SEQ ID NO: 143. In another embodiment, the humanized framework regions are 60%, 65%, 70%, 75%, 80%, 85%, 90%, 95% or more similar in length to the framework regions of SEQ ID NO: 143. Humanized variants of the heavy chain variable region of SEQ ID NO: 143 share at least 50%, at least 55%, at least 60%, at least 65%, at least 70%, at least 75%, at least 80%, at least 85%, at least 90%, at least 95% sequence identity along the entire length of SEQ ID 143.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 143. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 30, or a modified amino acid sequence thereof containing 1, 2, 3, or more amino acid residue modifications as compared to SEQ ID NO: 30; a H-CDR2 having the amino acid sequence of SEQ ID NO: 68, or a modified amino acid sequence thereof containing 1, 2, 3, or more amino acid residue modifications as compared to SEQ ID NO: 68; and a H-CDR3 comprising the amino acid sequence of SEQ ID NO: 106, or a modified amino acid sequence thereof, said modified amino acid sequence containing 1, 2, 3, or more amino acid modifications as compared to SEQ ID NO: 106.

An exemplary single domain antibody having this heavy chain variable region is referred to herein as the 68-T-sR2-2E6 antibody. The 68-T-sR2-2E6 antibody comprises a $V_H$ chain amino acid sequence of SEQ ID NO: 144 as shown below.

SEQ ID NO: 144
QVQLQESGGGLVQPGDSLRLSCAASGRTFSSYAMGWFRQAPGKEREFVA
AINWSGHSTYYADSVKGRFTISRDNAKNTVYLQMNMLKPEDTAVYYCKL
TRLLNTYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 144.

In one embodiment, the antibody or binding fragment thereof of the present disclosure comprises a humanized variant of the heavy chain variable region of SEQ ID NO: 144, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 144), or a combination of these approaches. The humanized framework regions are designed to be similar in length and sequence to the parental framework sequences of SEQ ID NO: 144. In one embodiment, the humanized framework regions share 50%, 55%, 60%, 65%, 70%, 75%, 80%, 85%, 90%, 95% or more sequence identity to the framework regions of SEQ ID NO: 144. In another embodiment, the humanized framework regions are 60%, 65%, 70%, 75%, 80%, 85%, 90%, 95% or more similar in length to the framework regions of SEQ ID NO: 144. Humanized variants of the heavy chain variable region of SEQ ID NO: 144 share at least 50%, at least 55%, at least 60%, at least 65%, at least 70%, at least 75%, at least 80%, at least 85%, at least 90%, at least 95% sequence identity along the entire length of SEQ ID 144.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 144. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 31, or a modified amino acid sequence thereof containing 1, 2, 3, or more amino acid residue modifications as compared to SEQ ID NO: 31; a H-CDR2 having the amino acid sequence of SEQ ID NO: 69, or a modified amino acid sequence thereof containing 1, 2, 3, or more amino acid residue modifications as compared to SEQ ID NO: 69; and a H-CDR3 comprising the amino acid sequence of SEQ ID NO: 107, or a modified amino acid sequence thereof, said modified amino acid sequence containing 1, 2, 3, or more amino acid modifications as compared to SEQ ID NO: 107.

An exemplary single domain antibody having this heavy chain variable region is referred to herein as the 69-T-sR2-2H8 antibody. The 69-T-sR2-2H8 antibody comprises a $V_H$ chain amino acid sequence of SEQ ID NO: 145 as shown below.

SEQ ID NO: 145
QVQLQESGGGLVQAGDSLRLSCAFSGRTFGLRTMGWFRQAPGKEREFVS
SLTWRDNNAYYADSVKGRFTISRDNAKKTLYLQMNSLKPEDTAVYFCNV
HLVFTNRDYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 145.

In one embodiment, the antibody or binding fragment thereof of the present disclosure comprises a humanized variant of the heavy chain variable region of SEQ ID NO: 145, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 145), or a combination of these approaches. The humanized framework regions are designed to be similar in length and sequence to the parental framework sequences of SEQ ID NO: 145. In one embodiment, the humanized framework regions share 50%, 55%, 60%, 65%, 70%, 75%, 80%, 85%, 90%, 95% or more sequence identity to the framework regions of SEQ ID NO:

145. In another embodiment, the humanized framework regions are 60%, 65%, 70%, 75%, 80%, 85%, 90%, 95% or more similar in length to the framework regions of SEQ ID NO: 145. Humanized variants of the heavy chain variable region of SEQ ID NO: 145 share at least 50%, at least 55%, at least 60%, at least 65%, at least 70%, at least 75%, at least 80%, at least 85%, at least 90%, at least 95% sequence identity along the entire length of SEQ ID 145.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 145. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 32, or a modified amino acid sequence thereof containing 1, 2, 3, or more amino acid residue modifications as compared to SEQ ID NO: 32; a H-CDR2 having the amino acid sequence of SEQ ID NO: 70, or a modified amino acid sequence thereof containing 1, 2, 3, or more amino acid residue modifications as compared to SEQ ID NO: 70; and a H-CDR3 comprising the amino acid sequence of SEQ ID NO: 108, or a modified amino acid sequence thereof, said modified amino acid sequence containing 1, 2, 3, or more amino acid modifications as compared to SEQ ID NO: 108.

An exemplary single domain antibody having this heavy chain variable region is referred to herein as the 74-T-sR2-1C10 antibody. The 74-T-sR2-1C10 antibody comprises a $V_H$ chain amino acid sequence of SEQ ID NO: 146 as shown below.

```
                                             SEQ ID NO: 146
QVQLQQSGGGLVQPGGSLRLSCAASWRIFSPNAMAWYRQAPGKQRELVA
RITWAGITNYADSVKGRFTISRDNAKNTVYLQMHSLKPEDTAIYYCVAD
RRSSYLGPRFDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 146.

In one embodiment, the antibody or binding fragment thereof of the present disclosure comprises a humanized variant of the heavy chain variable region of SEQ ID NO: 146, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 146), or a combination of these approaches. The humanized framework regions are designed to be similar in length and sequence to the parental framework sequences of SEQ ID NO: 146. In one embodiment, the humanized framework regions share 50%, 55%, 60%, 65%, 70%, 75%, 80%, 85%, 90%, 95% or more sequence identity to the framework regions of SEQ ID NO: 146. In another embodiment, the humanized framework regions are 60%, 65%, 70%, 75%, 80%, 85%, 90%, 95% or more similar in length to the framework regions of SEQ ID NO: 146. Humanized variants of the heavy chain variable region of SEQ ID NO: 146 share at least 50%, at least 55%, at least 60%, at least 65%, at least 70%, at least 75%, at least 80%, at least 85%, at least 90%, at least 95% sequence identity along the entire length of SEQ ID 146.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 146. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 33, or a modified amino acid sequence thereof containing 1, 2, 3, or more amino acid residue modifications as compared to SEQ ID NO: 33; a H-CDR2 having the amino acid sequence of SEQ ID NO: 71, or a modified amino acid sequence thereof containing 1, 2, 3, or more amino acid residue modifications as compared to SEQ ID NO: 71; and a H-CDR3 comprising the amino acid sequence of SEQ ID NO: 109, or a modified amino acid sequence thereof, said modified amino acid sequence containing 1, 2, 3, or more amino acid modifications as compared to SEQ ID NO: 109.

An exemplary single domain antibody having this heavy chain variable region is referred to herein as the 75-T-sR2-1G12 antibody. The 75-T-sR2-1G12 antibody comprises a $V_H$ chain amino acid sequence of SEQ ID NO: 147 as shown below.

```
                                             SEQ ID NO: 147
QVQLQESGGGLVQPGGSLRLSCAASRYIFGTMGWYRQAPGLQRELVASI
SRGGSTNYADSVKGRFAISRDNAKNTVYLQMNSLKPEDTAVYYCAARSS
LLEFWLGSRRGYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 147.

In one embodiment, the antibody or binding fragment thereof of the present disclosure comprises a humanized variant of the heavy chain variable region of SEQ ID NO: 147, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 147), or a combination of these approaches. The humanized framework regions are designed to be similar in length and sequence to the parental framework sequences of SEQ ID NO: 147. In one embodiment, the humanized framework regions share 50%, 55%, 60%, 65%, 70%, 75%, 80%, 85%, 90%, 95% or more sequence identity to the framework regions of SEQ ID NO:

147. In another embodiment, the humanized framework regions are 60%, 65%, 70%, 75%, 80%, 85%, 90%, 95% or more similar in length to the framework regions of SEQ ID NO: 147. Humanized variants of the heavy chain variable region of SEQ ID NO: 147 share at least 50%, at least 55%, at least 60%, at least 65%, at least 70%, at least 75%, at least 80%, at least 85%, at least 90%, at least 95% sequence identity along the entire length of SEQ ID 147.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 147. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 34, or a modified amino acid sequence thereof containing 1, 2, 3, or more amino acid residue modifications as compared to SEQ ID NO: 34; a H-CDR2 having the amino acid sequence of SEQ ID NO: 72, or a modified amino acid sequence thereof containing 1, 2, 3, or more amino acid residue modifications as compared to SEQ ID NO: 72; and a H-CDR3 comprising the amino acid sequence of SEQ ID NO: 110, or a modified amino acid sequence thereof, said modified amino acid sequence containing 1, 2, 3, or more amino acid modifications as compared to SEQ ID NO: 110.

An exemplary single domain antibody having this heavy chain variable region is referred to herein as the 76-T-sR2-2E7 antibody. The 76-T-sR2-2E7 antibody comprises a $V_H$ chain amino acid sequence of SEQ ID NO: 148 as shown below.

```
                                      SEQ ID NO: 148
QVQLQQSGGGLVQPGGSLRLACAASGRFFRINAMAWYRQAPGKQRELVA
TITRAGTTTYADSVKGRFTISRDNAKNTVYLQMISLKPEDTAVYYCAKY
PTITWYGRHDYRGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 148.

In one embodiment, the antibody or binding fragment thereof of the present disclosure comprises a humanized variant of the heavy chain variable region of SEQ ID NO: 148, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 148), or a combination of these approaches. The humanized framework regions are designed to be similar in length and sequence to the parental framework sequences of SEQ ID NO: 148. In one embodiment, the humanized framework regions share 50%, 55%, 60%, 65%, 70%, 75%, 80%, 85%, 90%, 95% or more sequence identity to the framework regions of SEQ ID NO: 148. In another embodiment, the humanized framework regions are 60%, 65%, 70%, 75%, 80%, 85%, 90%, 95% or more similar in length to the framework regions of SEQ ID NO: 148. Humanized variants of the heavy chain variable region of SEQ ID NO: 148 share at least 50%, at least 55%, at least 60%, at least 65%, at least 70%, at least 75%, at least 80%, at least 85%, at least 90%, at least 95% sequence identity along the entire length of SEQ ID 148.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 148. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 35, or a modified amino acid sequence thereof containing 1, 2, 3, or more amino acid residue modifications as compared to SEQ ID NO: 35; a H-CDR2 having the amino acid sequence of SEQ ID NO: 73, or a modified amino acid sequence thereof containing 1, 2, 3, or more amino acid residue modifications as compared to SEQ ID NO: 73; and a H-CDR3 comprising the amino acid sequence of SEQ ID NO: 111, or a modified amino acid sequence thereof, said modified amino acid sequence containing 1, 2, 3, or more amino acid modifications as compared to SEQ ID NO: 111.

An exemplary single domain antibody having this heavy chain variable region is referred to herein as the 84-T-sR2-2E8 antibody. The 84-T-sR2-2E8 antibody comprises a $V_H$ chain amino acid sequence of SEQ ID NO: 149 as shown below.

```
                                      SEQ ID NO: 149
QVQLQESGGGLVQHGGSLRLSCAASGSFFRINTMAWHRQAPGKQRELVA
SITRGGSTNYADSVKGRFTISRDNAKNTVYLQMNSLKSEDTAVYYCAAS
RFGINYYTARQYGYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 149.

In one embodiment, the antibody or binding fragment thereof of the present disclosure comprises a humanized variant of the heavy chain variable region of SEQ ID NO: 149, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 149), or a combination of these approaches. The humanized framework regions are designed to be similar in length and sequence to the parental framework sequences of SEQ ID NO: 149. In one embodiment, the humanized framework regions share 50%, 55%, 60%, 65%, 70%, 75%, 80%, 85%, 90%, 95% or more sequence identity to the framework regions of SEQ ID NO:

149. In another embodiment, the humanized framework regions are 60%, 65%, 70%, 75%, 80%, 85%, 90%, 95% or more similar in length to the framework regions of SEQ ID NO: 149. Humanized variants of the heavy chain variable region of SEQ ID NO: 149 share at least 50%, at least 55%, at least 60%, at least 65%, at least 70%, at least 75%, at least 80%, at least 85%, at least 90%, at least 95% sequence identity along the entire length of SEQ ID 149.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 149. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 36, or a modified amino acid sequence thereof containing 1, 2, 3, or more amino acid residue modifications as compared to SEQ ID NO: 36; a H-CDR2 having the amino acid sequence of SEQ ID NO: 74, or a modified amino acid sequence thereof containing 1, 2, 3, or more amino acid residue modifications as compared to SEQ ID NO: 74; and a H-CDR3 comprising the amino acid sequence of SEQ ID NO: 112, or a modified amino acid sequence thereof, said modified amino acid sequence containing 1, 2, 3, or more amino acid modifications as compared to SEQ ID NO: 112.

An exemplary single domain antibody having this heavy chain variable region is referred to herein as the 90-T-sR2-1D9 antibody. The 90-T-sR2-1D9 antibody comprises a $V_H$ chain amino acid sequence of SEQ ID NO: 150 as shown below.

```
                                              SEQ ID NO: 150
QVQLQASGGGLVQAGGSLRLSCAASGRTFSRYPMGWFRQAPGKEREFVA
RFGWSGLSTYYADSVKGRFTISRDNAKNTVYLQMNSLKPEDTAVYYCAA
GRFMGSYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 150.

In one embodiment, the antibody or binding fragment thereof of the present disclosure comprises a humanized variant of the heavy chain variable region of SEQ ID NO: 150, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 150), or a combination of these approaches. The humanized framework regions are designed to be similar in length and sequence to the parental framework sequences of SEQ ID NO: 150. In one embodiment, the humanized framework regions share 50%, 55%, 60%, 65%, 70%, 75%, 80%, 85%, 90%, 95% or more sequence identity to the framework regions of SEQ ID NO: 150. In another embodiment, the humanized framework regions are 60%, 65%, 70%, 75%, 80%, 85%, 90%, 95% or more similar in length to the framework regions of SEQ ID NO: 150. Humanized variants of the heavy chain variable region of SEQ ID NO: 150 share at least 50%, at least 55%, at least 60%, at least 65%, at least 70%, at least 75%, at least 80%, at least 85%, at least 90%, at least 95% sequence identity along the entire length of SEQ ID 150.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 150. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 37, or a modified amino acid sequence thereof containing 1, 2, 3, or more amino acid residue modifications as compared to SEQ ID NO: 37; a H-CDR2 having the amino acid sequence of SEQ ID NO: 75, or a modified amino acid sequence thereof containing 1, 2, 3, or more amino acid residue modifications as compared to SEQ ID NO: 75; and a H-CDR3 comprising the amino acid sequence of SEQ ID NO: 113, or a modified amino acid sequence thereof, said modified amino acid sequence containing 1, 2, 3, or more amino acid modifications as compared to SEQ ID NO: 113.

An exemplary single domain antibody having this heavy chain variable region is referred to herein as the 91-T-sR2-1H12 antibody. The 91-T-sR2-1H12 antibody comprises a $V_H$ chain amino acid sequence of SEQ ID NO: 151 as shown below.

```
                                              SEQ ID NO: 151
QVQLQESGGGLVQAGGSLRLSCAASGRTFSWYAMGWFRQAPGREREFVA
AIRRSGGITIYADSVKGRFAVSRDNAKNTVYLQMNSLKPEDTAVYYCAA
NLFQWRLNDNGNQYGSWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 151.

In one embodiment, the antibody or binding fragment thereof of the present disclosure comprises a humanized variant of the heavy chain variable region of SEQ ID NO: 151, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 151), or a combination of these approaches. The humanized framework regions are designed to be similar in length and sequence to the parental framework sequences of SEQ ID NO: 151. In one embodiment, the humanized framework regions share 50%, 55%, 60%, 65%, 70%, 75%, 80%, 85%, 90%, 95% or more sequence identity to the framework regions of SEQ ID NO: 151. In another embodiment, the humanized framework regions are 60%, 65%, 70%, 75%, 80%, 85%, 90%, 95% or more similar in length to the framework regions of SEQ ID NO: 151. Humanized variants of the heavy chain variable region of SEQ ID NO: 151 share at least 50%, at least 55%, at least 60%, at least 65%, at least 70%, at least 75%, at least 80%, at least 85%, at least 90%, at least 95% sequence identity along the entire length of SEQ ID 151.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 151. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 38, or a modified amino acid sequence thereof containing 1, 2, 3, or more amino acid residue modifications as compared to SEQ ID NO: 38; a H-CDR2 having the amino acid sequence of SEQ ID NO: 76, or a modified amino acid sequence thereof containing 1, 2, 3, or more amino acid residue modifications as compared to SEQ ID NO: 76; and a H-CDR3 comprising the amino acid sequence of SEQ ID NO: 114, or a modified amino acid sequence thereof, said modified amino acid sequence containing 1, 2, 3, or more amino acid modifications as compared to SEQ ID NO: 114.

An exemplary single domain antibody having this heavy chain variable region is referred to herein as the 92-T-sR2-2E9 antibody. The 92-T-sR2-2E9 antibody comprises a V$_H$ chain amino acid sequence of SEQ ID NO: 152 as shown below.

```
                                          SEQ ID NO: 152
QVQLQESGGGLVQAGGSLRLSCVVSGRTFSTSQMGWFRQPPGKERELVA
RISWRGKQHYADSVKGRFTISRDYAKNTVYLQMNGLKSEDTAVYYCAAG
PRAVLFGTYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 152.

In one embodiment, the antibody or binding fragment thereof of the present disclosure comprises a humanized variant of the heavy chain variable region of SEQ ID NO: 152, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 152), or a combination of these approaches. The humanized framework regions are designed to be similar in length and sequence to the parental framework sequences of SEQ ID NO: 152. In one embodiment, the humanized framework regions share 50%, 55%, 60%, 65%, 70%, 75%, 80%, 85%, 90%, 95% or more sequence identity to the framework regions of SEQ ID NO: 152. In another embodiment, the humanized framework regions are 60%, 65%, 70%, 75%, 80%, 85%, 90%, 95% or more similar in length to the framework regions of SEQ ID NO: 152. Humanized variants of the heavy chain variable region of SEQ ID NO: 152 share at least 50%, at least 55%, at least 60%, at least 65%, at least 70%, at least 75%, at least 80%, at least 85%, at least 90%, at least 95% sequence identity along the entire length of SEQ ID 152.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 152. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 202, or a modified amino acid sequence thereof containing 1, 2, 3, or more amino acid residue modifications as compared to SEQ ID NO: 202; a H-CDR2 having the amino acid sequence of SEQ ID NO: 203, or a modified amino acid sequence thereof containing 1, 2, 3, or more amino acid residue modifications as compared to SEQ ID NO: 203; and a H-CDR3 comprising the amino acid sequence of SEQ ID NO: 204, or a modified amino acid sequence thereof, said modified amino acid sequence containing 1, 2, 3, or more amino acid modifications as compared to SEQ ID NO: 204.

An exemplary single domain antibody having this heavy chain variable region is referred to herein as the T-sR2-2B8 antibody. This antibody comprises a V$_H$ chain amino acid sequence of SEQ ID NO: 205 as shown below.

```
                                          SEQ ID NO: 205
QVQLAESGGGLVQAGGSLRLSCVVSGRTFSTSQMGWFRQPPGKERELVA
RISWRGKQHYADSVKGRFTISRDYAKNTVYLQMNGLKSEDTAVYYCAAD
RRRTYLGQQHDYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 205.

In one embodiment, the antibody or binding fragment thereof of the present disclosure comprises a humanized variant of the heavy chain variable region of SEQ ID NO: 205, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 205), or a combination of these approaches. The humanized framework regions are designed to be similar in length and sequence to the parental framework sequences of SEQ ID NO: 205. In one embodiment, the humanized framework regions share 50%, 55%, 60%, 65%, 70%, 75%, 80%, 85%, 90%, 95% or more sequence identity to the framework regions of SEQ ID NO: 205. In another embodiment, the humanized framework regions are 60%, 65%, 70%, 75%, 80%, 85%, 90%, 95% or more similar in length to the framework regions of SEQ ID NO: 205. Humanized variants of the heavy chain variable region of SEQ ID NO: 205 share at least 50%, at least 55%, at least 60%, at least 65%, at least 70%, at least 75%, at least 80%, at least 85%, at least 90%, at least 95% sequence identity along the entire length of SEQ ID 205.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 205. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 206, or a modified amino acid sequence thereof containing 1, 2, 3, or more amino acid residue modifications as compared to SEQ ID NO: 206; a H-CDR2 having the amino acid sequence of SEQ ID NO: 207, or a modified amino acid sequence thereof containing 1, 2, 3, or more amino acid residue modifications as compared to SEQ ID NO: 207; and a H-CDR3 comprising the amino acid sequence of SEQ ID NO: 208, or a modified amino acid sequence thereof, said modified amino acid sequence containing 1, 2, 3, or more amino acid modifications as compared to SEQ ID NO: 208.

An exemplary single domain antibody having this heavy chain variable region is referred to herein as the T-sR2-2F12 antibody. This antibody comprises a $V_H$ chain amino acid sequence of SEQ ID NO: 209 as shown below.

```
                                          SEQ ID NO: 209
QVQLQESGGGLVQAGGSLRLSCAASGSIFRINGMGWHRQAPGKERELVA
TITRGGSISYADSVKGRFTISRDNAKNTLYLQMNNLKPEDTAVYYCAKY
RRPLFYSGSNYREGDFASWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity to SEQ ID NO: 209.

In one embodiment, the antibody or binding fragment thereof of the present disclosure comprises a humanized variant of the heavy chain variable region of SEQ ID NO: 209, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 209), or a combination of these approaches. The humanized framework regions are designed to be similar in length and sequence to the parental framework sequences of SEQ ID NO: 209. In one embodiment, the humanized framework regions share 50%, 55%, 60%, 65%, 70%, 75%, 80%, 85%, 90%, 95% or more sequence identity to the framework regions of SEQ ID NO: 209. In another embodiment, the humanized framework regions are 60%, 65%, 70%, 75%, 80%, 85%, 90%, 95% or more similar in length to the framework regions of SEQ ID NO: 209. Humanized variants of the heavy chain variable region of SEQ ID NO: 209 share at least 50%, at least 55%, at least 60%, at least 65%, at least 70%, at least 75%, at least 80%, at least 85%, at least 90%, at least 95% sequence identity along the entire length of SEQ ID 209.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 209. In accordance with this aspect of the disclosure, a competitive binding assay, such as Bio-competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 210, or a modified amino acid sequence thereof containing 1, 2, 3, or more amino acid residue modifications as compared to SEQ ID NO: 210; a H-CDR2 having the amino acid sequence of SEQ ID NO: 211, or a modified amino acid sequence thereof containing 1, 2, 3, or more amino acid residue modifications as compared to SEQ ID NO: 211; and a H-CDR3 comprising the amino acid sequence of SEQ ID NO: 212, or a modified amino acid sequence thereof, said modified amino acid sequence containing 1, 2, 3, or more amino acid modifications as compared to SEQ ID NO: 212.

An exemplary single domain antibody having this heavy chain variable region is referred to herein as the T-sR2-2B3 antibody. This antibody comprises a $V_H$ chain amino acid sequence of SEQ ID NO: 213 as shown below.

```
                                          SEQ ID NO: 213
QVQLQASGGGLVQAGGSLRLSCAASGRTFGSYTMGWFRQAPGKEREFVA
AISRSGGSTYYADSVKGRFTISRDNAKNTVYLQMNSLKPEDTAVYYCNV
RGRPFILSKPFDSWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity to SEQ ID NO: 213.

In one embodiment, the antibody or binding fragment thereof of the present disclosure comprises a humanized variant of the heavy chain variable region of SEQ ID NO: 213, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 213), or a combination of these approaches. The humanized framework regions are designed to be similar in length and sequence to the parental framework sequences of SEQ ID NO: 213. In one embodiment, the humanized framework regions share 50%, 55%, 60%, 65%, 70%, 75%, 80%, 85%, 90%, 95% or more sequence identity to the framework regions of SEQ ID NO: 213. In another embodiment, the humanized framework regions are 60%, 65%, 70%, 75%, 80%, 85%, 90%, 95% or more similar in length to the framework regions of SEQ ID NO: 213. Humanized variants of the heavy chain variable region of SEQ ID NO: 213 share at least 50%, at least 55%, at least 60%, at least 65%, at least 70%, at least 75%, at least 80%, at least 85%, at least 90%, at least 95% sequence identity along the entire length of SEQ ID 213.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 213. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 214, or a modified amino acid sequence thereof containing 1, 2, 3, or more amino acid residue modifications as compared to SEQ ID NO: 214; a H-CDR2 having the amino acid sequence of SEQ ID NO: 215, or a modified amino acid sequence thereof containing 1, 2, 3, or more amino acid residue modifications as compared to SEQ ID NO: 215; and a H-CDR3 comprising the amino acid sequence of SEQ ID NO: 216, or a modified amino acid sequence thereof, said modified amino acid sequence containing 1, 2, 3, or more amino acid modifications as compared to SEQ ID NO: 216.

An exemplary single domain antibody having this heavy chain variable region is referred to herein as the T-sR2-2C4 antibody. This antibody comprises a $V_H$ chain amino acid sequence of SEQ ID NO: 217 as shown below.

```
                                        SEQ ID NO: 217
QVQLQESGGGLVQAGNSLRLSCAASGRTFSNYAMGWFRQAPGKEREFVA
AITRNGGITYYAESVKGRFTISRDNAKNMVYLQMNSLKPEDTAVYYCNI
KARRGSFFNPVNNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 217.

In one embodiment, the antibody or binding fragment thereof of the present disclosure comprises a humanized variant of the heavy chain variable region of SEQ ID NO: 217, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 217), or a combination of these approaches. The humanized framework regions are designed to be similar in length and sequence to the parental framework sequences of SEQ ID NO: 217. In one embodiment, the humanized framework regions share 50%, 55%, 60%, 65%, 70%, 75%, 80%, 85%, 90%, 95% or more sequence identity to the framework regions of SEQ ID NO: 217. In another embodiment, the humanized framework regions are 60%, 65%, 70%, 75%, 80%, 85%, 90%, 95% or more similar in length to the framework regions of SEQ ID NO: 217. Humanized variants of the heavy chain variable region of SEQ ID NO: 217 share at least 50%, at least 55%, at least 60%, at least 65%, at least 70%, at least 75%, at least 80%, at least 85%, at least 90%, at least 95% sequence identity along the entire length of SEQ ID 217.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 217. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In another embodiment, the antibody or binding fragment thereof as disclosed herein comprises a heavy chain variable region having a H-CDR1 with an amino acid sequence selected from SEQ ID NOs: 153-164, 307, or a modified amino acid sequence thereof containing 1, 2, 3, 4, 5, 7, 8, or 9 amino acid residue modifications as compared to SEQ ID NOs: 153-164 and 307 that maintain or enhance binding specificity of the H-CDR1. In one embodiment, the amino acid sequence of the H-CDR1 contains no more than 1, 2, or 3 amino acid modifications as compared to SEQ ID NOs: 153-164 and 307, respectively. The HCVR further comprises a H-CDR2 with an amino acid sequence selected from SEQ ID NOs: 165-176, 308 or a modified amino acid sequence thereof containing 1, 2, 3, 4, 5, 6, 7, 8, 9, or 10, amino acid residue modifications as compared to SEQ ID NOs: 165-176 and 308 that maintain or enhance binding specificity of the H-CDR2. In one embodiment, the amino acid sequence of the H-CDR2 contains no more than 1, 2, or 3, amino acid modifications as compared to SEQ ID NOs: 165-176 and 308, respectively. The HCVR of the antibody or binding fragment thereof comprises a H-CDR3 with an amino acid sequence selected from SEQ ID NOs: 177-188, 309 or a modified amino acid sequence thereof containing 1, 2, 3, 4, 5, 6, 7, 8, 9, 10, or 11 amino acid residue modifications as compared to SEQ ID NOs: 177-188 and 309 that maintain or enhance binding specificity of the H-CDR3. In one embodiment, the amino acid sequence of the H-CDR3 contains no more than 1, 2, or 3 amino acid modifications as compared to SEQ ID NOs: 177-188 and 309, respectively. The amino acid sequences of SEQ ID NOs: 153-188 and 307-309 are provided in Table 2 below.

TABLE 2

Tau Single Domain Antibody Complementarity Determining Regions

| Antibody Description | descr | sequence | SEQ ID NO: | descr | sequence | SEQ ID NO: | descr | sequence | SEQ ID NO: |
|---|---|---|---|---|---|---|---|---|---|
| 01-T-bR3-1E2; 02-T-bR3-1D10; 07-T-bR3-1C1; 09-T-bR3-1E4; 10-T-bR3-1D11; 14-T-bR3-1B1; 15-T-bR3-1C2; 17-T-bR3-1C5; 23-T-bR3-1C3; 25-T-bR3-1C6; 31-T-bR3-1C4; 33-T-bR3-1C9; 41-T-bR3-1C10; 46-T-bR3-1B5; 49-T-bR3-1C12; 57-T-bR3-1D1; 65-T-bR3-1D5; 70-T-bR3-1B9; 73-T-bR3-1D6; 77-T-bR3-1A8; 81-T-bR3-1D7; 89-T-bR3-1D8; 93-T-bR3-1A10; 94-T-bR3-1B12 | CDR1 | SGRIFSNNVM | 153 | CDR2 | AISRSGGTTLYA | 165 | CDR3 | GKVDEIRPTVSASYD | 177 |
| 06-T-bR3-1A11 | CDR1 | SSGPFSRYAM | 154 | CDR2 | TISRSGSSTTYG | 166 | CDR3 | AVSRYYTAGASADTKTYD | 178 |
| 08-T-bR3-1E12; 16-T-bR3-1F8; 30-T-bR3-1B3; 39-T-bR3-1C7; 78-T-bR3-1B10; 80-T-bR3-1H11; 85-T-bR3-1A9; 38T-bR3-1B4 | CDR1 | SGFNFGSFAI | 155 | CDR2 | CISSTDDTSVYS | 167 | CDR3 | ATVGQSCDLWDHPQVPVRYRGR | 179 |
| 22-T-bR3-1B2 | CDR1 | SGSISSINAI | 156 | CDR2 | KITKGGTTIYT | 168 | CDR3 | GADVNYGSPDYID | 180 |
| 24-T-bR3-1F10; 48-T-bR3-1G5 | CDR1 | SGRTFSTYTM | 157 | CDR2 | AISWSSGTANYA | 169 | CDR3 | NAWSPVGHD | 181 |
| 32-T-bR3-1F12 | CDR1 | SGRTFSNYAM | 158 | CDR2 | AISWSGAYTFYG | 170 | CDR3 | AAARGGRWYSTYD | 182 |
| 40-T-bR3-1G3 | CDR1 | SGSTFSGYVI | 159 | CDR2 | IISSSGSTNYA | 171 | CDR3 | NARLWLNN | 183 |
| 47-T-bR3-1C8 | CDR1 | SGFTFSSYWM | 160 | CDR2 | TISPSGGTTYYT | 172 | CDR3 | AARRSGRYEYD | 184 |
| 62-T-bR3-1B8; 71-T-bR3-1D12 | CDR1 | SGFPFDDYPM | 161 | CDR2 | SVSPNGGSTFYA | 173 | CDR3 | AKVLDYYCSGYGCYASYD | 185 |
| 79-T-bR3-1E1 | CDR1 | SISIVSINTM | 162 | CDR2 | GITSGGSTNYA | 174 | CDR3 | NAGRYVPGAIVTN | 186 |
| 86-T-bR3-1B11 | CDR1 | SMTTLGFKTM | 163 | CDR2 | RISSGGQTNYA | 175 | CDR3 | NARRYYSLARYDYN | 187 |
| 95-T-bR3-1E11 | CDR1 | GGKSTAAVNGV | 164 | CDR2 | AIRPGGRRDYL | 176 | CDR3 | YAEGLLLPST | 188 |
| 55-T-bR3-1D4 | CDR1 | SGRTFSGYS | 307 | CDR2 | VGGISRSGGWT | 308 | CDR3 | AAAVSRINDYAPALSRAYD | 309 |

In one embodiment, the antibody or binding fragment thereof has a heavy chain variable region with a H-CDR1 having the amino acid sequence of SEQ ID NO: 153, or a modified amino acid sequence thereof containing 1, 2, 3, or more amino acid residue modifications as compared to SEQ ID NO: 153; a H-CDR2 having the amino acid sequence of SEQ ID NO: 165, or a modified amino acid sequence thereof containing 1, 2, 3, or more amino acid residue modifications as compared to SEQ ID NO: 165; and a H-CDR3 comprising the amino acid sequence of SEQ ID NO: 177, or a modified amino acid sequence thereof, said modified amino acid sequence containing 1, 2, 3, or more amino acid modifications as compared to SEQ ID NO: 177.

An exemplary single domain antibody having this heavy chain variable region is referred to herein as the 01-T-bR3-1E2 antibody. The 01-T-bR3-1E2 antibody comprises a $V_H$ chain amino acid sequence of SE ID NO: 189 as shown below.

SEQ ID NO: 189
QVQLQESGGGLVQAGGSLRLSCAASGRIFSNNVMGWFRQAPGKEREFVA
AISRSGGTTLYAESMKGRFTISRDNAKNTLYLQMNSLKSEDTAMYYCGK
VDEIRPTVSASYDLWGQGTLVTVSS

Other single domain antibodies described herein having the same $V_H$ chain amino acid sequence of SEQ ID NO: 189 include 02-T-bR3-1D10; 07-T-bR3-1C1; 09-T-bR3-1E4; 10-T-bR3-1D11; 14-T-bR3-1B1; 15-T-bR3-1C2; 17-T-bR3-1C5; 23-T-bR3-1C3; 25-T-bR3-1C6; 31-T-bR3-1C4; 33-T-bR3-1C9; 41-T-bR3-1C10; 46-T-bR3-1B5; 49-T-bR3-1C12; 57-T-bR3-1D1; 65-T-bR3-1D5, 70-T-bR3-1B9; 73-T-bR3-1D6; 77-T-bR3-1A8; 81-T-bR3-1D7; 89-T-bR3-1D8; 93-T-bR3-1A10; and 94-T-bR3-1B12.

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 189.

In one embodiment, the antibody or binding fragment thereof of the present disclosure comprises a humanized variant of the heavy chain variable region of SEQ ID NO: 189, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 189), or a combination of these approaches. The humanized framework regions are designed to be similar in length and sequence to the parental framework sequences of SEQ ID NO: 189. In one embodiment, the humanized framework regions share 50%, 55%, 60%, 65%, 70%, 75%, 80%, 85%, 90%, 95% or more sequence identity to the framework regions of SEQ ID NO: 189. In another embodiment, the humanized framework regions are 60%, 65%, 70%, 75%, 80%, 85%, 90%, 95% or more similar in length to the framework regions of SEQ ID NO: 189. Humanized variants of the heavy chain variable region of SEQ ID NO: 189 share at least 50%, at least 55%, at least 60%, at least 65%, at least 70%, at least 75%, at least 80%, at least 85%, at least 90%, at least 95% sequence identity along the entire length of SEQ ID 189.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 189. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 154, or a modified amino acid sequence thereof containing 1, 2, 3, or more amino acid residue modifications as compared to SEQ ID NO: 154; a H-CDR2 having the amino acid sequence of SEQ ID NO: 166, or a modified amino acid sequence thereof containing 1, 2, 3, or more amino acid residue modifications as compared to SEQ ID NO: 166; and a H-CDR3 comprising the amino acid sequence of SEQ ID NO: 178, or a modified amino acid sequence thereof, said modified amino acid sequence containing 1, 2, 3, or more amino acid modifications as compared to SEQ ID NO: 178.

An exemplary single domain antibody having this combination of heavy chain variable region CDRs is referred to herein as the 06-T-bR3-1A11 antibody. The 06-T-bR3-1A1 1 antibody comprises a $V_H$ chain amino acid sequence of SEQ ID NO: 190 as shown below.

SEQ ID NO: 190
QVQLQESGGGLVQAGDSLRLSCAASSGPFSRYAMGWFRQAPGKEREFVA
TISRSGSSTTYGDSVKGRFTISRDNAKNTLYLEMNSLTPEDTAVYYCAV
SRYYTAGASADTKTYDYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 190.

In one embodiment, the antibody or binding fragment thereof of the present disclosure comprises a humanized variant of the heavy chain variable region of SEQ ID NO: 190, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 190), or a combination of these approaches. The humanized framework regions are designed to be similar in length and sequence to the parental framework sequences of SEQ ID NO: 190. In one embodiment, the humanized framework regions share 50%, 55%, 60%, 65%, 70%, 75%, 80%, 85%, 90%, 95% or more sequence identity to the framework regions of SEQ ID NO: 190. In another embodiment, the humanized framework regions are 60%, 65%, 70%, 75%, 80%, 85%, 90%, 95% or more similar in length to the framework regions of SEQ ID NO: 190. Humanized variants of the heavy chain variable region of SEQ ID NO: 190 share at least 50%, at least 55%, at least 60%, at least 65%, at least 70%, at least 75%, at least 80%, at least 85%, at least 90%, at least 95% sequence identity along the entire length of SEQ ID NO: 190, respectively.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 190. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 155, or a modified amino acid sequence thereof containing 1, 2, 3, or more amino acid residue modifications as compared to SEQ ID NO: 155; a H-CDR2 having the amino acid sequence of SEQ ID NO: 167, or a modified amino acid sequence thereof containing 1, 2, 3, or more amino acid residue modifications as compared to SEQ ID NO: 167; and a H-CDR3 comprising the amino acid sequence of SEQ ID NO: 179, or a modified amino acid sequence thereof, said modified amino acid sequence containing 1, 2, 3, or more amino acid modifications as compared to SEQ ID NO: 179.

An exemplary single domain antibody having this combination of heavy chain variable region CDRs is referred to herein as the 08-T-bR3-1E12 antibody. The 08-T-bR3-1E12 antibody comprises a V$_H$ chain amino acid sequence of SEQ ID NO: 191 as shown below.

```
                                          SEQ ID NO: 191
QVQLQASGGGLVQPGGSLKLSCQASGFNFGSFAIAWFRQAPGKGREGIS
CISSTDDTSVYSDAVKGRFAISRDNAKRAAYLQMNSLIPEDTANYYCAT
VGQSCDLWDHPQVPVRYRGRGTLVTVSS
```

Another exemplary single domain antibody having this combination of heavy chain variable region CDRs is referred to herein as the 16-T-bR3-1F8 antibody. The 16-T-bR3-1F8 antibody comprises a V$_H$ chain amino acid sequence of SEQ ID NO: 192 as shown below.

```
                                          SEQ ID NO: 192
QVQLQASGGGLVQPGGSLKLSCQASGFNFGSFAIAWFRQAPGKGREGIS
CISSTDDTSVYSDAVKGRFAISRDNAKRAAYLQMNSLIPEDTANYYCAT
VGQSCDLWDHPQVPVRYRGRGTQVTVSS
```

Other antibodies of the disclosure comprising the amino acid sequence of SEQ ID NO: 192 include 30-T-bR3-1B3; 39-T-bR3-1C7; 78-T-bR3-1B10; 80-T-bR3-1H11; 85-T-bR3-1A9; and 38T-bR3-1B4.

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 191 or SEQ ID NO: 192.

In one embodiment, the antibody or binding fragment thereof of the present disclosure comprises a humanized variant of the heavy chain variable region of SEQ ID NO: 191 or SEQ ID NO: 192, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 191 or SEQ ID NO: 192), or a combination of these approaches. The humanized framework regions are designed to be similar in length and sequence to the parental framework sequences of SEQ ID NO: 191 or SEQ ID NO: 192. In one embodiment, the humanized framework regions share 50%, 55%, 60%, 65%, 70%, 75%, 80%, 85%, 90%, 95% or more sequence identity to the framework regions of SEQ ID NO: 191 or SEQ ID NO: 192. In another embodiment, the humanized framework regions are 60%, 65%, 70%, 75%, 80%, 85%, 90%, 95% or more similar in length to the framework regions of SEQ ID NO: 191 or SEQ ID NO: 192. Humanized variants of the heavy chain variable region of SEQ ID NO: 191 or SEQ ID NO: 192 share at least 50%, at least 55%, at least 60%, at least 65%, at least 70%, at least 75%, at least 80%, at least 85%, at least 90%, at least 95% sequence identity along the entire length of SEQ ID NO: 191 or SEQ ID NO: 192, respectively.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 191 or SEQ ID NO: 192. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 156, or a modified amino acid sequence thereof containing 1, 2, 3, or more amino acid residue modifications as compared to SEQ ID NO: 156; a H-CDR2 having the amino acid sequence of SEQ ID NO: 168, or a modified amino acid sequence thereof containing 1, 2, 3, or more amino acid residue modifications as compared to SEQ ID NO: 168; and a H-CDR3 comprising the amino acid sequence of SEQ ID NO: 180, or a modified amino acid sequence thereof, said modified amino acid sequence containing 1, 2, 3, or more amino acid modifications as compared to SEQ ID NO: 180.

An exemplary single domain antibody having this heavy chain variable region is referred to herein as the 22-T-bR3-1B2 antibody. The 22-T-bR3-1B2 antibody comprises a V$_H$ chain amino acid sequence of SEQ ID NO: 193 as shown below.

```
                                          SEQ ID NO: 193
QVQLQESGGGFVQAGTSLRLSCAASGSISSINAIAWYRQGRGNQRELLA
KITKGGTTIYTNSVKGRFTISRDNNKNTVYLQMDSLKPDDTAVYYCGAD
VNYGSPDYIDYWGQGTQVTVSS
```

In another embodiment, the antibody or binding fragment thereof comprises a heavy chain variable region having an amino acid sequence that shares at least 6000, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 193.

In one embodiment, the antibody or binding fragment thereof of the present disclosure comprises a humanized variant of the heavy chain variable region of SEQ ID NO: 193, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 193), or a combination of these approaches. The humanized framework regions are designed to be similar in length and sequence to the parental framework sequences of SEQ ID NO: 193. In one embodiment, the humanized framework regions share 50%, 55%, 60%, 65%, 70%, 75%, 80%, 85%, 90%, 95% or more sequence identity to the framework regions of SEQ ID NO: 193. In another embodiment, the humanized framework regions are 60%, 65%, 70%, 75%, 80%, 85%, 90%, 95% or more similar in length to the framework regions of SEQ ID NO: 193. Humanized variants of the heavy chain variable region of SEQ ID NO: 193 share at least 50%, at least 55%, at least 60%, at least 65%, at least 70%, at least 75%, at least 80%, at least 85%, at least 90%, at least 95% sequence identity along the entire length of SEQ ID 193.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 193. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 157, or a modified amino acid sequence thereof containing 1, 2, 3, or more amino acid residue modifications as compared to SEQ ID NO: 157; a H-CDR2 having the amino acid sequence of SEQ ID NO: 169, or a modified amino acid sequence thereof containing 1, 2, 3, or more amino acid residue modifications as compared to SEQ ID NO: 169; and a H-CDR3 comprising the amino acid sequence of SEQ ID NO: 181, or a modified amino acid sequence thereof, said modified amino acid sequence containing 1, 2, 3, or more amino acid modifications as compared to SEQ ID NO: 181.

Exemplary single domain antibodies having this heavy chain variable region are referred to herein as the 24-T-bR3-1F10 and 48-T-bR3-1G5 antibodies. These antibodies comprise a $V_H$ chain amino acid sequence of SEQ ID NO: 194 as shown below.

```
                                       SEQ ID NO: 194
QVQLQESGGGLVQSGGSLRLSCAASGRTFSTYTMGWFRQAPGKEREFVA
AISWSSGTANYADSVKGRFTISRDSAKNTVYLQMNSLKPEDTAVYYCNA
WSPVGHDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 194

In one embodiment, the antibody or binding fragment thereof of the present disclosure comprises a humanized variant of the heavy chain variable region of SEQ ID NO: 194, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 194), or a combination of these approaches. The humanized framework regions are designed to be similar in length and sequence to the parental framework sequences of SEQ ID NO: 194. In one embodiment, the humanized framework regions share 50%, 55%, 60%, 65%, 70%, 75%, 80%, 85%, 90%, 95% or more sequence identity to the framework regions of SEQ ID NO: 194. In another embodiment, the humanized framework regions are 60%, 65%, 70%, 75%, 80%, 85%, 90%, 95% or more similar in length to the framework regions of SEQ ID NO: 194. Humanized variants of the heavy chain variable region of SEQ ID NO: 194 share at least 50%, at least 55%, at least 60%, at least 65%, at least 70%, at least 75%, at least 80%, at least 85%, at least 90%, at least 95% sequence identity along the entire length of SEQ ID NO: 194, respectively.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 194. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 158, or a modified amino acid sequence thereof containing 1, 2, 3, or more amino acid residue modifications as compared to SEQ ID NO: 158; a H-CDR2 having the amino acid sequence of SEQ ID NO: 170, or a modified amino acid sequence thereof containing 1, 2, 3, or more amino acid residue modifications as compared to SEQ ID NO: 170; and a H-CDR3 comprising the amino acid sequence of SEQ ID NO: 182, or a modified amino acid sequence thereof, said modified amino acid sequence containing 1, 2, 3, or more amino acid modifications as compared to SEQ ID NO: 182.

An exemplary single domain antibody having this heavy chain variable region is referred to herein as the 32-T-bR3-1F12 antibody. The 32-T-bR3-1F12 antibody comprises a $V_H$ chain amino acid sequence of SEQ ID NO: 195 as shown below.

```
                                       SEQ ID NO: 195
QVQLQQSGGGLVQAGGSLRLSCAASGRTFSNYAMGWFRQAPGKEREFVA
AISWSGAYTFYGNSVRGRFTISRDNPNNTVYLQMNSLKPEDTATYYCAA
ARGGRWYSTYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 195.

In one embodiment, the antibody or binding fragment thereof of the present disclosure comprises a humanized variant of the heavy chain variable region of SEQ ID NO: 195, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 195), or a combination of these approaches. The humanized framework regions are designed to be similar in length and sequence to the parental framework sequences of SEQ ID NO: 195. In one embodiment, the humanized framework regions share 50%, 55%, 60%, 65%, 70%, 75%, 80%, 85%, 90%, 95% or more sequence identity to the framework regions of SEQ ID NO: 195. In another embodiment, the humanized framework regions are 60%, 65%, 70%, 75%, 80%, 85%, 90%, 95% or more similar in length to the framework regions of SEQ ID NO: 195. Humanized variants of the heavy chain variable region of SEQ ID NO: 195 share at least 50%, at least 55%, at least 60%, at least 65%, at least 70%, at least 75%, at least 80%, at least 85%, at least 90%, at least 95% sequence identity along the entire length of SEQ ID 195.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 195. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 159, or a modified amino acid sequence thereof containing 1, 2, 3, or more amino acid residue modifications as compared to SEQ ID NO: 159; a H-CDR2 having the amino acid sequence of SEQ ID NO: 171, or a modified amino acid sequence thereof containing 1, 2, 3, or more amino acid residue modifications as compared to SEQ ID NO: 171; and a H-CDR3 comprising the amino acid sequence of SEQ ID NO: 183, or a modified amino acid sequence thereof, said modified amino acid sequence containing 1, 2, 3, or more amino acid modifications as compared to SEQ ID NO: 183.

An exemplary single domain antibody having this heavy chain variable region is referred to herein as the 40-T-bR3-1G3 antibody. The 40-T-bR3-1G3 antibody comprises a $V_H$ chain amino acid sequence of SEQ ID NO: 196 as shown below.

```
                                        SEQ ID NO: 196
QVQLQESGGGLVQAGGSLRLSCAASGSTFSGYVIGWYRQAPGKQREEVA
IISSSGSTNYADSVKGRFTISRDNANAKTTFYLQMNSLKPEDTAVYYCN
ARLWLNNYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 196.

In one embodiment, the antibody or binding fragment thereof of the present disclosure comprises a humanized variant of the heavy chain variable region of SEQ ID NO: 196, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 196), or a combination of these approaches. The humanized framework regions are designed to be similar in length and sequence to the parental framework sequences of SEQ ID NO: 196. In one embodiment, the humanized framework regions share 50%, 55%, 60%, 65%, 70%, 75%, 80%, 85%, 90%, 95% or more sequence identity to the framework regions of SEQ ID NO: 196. In another embodiment, the humanized framework regions are 60%, 65%, 70%, 75%, 80%, 85%, 90%, 95% or more similar in length to the framework regions of SEQ ID NO: 196. Humanized variants of the heavy chain variable region of SEQ ID NO: 196 share at least 50%, at least 55%, at least 60%, at least 65%, at least 70%, at least 75%, at least 80%, at least 85%, at least 90%, at least 95% sequence identity along the entire length of SEQ ID 196.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 196. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 160, or a modified amino acid sequence thereof containing 1, 2, 3, or more amino acid residue modifications as compared to SEQ ID NO: 160; a H-CDR2 having the amino acid sequence of SEQ ID NO: 172, or a modified amino acid sequence thereof containing 1, 2, 3, or more amino acid residue modifications as compared to SEQ ID NO: 172; and a H-CDR3 comprising the amino acid sequence of SEQ ID NO: 184, or a modified amino acid sequence thereof, said modified amino acid sequence containing 1, 2, 3, or more amino acid modifications as compared to SEQ ID NO: 184.

An exemplary single domain antibody having this heavy chain variable region is referred to herein as the 47-T-bR3-1C8 antibody. The 47-T-bR3-1C8 antibody comprises a $V_H$ chain amino acid sequence of SEQ ID NO: 197 as shown below.

```
                                        SEQ ID NO: 197
QVQLQESGGGLVQPGGSLRLSCAASGFTFSSYWMYWVRQAPGKGLEWVS
TISPSGGTTYYTNSAKGRFTISRDNAKNTVYLQVNNLKPEDTAVYYCAA
RRSGRYEYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 197.

In one embodiment, the antibody or binding fragment thereof of the present disclosure comprises a humanized variant of the heavy chain variable region of SEQ ID NO: 197, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 197), or a combination of these approaches. The humanized framework regions are designed to be similar in length and sequence to the parental framework sequences of SEQ ID NO: 197. In one embodiment, the humanized framework regions share 50%, 55%, 60%, 65%, 70%, 75%, 80%, 85%, 90%, 95% or more sequence identity to the framework regions of SEQ ID NO: 197. In another embodiment, the humanized framework regions are 60%, 65%, 70%, 75%, 80%, 85%, 90%, 95% or more similar in length to the framework regions of SEQ ID NO: 197. Humanized variants of the heavy chain variable region of SEQ ID NO: 197 share at least 50%, at least 55%, at least 60%, at least 65%, at least 70%, at least 75%, at least 80%, at least 85%, at least 90%, at least 95% sequence identity along the entire length of SEQ ID 197.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 197. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 161, or a modified amino acid sequence thereof containing 1, 2, 3, or more amino acid residue modifications as compared to SEQ ID NO: 161; a H-CDR2 having the amino acid sequence of SEQ ID NO: 173, or a modified amino acid sequence thereof containing 1, 2, 3, or more amino acid residue modifications as compared to SEQ ID NO: 173; and a H-CDR3 comprising the amino acid sequence of SEQ ID NO: 185, or a modified amino acid sequence thereof, said modified amino acid sequence containing 1, 2, 3, or more amino acid modifications as compared to SEQ ID NO: 185.

Exemplary single domain antibodies having this heavy chain variable region are referred to herein as the 62-T-bR3-1B8 and 71-T-bR3-1D12 antibodies. These antibodies comprise a $V_H$ chain amino acid sequence of SEQ ID NO: 198 as shown below.

```
                                          SEQ ID NO: 198
QVQLQESGGDLVQPGGSLRLSCVASGFPFDDYPMSWVRQAPGKGLEWVS
SVSPNGGSTFYADSLKGRFTISRDNAKNTLYLQINSLKSDDTAVYHCAK
VLDYYCSGYGCYASYDLWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 198.

In one embodiment, the antibody or binding fragment thereof of the present disclosure comprises a humanized variant of the heavy chain variable region of SEQ ID NO: 198, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 198), or a combination of these approaches. The humanized framework regions are designed to be similar in length and sequence to the parental framework sequences of SEQ ID NO: 198. In one embodiment, the humanized framework regions share 50%, 55%, 60%, 65%, 70%, 75%, 80%, 85%, 90%, 95% or more sequence identity to the framework regions of SEQ ID NO: 198. In another embodiment, the humanized framework regions are 60%, 65%, 70%, 75%, 80%, 85%, 90%, 95% or more similar in length to the framework regions of SEQ ID NO: 198. Humanized variants of the heavy chain variable region of SEQ ID NO: 198 share at least 50%, at least 55%, at least 60%, at least 65%, at least 70%, at least 75%, at least 80%, at least 85%, at least 90%, at least 95% sequence identity along the entire length of SEQ ID 198.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 198. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 162, or a modified amino acid sequence thereof containing 1, 2, 3, or more amino acid residue modifications as compared to SEQ ID NO: 162; a H-CDR2 having the amino acid sequence of SEQ ID NO: 174, or a modified amino acid sequence thereof containing 1, 2, 3, or more amino acid residue modifications as compared to SEQ ID NO: 174; and a H-CDR3 comprising the amino acid sequence of SEQ ID NO: 186, or a modified amino acid sequence thereof, said modified amino acid sequence containing 1, 2, 3, or more amino acid modifications as compared to SEQ ID NO: 186.

An exemplary single domain antibody having this heavy chain variable region is referred to herein as the 79-T-bR3-1E1 antibody. The 79-T-bR3-1E1 antibody comprises a $V_H$ chain amino acid sequence of SEQ ID NO: 199 as shown below.

```
                                          SEQ ID NO: 199
QVQLQESGGGLVQPGGSLRLSCAASISIVSINTMAWYRQAPGKQRELVA
GITSGGSTNYADSVKGRFTISRDNAKNTVSLQMNSLKPEDTAVYYCNAG
RYVPGAIVTNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 199.

In one embodiment, the antibody or binding fragment thereof of the present disclosure comprises a humanized variant of the heavy chain variable region of SEQ ID NO: 199, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 199), or a combination of these approaches. The humanized framework regions are designed to be similar in length and sequence to the parental framework sequences of SEQ ID NO: 199. In one embodiment, the humanized framework regions share 50%, 55%, 60%, 65%, 70%, 75%, 80%, 85%, 90%, 95% or more sequence identity to the framework regions of SEQ ID NO: 199. In another embodiment, the humanized framework regions are 60%, 65%, 70%, 75%, 80%, 85%, 90%, 95% or more similar in length to the framework regions of SEQ ID NO: 199. Humanized variants of the heavy chain variable region of SEQ ID NO: 199 share at least 50%, at least 55%, at least 60%, at least 65%, at least 70%, at least 75%, at least 80%, at least 85%, at least 90%, at least 95% sequence identity along the entire length of SEQ ID 199.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 199. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 163, or a modified amino acid sequence thereof containing 1, 2, 3, or more amino acid residue modifications as compared to SEQ ID NO: 163; a H-CDR2 having the amino acid sequence of SEQ ID NO: 175, or a modified amino acid sequence thereof containing 1, 2, 3, or more amino acid residue modifications as compared to SEQ ID NO: 175; and a H-CDR3 comprising the amino acid sequence of SEQ ID NO: 187, or a modified amino acid sequence thereof, said modified amino acid sequence containing 1, 2, 3, or more amino acid modifications as compared to SEQ ID NO: 187.

An exemplary single domain antibody having this heavy chain variable region as described herein is the 86-T-bR3-1B11 antibody. This antibody comprises a $V_H$ chain amino acid sequence of SEQ ID NO: 200 as shown below.

```
                                          SEQ ID NO: 200
QVQLQEFGGGLVQAGGSLRLSCLASMTTLGFKTMGWYRQAPGKQRELVA
RISSGGQTNYADSVKGRFTISRDNAKNTVYLQMISLKPEDTAVYYCNAR
RYYSLARYDYNYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 200.

In one embodiment, the antibody or binding fragment thereof of the present disclosure comprises a humanized variant of the heavy chain variable region of SEQ ID NO: 200, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 200), or a combination of these approaches. The humanized framework regions are designed to be similar in length and sequence to the parental framework sequences of SEQ ID NO: 200. In one embodiment, the humanized framework regions share 50%, 55%, 60%, 65%, 70%, 75%, 80%, 85%, 90%, 95% or more sequence identity to the framework regions of SEQ ID NO: 200. In another embodiment, the humanized framework regions are 60%, 65%, 70%, 75%, 80%, 85%, 90%, 95% or more similar in length to the framework regions of SEQ ID NO: 200. Humanized variants of the heavy chain variable region of SEQ ID NO: 200 share at least 50%, at least 55%, at least 60%, at least 65%, at least 70%, at least 75%, at least 80%, at least 85%, at least 90%, at least 95% sequence identity along the entire length of SEQ ID NO: 200.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 200. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 164 or a modified amino acid sequence thereof containing 1, 2, 3, or more amino acid residue modifications as compared to SEQ ID NO: 164; a H-CDR2 having the amino acid sequence of SEQ ID NO: 176, or a modified amino acid sequence thereof containing 1, 2, 3, or more amino acid residue modifications as compared to SEQ ID NO: 176; and a H-CDR3 comprising the amino acid sequence of SEQ ID NO: 188, or a modified amino acid sequence thereof, said modified amino acid sequence containing 1, 2, 3, or more amino acid modifications as compared to SEQ ID NO: 188.

An exemplary single domain antibody having this heavy chain variable region is referred to herein as the 95-T-bR3-1E11 antibody. This antibody comprises a $V_H$ chain amino acid sequence of SEQ ID NO: 201 as shown below.

```
                                          SEQ ID NO: 201
QVQLQAFGGAAAQAGDSLRLSCVVGGKSTAAVNGVGWYRQAPGRQREFV
AAIRPGGRRDYLDSVKGRFSVFRNKTTVYLRMNDLRIEDTAVYYCYAEG
LLLPSTYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 201.

In one embodiment, the antibody or binding fragment thereof of the present disclosure comprises a humanized variant of the heavy chain variable region of SEQ ID NO: 201, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 201), or a combination of these approaches. The humanized framework regions are designed to be similar in length and sequence to the parental framework sequences of SEQ ID NO: 201. In one embodiment, the humanized framework regions share 50%, 55%, 60%, 65%, 70%, 75%, 80%, 85%, 90%, 95% or more sequence identity to the framework regions of SEQ ID NO: 201. In another embodiment, the humanized framework regions are 60%, 65%, 70%, 75%, 80%, 85%, 90%, 95% or more similar in length to the framework regions of SEQ ID NO: 201. Humanized variants of the heavy chain variable region of SEQ ID NO: 201 share at least 50%, at least 55%, at least 60%, at least 65%, at least 70%, at least 75%, at least 80%, at least 85%, at least 90%, at least 95% sequence identity along the entire length of SEQ ID 201.

In one embodiment, the antibody or binding fragment thereof has a heavy chain variable region with a H-CDR1 having the amino acid sequence of SEQ ID NO: 307 or a modified amino acid sequence thereof containing 1, 2, 3, or more amino acid residue modifications as compared to SEQ ID NO: 307; a H-CDR2 having the amino acid sequence of SEQ ID NO: 308, or a modified amino acid sequence thereof containing 1, 2, 3, or more amino acid residue modifications as compared to SEQ ID NO: 308; and a H-CDR3 comprising the amino acid sequence of SEQ ID NO: 309, or a modified amino acid sequence thereof, said modified amino acid sequence containing 1, 2, 3, or more amino acid modifications as compared to SEQ ID NO: 309.

An exemplary single domain antibody having this heavy chain variable region is referred to herein as the 55-T-bR3-1D4 antibody. This antibody comprises a $V_H$ chain amino acid sequence of SEQ ID NO: 310 as shown below.

```
                                            SEQ ID NO: 310
QVQLQEFGGGLVQAGGSLRLSCAASGRTFSGYSMGWFRQAPGKEREFVG
GISRSGGWTYYADSVKGRFTISRDNAKNTVYLQMNSLKPEDTAVYYCAA
AVSRINDYAPALSRAYDYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 310.

In one embodiment, the antibody or binding fragment thereof of the present disclosure comprises a humanized variant of the heavy chain variable region of SEQ ID NO: 310, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 310), or a combination of these approaches. The humanized framework regions are designed to be similar in length and sequence to the parental framework sequences of SEQ ID NO: 310. In one embodiment, the humanized framework regions share 50%, 55%, 60%, 65%, 70%, 75%, 80%, 85%, 90%, 95% or more sequence identity to the framework regions of SEQ ID NO: 310. In another embodiment, the humanized framework regions are 60%, 65%, 70%, 75%, 80%, 85%, 90%, 95% or more similar in length to the framework regions of SEQ ID NO: 310. Humanized variants of the heavy chain variable region of SEQ ID NO: 310 share at least 50%, at least 55%, at least 60%, at least 65%, at least 70%, at least 75%, at least 80%, at least 85%, at least 90%, at least 95% sequence identity along the entire length of SEQ ID 310.

Another aspect of the present disclosure relates to an antibody or binding portion thereof (e.g., a human antibody) that competes for binding to human tau protein with the anti-tau antibody comprising a heavy chain variable region with the amino acid sequence of SEQ ID NO: 310. In accordance with this aspect of the disclosure, a competitive binding assay, such as Bio-Layer Interferometry (BLI) can be utilized to identify an antibody or binding portion thereof that competes for binding to a tau protein with the enumerated monoclonal antibody. Other competitive binding assays known in the art can also be utilized to identify a competitive binding antibody in accordance with this aspect of the disclosure.

Antibody "specificity" refers to selective recognition of the antibody or binding portion thereof as described herein for a particular epitope of the tau protein. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. The epitope of the antibodies described herein may be "linear" or "conformational". In a linear epitope, all of the points of interaction between the protein and the antibody occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, 6, 7, 8, 9, 10, 11, 12, 13, 14, 15, 16, 17, 18, 19, 20 or more amino acids in a unique spatial conformation. Antibodies that recognize the same epitope can be verified in a simple immunoassay showing the ability of one antibody to block the binding of another antibody to a target antigen.

In one embodiment, the epitope recognized by the isolated antibody of the present invention is a non-linear or conformational epitope, i.e. a tertiary or quaternary structure that is shared by pathological proteins. For example, the non-linear or conformational epitope recognized by the antibodies described herein is a conformational epitope that is common or shared with one or more, or all, amyloidogenic proteins, e.g., tau, synuclein, Aβ, prion, etc. Accordingly, in one embodiment, the antibodies described herein have antigenic specificity for a shared conformational epitope common to all amyloidogenic proteins known in the art.

Another aspect of the present disclosure is directed to an antibody mimetic that binds tau protein. An "antibody mimetic" as referred to herein encompasses any organic compound, e.g., a peptide or polypeptide, that can specifically bind an antigen like an antibody, and is about 3-20 kDa. In one embodiment, the antibody mimetic comprises a scaffold which binds its antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety). In accordance with this aspect of the present disclosure, the loop binding regions of the antibody mimetic are adapted to comprise one or more of the heavy chain CDRs of the antibodies disclosed herein. For example, an antibody mimetic of the present disclosure may comprise a first loop region having an amino acid sequence of any one of SEQ ID NOs: 1-38, 202, 206, 210, 214, or a modified amino acid sequence of any one of SEQ ID NOs: 1-38, 202, 206, 210, and 214 said modified sequence containing 1, 2, 3, 4, 5, 6, 7, 8, 9, or 10 amino acid residue modifications as compared to any one of SEQ ID NOs: 1-38, 202, 206, 210, and 214. The antibody mimetic may comprise another loop region having an amino acid sequence of any one of SEQ ID NOs: 39-76, 203, 207, 211, 215 or a modified amino acid sequence of any one of SEQ ID NOs: 39-76, 203, 207, 211, and 215 said modified sequences containing 1, 2, 3, 4, 5, 6, or 7, amino acid residue modifications as compared to any one of SEQ ID NOs: 39-76, 203, 207, 211, and 215. The antibody mimetic may comprise another loop region having an amino acid sequence any one of SEQ ID NOs: 77-114, 204, 208, 212, 216, or a modified amino acid sequence of any one of SEQ ID NOs: 77-114, 204, 208, 212, and 216 said modified sequence containing 1, 2, 3, 4, 5, 6, or 7 amino acid residue modifications as compared to any one of SEQ ID NOs: 77-114, 204, 208, 212, and 216.

In another embodiment, an antibody mimetic of the present disclosure may comprise a first loop region having an amino acid sequence of any one of SEQ ID NOs: 153-164 and 307 or a modified amino acid sequence of any one of SEQ ID NOs: 153-164 and 307, said modified sequence containing 1, 2, 3, 4, 5, 6, 7, 8, or 9 amino acid residue modifications as compared to any one of SEQ ID NOs: 153-164 and 307. The antibody mimetic may comprise another loop region having an amino acid sequence of any one of SEQ ID NOs: 165-176 and 308, or a modified amino acid sequence of any one of SEQ ID NOs: 165-176 and 308, said modified sequences containing 1, 2, 3, 4, 5, 6, 7, 8, 9, or 10, amino acid residue modifications as compared to any one of SEQ ID NOs: 165-176 and 308. The antibody mimetic may comprise another loop region having an amino acid sequence any one of SEQ ID NOs: 177-188 and 309, or a modified amino acid sequence of any one of SEQ ID NOs: 177-188 and 309, said modified sequence containing 1, 2, 3, 4, 5, 6, 7, 8, 9, 10, or 11 amino acid residue modifications as compared to any one of SEQ ID NOs: 177-188 and 309.

In one embodiment, the antibody mimetic comprises one or more modified fibronectin type III (FN3) domains (e.g., an adnectin or centyrin molecule), where each modified FN3 domain has one or more loop regions that comprise one or more CDR sequences or modified CDR sequences as disclosed herein.

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. In accordance with the present disclosure, one or more of the loop regions of each FN3 domain of the binding molecule are modified to comprise one or more CDR sequences disclosed herein.

The modified FN3 domain can be a FN3 domain derived from any of the wide variety of animal, yeast, plant, and bacterial extracellular proteins containing these domains. In one embodiment, the FN3 domain is derived from a mammalian FN3 domain. Exemplary FN3 domains include, for example and without limitation, any one of the 15 different FN3 domains present in human tenascin C, or the 15 different FN3 domains present in human fibronectin (FN) (e.g., the $10^{th}$ fibronectin type III domain). Exemplary FN3 domains also include non-natural synthetic FN3 domains, such as those described in U.S. Pat. Publ. No. 2010/0216708 to Jacobs et al., which is hereby incorporated by reference in its entirety. Individual FN3 domains are referred to by domain number and protein name, e.g., the $3^{rd}$ FN3 domain of tenascin (TN3), or the $10^{th}$ FN3 domain of fibronectin (FN10).

Another aspect of the present disclosure is directed to isolated polynucleotides encoding the antibody or binding fragment thereof or antibody mimetic as described herein. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

In one embodiment, an isolated polynucleotide encodes any one or more of a H-CDR1 of any one of SEQ ID NOs: 1-38, 202, 206, 210, 214, and variants thereof, a H-CDR2 of any one of SEQ ID NOs: 39-76, 203, 207, 211, 215, and variants thereof, and a H-CRD3 of any one of SEQ ID NOs: 77-114, 204, 208, 212, 216, and variants thereof. In another embodiment, an isolated polynucleotide as described herein encodes any one or more of a H-CDR1 of any one of SEQ ID NOs: 153-164, 307, and variants thereof, a H-CDR2 of any one of SEQ ID NOs: 165-176, 308, and variants thereof, and a H-CDR3 of any one of SEQ ID NOs: 177-188, 309, and variants thereof.

In another embodiment, an isolated polynucleotide as described herein encodes a heavy chain variable region of a tau antibody having the amino acid sequence of any one of SEQ ID NOs: 115-152, 205, 209, 213, 217, and variants thereof. The nucleotide sequences of these isolated polynucleotides are enumerated in Table 3 herein and include SEQ ID NOs: 218-260. In another embodiment, the isolated polynucleotide encodes a heavy chain variable region having the amino acid sequence of any one of SEQ ID NOs: 189-201, 310 and variants thereof. The nucleotide sequences of these isolated polynucleotides are enumerated in Table 4 herein and include SEQ ID NOs: 261-306. Nucleic acid molecules having nucleotide sequences that differ from SEQ ID NOs: 218-306, which as a result of the degeneracy of the genetic code, also encode the tau antibody described herein are also encompassed by the present disclosure. Such nucleic acid molecules may share 80%, 85%, 90%, or 95% sequence identity to any one of the sequences of SEQ ID NOs: 218-306.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that provide, for example, a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the disclosure is directed to a vector comprising at least one polynucleotide encoding the antibody or binding fragment thereof or antibody mimetic as described herein. Such vectors include, without limitation, plasmid vectors, viral vectors, including without limitation, vaccina vector, lentiviral vector, adenoviral vector, adeno-associated viral vector, vectors for baculovirus expression, transposon based vectors or any other vector suitable for introduction of the polynucleotides described herein into a given organism or genetic background by any means to facilitate expression of the encoded antibody polypeptide. The polynucleotide sequences encoding the heavy chain variable domains as described herein are combined with sequences of a promoter, a translation initiation segment (e.g., a ribosomal binding sequence and start codon), a 3' untranslated region, polyadenylation signal, a termination codon, and transcription termination to form one or more expression vector constructs.

In one embodiment, the vector is an adenoviral-associated viral (AAV) vector. A number of therapeutic AAV vectors suitable for delivery of the polynucleotides encoding tau antibodies described herein to the central nervous system are known in the art. See e.g., Deverman et al., "Gene Therapy for Neurological Disorders: Progress and Prospects," *Nature Rev.* 17:641-659 (2018), which in hereby incorporated by reference in its entirety. Suitable AAV vectors include serotypes AAV1, AAV2, AAV3, AAV4, AAV5, AAV6, AAV7, AAV8, AAV9, AAV10, or AAV 11 in their native form or engineered for enhanced tropism. AAV vectors known to have tropism for the CNS that are particularly suited for therapeutic expression of the tau antibodies described herein include, AAV1, AAV2, AAV4, AAV5, AAV8 and AAV9 in their native form or engineered for enhanced tropism. In one embodiment, the AAV vector is an AAV2 vector. In another embodiment, the AAV vector is an AAV5 vector as described by Vitale et al., "Anti-tau Conformational scFv MC1 Antibody Efficiently Reduces Pathological Tau Species in Adult JNPL3 Mice," *Acta Neuropathol. Commun.* 6:82 (2018), optionally containing the GFAP or CAG promoter and the Eoodchuck hepatitis virus (WPRE) post-translational regulatory element. In another embodiment, the AAV vector is an AAV9 vector as described by Haiyan et al., "Targeting Root Cause by Systemic scAAV9-hIDS Gene Delivery: Functional Correction and Reversal of Severe MPSII in Mice," *Mol. Ther. Methods Clin. Dev.* 10:327-340 (2018), which is hereby incorporated by reference in its entirety. In another embodiment, the AAV vector is an AAVrh10 vector as described by Liu et al., "Vectored Intracerebral Immunizations with the Anti-Tau Monoclonal Antibody PHF1 Markedly Reduces Tau Pathology in Mutant Transgenic Mice," *J. Neurosci.* 36(49): 12425-35 (2016), which is hereby incorporated by reference in its entirety.

In another embodiment the AAV vector is a hybrid vector comprising the genome of one serotype, e.g., AAV2, and the capsid protein of another serotype, e.g., AAV1 or AAV3-9 to control tropism. See e.g., Broekman et al., "Adeno-associated Virus Vectors Serotyped with AAV8 Capsid are More Efficient than AAV-1 or -2 Serotypes for Widespread Gene Delivery to the Neonatal Mouse Brain," *Neuroscience* 138: 501-510 (2006), which is hereby incorporated by reference in its entirety. In one embodiment, the AAV vector is an AAV2/8 hybrid vector as described by Ising et al., "AAV-mediated Expression of Anti-Tau ScFv Decreases Tau Accumulation in a Mouse Model of Tauopathy," *J. Exp. Med.* 214(5):1227 (2017), which is hereby incorporated by reference in its entirety. In another embodiment the AAV vector is an AAV2/9 hybrid vector as described by Simon et al., "A Rapid Gene Delivery-Based Mouse Model for Early-Stage Alzheimer Disease-Type Tauopathy," *J. Neuropath. Exp. Neurol.* 72(11): 1062-71 (2013), which is hereby incorporated by reference in its entirety.

In another embodiment, the AAV vector is one that has been engineered or selected for its enhanced CNS transduction after intraparenchymal administration, e.g., AAV-DJ (Grimm et al., *J. Viol.* 82:5887-5911 (2008), which is hereby incorporated by reference in its entirety); increased transduction of neural stem and progenitor cells, e.g., SCH9 and AAV4.18 (Murlidharan et al., *J. Virol.* 89: 3976-3987 (2015) and Ojala et al., *Mol. Ther.* 26:304-319 (2018), which are hereby incorporated by reference in their entirety); enhanced retrograde transduction, e.g., rAAV2-retro (Muller et al., *Nat. Biotechnol.* 21:1040-1046 (2003), which is hereby incorporated by reference in its entirety); selective transduction into brain endothelial cells, e.g., AAV-BRI (Korbelin et al., *EMBO Mol. Med.* 8: 609-625 (2016), which is hereby incorporated by reference in its entirety); or enhanced transduction of the adult CNS after IV administration, e.g., AAV-PHP.B and AAVPHP.eB (Deverman et al., *Nat. Biotechnol.* 34: 204-209 (2016) andChan et al., *Nat. Neurosci.* 20: 1172-1179 (2017), which are hereby incorporated by reference in their entirety.

In accordance with this embodiment, the expression vector construct encoding the anti-tau antibody or binding portion thereof can include the nucleic acid encoding the heavy chain variable region polypeptide, a fragment thereof, a variant thereof, or combinations thereof. In one embodiment, the heavy chain variable region polynucleotide encodes only a variable heavy chain (VH) region. In another embodiment, the heavy chain variable region polynucleotide is engineered to further comprise a region encoding at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

The promoter sequence of the expression vector construct is suitable for driving expression of the antibody or binding fragment thereof. The promoter can be inducible or constitutive. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), artificial CMV-chicken β-actin promoter with β-globin splice acceptor (CAG), chicken β-actin (CBA) promoter, a chimeric liver-specific promoter (LSP) a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein. The expression construct can further encode enhance-promoter elements that control or restrict expression of the encoded antibody. Enhancer-promoter elements that restrict expression to several neuronal and glial cell types in the CNS are known in the art and suitable for inclusion in the vector expression constructs described herein. See e.g., Lee et al., "GFAP Promoter Elements Required for Region-Specific and Astrocyte-Specific Expression," *Glia* 56: 481-493 (2008); Dimidschstein et al., "A Viral Strategy for Targeting and Manipulating Interneurons Across Vertebrate Species," *Nat. Neuroscience*" 19:1743-49 (2016); and de Leeuq et al., "rAAV-compatible MiniPromoters for Restricted Expression in the Brain and Eye," *Mol. Brain* 9:52 (2016), which are hereby incorporated by reference in their entirety.

The expression construct can further encode a linker sequence. The linker sequence can encode an amino acid sequence that spatially separates and/or links the one or more components of the expression construct.

Another embodiment of the invention is a host cell comprising the vectors described herein. The antibodies and binding fragments thereof described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

The host cell chosen for expression may be of mammalian origin or may be selected from COS-1, COS-7, HEK293, BHK21, CHO, BSC-1, He G2, SP2/0, HeLa, myeloma, lymphoma, yeast, insect, or plant cells, or any derivative, immortalized or transformed cell thereof. Alternatively, the host cell may be selected from a species or organism incapable of glycosylating polypeptides, e.g., a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The antibodies described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA,* 77: 4216-4220 (1980), which is hereby incorporated by reference in its entirety). Other suitable mammalian host cells include, without limitation, NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibodies and fragments thereof. It is understood that variations on the above procedure are within the scope of the present disclosure. For example, it may be desirable to transfect a host cell with DNA encoding functional fragments the heavy chain of an antibody described herein. Recombinant DNA technology may also be used to remove some or all of the DNA encoding portions of the heavy chain that are not necessary for binding to the antigens of interest. The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

In another embodiment, the antibody or binding fragment thereof, or the polynucleotide encoding the antibody or binding fragment thereof is a component of a pharmaceutical composition. In one embodiment, the pharmaceutical composition comprises a monoclonal antibody composition. In another embodiment, the pharmaceutical composition comprises two or more different single-domain antibodies, e.g., a polyclonal antibody composition. In another embodiment, the pharmaceutical composition comprises polynucleotides encoding the monoclonal antibody composition. In another embodiment, the pharmaceutical composition comprises polynucleotides encoding two or more different single-domain antibodies as described herein. In another embodiment, the pharmaceutical composition comprises one or more antibodies or polynucleotides encoding the same as described herein and one or more prophylactic or therapeutic agents other than the antibodies described herein that are useful for preventing or treating a condition mediated by a toxic tau protein.

The therapeutically effective amount of antibody present in the pharmaceutical composition or formulation is determined by taking into account the desired dose volumes and mode(s) of administration. Exemplary antibody concentrations in the pharmaceutical compositions of the present disclosure include from about 0.1 mg/mL to about 50 mg/mL, from about 0.5 mg/mL to about 25 mg/mL, and from about 2 mg/mL to about 10 mg/mL.

An aqueous formulation is prepared comprising the antibody in a pH-buffered solution. The buffer has a pH in the range from about 4.5 to about 10, from about 5 to about 9, or from about 6 to 8. Examples of buffers include phosphate buffers (e.g., phosphate buffered saline), acetate (e.g. sodium acetate), succinate (such as sodium succinate), gluconate, histidine, citrate and other organic acid buffers.

A polyol, which acts as a tonicifier and may stabilize the antibody, may be included in the formulation. In one embodiment, the tonicifying polyol is a salt such as sodium chloride. In another embodiment, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, or in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant may also be added to the pharmaceutical composition containing the antibody. Exemplary surfactants include nonionic surfactants such as polysorbates (e.g. polysorbates 20, 80 etc), poloxamers (e.g. poloxamer 188), Pluronic F68, and PEG (polyethylene glycol). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, or from about 0.01% to about 0.1%.

In one embodiment, the pharmaceutical composition contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the pharmaceutical composition, particularly where the formulation is a multi-dose formulation. Suitable preservatives include, without limitation phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. The concentration of preservative may be in the range from about 0.01% to about 5%, from about 0.5% to about 2% and any range or value therein. Non-limiting examples include, no preservative, 0.1-2% m-cresol, 0.1-3% benzyl alcohol, 0.001-0.5% thimerosal, 0.001-2.0% phenol, 0.0005-1.0% alkylparaben(s), and the like. One or more other pharmaceutically acceptable carriers, excipients or stabilizers such as those described in *Remington's Pharmaceutical Sciences* 16th edition, Osol, A. Ed. (1980), which is hereby incorporated by reference in its entirety, may be included in the composition provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions to be used for in vivo administration must be sterile. This is readily accomplished by filtration through sterile filtration membranes, prior to, or following, preparation of the composition.

The pharmaceutical compositions comprising antibodies or binding fragments thereof, or polynucleotides encoding the antibodies or binding fragments thereof, are for use in, but not limited to, preventing, treating, managing, or ameliorating one or more symptoms of a condition involving a pathological tau protein, e.g., Alzheimer's disease or other tauopathy.

In another aspect of the present disclosure the anti-tau antibodies described herein, binding fragments thereof, or a pharmaceutical composition containing the same, are employed in a method of inhibiting onset of one or more symptoms of a condition involving pathological tau protein in a subject. This method involves administering to the subject the anti-tau antibodies described, polynucleotides encoding the anti-tau antibodies described herein, or a pharmaceutical composition containing the same to the subject in an amount effective to inhibit the onset of one or more symptoms of the condition involving pathological tau protein in the subject.

In another aspect of the present disclosure the tau antibodies described herein, polynucleotides encoding the tau antibodies described herein, or a pharmaceutical composition containing the same, are employed in a method of treating a subject having a condition involving pathological tau protein. This method involves selecting a subject having one or more symptoms of the condition involving a pathological tau protein and administering to the subject the tau antibody, a polynucleotide encoding a tau antibody, or a pharmaceutical composition containing the same in an amount effective to treat the condition involving the pathological tau protein in the subject.

In accordance with these embodiments, the condition involving a pathological tau protein may include Alzheimer's disease, Pick's disease, progressive supranuclear palsy, corticobasal degeneration, argyrophilic grain disease, primary age-related tauopathy, globular glial tauopathy, frontotemporal dementia, parkinsonism linked to chromosome 17, chronic traumatic encephalopathy, Huntington's disease, Amyotrophic Lateral Sclerosis (ALS), Niemann-Pick-C, Guam-ALS-Parkinson's dementia, post-encephalitic Parkinson's disease, aluminum toxicity, or prion disease.

In accordance with these embodiments, the "subject" is typically a human. However, other non-human mammals amenable to treatment in accordance with the methods described herein include, without limitation, primates, dogs, cats, rodents (e.g., mouse, rat, guinea pig), horses, deer, cervids, cattle and cows, sheep, and pigs.

In prophylactic applications, the pharmaceutical compositions of the present invention are administered to a subject that is susceptible to, or otherwise at risk of developing a particular condition mediated by a pathological form of tau protein, e.g., Pick's disease, progressive supranuclear palsy, corticobasal degeneration, argyrophilic grain disease, primary age-related tauopathy, globular glial tauopathy, frontotemporal dementia, parkinsonism linked to chromosome 17, chronic traumatic encephalopathy, Huntington's disease, Amyotrophic Lateral Sclerosis (ALS), Niemann-Pick-C, Guam-ALS-Parkinson's dementia, post-encephalitic Parkinson's disease, aluminum toxicity, and prion disease. In accordance with this embodiment, the composition is administered in an amount sufficient to eliminate or reduce the risk of the condition or to delay, inhibit, or prevent the onset of the condition. Prophylactic application also includes the administration of an antibody composition to prevent or delay the recurrence or relapse of a condition mediated by the tau protein or peptide in its pathological form. The present methods and compositions are especially suitable for prophylactic treatment of individuals who have a known genetic risk of developing a condition involving pathological tau protein. For example, several mutations in tau protein are known to be associated with the frontotemporal dementia and parkinsonism linked to chromosome 17 (FTDP-17) (see Goedert and Jakes, "Mutations Causing Neurodegenerative Tauopathies," *Biochimica et Biophysica Acta* 1739(2-3): 240-50 (2005), which is hereby incorporated by reference in its entirety). Genetic markers of other tau related diseases, such as Alzheimer's disease are also known in the art. For example, mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis.

In therapeutic applications, pharmaceutical compositions are administered to a subject suspected of, or already suffering from a condition associated with or caused by a pathological form of tau protein in an amount sufficient to cure, or at least partially arrest or alleviate, one or more symptoms of the condition and its complications. An amount adequate to accomplish this is defined as a therapeutically- or pharmaceutically-effective dose. In both prophylactic and therapeutic regimes, agents are usually administered in several dosages until a sufficient response has been achieved. An effective dose of the composition of the present invention, for the treatment of the above described conditions will vary depending upon many different factors, including means of administration, target site, physiological state of the patient, whether the patient is human or an animal, other medications administered, and whether treatment is prophylactic or therapeutic.

In accordance with the prophylactic and therapeutic methods described herein, compositions comprising the antibody or binding fragments thereof are administered in a dosage ranging from about 0.0001 to 100 mg/kg, and more usually 0.01 to 10 mg/kg of the recipient's body weight. For example, the antibody or binding fragment thereof is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. Intervals between single dosages can be weekly, monthly or yearly. Intervals can also be irregular as indicated by measuring blood levels of antibody in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody, binding fragment thereof, or pharmaceutical composition described herein may be any suitable route that delivers the compositions to the host, such as parenteral administration, e.g., intradermal, intramuscular, intraperitoneal, intravenous or subcutaneous, pulmonary; transmucosal (e.g., oral, intranasal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by, for example, intraarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapericardiac, intraperitoneal, intrapleural, intraprostatic, intrapulmonary, intrarenal, intraretinal, intraspinal, intrasynovial, intrathoracic, intravascular, intravesical, intralesional, sublingual, intranasal, or transdermal delivery.

Administration can be systemic or local. In one embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices.

In another embodiment, compositions containing the antibody or binding fragment thereof are delivered in a controlled release or sustained release system. In one embodiment, a pump is used to achieve controlled or sustained release. In another embodiment, polymeric materials can be used to achieve controlled or sustained release of the antibody compositions described herein. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is preferably inert, free of leachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibodies known in the art are suitable for use and delivery of compositions containing the antibodies and binding fragments thereof as described herein, see e.g., Song et al, "Antibody Mediated Lung Targeting of Long-Circulating Emulsions," *PDA Journal of Pharmaceutical Science & Technology* 50:372-397 (1995); Cleek et al, "Biodegradable Polymeric Carriers for a bFGF Antibody for Cardiovascular Application," *Pro. Int'l. Symp. Control. Rel. Bioact. Mater.* 24:853-854 (1997); and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where the pharmaceutical composition comprises polynucleotides encoding the antibody or binding fragment thereof as described herein, the nucleic acid can be administered in vivo to promote expression of its encoded antibody, by constructing it as part of an appropriate nucleic acid expression vector and administering it so that it becomes intracellular, e.g., the by use of a retroviral vector (see e.g., U.S. Pat. No. 4,980,286 to Morgan et al., which is hereby incorporated by reference in its entirety). In one embodiment, polynucleotides encoding the tau antibody as described herein are incorporated into an AAV vector as described supra (e.g., AAV2, AAV4, AAV5, AAV7, AABV8, AAV9, AAVrh10, AAV2/8, AAV2/9, etc.) and delivered via intraparenchymal administration, including convection enhanced delivery (CED), intrathecal administration, intracerebroventricular administration, subpial administration, intramuscular administration, or intravenous administration. Other forms of nucleic acid delivery can also be employed, e.g., direct injection, use of microparticle bombardment (see e.g., a gene gun; Biolistic, Dupont), coating with lipids or cell-surface receptors or transfecting agents, or by administering it in linkage to a homeobox-like peptide which is known to enter the nucleus (see e.g., Joliot et al, *Proc. Natl. Acad. Sci. USA* 88: 1864-1868 (1991), which is hereby incorporated by reference in its entirety). Alternatively, a nucleic acid can be introduced intracellularly and incorporated within host cell DNA for expression by homologous recombination.

If the methods described herein involve intranasal administration of the antibody composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the methods described herein involve oral administration of the antibody compositions described herein, the compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate.

In another embodiment, a pharmaceutical composition comprising a recombinant nucleic acid sequence encoding an antibody or binding portion thereof as described herein, is administered to a subject to facilitate in vivo expression and formation of the antibody for the treatment or prevention of conditions mediated by toxic oligomeric proteins or peptides in a subject. Expression vector constructs suitable for use in this embodiment of the disclosure are described supra.

The polynucleotide compositions can result in the generation of the antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody in the subject. The composition can result in the generation of the antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The antibodies, binding fragments thereof, or pharmaceutical compositions containing the same can be packaged in hermetically sealed containers such as an ampoule or sachette indicating the quantity of the antibody or binding fragment thereof. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention are supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies and binding fragments described herein can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Additional surfactants include but are not limited to polysorbate 20 and BRIJ surfactants. The pharmaceutical composition comprising the antibodies described herein prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions (see WO 04/078140 to Bookbinder et al., and U.S. Patent Appl. Publication No. US2006104968 to Bookbinder et al., which are hereby incorporated herein by reference in their entirety).

The antibodies and binding fragments described herein can also be employed in a number of diagnostic, prognostic and research applications.

Another aspect of the present disclosure is directed to a method of diagnosing Alzheimer's disease or a tauopathy in a subject. This method involves detecting, in the subject, the presence of tau protein or peptide using a diagnostic reagent, wherein the diagnostic reagent comprises an antibody or binding fragment described herein. The diagnosis of Alzheimer's disease or a tauopathy in the subject is based on the detection of tau protein or peptide in the subject.

In one embodiment, the method of diagnosing Alzheimer's disease and/or a tauopathy in a subject involves the detection of tau protein or peptide in the subject. In one embodiment, the method of diagnosing Alzheimer's disease and/or a tauopathy in the subject involves the detection of accumulated tau protein or peptide. In another embodiment, the method of diagnosing Alzheimer's disease and/or a tauopathy in the subject involves the detection of pathological tau protein in the subject.

Detecting the presence of tau protein or peptide in a subject using the antibodies or antibody fragments thereof as described herein can be achieved by obtaining a biological sample from the subject (e.g., blood, urine, cerebral spinal fluid, ocular lacrimal secretion, saliva, feces, nasal brushings and tissue or organ biopsy), contacting the biological sample with the diagnostic antibody reagent, and detecting binding of the diagnostic antibody reagent to tau protein or peptide if present in the sample from the subject. Assays for carrying out the detection of tau protein or peptide in a biological sample using a diagnostic antibody are well known in the art and include, without limitation, ELISA, immunohistochemistry, SIMOA (single molecule array), and Western blot.

In accordance with this and other embodiments described herein, the tau antibody or binding fragments described herein are coupled to a detectable label. The label can be any detectable moiety known and used in the art. Suitable labels include, without limitation, radioisotopes or radionuclides (e.g., $^{3}$H, $^{14}$C, $^{18}$F, $^{35}$S, $^{90}$Y $^{99}$Tc, $^{111}$In, $^{124}$I, $^{113}$I, $^{177}$Lu, $^{166}$Ho, $^{89}$Zr, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

Detecting the presence of tau in a subject using the diagnostic antibody reagent of the present invention can also be achieved using in vivo imaging techniques. In vivo imaging involves administering to the subject the antibody or binding fragments thereof described herein, and detecting the binding of the antibody or binding fragment thereof to the tau in vivo.

Diagnostic antibodies or similar reagents can be administered by intravenous injection into the body of the patient, by injection into the cerebrospinal fluid, by intracranial injection directly into the brain, or by drilling a hole through the skull. The dosage of antibody should be within the same ranges as for treatment methods. In accordance with this embodiment, the antibody or binding fragment is coupled to an imaging agent to facilitate in vivo imaging. The imaging agent can be any agent known to one of skill in the art to be useful for imaging, preferably being a medical imaging agent. Examples of medical imaging agents include, but are not limited to, single photon emission computed tomography (SPECT) agents, positron emission tomography (PET) agents, magnetic resonance imaging (MRI) agents, nuclear magnetic resonance imaging (NMR) agents, x-ray agents, optical agents (e.g., fluorophores, bioluminescent probes, near infrared dyes, quantum dots), ultrasound agents and neutron capture therapy agents, computer assisted tomography agents, two photon fluorescence microscopy imaging agents, and multi-photon microscopy imaging agents. Exemplary detectable markers include radioisotopes (e.g., $^{18}F$, $^{11}C$, $^{13}N$, $^{64}Cu$, $^{124}I$, $^{76}Br$, $^{82}Rb$, $^{68}Ga$ $^{99m}Tc$, $^{111}In$, $^{125}I$, $^{201}Tl$, $^{89}Zr$, or $^{15}O$, which are suitable for PET and/or SPECT use) and ultra-small superparamagnetic particles of iron oxide (USPIO) which are suitable for MRI.

Diagnosis of a condition involving pathological tau is performed by comparing the amount, size, and/or intensity of detected tau in a sample from the subject or in the subject, to corresponding baseline values. An appropriate baseline value can be the average level of tau found in a population of undiseased individuals. Alternatively, an appropriate baseline value may be the level of tau in the same subject determined at an earlier time.

The diagnostic methods described herein can also be used to monitor a subject's response to therapy. In this embodiment, detection of tau in the subject is determined prior to or concurrent with the commencement of treatment. The level of tau in the subject at this timepoint is used as a baseline value. At various times during the course of treatment the detection of tau is repeated, and the measured values thereafter compared with the baseline values. A decrease in values relative to baseline signals a positive response to treatment. No change or an increase in values relative to baseline signals an inadequate response to treatment. The treatment plan of an individual can be modified based on the results of monitoring the levels of tau in the subject.

A related aspect of the disclosure is directed to a method of identifying a subject's risk for developing a condition mediated by or associated with a pathological form of tau. This method involves detecting, in the subject, the presence of accumulated tau protein or peptide using a diagnostic reagent comprising the antibody or binding fragment thereof described herein, and identifying the subject's risk of developing a condition mediated by or associated with accumulated tau based on the results of the detecting step.

Methods of detecting the presence of tau in the subject or in a sample from the subject include the in vitro and in vivo methods described supra. In one embodiment, the subject is not exhibiting any definitive signs or symptoms of a condition involving a pathological tau protein, and employment of this method serves as an early diagnostic. In another embodiment, the subject is not exhibiting any signs or symptoms of a condition involving a pathological tau protein, but has a genetic predisposition to a condition and employment of this method serves to predict the likelihood that the individual will develop the condition involving a pathological tau protein in the future. In either embodiment, appropriate therapeutic and/or prophylactic intervention can be employed, e.g., administration of a therapeutic composition containing an antibody or polynucleotides encoding an antibody in an amount effective to slow or prevent the onset or progression of the condition.

Another aspect of the present disclosure is directed to a diagnostic kit that comprises the antibody or binding fragment thereof as described herein and a detectable label.

A suitable detectable label is any moiety attached to an antibody or an analyte to render the reaction between the antibody and the analyte detectable. A label can produce a signal that is detectable by visual or instrumental means. Various labels include signal-producing substances, such as chromogens, fluorescent compounds, chemiluminescent compounds, radioactive compounds, and the like. Representative examples of detectable labels include moieties that produce light, e.g., acridinium compounds, and moieties that produce fluorescence, e.g., fluorescein. In this regard, the moiety itself may not be detectable, but becomes detectable upon reaction with yet another moiety.

Other suitable detectable labels include radioactive labels (e.g., H, I, S, C, F, and P), enzymatic labels (e.g., horseradish peroxidase, alkaline peroxidase, glucose 6-phosphate dehydrogenase, and the like), chemiluminescent labels (e.g., acridinium esters, thioesters, or sulfonamides; luminol, isoluminol, phenanthridinium esters, and the like), fluorescent labels (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label.

TABLE 3

Polynucleotide Sequences of Tau Antibodies Enriched by Solid Phase Panning

| Antibody ID | Nucleotide Sequence | NA SEQ ID NO: | AA SEQ ID NO: |
|---|---|---|---|
| 03-T-sR2-1D10 | ATGAAATACCTATTGCCTACGGCGGCCGCTGGATTGTTATTACTCGC GGCCCAGCCGGCCATGGCGCAGGTGCAGCTGCAGGAGTCTGGGGG AGGATTGGTGCAGGCTGGGGGCTCTCTGAGACTCTCCTGTACAGCC TCTGGACGCACCTTCCGTGCCTATGCCATGGGGTGGTTCCGCCAGGC TCCAGGGAAGGAGCGTGAGTTGGTAGCAGCTATTAGCCGCACTGGT GGTGTCACAACCTATGCAGACTCCGTGAAGGGCCGATTCACCATCTC | 218 | 115 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | CAGAGACAACGCCAAGAATACGGTGTATCTGCAAATGAACAACCTG<br>AAGACTGAGGACACGGCCGTCTATTATTGTAATGCATACTTCCGTTG<br>GGGTACTCGCTACTGGGGCCAGGGGACCCAGGTCACCGTCTCCTCA<br>ACTAGTGGCCCGGGAGGCCAACACCATCACCACCATCATGGCGCAG<br>AACAAAAACTCATCTCAGAAGAGGATCTGTCTTAG | | |
| 04-T-sR2-2A11 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGCCTGGGGGGTCTCTGAGACTCTCCTGTGCAGCC<br>TCTGGAAGGATCTTCAGTATTTGGACCATGGGCTGGTACCGCCAGG<br>CTCCAGGGAAGCAGCGCGAGTTGGTCGCGGCTATTACTAGTGTTGG<br>TAACACAGACTATGCAGACTCCGTGAAGGGCCGATTCACCATCTCCA<br>GAGAGACTGCCAAGAAGACGGTGTATCTGCAAATGAACAGCCTGAA<br>ACCTGAGGACACGGCCGTCTATTACTGTAATGTAGAATCTCGGCGTG<br>GTATAGGCTTCCTACGTAAAACGTATAGCTACTGGGGCCAGGGGAC<br>CCAGGTCACCGTCTCCTCAACTAGTGGCCCGGGAGGCCAACACCATC<br>ACCACCATCATGGCGCAGAACAAAAACTCATCTCAGAAGAGGATCT<br>GTCTTAG | 219 | 116 |
| 11-T-sR2-1E4 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGCCTGGGGGGTCTCTGACACTCTCCTGTGCAGCCT<br>CTGGAAGCATCTTCAGAATCAATAACATGGGCTGGTTCCGCCAGGCT<br>CCAGGGAAGCAGCGCGAGTTGGTCGCAACTATTACTCGTGGTGGTA<br>ACACAAACTATGCAGACTCCGTGAAGGGCCGATTCACCATCTCCAGA<br>GACAACGCCAAGAAAACGCTGTATCTGCAAATGAACAGCCTGAAAC<br>CTGAGGACACGGCCGTCTATTACTGTAATGCAAATTATCTTATTCGAT<br>CATACTGGGGCCAGGGGACCCAGGTCACCGTCTCCTCAACTAGTGG<br>CCCGGGAGGCCAACACCATCACCACCATCATGGCGCAGAACAAAAA<br>CTCATCTCAGAAGAGGATCTGTCTTAG | 220 | 117 |
| 12-T-sR2-2B4 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGCTTGGTGCAGCCTGGGGGGTCTCTGACACTCTCCTGTGCAGCCT<br>CTGGAAGCATCTTCAGAATCAATAACATGGGCTGGTTCCGCCAGGCT<br>CCAGGGAAGCAGCGCGAGTTGGTCGCAACTATTACTCGTGGTGGTA<br>ACACAAACTATGCAGACTCCGTGAAGGGCCGATTCACCATCTCCAGA<br>GACAACGCCAAGAACACGGTGTATCTGCAAATGGACAGCCTGAAAC<br>CTGAGGACACGGCCGTCTATTACTGTAATGTAAAAAAGCATTTCGGC<br>ATTCGATATGACTACTGGGGCCAGGGGACCCAGGTCACCGTCTCCTC<br>AACTAGTGGCCCGGGAGGCCAACACCATCACCACCATCATGGCGCA<br>GAACAAAAACTCATCTCAGAAGAGGATCTGTCTTAG | 221 | 118 |
| 13-T-sR2-2F8 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGGCTGGGGGCTCTCTGAGACTCTCCTGCGCAGCC<br>TCTGGACGCACCTTCAGCAACTATGCCTTGGCCTGGTTCCGCCAGGC<br>TCCAGGGTTGGAGCGTGAGTTTGTGTCAAGTATTAGCTGGAGTGGT<br>GGTGTACTATACTATGCAGACTCCGTGAAGGGCCGATTCACCATGTC<br>CAGAGACAACGGCAAGAACACGGTGTACCTGCAAATGAACAGCCTG<br>AAACCTGAGGACACGGCCGTTTATTACTGTGCAGCGAACGCCGGGT<br>TGAGTTTATTAAGGAATTGGAGGACTAATGAGTATGCCTACTGGGG<br>CCAGGGGACCCAGGTCACCGTCTCCTCAACTAGTGGCCCGGGAGGC<br>CAACACCATCACCACCATCATGGCGCAGAACAAAAACTCATCTCAGA<br>AGAGGATCTGTCTTAG | 222 | 119 |
| 18-T-sR2-1A8 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGCTTGGTGCAGGCTGGGGGCTCTCTGAGACTCTCCTGTGCAGCC<br>TCTGGAAGCATCTTCCGTATCAATGCCATGGGCTGGTACCGCCAGGC<br>TCCAGGGAAGCAGCGCGAGTTGGTCGCTAGAATTAATACTGGTGGT<br>AACACAAACTATGCAGGCTCCGTGAAGGGCCGATTCACCATCTCCAG<br>AGACAACGGCAAGAACACGGTGTATCTGCAAATGAACAGCCTGAAA<br>CCTGAGGACACGGCCGTCTATTACTGTAATGTACAGAGATTCATCAC<br>TACCTATTGGGGCCAGGGGACCCAGGTCACCGTCTCCTCAACTAGTG<br>GCCCGGGAGGCCAACACCATCACCACCATCATGGCGCAGAACAAAA<br>ACTCATCTCAGAAGAGGATCTGTCTTAG | 223 | 120 |
| 20-T-sR2-2B7 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGATTGGTGCAGGCTGGGGGCTCTCTGAGACTCTCCTGTGCAGCC<br>TCTGGACGCACCTTCAGTACCTATAGGATGGGCTGGTTCCGCCAGGC<br>TCCAGGGAAGGAGCGTGAGTTTGTAGCAGCTATTAGGTGGAGTACA | 224 | 121 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | AGTTATGCAGATTCCGTGAAGGGCCGATTCATCATCTCCAGAGACAA<br>CGCCAAGAACACGGTGTATCTGCAAATGAACAGCCTGAAACCTGAG<br>GACACGGCCGTTTATTACTGTGCAACAGGGAGGGCCTGGAGTACAC<br>TGGCCACGACATATGTTTACTGGGGCCAGGGGACCCAGGTCACCGT<br>CTCCTCAACTAGTGGCCCGGGAGGCCAACACCATCACCACCATCATG<br>GCGCAGAACAAAAACTCATCTCAGAAGAGGATCTGTCTTAG | | |
| 21-T-sR2-2G7 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGGCCGGGGGCTCTCTGAGACTCTCCTGTGCAGCC<br>TCTGGACGCACCTTCAGTAGATATGCCACGGCCTGGTTCCGCCAGGC<br>TCCAGGGAAGGAGCGTGAGTTTGTAGCAGGTATTAGCTGGAGTGG<br>AACATCGTATGCAGACTCCGTGAAGGGCCGATTCACCATCTCCAGAG<br>ACAACGCCAAGAACACGCTGTATCTGCAAATGAACAGTCTGAAATCT<br>GAGGACACGGCCGTGTATTACTGTGCAAACTTTAAATACCGGTACG<br>GGTTGGGGCCCCGCGACTACTGGGGCCAGGGGACCCTGGTCACCGT<br>TTCCTCAACTAGTGGCCCGGGAGGCCAACACCATCACCACCATCATG<br>GCGCAGAACAAAAACTCATCTCAGAAGAGGATCTGTCTTAG | 225 | 122 |
| 26-T-sR2-1B2 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCCTGGTGCAGGCTGGGGGGTCTCTGAGACTCTCCTGTGTAGCC<br>TCTGGAAGCATCTTCAGGTTCAATGCCATCGGCTGGTACCGCCAGGC<br>TCCAGGGAAGGAGCGCGAGTTGGTCGCACGTATTAGGCGTCTTGGA<br>AGCACGTCCTATGCAGACTCCGTGAAGGGCCGATTCTCCATCTCCAG<br>AGACAGCGCCAAGAACACGGTGTATCTGCAGATGAACAGCCTGAAA<br>CCTGAGGACACGGCCGTCTATTACTGTAATGCCGACACTCACTTTTC<br>GACGCGCAACTATTGGGGCCAGGGGACCCAGGTCACCGTCTCCTCA<br>ACTAGTGGCCCGGGAGGCCAACACCATCACCACCATCATGGCGCAG<br>AACAAAAACTCATCTCAGAAGAGGATCTGTCTTAG | 226 | 123 |
| 27-T-sR2-1E9- | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGCTTGGTGCAGGCTGGGGGCTCTCTGAGACTCTCCTGTGCAGCC<br>TCTGGAAGCATCTTCCGTATCAATGGCATGGGCTGGCATCGCCAGGC<br>TCCAGGGAAGGAGCGCGAGTTGGTCGCAACTATTACTCGTGGTGGG<br>AGCACAAACTATGCAGACTCCGTGAAGGGCCGATTCACCATCTCCAG<br>AGACAACGCCAAGAACACGGTGTATCTGCAAATGAACAGCCTGAAA<br>CCTGAGGACACGGCCGTTTATTACTGTGCAGCAGACCCGCGGTGGC<br>GACTCCCTTTTCCCGGGTACGGCATGGACTACTGGGGCAAAGGGAC<br>CCAGGTCACCGTTTCCTCAACTAGTGGCCCGGGAGGCCAACACCATC<br>ACCACCATCATGGCGCAGAACAAAAACTCATCTCAGAAGAGGATCT<br>GTCTTAG | 227 | 124 |
| 28-T-sR2-2B11 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGCCTGGGGGGTCGCTGAGACTCTCCTGTGCAGCC<br>TCTGGACGTATCCTTATCAGTTCCATGGGCTGGTACCGCCAGGCTCA<br>AGGAGAGCAGCGCGAGTTGGTCGCTACTATCACTAGAGGCGGTACC<br>ACAAACTATGCAGATTCCGTGAAGGGCCGATTCACCATCTCCAGAGA<br>CAACGCCAAGAACATGGTGTATCTGCAAATGAACAAACTGAAATCT<br>GAGGACACGGCCGTGTATTACTGTGCAAGGGTGTACGGTCGTGTCT<br>GGTCCCGCCCTTATGACTACTGGGGCCAGGGGACCCAGGTCACCGT<br>CTCCTCAACTAGTGGCCCGGGAGGCCAACACCATCACCACCATCATG<br>GCGCAGAACAAAAACTCATCTCAGAAGAGGATCTGTCTTAG | 228 | 125 |
| 82-T-sR2-1D3 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGCCTGGGGGGTCGCTGAGACTCTCCTGTGCAGCC<br>TCTGGACGTATCCTTATCAGTTCCATGGGCTGGTACCGCCAGGCTCA<br>AGGAGAGCAGCGCGAGTTGGTCGCTACTATCACTAGAGGCGGTACC<br>ACAAACTATGCAGATTCCGTGAAGGGCCGATTCACCATCTCCAGAGA<br>CAACGCCAAGAACATGGTGTATCTGCAAATGAACAAACTGAAATCT<br>GAGGACACGGCCGTGTATTACTGTGCAAGGGTGTACGGTCGTGTCT<br>GGTCCCGCCCTTATGACTACTGGGGCCAGGGGACCCAGGTCACCGT<br>TTCCTCAACTAGTGGCCCGGGAGGCCAACACCATCACCACCATCATG<br>GCGCAGAACAAAAACTCATCTCAGAAGAGGATCTGTCTTAG | 229 | 125 |
| 29-T-sR2-2G8 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGCTTCGTGCAGGCTGGGGGGTCTCTGAGACTCTCCTGTACAGTCT<br>CTGGAAGGACCTTCAGGATCAATGGCATCGACTGGTACCGCCAGGC<br>TCCAGGGAAGCAGCGCGAGTTGGTCGCAGGGATTAGTAGTACTGGT | 230 | 126 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | AGCACAAACTATGCAGACTCCGTGAAGGGCCGATTCACCATCTCCAG<br>AGACAACGCAGGGAATGCGGTCTATCTGCAAATGAACAACCTGAAA<br>CCTGAGGACACGGGCCGATATTACTGTGCAGCCTCGCGTGGTTTGA<br>GTGGTAGCTGGTATCTCCGGTCGTCGTATCCTTATTGGGGCCAGGG<br>GACCCAGGTCACCGTCTCCTCAACTAGTGGCCCGGGAGGCCAACAC<br>CATCACCACCATCATGGCGCAGAACAAAAACTCATCTCAGAAGAGG<br>ATCTGTCTTAG | | |
| 34-T-sR2-1B7 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGCTTGGTGCAGCCTGGGGGGTCTCTGAGACTCTCCTGTGCAGCC<br>TCCCGCTACATCTTCGGTACCATGGGCTGGTACCGCCAGGCTCCAGG<br>GCTGCAGCGCGAGTTGGTCGCATCAATTTCTCGTGGTGGTAGTACAA<br>ACTATGCAGACTCCGTGAAGGGCCGATTCGCCATCTCCAGAGACAA<br>CGCCAAGAAAACGGTGTATCTGCAAATGAACAGCCTGAAACCTGAG<br>GACACGGCCGTCTATTACTGTAATGCAGTACCATACCGTTGGGGTAG<br>TAGCTGGTACGCTGGTCGCTACTGGGGCCAGGGGACCCTGGTCACC<br>GTCTCCTCAACTAGTGGCCCGGGAGGCCAACACCATCACCACCATCA<br>TGGCGCAGAACAAAAACTCATCTCAGAAGAGGATCTGTCTTAG | 231 | 127 |
| 35-T-sR2-1F5 | ATGAAATACCTATTGCCTACGGCGGCCGCTGGATTGTTATTACTCGC<br>GGCCCAGCCGGCCATGGCGCAGGTGCAGCTGCAGCAGTCTGGGGG<br>AGGCTTGGTCCAGGCTGGGGGGTCTCTGACGCTCTCCTGTGTAGCCT<br>CTGGAAGCCGCTTCAGTATCAATACCATGGGCTGGTACCGCCAGGCT<br>CCAGGGAAGCAGCGCGAGTTGGTCGCAGGTATTACTCGTGGTGGG<br>AGCACAAACTATGCAGACTCCGTGAAGGGCCGATTCACCATCTCTAG<br>AGAGAACGCCAAGAACACGGTGTATCTGCAAATGAATAGCCTGAAA<br>CCTGAGGACACGGCCGTTTATTACTGTGCAGCCACACTCCGTGCGTG<br>GGCCCTTACTTTCGCGACTTCGTATGCCTACTGGGGCCAGGGGACCC<br>AGGTCACCGTCTCCTCAACTAGTGGCCCGGGAGGCCAACACCATCAC<br>CACCATCATGGCGCAGAACAAAAACTCATCTCAGAAGAGGATCTGT<br>CTTAG | 232 | 128 |
| 36-T-sR2-2C1 | ATGAAATACCTATTGCCTACGGCGGCCGCTGGATTGTTATTACTCGC<br>GGCCCAGCCGGCCATGGCGCAGGTGCAGCTGCAGGCGTCTGGGGG<br>AGGCTTGGTGCAGCCTGGGGGCTCTCTGACACTCTCCTGTGCAGCCT<br>CTGGACGCACCTTCAGTCGCTATGCCATGGGCTGGTTCCGCCAGGCT<br>CCAGGGAAGGAGCGTGAGTTTGTAGCACGTATTAGCTGGAGTGGTG<br>GTTGGACATACTATGCAGACTCCGTGAAGGGCCGATTCGCCATCTCC<br>AGAGACAACGCCAAGAACACGGTGTATCTGCAAATGAACAGCCTGA<br>AACCTGAGGACACGGCCGTTTATTACTGTGCAGCAGGTTCCCGCGC<br>GGTACTATTTGGTACCTATGACTACTGGGGCCAGGGGACCCAGGTC<br>ACCGTCTCCTCAACTAGTGGCCCGGGAGGCCAACACCATCACCACCA<br>TCATGGCGCAGAACAAAAACTCATCTCAGAAGAGGATCTGTCTTAG | 233 | 129 |
| 37-T-sR2-2G9 | ATGAAATACCTATTGCCTACGGCGGCCGCTGGATTGTTATTACTCGC<br>GGCCCAGCCGGCCATGGCGCAGGTGCAGCTGCAGTTGCAGGAGTCTGGGGG<br>AGGATTGGTGCAGGCTGGGGGCTCTCTGAGACTCTCCTGTGCAGCC<br>TCTGGACGCACCTTGAGCAGCTATCGCATGGGCTGGTTCCGCCAGG<br>TTCCAGGGAAGGAGCGTGAGCTTGTAGCAGCTATTAACTGGAGAGG<br>TAGTTGGACATACTATGCAGACTCCGTGAAGGGCCGGGTCACCATCT<br>CCAGAGACAACGCCAAGAACACGGTGTATCTGCAAATGAACAGCCT<br>ACAACCTGAGGACACGGCCCTGTATTACTGTGCAAGGCCGACTGCG<br>CGTTGGGACCTGTTCAGGGAAAAGTATGACTTCCGGGGCCAGGGGA<br>CCCAGGTCACCGTCTCCTCAACTAGTGGCCCGGGAGGCCAACACCAT<br>CACCACCATCATGGCGCAGAACAAAAACTCATCTCAGAAGAGGATC<br>TGTCTTAG | 234 | 130 |
| 42-T-sR2-1B8 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGATTGGTGCAGGCTGGGGGCTCTCTGAGACTCTCCTGTGCAGCC<br>TCTGGACGCACCTTCAGTAGTTATGCCATGGGCTGGTTCCGCCAGGC<br>TCCAGGGAAGGAGCGTGAGTTTGTAGCAGCTATTAGCAGGAGTGGT<br>GGTATTACATCTATGCAGACTCCGTGAAGGGCCGATTCGCCATCTC<br>CAGAGACAATGCCAAGAACACGGTGTATCTGCAAATGAACAGCCTG<br>AAACCTGAGGACACGGGCGTCTATTACTGTAATGTACAGAGATTCAT<br>CACTACCTATTGGGGCCAGGGGACCCTGGTCACCGTTTCCTCAACTA<br>GTGGCCCGGGAGGCCAACACCATCACCACCATCATGGCGCAGAACA<br>AAAACTCATCTCAGAAGAGGATCTGTCTTAG | 235 | 131 |
| 43-T-sR2-1F8 | ATGAAATACCTATTGCCTACGGCGGCCGCTGGATTGTTATTACTCGC<br>GGCCCAGCCGGCCATGGCGCAGGTGCAGTTGCAGGCGTCTGGGGG<br>AGGATTGGTGCAGGCTGGGGGCTCTCTGAGCCTCTCCTGTGCAGCC | 236 | 132 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | TCTGGACGCACCTTCGGTCTGTATACCATGGGCTGGTTCCGCCAGGC<br>TCCAGAGAAGGAGCGTGAGTTTGTAGCAGCTATTAGTTGGAGAGGT<br>CTTAGTATAATGTATGCAGACTCCGTGAAGGGCCGATTCACCATCTC<br>CAGAGACAACGTCAAGAACACGGTGTATCTGCAAATGAACAGCCTG<br>AAACCTGAGGACACGGCCGTTTATTACTGTGCAGCGAACGCCGGGT<br>TGAGTTTATTAAGGAATTGGAGGACTAATGAGTATGCCTACTGGGG<br>CCAGGGGACCCAGGTCACCGTCTCCTCAACTAGTGGCCCGGGAGGC<br>CAACACCATCACCACCATCATGGCGCAGAACAAAAACTCATCTCAGA<br>AGAGGATCTGTCTTAG | | |
| 44-T-sR2-2C5 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGGCTGGGGGCTCTCTGAGACTCTCCTGTGAAGCC<br>TCTGCGCGTACTTTCAGTAGTTATGCCGTGGGCTGGTTCCGCCAGGC<br>TCCGGGGAAGGAGCGTGAGTTTGTAGCAGCTATTAACTGGAGTGGG<br>CGTCGCACAAACTATGCAGACTCCGTGAAGGGCCGATTCTCCATCTC<br>CAGAGACAACGCCAAGAACACGATGTATCTGCAAATGAACAGCCTG<br>AAACCTGAGGACACGGCCGTTTATTACTGTGCAGCAAGGTCGTCTCT<br>TCTAGAGTTCTGGTTGGGGTCCCGAAGAGGGTATGACTACTGGGGC<br>CAGGGGACCCAGGTCACCGTCTCCTCAACTAGTGGCCCGGGAGGCC<br>AACACCATCACCACCATCATGGCGCAGAACAAAAACTCATCTCAGAA<br>GAGGATCTGTCTTAG | 237 | 133 |
| 45-T-sR2-2H4 | ATGAAATACCTATTGCCTACGGCGGCCGCTGGATTGTTATTACTCGC<br>GGCCCAGCCGGCCATGGCGCAGGTGCAGCTGCAGCAGTTTGGGGG<br>AGGCTTGGTGCAGCCTGGGGGTCTCTGAGACTCTCCTGTGCAGCC<br>TCTGGAAGGATCTTCAGTATTTGGACCATGGGCTGGTACCGCCAGG<br>CTCCAGGGAAGCAGCGCGAGTTGGTCGCGGCTATTACTAGTGGTGG<br>TAGCACAAACTATGCAGACTCCGTGAAGGGCCGATTCACCATCTCCA<br>GAGACAACGCCAAAACACGGTGTATCTGCAAATGAACAGCCTGAA<br>ACCTGAGGACACGGCCGTCTATTACTGTAATGCTGATATACGCCCCC<br>GTATTATCTCGTTCTTTAAGGATTACTGGGGCCAGGGGACCCAGGT<br>CACCGTCTCCTCAACTAGTGGCCCGGGAGGCCAACACCATCACCACCA<br>TCATGGCGCAGAACAAAAACTCATCTCAGAAGAGGATCTGTCTTAG | 238 | 134 |
| 50-T-sR2-1C5 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGCCTGGGGGCTCTCTGAGACTCTCCTGTGCAGCC<br>TCTGGACGCACCTTCAGTCGCTATGCTATGGGCTGGTTCCGCCAGGC<br>TCCAGGGAAGGAGCGTGAGTTTGTAGCAGCTATTACCTGGAGTGGT<br>GGTATCATATATTATGCAGACTCCGTGAAGGGCCGATTCACCATCTC<br>CAGAGACAACGCCAAGAACACGGTGTATCTGCAAATGAACAACCTG<br>AAGACTGAGGACACGGCCGTCTATTATTGTAATGCATACTTCCGTTG<br>GGGTACTCGCTACTGGGGCCAGGGGACCCTGGTCACCGTCTCCTCA<br>ACTAGTGGCCCGGGAGGCCAACACCATCACCACCATCATGGCGCAG<br>AACAAAAACTCATCTCAGAAGAGGATCTGTCTTAG | 239 | 135 |
| 51-T-sR2-1G1 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGGCTGGGGGCTCTCTGAGACTTTCCTGTGCAGCC<br>TCTGGACGCTCCTTCAGTTGGTTGACCATGGCATGGTTCCGCCAGGC<br>TCCAGGGAAGGAGCGTGAAATTGTGGCTCGTATTACGTGGCGTGGT<br>ACCCCATACTATGCAGACTCTGTGAAGGGCCGGTTCGCCATCTCCAG<br>AGACAACGCCAAGAACACGGTGTATCTGCAAATGAACAGCCTGAAA<br>CCTGAGGACACGGCCATTTATTACTGTGCAGCCGCAAAACAGATACT<br>GATTAGACCGGATGCATATGTCTACTGGGGCCAGGGGACCCAGGTC<br>ACCGTTTCCTCAACTAGTGGCCCGGGAGGCCAACACCATCACCACCA<br>TCATGGCGCAGAACAAAAACTCATCTCAGAAGAGGATCTGTCTTAG | 240 | 136 |
| 52-T-sR2-2C9 | ATGAAATACCTATTGCCTACGGCGGCCGCTGGATTGTTATTACTCGC<br>GGCCCAGCCGGCCATGGCGCAGGTGCAGCTGCAGGCGTCTGGGGG<br>AGGCCTGGTGCAGGCTGGGGGGTCTCTGAGACTCTCCTGTGTAGCC<br>TCTGGAAGCATCTTCAGGTTCAATGCCATCGGCTGGTACCGCCAGGC<br>TCCAGGGAAGGAGCGCGAGTTGGTCGCACGTATTAGGCGTCTTGGA<br>AGCACGTCCTATGCAGACTCCGTGAAGGGCCGATTCTCCATCTCCAG<br>AGACAGCGCCAAGAACACGGTGTATCTGCAAATGGACAACCTGAAA<br>CCTGAGGACACGGCCGTTTATTACTGTAAAGCAGGCAGGCATCCCC<br>ATTTTAGTATGGATTAGTACCCTGACTTAGGCCAGGGGACCCAGGTC<br>ACCGTCTCCTCAACTAGTGGCCCGGGAGGCCAACACCATCACCACCA<br>TCATGGCGCAGAACAAAAACTCATCTCAGAAGAGGATCTGTCTTAG | 241 | 137 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| 53-T-sR2-2H5 | ATGAAATACCTATTGCCTACGGCGGCCGCTGGATTGTTATTACTCGC GGCCCAGCCGGCCATGGCGCAGGTGCAGTTGCAGGAGTCTGGGGG AGGCTTGGTGCAGCCTGGGGGGTCTCTGAGACTCTCCTGTGCAGCC TCCCGCTACATCTTCGGTACCATGGGCTGGTACCGCCAGGCTCCAGG GCTGCAGCGCGAGTTGGTCGCATCAATTTCTCGTGGTGGTAGTACAA ACTATGCAGACTCCGTGAAGGGCCGATTCGCCATCTCCAGAGACAA CGCCAAGAACACGGTGTATCTGCAAATGAACAACCTGAAACCTGAG GACACGGCCGTCTATTACTGTGCCCTGGCTCTAGGTTTCTTTACTAAT TACTACGTTCCGCGAGTCAAGCTATCGCTACTGGGGCCAGGGGACCC AGGTCACCGTCTCCTCAACTAGTGGCCCGGGAGGCCAACACCATCAC CACCATCATGGCGCAGAACAAAAACTCATCTCAGAAGAGGATCTGT CTTAG | 242 | 138 |
| 58-T-sR2-1C6 | ATGAAATACCTATTGCCTACGGCGGCCGCTGGATTGTTATTACTCGC GGCCCAGCCGGCCATGGCGCAGGTGCAGCTGCAGGAGTCTGGGGG AGGATTGGTACAGACTGGGGGCTCTCTGAGACTCTCCTGTGCAGCC TCTGGACGCACCTTCCGTCTTTATTCCATGGCCTGGTTTCGCCAGGCG CCAGGGAAGGAGCGCGAGTTTTTAGGATCGATTAGGTGGAATGGT GGCAACATATACTATACAGACTCCGTGAAGGGCCGATTCACCATCTC CAGAGACAACGCCAAGAACACGGCGTATCTGCAAATGAACAGCCTG ACACCTGAGGACACGGCCGTTTATTACTGTGCAGCAGGTCCTCGGAT AGCGGTATGGCGCTATGAGTATAACTACTGGGGCCAGGGGACCCAG GTCACCGTCTCCTCAACTAGTGGCCCGGGAGGCCAACACCATCACCA CCATCATGGCGCAGAACAAAAACTCATCTCAGAAGAGGATCTGTCTT AG | 243 | 139 |
| 59-T-sR2-1G5 | ATGAAATACCTATTGCCTACGGCGGCCGCTGGATTGTTATTACTCGC GGCCCAGCCGGCCATGGCGCAGGTGCAGCTGCAGGAGTCTGGGGG AGGCTTGGTGCAGCCTGGGGGGTCTCTGAGACTCTCCTGTGCAGCC TCTGGAAGCATCGGCAGTTTCAAGACCATGGGCTGGTACCGCCAGG CTCCAGGGAAGCAGCGCGAGTTGGTCGCAACTATTACTCGTTGGGG TTTTACAAACTATGCAGACTCCGTGAAGGGCCGATTCACCATCGCCA GAGACAACGCCAAGAGCACGCTGTATCTGCAAATGAACAGCCTGAA ACCTGAGGACACGGCCATTTATTACTGTGCAGCAGCGCAGGGGGGG TTTTATGAAACCGCGCGCCAATTGGTATAACTCGTGGGGCCAGGGA CCCTGGTCACCGTCTCCTCAACTAGTGGCCCGGGAGGCCAACACCAT CACCACCATCATGGCGCAGAACAAAAACTCATCTCAGAAGAGGATC TGTCTTAG | 244 | 140 |
| 60-T-sR2-2D8 | ATGAAATACCTATTGCCTACGGCGGCCGCTGGATTGTTATTACTCGC GGCCCAGCCGGCCATGGCGCAGGTGCAGTTGCAGGAGTCTGGGGG CGGATTGGTGCAGGCTGGGGCCTCTCTGAGACTCTCCTGTGTAGCCT CTGGACGCACCTTCAGCCGCTATGGTATGGGCTGGTTCCGCCAGGCT CCAGGGAAGGAGCGTGAGTTTGTAGCAGCCATTAGCCGGAGTGGT GCAATCTCATACTATGCAGACTCCGTGAAGGGCCGATTCACCATCTC CAGAGGCGACGCCACGAACACGGTCGTCCTGCAAATGAGCAGCCTG AAACCTGGGGACACGGCCGTTTATTACTGTGCAGCTTCAAGCAGAC GTCTGCTTGGTGGTCCATTTGCGTACGACTACTGGGGCCAGGGGAC CCTGGTCACCGTCTCCTCAACTAGTGGCCCGGGAGGCCAACACCATC ACCACCATCATGGCGCAGAACAAAAACTCATCTCAGAAGAGGATCT GTCTTAG | 245 | 141 |
| 61-T-sR2-2H7 | ATGAAATACCTATTGCCTACGGCGGCCGCTGGATTGTTATTACTCGC GGCCCAGCCGGCCATGGCGCAGGTGCAGCTGCAGGAGTCTGGGGG AGGCTTGGTGCAGCCTGGGGGGTCTCTGAGACTCTCCTGTGCAGCC TCCCGCTACATCTTCGGTACCATGGGCTGGTACCGCCAGGCTCCAGG GCTGCAGCGCGAGTTGGTCGCATCAATTTCTCGTGGTGGTAGTACAA ACTATGCAGACTCCGTGAAGGGCCGATTCGCCATCTCCAGAGACAA CGCCAAGAACACGGTTTATCTGCAAATGAACAGCCTTAAACCTGAG GACACGGCCGTCTATTACTGTAATGCAAACCGTCGCGGGTGGAACT ACTGGGGCCAGGGGACCCAGGTCACCGTTTCCTCAACTAGTGGCCC GGGAGGCCAACACCATCACCACCATCATGGCGCAGAACAAAAACTC ATCTCAGAAGAGGATCTGTCTTAG | 246 | 142 |
| 66-T-sR2-1C7 | ATGAAATACCTATTGCCTACGGCGGCCGCTGGATTGTTATTACTCGC GGCCCAGCCGGCCATGGCGCAGGTGCAGCTGCAGGAGTCTGGGGG AGGCTTGGTGCAGGCTGGGGGGTCTCTGAGACTCTCCTGTGCAGCC TCTGGAACCATCTTCACTATGAAGAACATGGCTTGGTACCGCCAGGC TCCAGGGAAGGAGCGTGAGTTTGTAGCAGCTATTAGCACGAGTGGT GGTGTGACATGGTATGCAGACTCCTCCGTGAAGGGCCGATTCACCA TCTCCCGAGACAACGCCAAGAACACGCTGTATCTGCAAATGGACAG CCTGAAACCTGAGGACACGGCCGTCTATTACTGTAAAGTCAGATCG GGCCCCCGAATTATACCCCAATTGCGCCGTGAGTACTGGGGCCAGG | 247 | 143 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | GGACCCAGGTCACCGTCTCCTCAACTAGTGGCCCGGGAGGCCAACA CCATCACCACCATCATGGCGCAGAACAAAAACTCATCTCAGAAGAG GATCTGTCTTAG | | |
| 68-T-sR2-2E6 | ATGAAATACCTATTGCCTACGGCGGCCGCTGGATTGTTATTACTCGC GGCCCAGCCGGCCATGGCGCAGGTGCAGTTGCAGGAGTCTGGGGG AGGCTTGGTGCAGCCTGGGGACTCTCTGAGACTCTCCTGTGCAGCCT CTGGACGCACCTTCAGTAGCTATGCCATGGGCTGGTTCCGCCAGGCT CCAGGGAAGGAGCGTGAGTTTGTGGCGGCTATTAACTGGAGTGGTC ATAGCACATACTATGCAGACTCCGTGAAGGGCCGATTCACCATCTCC AGAGACAACGCCAAGAACACGGTGTATCTGCAAATGAACATGCTGA AACCTGAGGACACGGCCGTCTACTATTGTAAACTTACTCGTTTGCTA AATACGTACTGGGGCCAGGGGACCCTGGTCACCGTCTCCTCAACTA GTGGCCCGGGAGGCCAACACCATCACCACCATCATGGCGCAGAACA AAAACTCATCTCAGAAGAGGATCTGTCTTAG | 248 | 144 |
| 69-T-sR2-2H8 | ATGAAATACCTATTGCCTACGGCGGCCGCTGGATTGTTATTACTCGC GGCCCAGCCGGCCATGGCGCAGGTGCAGCTGCAGGAGTCTGGGGG AGGATTGGTTCAGGCTGGGGACTCTCTGAGACTCTCCTGTGCATTCT CTGGACGCACCTTCGGCCTTCGCACCATGGGCTGGTTCCGCCAGGCT CCAGGGAAGGAGCGTGAGTTTGTATCAAGTCTTACATGGCGTGATA ATAATGCATACTATGCAGACTCCGTGAAGGGCCGATTCACCATCTCC AGAGACAACGCCAAGAAAACGCTGTATCTGCAAATGAACAGCCTGA AACCTGAGGACACGGCCGTCTATTTCTGTAATGTACATCTAGTCTTTA CCAACCGAGATTACTGGGGCCAGGGGACCCAGGTCACCGTCTCCTC AACTAGTGGCCCGGGAGGCCAACACCATCACCACCATCATGGCGCA GAACAAAAACTCATCTCAGAAGAGGATCTGTCTTAG | 249 | 145 |
| 74-T-sR2-1C10 | ATGAAATACCTATTGCCTACGGCGGCCGCTGGATTGTTATTACTCGC GGCCCAGCCGGCCATGGCGCAGGTGCAGTTGCAGCAGTCTGGGGG AGGCTTGGTGCAGCCTGGGGGGTCTCTGAGACTCTCCTGTGCAGCC TCTTGGCGCATCTTCAGTCCCAATGCCATGGCCTGGTACCGCCAGGC TCCAGGGAAGCAGCGCGAGTTGGTCGCACGAATTACGTGGGCTGGT ATCACAAACTATGCAGACTCCGTGAAGGGCCGATTCACCATCTCCAG AGACAACGCCAAAAACACGGTGTATCTGCAAATGCACAGCCTGAAA CCTGAGGATACGGCCATTTATTACTGTGTCGCAGATCGTCGAAGCAG CTACCTAGGGCCACGGTTTGACTACTGGGGCCAGGGGACCCAGGTC ACCGTCTCCTCAACTAGTGGCCCGGGAGGCCAACACCATCACCACCA TCATGGCGCAGAACAAAAACTCATCTCAGAAGAGGATCTGTCTTAG | 250 | 146 |
| 75-T-sR2-1G12 | ATGAAATACCTATTGCCTACGGCGGCCGCTGGATTGTTATTACTCGC GGCCCAGCCGGCCATGGCGCAGGTGCAGCTGCAGGAGTCTGGGGG AGGCTTGGTGCAGCCTGGGGGGTCTCTGAGACTCTCCTGTGCAGCC TCCCGCTACATCTTCGGTACCATGGGCTGGTACCGCCAGGCTCCAGG GCTGCAGCGCGAGTTGGTCGCATCAATTTCTCGTGGTGGTAGTACAA ACTATGCAGACTCCGTGAAGGGCCGATTCGCCATCTCCAGAGACAA CGCCAAGAACACGGTGTATCTGCAAATGAACAGCCTGAAACCTGAG GACACGGCCGTTTATTACTGTGCAGCAAGGTCGTCTCTTCTAGAGTT CTGGTTGGGGTCCCGAAGAGGGTATGACTACTGGGGCCAGGGGAC CCAGGTCACCGTCTCCTCAACTAGTGGCCCGGGAGGCCAACACCATC ACCACCATCATGGCGCAGAACAAAAACTCATCTCAGAAGAGGATCT GTCTTAG | 251 | 147 |
| 76-T-sR2-2E7 | ATGAAATACCTATTGCCTACGGCGGCCGCTGGATTGTTATTACTCGC GGCCCAGCCGGCCATGGCGCAGGTGCAGTTGCAGCAGTCTGGGGG AGGCTTGGTGCAGCCTGGGGGGTCTCTGAGACTCGCCTGTGCAGCC TCCGGAAGGTTCTTCAGGATCAATGCCATGGCCTGGTACCGCCAGG CTCCAGGGAAGCAGCGCGAATTGGTCGCAACTATTACGCGTGCTGG TACTACAACCTATGCAGACTCCGTGAAGGGCCGATTCACCATCTCCA GAGACAACGCCAAGAACACGGTGTATCTGCAAATGATCAGCCTGAA ACCTGAGGACACGGCCGTGTATTACTGTGCAAAATACCCTACTATTA CGTGGTATGGCCGGCATGACTACCGGGGTCAGGGGACCCAGGTCAC CGTCTCCTCAACTAGTGGCCCGGGAGGCCAACACCATCACCACCATC ATGGCGCAGAACAAAAACTCATCTCAGAAGAGGATCTGTCTTAG | 252 | 148 |
| 84-T-sR2-2E8 | ATGAAATACCTATTGCCTACGGCGGCCGCTGGATTGTTATTACTCGC GGCCCAGCCGGCCATGGCGCAGGTGCAGTTGCAGGAGTCTGGGGG AGGCTTGGTGCAGCATGGGGGGTCTCTGAGACTCTCCTGTGCAGCC TCTGGAAGCTTCTTCAGAATCAATACCATGGGCTGGCACCGCCAGGC TCCAGGGAAGCAGCGCGAGTTGGTCGCATCGATCACTCGTGGTGGT AGCACAAACTATGCAGACTCCGTGAAGGGCCGATTCACCATCTCCAG AGACAACGCCAAGAACACGGTGTATCTGCAAATGAACAGCCTGAAA TCTGAGGACACAGCCGTCTATTACTGTGCAGCAAGCCGGTTTGGTAT | 253 | 149 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | TAACTACTACACCGCCCGACAGTATGGTTATTGGGGCCAGGGGACC<br>CAGGTCACCGTCTCCTCAACTAGTGGCCCGGGAGGCCAACACCATCA<br>CCACCATCATGGCGCAGAACAAAAACTCATCTCAGAAGAGGATCTG<br>TCTTAG | | |
| 90-T-sR2-1D9 | ATGAAATACCTATTGCCTACGGCGGCCGCTGGATTGTTATTACTCGC<br>GGCCCAGCCGGCCATGGCGCAGGTGCAGTTGCAGGCGTCTGGGGG<br>AGGATTGGTGCAGGCTGGGGGCTCTCTGAGACTCTCCTGTGCAGCC<br>TCTGGACGCACCTTCAGTCGCTATCCCATGGGCTGGTTCCGCCAGGC<br>TCCAGGGAAGGAGCGTGAGTTTGTAGCACGTTTTGGGTGGAGTGGT<br>CTTAGCACCTACTATGCCGACTCCGTGAAGGGCCGATTCACCATCTC<br>CAGAGACAACGCCAAGAATACGGTGTATCTGCAAATGAACAGCCTG<br>AAACCTGAGGACACGGCCGTTTATTACTGTGCAGCCGGGCGCTTCAT<br>GGGTTCGTATGACTACTGGGGCCAGGGGACCCAGGTCACCGTCTCC<br>TCAACTAGTGGCCCGGGAGGCCAACACCATCACCACCATCATGGCG<br>CAGAACAAAAACTCATCTCAGAAGAGGATCTGTCTTAG | 254 | 150 |
| 91-T-sR2-1H12 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGGCTGGGGGCTCTCTGAGACTCTCCTGTGCAGCC<br>TCTGGACGCACCTTCAGTTGGTATGCCATGGGCTGGTTCCGCCAGGC<br>TCCAGGGAGGGAGCGTGAGTTTGTAGCAGCTATTAGGCGGAGTGG<br>TGGTATCACAATCTATGCAGACTCCGTGAAGGGCCGATTCGCCGTCT<br>CCAGAGACAACGCCAAGAACACGGTGTATCTGCAAATGAATAGCCT<br>GAAACCTGAGGACACGGCCGTTTATTACTGTGCAGCAAACTTATTTC<br>AGTGGCGACTAAACGACAACGGCAACCAGTATGGCTCCTGGGGCCA<br>GGGGACCCTGGTCACCGTCTCCTCAACTAGTGGCCCGGGAGGCCAA<br>CACCATCACCACCATCATGGCGCAGAACAAAAACTCATCTCAGAAGA<br>GGATCTGTCTTAG | 255 | 151 |
| 92-T-sR2-2E9 | ATGAAATACCTATTGCCTACGGCGGCCGCTGGATTGTTATTACTCGC<br>GGCCCAGCCGGCCATGGCGCAGGTGCAGCTGCAGGAGTCTGGGGG<br>AGGATTGGTGCAGGCTGGGGGCTCTCTGAGACTCTCCTGTGTAGTTT<br>CTGGACGCACCTTCAGTACTTCTCAGATGGGCTGGTTCCGCCAGCCT<br>CCAGGGAAGGAGCGTGAGTTGGTAGCACGTATTAGTTGGCGTGGTA<br>AGCAACACTATGCAGATTCCGTGAAGGGCCGCTTCACCATTTCCAGA<br>GACTACGCCAAGAACACGGTGTACCTGCAAATGAATGGCCTGAAAT<br>CTGAGGACACGGCCGTTTATTACTGTGCAGCAGGTCCCCGTGCGGT<br>ACTTTTTGGCACCTATGACTACTGGGGCCAGGGGACCCAGGTCACC<br>GTCTCCTCAACTAGTGGCCCGGGAGGCCAACACCATCACCACCATCA<br>TGGCGCAGAACAAAAACTCATCTCAGAAGAGGATCTGTCTTAG | 256 | 152 |
| T-sR2-2B8 | ATGAAATACCTATTGCCTACGGCGGCCGCTGGATTGTTATTACTCGC<br>GGCCCAGCCGGCCATGGCGCAGGTGCAGCTGGCAGAGTCTGGGGG<br>AGGATTGGTGCAGGCTGGGGGCTCTCTGAGACTCTCCTGTGTAGTTT<br>CTGGACGCACCTTCAGTACTTCTCAGATGGGCTGGTTCCGCCAGCCT<br>CCAGGGAAGGAGCGTGAGTTGGTAGCACGTATTAGTTGGCGTGGTA<br>AGCAACACTATGCAGATTCCGTGAAGGGCCGCTTCACCATTTCCAGA<br>GACTACGCCAAGAACACGGTGTACCTGCAAATGAATGGCCTGAAAT<br>CTGAGGACACGGCCGTGTATTACTGTGCAGCAGATCGTCGGAGGAC<br>CTACTTGGGGCAACAACATGACTACTGGGGCCAGGGGACCCTGGTC<br>ACCGTCTCCTCAACTAGTGGCCCGGGAGGCCAACACCATCACCACCA<br>TCATGGCGCAGAACAAAAACTCATCTCAGAAGAGGATCTGTCTTAG | 257 | 205 |
| T-sR2-2F12 | ATGAAATACCTATTGCCTACGGCGGCCGCTGGATTGTTATTACTCGC<br>GGCCCAGCCGGCCATGGCGCAGGTGCAGTTGCAGGAGTCTGGGGG<br>AGGCTTGGTGCAGGCTGGGGGCTCTCTGAGACTCTCCTGTGCAGCC<br>TCTGGAAGCATCTTCCGTATCAATGGCATGGGCTGGCATCGCCAGGC<br>TCCAGGGAAGGAGCGCGAGTTGGTCGCAACTATTACTCGTGGTGGT<br>AGCATAAGCTATGCAGACTCCGTGAAGGGCCGATTCACCATCTCCAG<br>AGACAACGCCAAGAACACGCTGTATCTGCAAATGAACAACCTGAAA<br>CCTGAGGACACGGCCGTGTATTACTGTGCAAAATACCGAAGACCGT<br>TATTTTATAGTGGTAGTAACTACCGTGAAGGTGACTTTGCTTCCTGG<br>GGCCAGGGGACCCAGGTCACCGTCTCCTCAACTAGTGGCCCGGGAG<br>GCCAACACCATCACCACCATCATGGCGCAGAACAAAAACTCATCTCA<br>GAAGAGGATCTGTCTTAG | 258 | 209 |
| T-sR2-2B3: | CAGGTGCAGTTGCAGGCGTCTGGGGGAGGATTGGTGCAGGCTGGG<br>GGCTCTCTGAGACTCTCCTGTGCAGCCTCTGGACGCACGTTCGGTAG<br>CTATACCATGGGCTGGTTCCGCCAGGCTCCAGGGAAGGAGCGTGAG<br>TTTGTAGCAGCTATTAGTAGGAGCGGTGGTAGCACATACTATGCAG<br>ACTCCGTGAAGGGCCGATTCACCATCTCCCGAGACAACGCCAAGAA<br>CACGGTGTATCTGCAAATGAACAGCCTGAAACCTGAGGACACGGCC | 259 | 213 |

TABLE 3-continued

Polynucleotide Sequences of Tan Antibodies Enriched by Solid Phase Panning

| Antibody ID | Nucleotide Sequence | NA SEQ ID NO: | AA SEQ ID NO: |
|---|---|---|---|
| | GTCTATTACTGTAATGTACGAGGGAGACCGTTTATATTGAGCAAACC<br>GTTTGATTCCTGGGGCCAGGGGACCCTGGTCACCGTCTCCTCAACTA<br>GTGGCCCGGGAGGCCAA | | |
| T-sR2-2C4: | CAGGTGCAGCTGCAGGAGTCTGGGGGAGGATTGGTGCAGGCTGGG<br>AACTCTCTGAGACTCTCCTGTGCAGCCTCTGGACGCACCTTCAGTAAT<br>TATGCCATGGGCTGGTTCCGCCAGGCTCCAGGGAAGGAGCGTGAGT<br>TTGTAGCAGCTATTACCAGGAATGGTGGTATTACATACTATGCAGAG<br>TCCGTGAAGGGCCGATTCACCATCTCCAGAGACAACGCCAAGAACA<br>TGGTGTATCTGCAAATGAACAGCCTGAAACCTGAGGACACGGCCGT<br>CTATTACTGTAATATTAAGGCAAGACGCGGTAGTTTCTTCAATCCCGT<br>AAATAACTACTGGGGCCAGGGGACCCAGGTCACCGTCTCCTCAACT<br>AGTGGCCCGGGAGGCCAA | 260 | 217 |

TABLE 4

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| 01-T-bR3-1E2 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGATCTGTCTTA<br>G | 261 | 189 |
| 02-T-bR3-1D10 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGATCTGTCTTA<br>G | 262 | 189 |
| 07-T-bR3-1C1 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGCCCGGGAGGCCAACACCATCACCAC<br>CATCATGGCGCAGAACAAAAACTCATCTCAGAAGAGGATCTGTCTTA<br>G | 263 | 189 |
| 09-T-bR3-1E4 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG | 264 | 189 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | | |
| 10-T-bR3-1D11 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 265 | 189 |
| 14-T-bR3-1B1 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 266 | 189 |
| 15-T-bR3-1C2 | ATGAAATACCTATTNCNTNCGGCGNNCGCTGGATTGTTATTACTCGC GGCCCANCCGNCCATGGCGCAGGTGCAGCTGCAGGAGTCTGGGGG AGGATTGGTGCAGGCTGGGGGCTCTCTGAGACTCTCCTGTGCAGCCT CTGGACGCATCTTCAGTAACAATGTGATGGGCTGGTTCCGCCAGGCT CCAGGGAAGGAGCGTGAATTTGTAGCAGCTATTAGCCGGAGCGGTG GTACCACATTGTATGCAGAATCCATGAAGGGCCGATTCACCATCTCC AGAGACAACGCCAAGAACACGCTGTATCTGCAAATGAACAGTCTGAA ATCTGAAGACACGGCCATGTATTACTGTGGGAAAGTTGATGAGATCC GGCCAACCGTCTCTGCTTCGTATGACCTCTGGGGCCAGGGGACCCTG GTCACCGTCTCCTCAACTAGTGGCCCGGGAGGCCAACACCATCACCA CCATCATGGCGCAGAACAAAAACTCATCTCAGAAGAGGATCTGTCTT AG | 267 | 189 |
| 17-T-bR3-1C5 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAN CATCATGGCGCAGAACAAAAACTCATCTCAGAAGAGGATCTGTCTTA G | 268 | 189 |
| 23-T-bR3-1C3 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 269 | 189 |
| 25-T-bR3-1C6 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC | 270 | 189 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGATCTGTCTTA<br>G | | |
| 31-T-bR3-1C4 | ATNAAATNCNTATTGCNTACGGCGNCCGCTGGATTGTTATTACTCGC<br>GGCCCAGCCGGCCATGGCGCAGGTGCAGCTGCAGGAGTCTGGGGG<br>AGGATTGGTGCAGGCTGGGGGCTCTCTGAGACTCTCCTGTGCAGCCT<br>CTGGACGCATCTTCAGTAACAATGTGATGGGCTGGTTCCGCCAGGCT<br>CCAGGGAAGGAGCGTGAATTTGTAGCAGCTATTAGCCGGAGCGGTG<br>GTACCACATTGTATGCAGAATCCATGAAGGGCCGATTCACCATCTCC<br>AGAGACAACGCCAAGAACACGCTGTATCTGCAAATGAACAGTCTGAA<br>ATCTGAAGACACGGCCATGTATTACTGTGGGAAAGTTGATGAGATC<br>CGGCCAACCGTCTCTGCTTCGTATGACCTCTGGGGCCAGGGGACCCTG<br>GTCACCGTCTCCTCAACTAGTGGCCCGGGAGGCCAACACCATCACCA<br>CCATCATGGCGCAGAACAAAAACTCATCTCAGAAGAGGATCTGTCTT<br>AG | 271 | 189 |
| 33-T-bR3-1C9 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGATCTGTCTTA<br>G | 272 | 189 |
| 41-T-bR3-1C10 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGATCTGTCTTA<br>G | 273 | 189 |
| 46-T-bR3-1B5 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG<br>GCCAACCGTCTCTGCTTCGTATGACCTCTGGGGCCAGGGGACCCTGG<br>TCACCGTCTCCTCAACTAGTGGCCCGGGAGGCCAACACCATCACCAC<br>CATCATGGCGCAGAACAAAAACTCATCTCAGAAGAGGNTCTGTCTTA<br>G | 274 | 189 |
| 49-T-bR3-1C12 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGATTGGTGCAGGCTGGGGGCTCTCTGAGACTCTCCTGTGCAGCCTC<br>TGGACGCATCTTCAGTAACAATGTGATGGGCTGGTTCCGCCAGGCTC<br>CAGGGAAGGAGCGTGAATTTGTAGCAGCTATTAGCCGGAGCGGTGG<br>TACCACATTGTATGCAGAATCCATGAAGGGCCGATTCACCATCTCCA<br>GAGACAACGCCAAGAACACGCTGTATCTGCAAATGAACAGTCTGAAA<br>TCTGAAGACACGGCCATGTATTACTGTGGGAAAGTTGATGAGATCCG | 275 | 189 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | | |
| 57-T-bR3-1D1 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 276 | 189 |
| 65-T-bR3-1D5 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGNTCTGTCTTA G | 277 | 189 |
| 70-T-bR3-1B9 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCNTCTCAGAAGAGGNTCTGTCTTA G | 278 | 189 |
| 73-T-bR3-1D6 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 279 | 189 |
| 77-T-bR3-1A8 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCNTCTCAGAAGAGGATCTGTCTTA G | 280 | 189 |
| 81-T-bR3-1D7 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC | 281 | 189 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | | |
| 89-T-bR3-1D8 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGNTCTGTCTTA G | 282 | 189 |
| 93-T-bR3-1A10 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAACAAAAACTCATCTCAGAAGAGGATCTGTCTTA G | 283 | 189 |
| 94-T-bR3-1B12 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGCTCTCTGAGACTCTCCTGTGCAGCCTC TGGACGCATCTTCAGTAACAATGTGATGGGCTGGTTCCGCCAGGCTC CAGGGAAGGAGCGTGAATTTGTAGCAGCTATTAGCCGGAGCGGTGG TACCACATTGTATGCAGAATCCATGAAGGGCCGATTCACCATCTCCA GAGACAACGCCAAGAACACGCTGTATCTGCAAATGAACAGTCTGAAA TCTGAAGACACGGCCATGTATTACTGTGGGAAAGTTGATGAGATCCG GCCAACCGTCTCTGCTTCGTATGACCTCTGGGGCCAGGGGACCCTGG TCACCGTCTCCTCAACTAGTGGCCCGGGAGGCCAACACCATCACCAC CATCATGGCGCAGAANAAAAACTCATCTCAGAAGAGGATCTGTCTTA G | 284 | 189 |
| 06-T-bR3-1A11 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGGCTGGGGGACTCTCTGAGACTCTCCTGTGCAGCCTC TAGCGGCCCCTTCAGTAGATATGCCATGGGCTGGTTCCGCCAGGCTC CAGGGAAGGAGCGTGAGTTTGTAGCAACTATTAGCCGGAGTGGTAG TAGTACAACTTATGGAGACTCCGTGAAGGGCCGATTCACCATCTCCA GAGACAACGCCAAGAACACACTATATCTCGAAATGAACAGCCTGACG CCTGAGGACACGGCCGTTTATTACTGTGCAGTCTCGAGGTACTATAC AGCAGGTGCTAGTGCTGATACAAAAACATATGACTACTGGGGCCAG GGGACCCTGGTCACCGTCTCCTCAACTAGTGGCCCGGGAGGCCAACA CCATCACCACCATCATGGCGCAGAACAAAAACTCATCTCAGAAGAGG ATCTGTCTTAG | 285 | 190 |
| 08-T-bR3-1E12 | ATGAAATACCTATTGCCTACGGCGGCCGCTGGATTGTTATTACTCGCG GCCCAGCCGGCCATGGCGCAGGTGCAGTTGCAGGCGTCTGGGGGAG GCTTGGTGCAGCCTGGGGGGTCGCTGAAACTCTCCTGTCAAGCCTCT GGATTCAATTTTGGCAGTTTTGCCATAGCCTGGTTCCGCCAGGCCCCA GGGAAGGGCCGCGAGGGGATCTCATGTATCAGTAGTACAGACGATA CATCAGTCTATTCAGACGCCGTCAAGGGCCGATTCGCCATTTCCAGA GACAATGCCAAGAGAGCGGCGTACTTGCAGATGAACAGTCTGATTCC TGAGGACACGGCCAATTATTACTGCGCAACCGTGGGCCAGTCCTGTG | 286 | 191 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | ATTTGTGGGACCACCCCCAGGTTCCAGTGCGCTACCGGGGCCGCGG GACCCTGGTCACCGTCTCCTCAACTAGTGGCCCGGGAGGCCAACACC ATCACCACCATCATGGCGCAGAACAAAAACTCATCTCAGAAGAGGNT CTGTCTTAG | | |
| 16-T-bR3-1F8 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTTTCCTCAACTAGTGGCCCGGGAGGCCAACAC CATCACCACCATCATGGCGCAGAACAAAAACTCATCTCAGAAGAGGN TCTGTCTTAG | 287 | 192 |
| 30-T-bR3-1B3 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTTTCCTCAACTAGTGGCCCGGGAGGCCAACAC CATCACCACCATCATGGCGCAGAACAAAAACTCATCTCAGAAGAGGA TCTGTCTTAG | 288 | 192 |
| 39-T-bR3-1C7 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTTTCCTCAACTAGTGGCCCGGGAGGCCAACAC CATCACCACCATCATGGCGCAGAACAAAAACTCATCTCAGAAGAGGA TCTGTCTTAG | 289 | 192 |
| 78-T-bR3-1B10 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTTTCCTCAACTAGTGGCCCGGGAGGCCAACAC CATCACCACCATCATGGCGCAGAACAAAAACTCNTCTCAGAAGAGGN TCTGTCTTAG | 290 | 192 |
| 80-T-bR3-1H11 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTCTCCTCAACTAGTGGCCCGGGAGGCCAACAC CATCACCACCATCATGGCGCAGAACAAAAACTCATCTCAGAAGAGGA TCTGTCTTAG | 291 | 192 |
| 85-T-bR3-1A9 | ATGAAATACCTATTGCCTACGGCGGCCGCTGGATTGTTATTACTCGCG GCCCAGCCGGCCATGGCGCAGGTGCAGCTGCAGGCGTCTGGGGGA GGCTTGGTGCAGCCTGGGGGGTCGCTGAAACTCTCCTGTCAAGCCTC | 293 | 192 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | TGGATTCAATTTTGGCAGTTTTGCCATAGCCTGGTTCCGCCAGGCCCC AGGGAAGGGCCGCGAGGGGATCTCATGTATCAGTAGTACAGACGAT ACATCAGTCTATTCAGACGCCGTCAAGGGCCGATTCGCCATTTCCAG AGACAATGCCAAGAGAGCGGCGTACTTGCAGATGAACAGTCTGATTC CTGAGGACACGGCCAATTATTACTGCGCAACCGTGGGCCAGTCCTGT GATTTGTGGGACCACCCCCAGGTTCCAGTGCGCTACCGGGGCCGCG GGACCCAGGTCACCGTTTCCTCAACTAGTGGCCCGGGAGGCCAACAC CATCACCACCATCATGGCGCAGAACAAAAACTCATCTCAGAAGAGGA TCTGTCTTAG | | |
| 22-T-bR3-1B2 | ATGAAATACCTATTGCCTACGGCGGCCGCTGGATTGTTATTACTCGCG GCCCAGCCGGCCATGGCGCAGGTGCAGTTGCAGGAGTCAGGGGGA GGCTTCGTGCAGGCTGGGACTTCTCTGAGACTGTCCTGTGCAGCCTC TGGAAGTATCTCGAGTATCAATGCCATCGCCTGGTACCGCCAGGGTC GCGGGAACCAGCGCGAGTTGCTCGCGAAAATTACTAAAGGTGGTAC TACAATATATACAAACTCCGTGAAGGGCCGATTCACCATCTCTAGAG ACAACAACAAGAACACGGTGTATCTACAAATGGACAGCCTGAAACCT GACGACACAGCTGTCTATTATTGTGGAGCAGATGTGAACTACGGAAG CCCTGATTACATAGACTACTGGGGCCAAGGGACCCAGGTCACCGTCT CCTCAACTAGTGGCCCGGGAGGCCAACACCATCACCACCATCATGGC GCAGAACAAAAACTCATCTCAGAAGAGGATCTGTCTTAG | 294 | 193 |
| 24-T-bR3-1F10 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGTCTGGGGGCTCTCTGAGACTCTCCTGTGCAGCCTC TGGACGCACCTTCAGTACCTATACCATGGGCTGGTTCCGCCAGGCTC CAGGGAAGGAGCGTGAGTTTGTAGCAGCTATTAGCTGGAGTTCTGG TACCGCTAACTATGCAGACTCCGTGAAGGGCCGATTCACCATCTCCA GAGACAGCGCCAAGAACACGGTGTATCTGCAAATGAACAGCCTGAA ACCTGAGGATACGGCCGTCTATTACTGTAATGCGTGGAGTCCGGTTG GTCATGACTACTGGGGTCAGGGGACCCAGGTCACCGTCTCCTCAACT AGTGGCCCGGGAGGCCAACACCATCACCACCATCATGGCGCAGAAC AAAAACTCATCTCAGAAGAGGATCTGTCTTAG | 295 | 194 |
| 48-T-bR3-1G5 | ATGAAATACCTATTGCCTACGGCGGCCGCTGGATTGTTATTACTCGCG GCCCAGCCGGCCATGGCGCAGGTGCAGCTGCAGGAGTCTGGGGGA GGATTGGTGCAGTCTGGGGGCTCTCTGAGACTCTCCTGTGCAGCCTC TGGACGCACCTTCAGTACCTATACCATGGGCTGGTTCCGCCAGGCTC CAGGGAAGGAGCGTGAGTTTGTAGCAGCTATTAGCTGGAGTTCTGG TACCGCTAACTATGCAGACTCCGTGAAGGGCCGATTCACCATCTCCA GAGACAGCGCCAAGAACACGGTGTATCTGCAAATGAACAGCCTGAA ACCTGAGGATACGGCCGTCTATTACTGTAATGCGTGGAGTCCGGTTG GTCATGACTACTGGGGTCAGGGGACCCAGGTCACCGTCTCCTCAACT AGTGGCCCGGGAGGCCAACACCATCACCACCATCATGGCGCAGAAC AAAAACTCATCTCAGAAGAGGATCTGTCTTAG | 296 | 194 |
| 32-T-bR3-1F12 | ATGAAATNCNTATTGCCTACGGCGGCCGCTGGATTGTTATTACTCGC GGCCCAGCCGGCCATGGCGCAGGTGCAGCTGCAGCAGTCTGGGGGA GGATTGGTGCAGGCTGGGGGCTCTCTGAGACTCTCCTGTGCAGCCTC TGGGCGCACCTTCAGTAACTACGCCATGGGCTGGTTCCGCCAGGCTC CAGGGAAGGAGCGTGAATTCGTAGCAGCTATTAGTTGGAGTGGTGC TTACACATTTTATGGAAACTCCGTGAGGGGCCGATTCACCATCTCCAG AGACAACCCCAACAACACGGTGTATCTGCAAATGAACAGCCTGAAAC CTGAGGACACGGCCACTTATTACTGCGCAGCAGCCCGAGGAGGTAG ATGGTACAGTACCTATGACTACTGGGGCCAGGGGACCCAGGTCACC GTCTCCTCAACTAGTGGCCCGGGAGGCCAACACCATCACCACCATCA TGGCGCAGAACAAAAACTCATCTCAGAAGAGGNTCTGTCTTAG | 297 | 195 |
| 40-T-bR3-1G3 | ATGAAATACCTATTGCCTACGGCGGCCGCTGGATTGTTATTACTCGCG GCCCAGCCGGCCATGGCGCAGGTGCAGCTGCAGGAGTCTGGGGGA GGCTTGGTGCAGGCTGGGGGGTCTCTGAGACTCTCCTGTGCAGCCTC TGGAAGCACCTTCAGCGGCTATGTCATCGGCTGGTACCGGCAGGCTC CAGGGAAGCAGCGCGAGGAGGTCGCAATTATTAGTAGTAGTGGTAG CACAAACTATGCAGACTCCGTGAAGGGCCGATTCACCATCTCCAGAG ACAACGCCAACGCCAAGACCACGTTTTATCTGCAAATGAACAGCCTG AAACCTGAGGACACGGCCGTCTATTACTGTAATGCGAGACTTTGGCT AAATAACTACTGGGGCCAGGGGACCCTGGTCACCGTCTCCTCAACTA GTGGCCCGGGAGGCCAACACCATCACCACCATCATGGCGCAGAACA AAAACTCATCTCAGAAGAGGATCTGTCTTAG | 298 | 196 |
| 47-T-bR3-1C8 | ATGAAATACCTATTGCCTACGCGGCCGCTGGATTGTTATTACTCGCG GCCCAGCCGGCCATGGCGCAGGTGCAGCTGCAGGAGTCTGGGGGA GGCTTGGTGCAGCCTGGGGGGTCTCTGAGACTCTCCTGTGCAGCCTC | 299 | 197 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| | TGGATTCACCTTCAGTAGCTACTGGATGTATTGGGTCCGTCAGGCTCC<br>AGGGAAGGGGCTCGAATGGGTCTCAACTATTAGTCCTAGTGGTGGT<br>ACAACATACTATACAAACTCCGCGAAGGGCCGATTCACCATCTCCAG<br>AGACAACGCCAAGAACACGGTGTATCTGCAAGTGAACAACCTGAAA<br>CCTGAGGACACGGCCGTTTATTACTGTGCAGCCCGACGAAGTGGTAG<br>ATATGAGTATGACTACTGGGGCCAGGGGACCCAGGTCACCGTCTCCT<br>CAACTAGTGGCCCGGGAGGCCAACACCATCACCACCATCATGGCGCA<br>GAACAAAAACTCATCTCAGAAGAGGATCTGTCTTAG | | |
| 62-T-bR3-1B8 | ATGAAATACCTATTGCCTACGGCGGCCGCTGGATTGTTATTACTCGCG<br>GCCCAGCCGGCCATGGCGCAGGTGCAGTTGCAGGAGTCTGGGGGA<br>GACTTGGTGCAGCCTGGGGGGTCTCTGAGACTCTCCTGTGTAGCCTC<br>TGGATTCCCTTTTGATGATTATCCCATGAGCTGGGTCCGACAGGCTCC<br>AGGGAAGGGGCTGGAGTGGGTCTCGTCTGTTAGCCCGAATGGTGGT<br>AGCACATTCTATGCAGACTCCCTGAAGGGCCGATTCACCATCTCCAG<br>AGACAACGCCAAGAACACGCTGTATCTGCAAATAAACAGTCTGAAAT<br>CAGACGACACGGCCGTGTATCACTGTGCAAAGGTTCTCGACTACTAC<br>TGCTCAGGCTATGGGTGTTATGCCTCATATGACCTTTGGGGCCAGGG<br>GACCCAGGTCACCGTCTCCTCAACTAGTGGCCCGGGAGGCCAACACC<br>ATCACCACCATCATGGCGCAGAACAAAAACTCATCTCAGAAGAGGAT<br>CTGTCTTAG | 300 | 198 |
| 71-T-bR3-1D12 | ATGAAATACCTATTGCCTACGGCGGCCGCTGGATTGTTATTACTCGCG<br>GCCCAGCCGGCCATGGCGCAGGTGCAGTTGCAGGAGTCTGGGGGA<br>GACTTGGTGCAGCCTGGGGGGTCTCTGAGACTCTCCTGTGTAGCCTC<br>TGGATTCCCTTTTGATGATTATCCCATGAGCTGGGTCCGACAGGCTCC<br>AGGGAAGGGGCTGGAGTGGGTCTCGTCTGTTAGCCCGAATGGTGGT<br>AGCACATTCTATGCAGACTCCCTGAAGGGCCGATTCACCATCTCCAG<br>AGACAACGCCAAGAACACGCTGTATCTGCAAATAAACAGTCTGAAAT<br>CAGACGACACGGCCGTGTATCACTGTGCAAAGGTTCTCGACTACTAC<br>TGCTCAGGCTATGGGTGTTATGCCTCATATGACCTTTGGGGCCAGGG<br>GACCCAGGTCACCGTCTCCTCAACTAGTGGCCCGGGAGGCCAACACC<br>ATCACCACCATCATGGCGCAGAACAAAAACTCATCTCAGAAGAGGAT<br>CTGTCTTAG | 301 | 198 |
| 79-T-bR3-1E1 | ATGAAATACCTATTGCCTACGGCGGCCGCTGGATTGTTATTACTCGCG<br>GCCCAGCCGGCCATGGCGCAGGTGCAGCTGCAGGAGTCTGGGGGA<br>GGCTTGGTGCAGCCTGGGGGGTCTCTGAGACTCTCCTGTGCAGCCTC<br>TATAAGCATCGTCAGTATCAATACCATGGCCTGGTACCGCCAGGCTC<br>CAGGGAAGCAGCGCGAGTTGGTCGCAGGTATTACTAGTGGTGGTAG<br>CACAAACTATGCAGACTCCGTGAAGGGCCGATTCACCATTTCCAGAG<br>ACAACGCCAAGAACACGGTGTCGCTGCAAATGAACAGCCTGAAACCT<br>GAGGACACGGCCGTCTATTACTGTAATGCAGGCCGCTACGTCCCTGG<br>TGCGATTGTTACTAACTACTGGGGCCAGGGGACCCAGGTCACCGTCT<br>CCTCAACTAGTGGCCCGGGAGGCCAACACCATCACCACCATCATGGC<br>GCAGAACAAAAACTCATCTCAGAAGAGGATCTGTCTTAG | 302 | 199 |
| 86-T-bR3-1B11 | ATGAAATACCTATTGCCTACGGCGGCCGCTGGATTGTTATTACTCGCG<br>GCCCAGCCGGCCATGGCGCAGGTGCAGTTGCAGGAGTTTGGGGGA<br>GCTTGGTGCAGGCTGGGGGGTCTCTGAGACTCTCCTGTTTAGCCTCT<br>ATGACTACCCTCGGGTTCAAGACCATGGGCTGGTACCGCCAGGCTCC<br>AGGGAAGCAGCGCGAGTTGGTCGCACGTATTAGTAGTGGTGGTCAG<br>ACAAACTATGCAGACTCCGTGAAGGGCCGATTCACCATCTCCAGAGA<br>CAACGCCAAGAACACAGTGTATCTGCAAATGATCAGTCTGAAACCTG<br>AGGATACGGCCGTCTATTATTGTAATGCGCGGCGTTACTATAGTCTA<br>GCGCGCTACGACTATAACTACTGGGGCCAGGGGACCCAGGTCACCG<br>TCTCCTCAACTAGTGGCCCGGGAGGCCAACACCATCACCACCATCAT<br>GGCGCAGAACAAAAACTCATCTCAGAAGAGGATCTGTCTTAG | 303 | 200 |
| 95-T-bR3-1E11 | ATGAAATACCTATTGCCTACGGCGGCCGCTGGATTGTTATTACTCGCG<br>GCCCAGCCGGCCATGGCGCAGGTGCAGCTGCAGGCGTTTGGGGGAG<br>CCGCGGCACAGGCTGGAGACTCTTTGAGACTTTCCTGTGTCGTTGGT<br>GGAAAGAGCACCGCCGCCGTCAATGGCGTGGGGTGGTACCGCCAGG<br>CTCCGGGTCGTCAGCGCGAATTTGTCGCGGCTATTAGACCTGGCGGT<br>AGACGAGATATCTGGATTCCGTGAAAGGCCGTTTCTCGGTATTTAG<br>GAATAAGACCACAGTTTACTTGCGAATGAACGATCTGAGGATTGAAG<br>ACACGGCCGTCTACTACTGTTATGCAGAGGGTCTTCTATTACCGTCGA<br>CGTACTGGGGCCAGGGGACCCTGGTCACCGTCTCCTCAACTAGTGGC<br>CCGGGAGGCCAACACCATCACCACCATCATGGCGCAGAACAAAAACT<br>CATCTCAGAAGAGGNTCTGTCTTAG | 304 | 201 |

TABLE 4-continued

Polynucleotide Sequences of Tan Antibodies Enriched by Solution Phase Panning

| Antibody ID | Nucleotide Sequence | NA SEQ ID NO: | AA SEQ ID NO: |
|---|---|---|---|
| 38-T-bR3-1B4 | ATGAAATACCTATTGCCTACGGCGGCCGCTGGATTGTTATTACTCGCG GCCCAGCCGGCCATGGCGCAGGTGCAGTTGCAGGCGTCTGGGGGAG GCTTGGTGCAGCCTGGGGGGTCGCTGAAACTCTCCTGTCAAGCCTCT GGATTCAATTTTGGCAGTTTTGCCATAGCCTGGTTCCGCCAGGCCCCA GGGAAGGGCCGCGAGGGGATCTCATGTATCAGTAGTACAGACGATA CATCAGTCTATTCAGACGCCGTCAAGGGCCGATTCGCCATTTCCAGA GACAATGCCAAGAGAGCGGCGTACTTGCAGATGAACAGTCTGATTCC TGAGGACACGGCCAATTATTACTGCGCAACCGTGGGCCAGTCCTGTG ATTTGTGGGACCACCCCCAGGTTCCAGTGCGCTACCGGGGCCGCGG GACCCTGGTCACCGTCTCCTCAACTAGTGGCCCGGGAGGCCAACACC ATCACCACCATCATGGCGCAGAACAAAAACTCATCTCAGAAGAGGAT CTGTCTTAG | 305 | 192 |
| 55-T-bR3-1D4 | ATGAAATACCTATTGCCTACGGCGGCCGCTGGATTGTTATTACTCGCG GCCCAGCCGGCCATGGCGCAGGTGCAGCTGCAGGAGTTTGGGGGA GGATTGGTGCAGGCTGGGGGCTCTCTGAGACTCTCCTGTGCAGCCTC TGGACGCACCTTCAGTGGCTATTCCATGGGCTGGTTCCGCCAGGCTC CAGGGAAGGAGCGTGAGTTTGTAGGAGGTATTAGCCGGAGTGGTG GGTGGACATACTATGCAGACTCCGTGAAGGGCCGATTCACCATCTCC AGAGACAACGCCAAGAACACAGTGTATCTGCAAATGAACAGCCTGA AACCTGAGGACACGGCCGTTTATTACTGTGCAGCAGCAGTTTCCCGT ATTAACGACTATGCGCCGGCCTTAAGCAGGGCGTATGACTACTGGGG CCAGGGGACCCAGGTCACCGTCTCCTCAACTAGTGGCCCGGGAGGC CAACACCATCACCACCATCATGGCGCAGAACAAAAACTCATCTCAGA AGAGGATCTGTCTTAG | 306 | 310 |

EXAMPLES

Examples are provided herein to illustrate the present invention. These examples are not meant to constrain the present invention to any particular application or theory of operation.

Example 1—Production of Llama Single Domain Antibodies Against Human Tau

Immunizations: A llama was immunized with Tau441 according to the following schedule. In general, immunizations occurred once per month, with serum and/or PBMCs taken 1 week after boosts.

| Tau441 Immunization Schedule | | |
|---|---|---|
| Pre-bleed | | Day 0 |
| Immunization 1 | 200 ug CFA, SQ | Day 0 |
| Immunization 2 | 100 ug IF A, SQ | Day 21 |
| Bleed 1 | | Day 28 |
| Immunization 3 | 100 ug IF A 100 ug Adjuplex, SQ | Day 49 |
| Bleed 2 | | Day 56 |
| Immunization 4 | 100 ug IF A 100 ug Adjuplex, SQ | Day 77 |
| Bleed 3 | | Day 84 |
| Immunization 5 | 100 ug IF A 100 ug Adjuplex, SQ | Day 105 |
| Bleed 4 | | Day 112~1 × 10$^8$ PBMCs |
| Immunization 6 | 200 ug Adjuplex split IM/SQ | Day 142 |
| Bleed 5 | | Day 149 |
| Immunization 7 | 200 ug Adjuplex split IM/SQ | Day 188 |
| Bleed 6 | | Day 196~1 × 10$^8$ PBMCs |

Complete Freund's Adjuvant (CFA), Incomplete Freund's Adjuvant (IFA), Adjuplex Adjuvant (Sigma), Subcutaneous (SQ), Intramuscular (IM).

Serum titer levels were determined by indirect ELISA using the following protocol:
1) Antigen was coated in 96 well Corning 9018 high-binding polystyrene assay plates at 2 μg/mL in PBS, 4 degrees ON.
2) Wash plate 4 times with PBS containing 0.05% Tween20 (PBST).
3) Block with PBST/5% non-fat dried milk (PBST/milk) for 2 hr at room temperature. 4) Wash 4 times with PBST.
5) Dilutions of sera were made in PBST/milk and incubated in plate for 1 hr at room temperature.
6) Wash 4 times with PBST.
7) Incubate with Rabbit anti-Llama IgG(H+L) (Life Technologies), 1:10,000 dilution in PBST/milk, 1 hr room temperature.
8) Wash 4 times with PBST.
9) Bound antibody was detected with Gt anti-Rb IgG(H+L)-HRP (Jackson), 1:10,000 in PBST/milk, 45 min room temperature.

Library Construction: Approximately 100 mL of llama blood was collected in EDTA-coated tubes (Becton Dickenson) and peripheral blood mononuclear cells (PBMCs) were isolated using Hisotpaque-1077 (Sigma). Approximately 1×10$^8$ PBMCs were isolated from the specific bleeds listed above and RNA prepared using RNeasy (Qiagen). cDNA was synthesized from a total of 50 μg of RNA (25 ug from each bleed) using random hexanucleotide primers and SuperScript reverse transcriptase (Life Technologies). Single domain antibodies (VHH) were cloned in a two step PCR process using the cDNA as template. The first PCR amplified the variable domains of all immunoglobulin heavy chains, both single chain (VHH) and conventional antibodies (VH) using CaL1/CaL2 primers:

5'-GTCCTGGCTGCTCTTCTACAAGG-3' (SEQ ID NO: 311)

5'-GGTACGTGCTGTTGAACTGTTCC-3'. (SEQ ID NO: 312)

The second nested PCR specifically amplified llama single domain antibodies (ProSci proprietary primers). PCR products were gel purified and the DNA fragments encoding the VHH domains were cloned into phage display vector pADL-23c (Antibody Design Labs) and electroporated into *E. coli* TG1 cells, yielding a library of approximately $1 \times 10^9$ in size.

Example 2: Selection of Single Domain Antibodies Against Tau

Phage displaying VHH antibodies were rescued from individual libraries with helper phage M13K07 and subjected to biopanning in two different ways: solid-phase and solution-phase panning. For solid-phase panning, Tau was adsorbed on 2 um diameter polystyrene beads (Polysciences, Inc), blocked with PBST containing 5% non-fat dried milk, and incubated with $2 \times 10^{11}$ phage in 1 mL PBST/milk for 1 hr at room temperature. For solution-phase panning, proteins were biotinylated using Lightning-Link Rapid Biotin (Innova Biosciences) and 1ug of biotinylated Tau incubated with $2 \times 10^{11}$ phage in 1 mL PBST/milk for 1 hr at room temperature. Polystyrene beads were captured by centrifugation and washed extensively with PBST. Biotinylated proteins bound to phage were captured with streptavidin-coated magnetic Dynabeads (Life Technologies) and extensively washed with PBST. In both cases, bound phage were eluted with both high pH (100 mM triethylamine, pH~10) and low pH (100 mM glycine, pH~2.5) for 5 min and neutralized with 1M Tris pH 7.5. *E. coli* strains TG1 and SS320 were then infected with eluted phage and used for a subsequent round of panning (TG1) or to express antibodies (SS320).

Example 3—Expression of Single Domain Antibodies for Screening

Individual SS320 clones were grown in 96 well plate format in 100 uL of 2YT/1% glucose/100 µg/mL ampicillin overnight at 37° C. 10 uL of the overnight cultures were inoculated into 1 mL each of 2YT/0.1% glucose/100 µg/mL ampicillin in deep 96 well blocks and grown at 37° C., 200 rpm for 3 hrs until cells were in log phase. Single domain antibody expression was then induced with IPTG (1 mM final) and the temperature reduced to 30° C. overnight. The next day, bacterial cultures were centrifuged at 3200 g for 10 min and supernatant removed. The remaining bacterial pellets were frozen at −70° C. Bacterial pellets were then thawed, resuspended in 300 uL of PBS, and incubated for 30 min at room temperature. Cellular debris was removed by centrifugation at 3200 g for 10 min and the antibody-containing supernatants transferred to a fresh 96 well plate for storage at −70° C. until used.

ELISA screening of the supernatants was performed using the following protocol:
1) coat antigen at 2 µg/mL in PBS, 4° C. ON (use 96 well Corning 9018 high-binding polystyrene assay plates).
2) wash 4 times with PBST
3) 2 hr block with PBST/5% milk, room temp
4) wash 4 times PBST
5) add dilutions of sdAb supes (1:1) in PBST/5% milk, 1 hr room temp
6) wash 4 times PBST
7) add ProSci's anti-c-myc-tag antibody (Cat. No. PM-7669), 1:1,000 in PBST/5% milk, 1 hr room temp
8) wash 4 times PBST
9) detect with goat anti-mouse IgG-HRP (Jackson Cat. No. 115-035-164), 1:5,000 in PBST/5% milk, incubate 30 to 45 min room temperature
10) wash 4 times PBST
11) develop 10 min to 1 hr depending on signal Example 4—Single Domain Antibody Purification Single Domain Antibodies were purified from 50 mL cultures as follows. Inoculated 3 mL of 2YT/1% glucose/100 µg/mL Amp with specific clone in SS320 cells and grew overnight 37 degrees, 200 rpm. Next day, 500 uL of overnight culture was added to 50 mL of 2YT/0.1% glucose/100 µg/mL ampicillin and grown at 37 degrees, 200 rpm. After $OD_{600}$ reached 0.7, induced the culture with IPTG (1 mM final) and grown overnight at 30 degrees.

The next day, bacteria were collected by centrifugation for 15 min, 3500 g at room temperature. The cell pellet was resuspended in 2.5 mL of ice-cold TES (20 mM Tris, 0.5 mM EDTA, 17% sucrose), and incubated for 1 hr on ice. 5 mL of TES/4 (TES diluted 1 to 4 in water) was added, and incubation on ice continued for 45 min mixing occasionally. The suspension was centrifuged at 10,000 g for 30 min, 4 degrees and the supernatant was collected. The His-tagged single domain antibodies were purified by using IMAC (Immobilized Metal Affinity Chromatography) according to the manufacturer's instructions (Qiagen).

Example 5—Single Domain Antibody Characterization

Single domain antibody (sdAb) titer following administration of tau441 as described in Example 1 was measured by ELISA. ELISA plates were coated with 2 µg/ml of the longest tau isoform (441 aa), and reacted with various bleeds obtained after several immunizations with tau441. The hydrogen peroxidase (HRP)-linked secondary antibody recognizes single-domain llama antibodies. Some auto-sdAbs against tau were detected in the pre-bleed. FIG. 1A shows that sdAb titer in the tau protein immunized llama peaks at bleed 2 and remains stable through bleed 6.

Figure 1B:
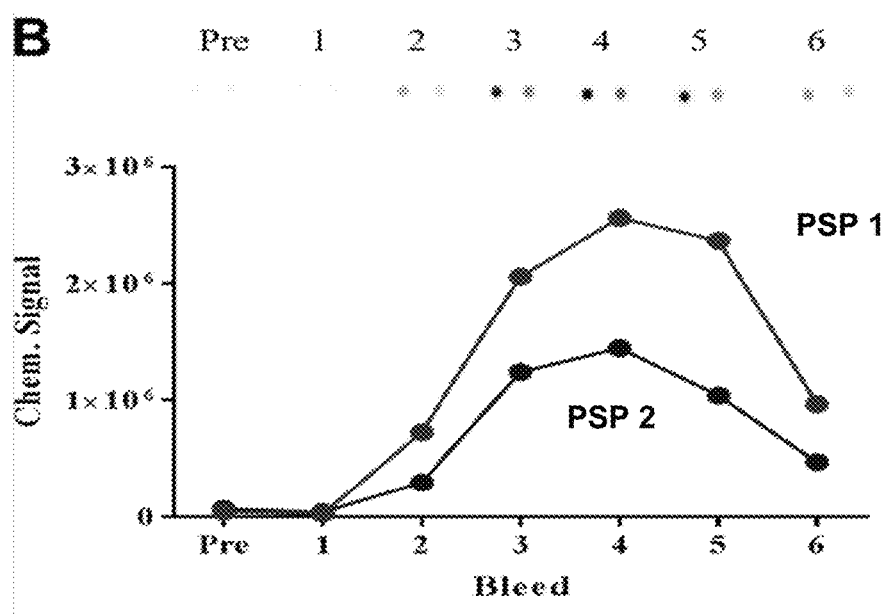
FIG. 1B shows immunoreactivity of the tau sdAb with brain homogenates having different Progressive Supranuclear Palsy (PSP) human tauopathy.

To test the reactivity of the tau sdAb to human tauopathy brains, paired helical filament (PHF) enriched tau fractions from two different Progressive Supranuclear Palsy (PSP) human tauopathy cases were spotted onto nitrocellulose membranes and incubated with plasma from each of the seven time points, pre-treatment through bleed 6, at a 1:1000 dilution overnight. Following this, blots were washed and incubated with HRP-conjugated llama secondary antibody at 1:2000 and developed together to ensure that time in the developing fluid and exposure would be identical. For both cases, signal increased reaching a maximum at bleed 4, followed by a small decrease in signal at bleed 5 and a larger decrease at bleed 6 (FIG. 1). sdAb clones were obtained from B-cells from bleeds 4 and 5 using the services of ProSci Inc. (Poway, CA).

Phage display library panning against biotinylated solution phase (FIG. 2A) and solid phase (FIG. 2B) recTau441 was used to enrich for clones (Abs>0.1) with 85% ($3^{rd}$ round: one plate) and 24% ($2^{nd}$ round—2 plates) positivity, respectively.

The sdAb clones have a diverse binding profile as shown in FIGS. 3A-3D. Some preferably bind to paired helical filament (PHF) enriched fraction from Alzheimer's brain, whereas others bind better to recTau441 or bind well to both PHF and recTau441. Note that these are culture supernatants and clone expression may vary, which will affect absorbance values. Supernatants can be expected to contain 0.1-1 µg/ml. X and Y axes are absorbance values for recTau441 and PHF, respectively.

The anti-tau sdAbs recognize tau pathology in human tauopathy brains. A monoclonal sdAb, 2B8, stains numerous tangles and pretangles in a human tauopathy brain as shown in the image of FIG. 4A. Its epitope has yet to be characterized. Several other anti-tau sdAb recognize pathological tau on tissue sections with varying reactivity towards tangles, pretangles, somal, axonal and dendritic tau, reflecting their diversity. For comparison, PHF1 staining of a phospho-tau epitope of adjacent section of the same brain reveals mostly mature tangles, dystrophic neurites and possibly glial cells (FIG. 4B).

To examine whether the tau sdAb can clear tau from neurons, primary neurons were prepared from day 0 Tg JNPL3 tauopathy pups, incubated with 1 µg/ml of the 2B8 anti-tau sdAb, and compared to untreated neurons from the same animal. Immunblotting was carried out for neuronal marker NeuN and total tau levels. NeuN levels were unchanged between control and treated cells, indicating that the sdAb is not toxic to neurons (FIG. 5A). Neurons treated with 2B8 for 3 days had significantly lower tau levels compared to untreated controls ($p=0.03$) as shown in the graph of FIG. 5B.

Figure 6A:
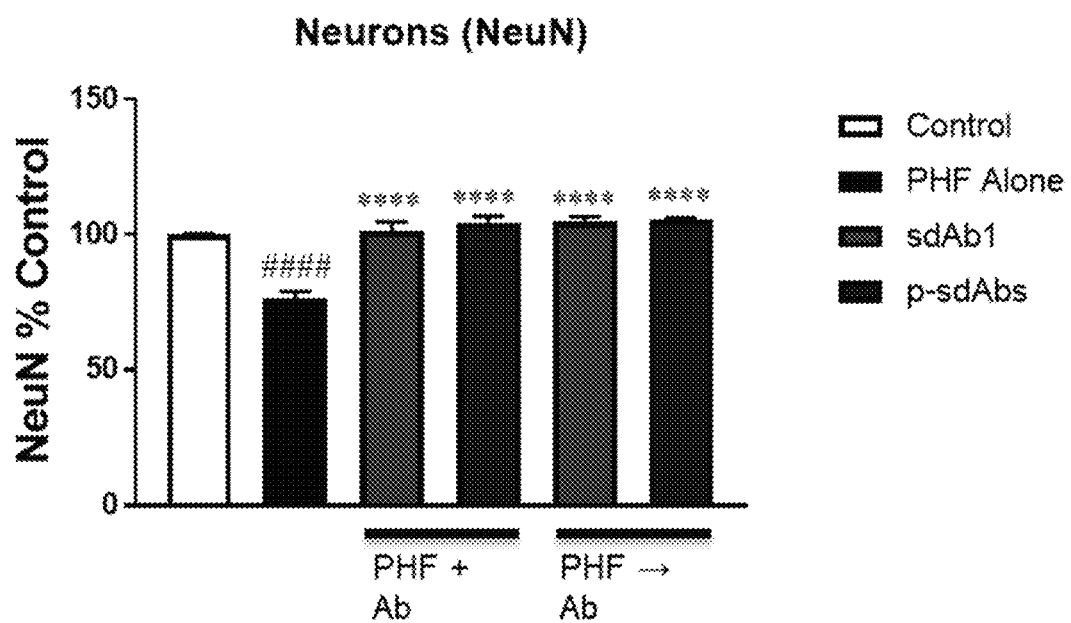
FIGS. 6A-6B are graphs showing anti-tau sdAb prevents toxicity of PHF both extracellularly and intracellularly (FIG. 6A), and clears human Alzheimer's brain derived tau protein (FIG. 6B) in tauopathy mouse primary neuronal culture. To examine extracellular effects, antibodies (1 µg/ml) were administrated with enriched human paired helical filaments (PF: 1 µg/ml) derived from AD brain to primary tauopathy JNPL3 mouse cultures (PHF+Ab) for 7 days. Under these conditions, monoclonal sdAb (sdAb1) and polyclonal sdAbs (p-sdAbs) work equally well extracellularly in preventing PHF neurotoxicity (FIG. 6A) and in clearing tau pathology (FIG. 6B). To examine intracellular effects, antibodies were administered 24 h after PHF (PHF→Ab), which by then has been taken up into the neurons. Under these conditions (PHF→Ab), both the m-sdAb (sdAb1) and p-sdAbs were equally effective in preventing PHF neurotoxicity (FIG. 6A), and in clearing tau pathology (FIG. 6B), examined 7 days later, with comparable efficacy to the extracellular condition. ##, ###$p<0.01$, 0.001 compared to untreated control. **$p<0.0001$ compared to PHF alone. sdAb1: 2B8; p-sdAbs: polyclonal sdAb
Figure 6B:
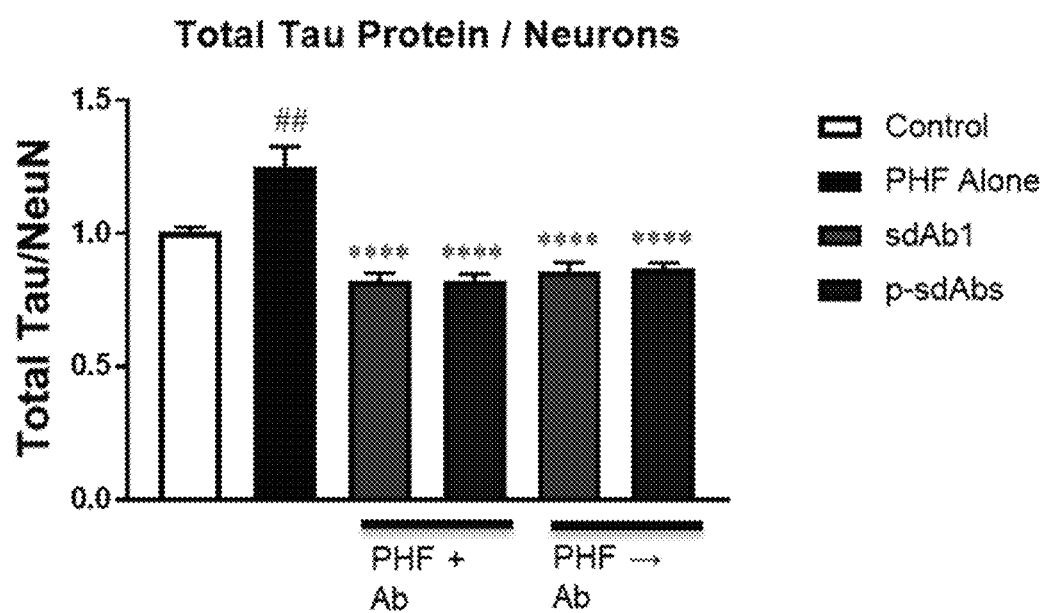

The ability of monoclonal (m) and polyclonal (p) tau sdAbs to prevent toxicity of AD brain derived pathological tau protein was investigated. To examine extracellular effects, antibodies (1 µg/ml) were administered with enriched human paired helical filaments (PHF; 1 µg/ml) derived from AD brain to primary tauopathy JNPL3 mouse cultures (PHF+Ab) for 7 days. Under these conditions, m-sdAb (sdAb1=2B8) and p-sdAbs work equally well extracellularly in preventing PHF neurotoxicity (FIG. 6A) and in clearing tau pathology (FIG. 6B). To examine intracellular effects, antibodies are administered 24 h after PHF (PHF→Ab), which by then has been taken up into the neurons. Under these conditions (PHF→Ab), both the m-sdAb (sdAb1) and p-sdAbs were equally effective in preventing PHF neurotoxicity (FIG. 6A), and in clearing tau pathology (FIG. 6B), examined 7 days later, with comparable efficacy to the extracellular condition.

Figure 7A:
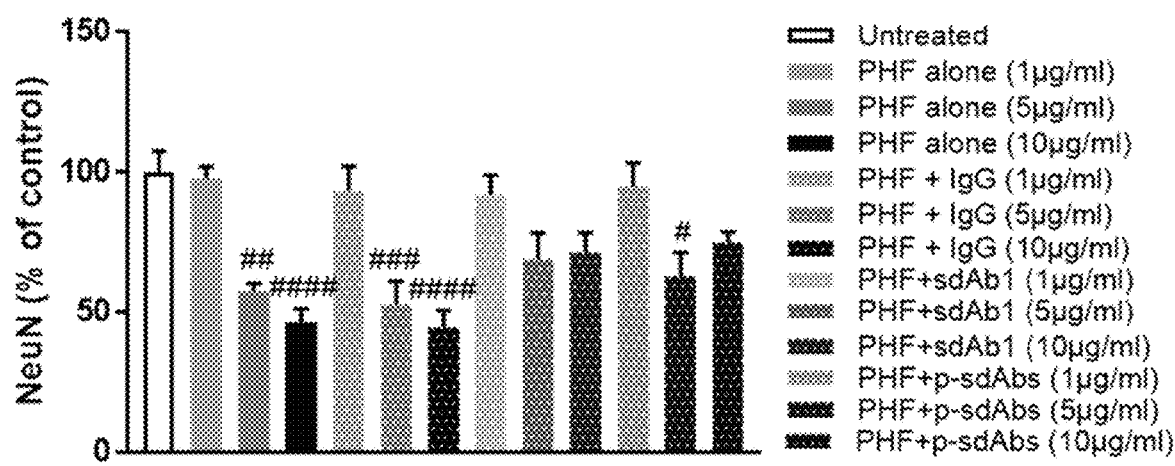
FIGS. 7A-7C show that anti-tau sdAb prevents toxicity of and clears human Alzheimer's brain derived tau protein in tauopathy human neuron-like culture. Differentiated SH-SY5Y human neuroblastoma cells were treated with PHF-enriched tau for 24 h, washed to remove extracellular PHF, treated with sdAb for 72 h, and then processed for western blots. PHF showed a dose-dependent neurotoxicity that was partially alleviated by the sdAbs (FIG. 7A). Likewise, PHF treatment led to a dose-dependant increase in total- (FIG. 7B) and phospho-tau (FIG. 7C) that was strongly attenuated by the sdAbs. #, ##, ###, ####: $p<0.05$, 0.01, 0.001, 0.0001, compared to untreated control. , *, **: $p<0.01$, 0.001, 0.0001, compared to PHF alone. sdAb1: 2B8; p-sdAbs: polyclonal sdAb
Figure 7B:
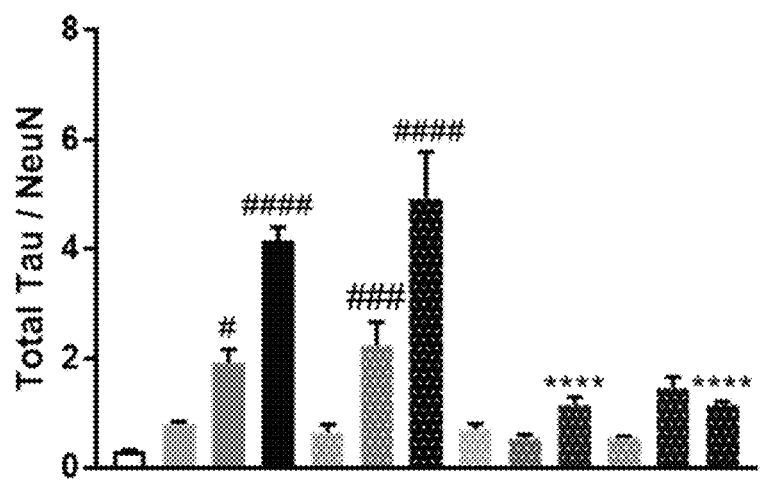
Figure 7C:
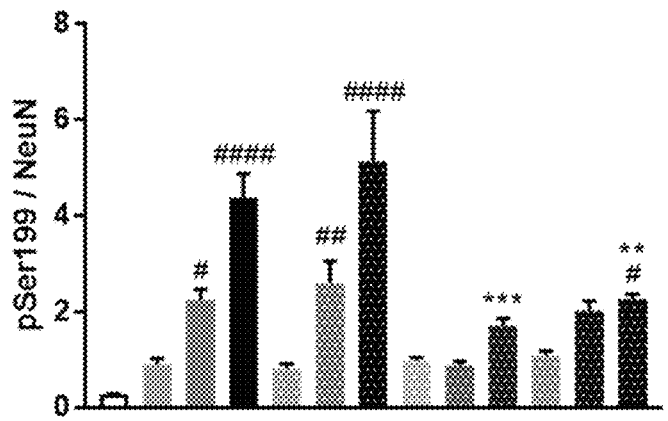

The anti-tau sdAbs also prevent toxicity of and clear human Alzheimer's brain derived tau protein in tauopathy human neuron-like cultures. Differentiated SH-SY5Y human neuroblastoma cells were treated with PHF-enriched tau for 24 h, washed to remove extracellular PHF, treated with sdAb for 72 h, and then processed for western blots. PHF showed a dose-dependent neurotoxicity that was partially alleviated by the sdAbs as shown in FIG. 7A. Likewise, PHF treatment led to a dose-dependant increase in total- (FIG. 7B) and phospho-tau (FIG. 7C) that was strongly attenuated by the sdAbs. #, ##, ###, ####: $p<0.05$, 0.01, 0.001, 0.0001, compared to untreated control. , *, ****: $p<0.01$, 0.001, 0.0001, compared to PHF alone. sdAb1: 2B8; p-sdAbs: polyclonal sdAb.

Figures 8A, 8B:
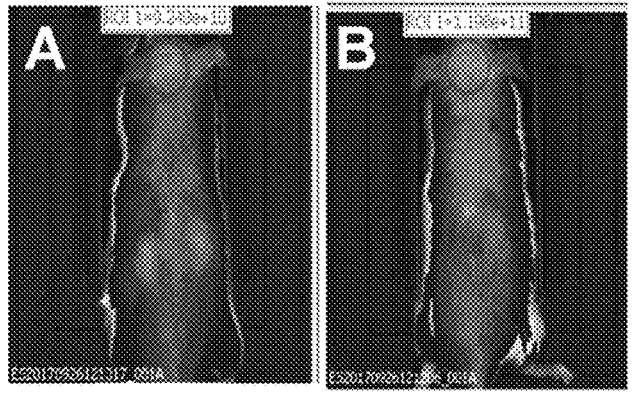
FIGS. 8A-8C show that anti-tau sdAb provides strong specific brain signal in tauopathy mice but not in wildtype mice. Mice received an intravenous injection of 250 µg of sdAb labeled with a near infrared dye. IVIS signal was obtained from the anesthetized mice several times within the first hour. Brain signal was strong in JNPL3 mouse G47 (FIG. 8A; 17 min), and G48 (FIG. 8B; 10 min) with strong signal seen also presumably in the kidneys (FIG. 8A) reflecting probe clearance and in the spinal cord (FIG. 8A and FIG. 8B), which in the JNPL3 model has extensive tau pathology. Quantitative analysis of IVIS brain signal over time (FIG. 8C), shows strong (G48 and G47) and moderate (rest of animals) specific signal from the tauopathy mice, presumably reflecting their degree of tau pathology, and minimal signal in wt mice (WT1 and WT2). One mouse (F45) received both sdAb1 and p-sdAbs resulting in a similar brain signal. sdAb1: 2B8; p-sdAbs: polyclonal sdAb.
Figure 8C:
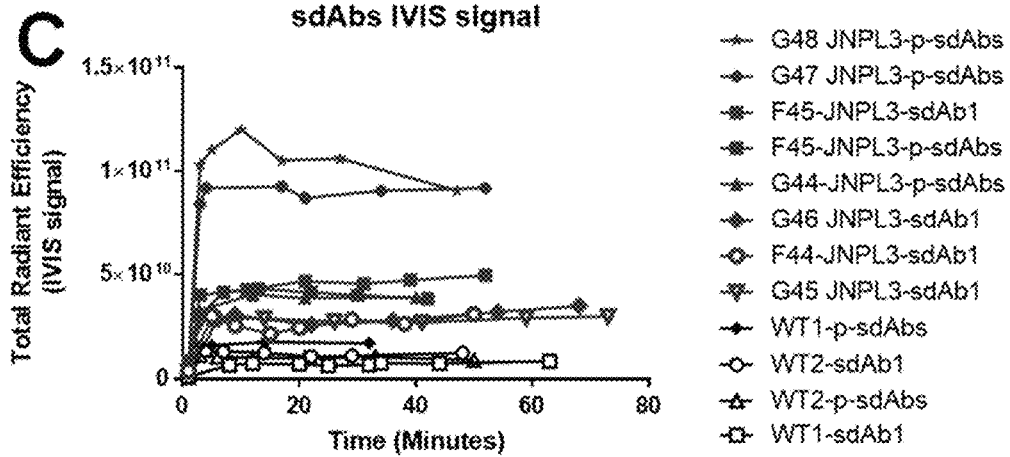

To test distribution of sdAb upon systemic administration, mice received an intravenous injection of 250 µg of sdAb labeled with a near infrared dye as previously described for anti-tau scFc (Krishnaswamy et al., "Antibody-derived In vivo Imaging of tau Pathology," *J Neuroscie* 10:34(50): 16835-50 (2014), which is hereby incorporated by reference in its entirety). In vivo imaging system (IVIS) signal was obtained from the anesthetized mice several times within the first hour. Brain signal (blue circle) was strong (yellow) in JNPL3 mouse G47 (FIG. 8A; 17 min), and G48 (FIG. 8B; 10 min) with strong signal (yellow) seen also presumably in the kidneys (FIG. 8A) reflecting probe clearance and in the spinal cord (FIGS. 8A and 8B), which in the JNPL3 model has extensive tau pathology. A quantitative analysis of IVIS brain signal over time (FIG. 8C), shows strong (G48 and G47) and moderate (rest of animals) specific signal from the tauopathy mice, presumably reflecting their degree of tau pathology, and minimal signal in wt mice (WT1 and WT2). One mouse (F45) received both sdAb 2B8 (sdAb1) and polyclonal sdAbs (p-sdAbs) resulting in a similar brain signal. The signal peaks within a few minutes and is stable within the first hour. The sdAb signal is cleared faster (within the first day) than with scFv or mAb that takes several days to dissipate (Krishnaswamy et al., "Antibody-derived In vivo Imaging of tau Pathology," *JNeuroscie* 10:34(50): 16835-50 (2014), which is hereby incorporated by reference in its entirety).

Figure 9:
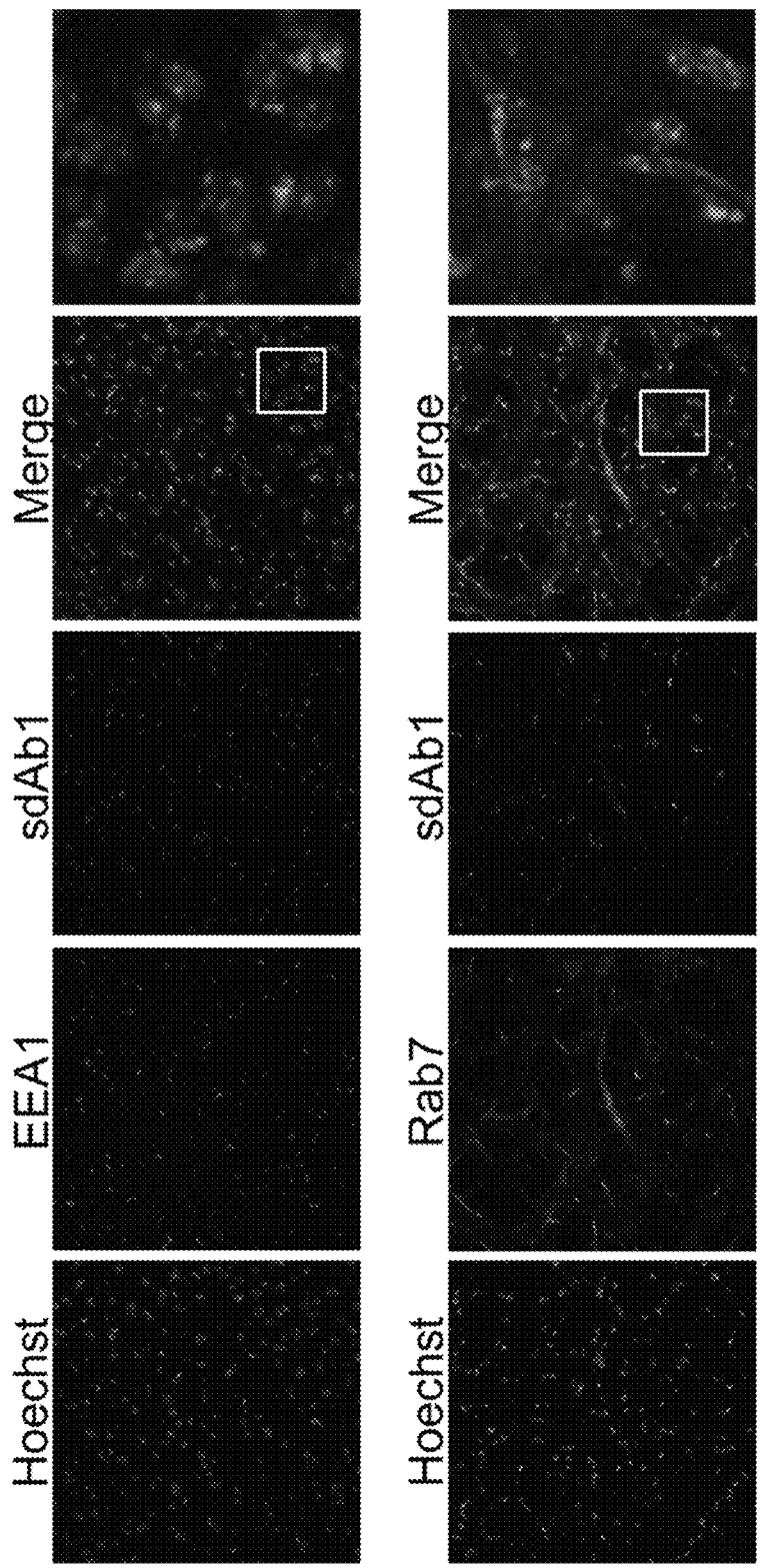
FIG. 9 is a panel of immunocytochemcial images showing anti-tau sdAb distribution to the endosomal-lysosomal system in the brain after intravenous injection in tauopathy mice. In a subset of IVIS imaged mice (near-infrared dye labeled sdAb (250 µg) injected intravenously (i.v)), brains were removed 1 h after injection, sectioned and stained with a nuclear stain (Hoechst.

Distribution of the tau sdAb in the brain after intravenous administration was also determined. In a subset of IVIS imaged mice (near-infrared dye labeled sdAb 2B8 (SdAbl) (250 µg) injected intravenously (i.v)), brains were removed 1 h after injection, sectioned and stained with a nuclear stain (Hoechst) (FIG. 9, far left images), and an antibody against early endosomes (EEA1; FIG. 9, top panel, second image from left) or late endosomes/lysosomes (Rab7; FIG. 9, bottom panel, second image from left). Merged images and their magnification (as per white boxes; FIG. 9, top and bottom panel, last two images on the right) revealed that sdAb1 enters the brain following intravenous injection and is taken up into neurons into the endosomal-lysosomal system.

Figure 10:
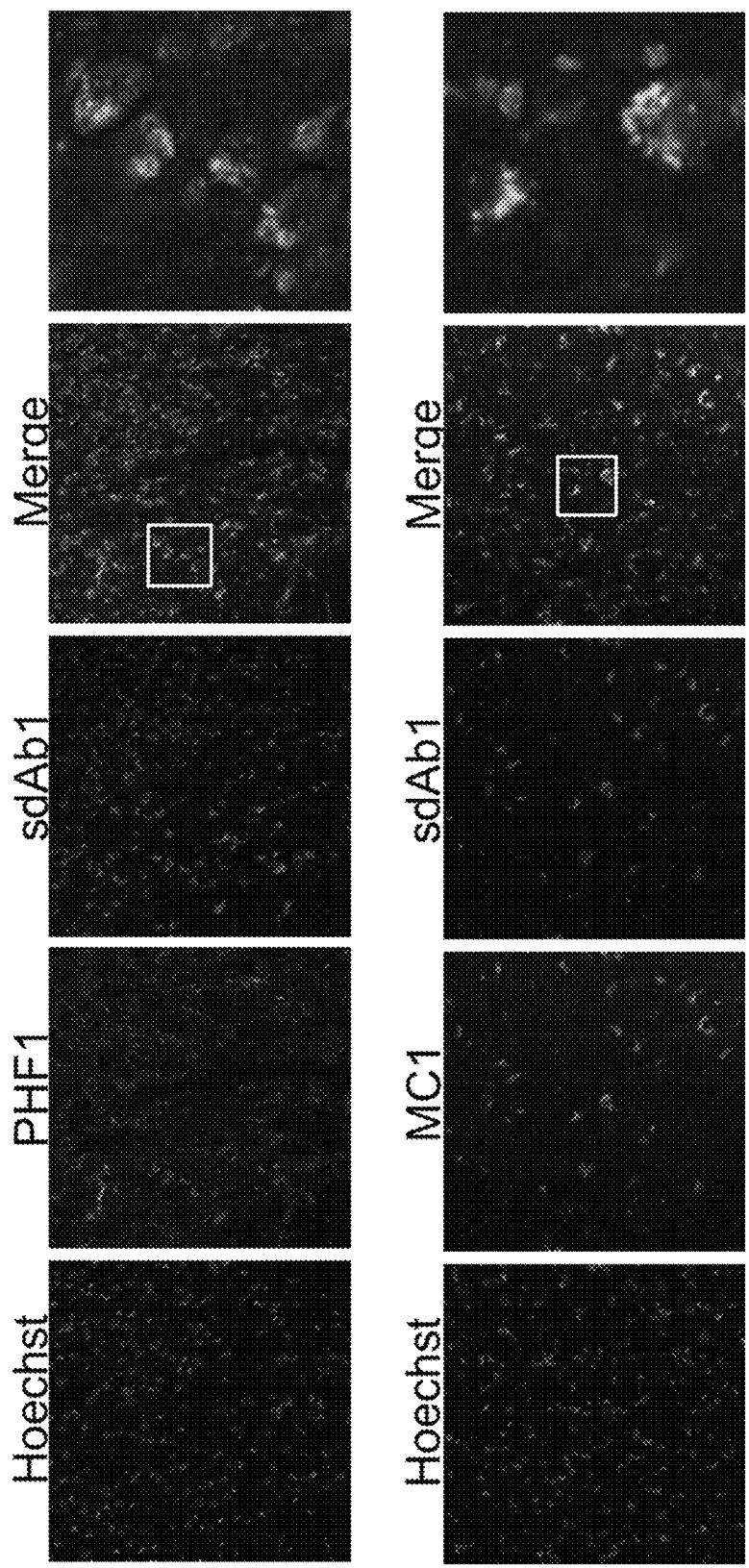
FIG. 10. is a panel of immunocytochemical images showing anti-tau sdAb binding to pathological tau in the brain after intravenous injection in tauopathy mice. In a subset of IVIS imaged mice (near-infrared dye labeled sdAb (250 µg) injected intravenously (i.v)), brains were removed 1 h after injection, sectioned and stained with a nuclear stain (Hoechst.

Binding of anti-tau sdAb to pathological tau in the brain after intravenous injection in tauopathy mice was also examined. In a subset of IVIS imaged mice (near-infrared dye labeled sdAb 2B8 (sdAb1) (250 µg) injected intravenously (i.v)), brains were removed 1 h after injection, sectioned and stained with a nuclear stain (Hoechst; FIG. 10, far left images), and an antibody against hyperphosphorylated tau epitope (PHF1; FIG. 10, top panel, second from left) or a conformational tau epitope (MC1; FIG. 10, bottom panel, second from left). Merged images and their magnification (as per white boxes; FIG. 10, top and bottom panel, last two images on the right) revealed that sdAb1 enters the brain following intravenous injection and is taken up into neurons, where it binds to pathological tau protein (in the endosomal-lysosomal system as per FIG. 9).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An antibody or fragment thereof, said antibody or binding fragment thereof comprising a heavy chain variable region selected from the group consisting of:

(i) a heavy chain variable region comprising the CDR-H1 of SEQ ID NO: 1, the CDR-H2 of SEQ ID NO: 39, and the CDR-H3 of SEQ ID NO: 77;

(ii) a heavy chain variable region comprising the CDR-H1 of SEQ ID NO: 2, the CDR-H2 of SEQ ID NO: 40, and the CDR-H3 of SEQ ID NO: 78;

(iii) a heavy chain variable region comprising the CDR-H1 of SEQ ID NO: 3, the CDR-H2 of SEQ ID NO: 41, and the CDR-H3 of SEQ ID NO: 79;

(iv) a heavy chain variable region comprising the CDR-H1 of SEQ ID NO: 4, the CDR-H2 of SEQ ID NO: 42, and the CDR-H3 of SEQ ID NO: 80;

(v) a heavy chain variable region comprising the CDR-H1 of SEQ ID NO: 5, the CDR-H2 of SEQ ID NO: 43, and the CDR-H3 of SEQ ID NO: 81;

(vi) a heavy chain variable region comprising the CDR-H1 of SEQ ID NO: 6, the CDR-H2 of SEQ ID NO: 44, and the CDR-H3 of SEQ ID NO: 82;

(vii) a heavy chain variable region comprising the CDR-H1 of SEQ ID NO: 7, the CDR-H2 of SEQ ID NO: 45, and the CDR-H3 of SEQ ID NO: 83;

(viii) a heavy chain variable region comprising the CDR-H1 of SEQ ID NO: 8, the CDR-H2 of SEQ ID NO: 46, and the CDR-H3 of SEQ ID NO: 84;

(ix) a heavy chain variable region comprising the CDR-H1 of SEQ ID NO: 9, the CDR-H2 of SEQ ID NO: 47, and the CDR-H3 of SEQ ID NO: 85;

(x) a heavy chain variable region comprising the CDR-H1 of SEQ ID NO: 10, the CDR-H2 of SEQ ID NO: 48, and the CDR-H3 of SEQ ID NO: 86;

(xi) a heavy chain variable region comprising the CDR-H1 of SEQ ID NO: 11, the CDR-H2 of SEQ ID NO: 49, and the CDR-H3 of SEQ ID NO: 87;

(xii) a heavy chain variable region comprising the CDR-H1 of SEQ ID NO: 12, the CDR-H2 of SEQ ID NO: 50, and the CDR-H3 of SEQ ID NO: 88;

(xiii) a heavy chain variable region comprising the CDR-H1 of SEQ ID NO: 13, the CDR-H2 of SEQ ID NO: 51, and the CDR-H3 of SEQ ID NO: 89;

(xiv) a heavy chain variable region comprising the CDR-H1 of SEQ ID NO: 14, the CDR-H2 of SEQ ID NO: 52, and the CDR-H3 of SEQ ID NO: 90;

(xv) a heavy chain variable region comprising the CDR-H1 of SEQ ID NO: 15, the CDR-H2 of SEQ ID NO: 53, and the CDR-H3 of SEQ ID NO: 91;

(xvi) a heavy chain variable region comprising the CDR-H1 of SEQ ID NO: 16, the CDR-H2 of SEQ ID NO: 54, and the CDR-H3 of SEQ ID NO: 92;

(xvii) a heavy chain variable region comprising the CDR-H1 of SEQ ID NO: 17, the CDR-H2 of SEQ ID NO: 55, and the CDR-H3 of SEQ ID NO: 93;

(xviii) a heavy chain variable region comprising the CDR-H1 of SEQ ID NO: 18 the CDR-H2 of SEQ ID NO: 56, and the CDR-H3 of SEQ ID NO: 94;

(xix) a heavy chain variable region comprising the CDR-H1 of SEQ ID NO: 19, the CDR-H2 of SEQ ID NO: 57, and the CDR-H3 of SEQ ID NO: 95;

(xx) a heavy chain variable region comprising the CDR-H1 of SEQ ID NO: 20, the CDR-H2 of SEQ ID NO: 58, and the CDR-H3 of SEQ ID NO: 96;

(xxi) a heavy chain variable region comprising the CDR-H1 of SEQ ID NO: 21, the CDR-H2 of SEQ ID NO: 59, and the CDR-H3 of SEQ ID NO: 97;

(xxii) a heavy chain variable region comprising the CDR-H1 of SEQ ID NO: 22, the CDR-H2 of SEQ ID NO: 60, and the CDR-H3 of SEQ ID NO: 98;

(xxiii) a heavy chain variable region comprising the CDR-H1 of SEQ ID NO: 23, the CDR-H2 of SEQ ID NO: 61, and the CDR-H3 of SEQ ID NO: 99;

(xxiv) a heavy chain variable region comprising the CDR-H1 of SEQ ID NO: 24, the CDR-H2 of SEQ ID NO: 62, and the CDR-H3 of SEQ ID NO: 100;

(xxv) a heavy chain variable region comprising the CDR-H1 of SEQ ID NO: 25, the CDR-H2 of SEQ ID NO: 63, and the CDR-H3 of SEQ ID NO: 101;

(xxvi) a heavy chain variable region comprising the CDR-H1 of SEQ ID NO: 26, the CDR-H2 of SEQ ID NO: 64, and the CDR-H3 of SEQ ID NO: 102;

(xxvii) a heavy chain variable region comprising the CDR-H1 of SEQ ID NO: 27, the CDR-H2 of SEQ ID NO: 65, and the CDR-H3 of SEQ ID NO: 103;

(xxviii) a heavy chain variable region comprising the CDR-H1 of SEQ ID NO: 28, the CDR-H2 of SEQ ID NO: 66, and the CDR-H3 of SEQ ID NO: 104;

(xxix) a heavy chain variable region comprising the CDR-H1 of SEQ ID NO: 29, the CDR-H2 of SEQ ID NO: 67, and the CDR-H3 of SEQ ID NO: 105;

(xxx) a heavy chain variable region comprising the CDR-H1 of SEQ ID NO: 30, the CDR-H2 of SEQ ID NO: 68, and the CDR-H3 of SEQ ID NO: 106;

(xxxi) a heavy chain variable region comprising the CDR-H1 of SEQ ID NO: 31, the CDR-H2 of SEQ ID NO: 69, and the CDR-H3 of SEQ ID NO: 107;

(xxxii) a heavy chain variable region comprising the CDR-H1 of SEQ ID NO: 32, the CDR-H2 of SEQ ID NO: 70, and the CDR-H3 of SEQ ID NO: 108;

(xxxiii) a heavy chain variable region comprising the CDR-H1 of SEQ ID NO: 33, the CDR-H2 of SEQ ID NO: 71, and the CDR-H3 of SEQ ID NO: 109;

(xxxiv) a heavy chain variable region comprising the CDR-H1 of SEQ ID NO: 34 the CDR-H2 of SEQ ID NO: 72, and the CDR-H3 of SEQ ID NO: 110;
(xxxv) a heavy chain variable region comprising the CDR-H1 of SEQ ID NO: 35, the CDR-H2 of SEQ ID NO: 73, and the CDR-H3 of SEQ ID NO: 111;
(xxxvi) a heavy chain variable region comprising the CDR-H1 of SEQ ID NO: 36, the CDR-H2 of SEQ ID NO: 74, and the CDR-H3 of SEQ ID NO: 112;
(xxxvii) a heavy chain variable region comprising the CDR-H1 of SEQ ID NO: 37, the CDR-H2 of SEQ ID NO: 75, and the CDR-H3 of SEQ ID NO: 113;
(xxxviii) a heavy chain variable region comprising the CDR-H1 of SEQ ID NO: 38, the CDR-H2 of SEQ ID NO: 76, and the CDR-H3 of SEQ ID NO: 114;
(xxxix) a heavy chain variable region comprising the CDR-H1 of SEQ ID NO: 202, the CDR-H2 of SEQ ID NO: 203, and the CDR-H3 of SEQ ID NO: 204;
(xl) a heavy chain variable region comprising the CDR-H1 of SEQ ID NO: 206, the CDR-H2 of SEQ ID NO: 207, and the CDR-H3 of SEQ ID NO: 208;
(xli) a heavy chain variable region comprising the CDR-H1 of SEQ ID NO: 210, the CDR-H2 of SEQ ID NO: 211, and the CDR-H3 of SEQ ID NO: 212; and
(xlii) a heavy chain variable region comprising the CDR-H1 of SEQ ID NO: 214, the CDR-H2 of SEQ ID NO: 215, and the CDR-H3 of SEQ ID NO: 216.

2. The antibody or binding fragment thereof of claim 1, wherein said antibody or binding fragment thereof binds to human tau protein.

3. The antibody or binding fragment thereof of claim 1, wherein said antibody or binding fragment thereof is a camelid antibody or binding fragment thereof.

4. The antibody or binding fragment thereof of claim 1, wherein said antibody or binding fragment thereof is a monoclonal antibody or binding fragment thereof.

5. The antibody or binding fragment thereof of claim 1, wherein said heavy chain variable region further comprises human or a humanized immunoglobulin heavy chain framework regions.

6. The antibody or binding fragment thereof of claim 5, wherein the heavy chain variable region comprises an amino acid sequence that is at least 80% identical to an amino acid sequence selected from the group consisting of SEQ ID NOs: 115-152, 205, 209, 213, and 217216.

7. The antibody or binding fragment thereof of claim 5, wherein the heavy chain variable region comprises an amino acid sequence selected from the group consisting of SEQ ID NOs: 115-152, 205, 209, 213, and 217.

8. The antibody or binding fragment thereof of claim 1, wherein said antibody or binding fragment thereof is selected from the group consisting of: a single domain antibody (Fv), a minibody, and a bispecific antibody.

9. A polyclonal antibody composition comprising two or more antibodies or fragments thereof of claim 1.

10. A pharmaceutical composition comprising:
the antibody or binding fragment thereof of claim 6 and a pharmaceutical carrier.

11. A method of treating a subject to inhibit onset of one or more symptoms of a condition involving pathological tau protein, said method comprising:
administering to the subject the pharmaceutical composition of claim 10, wherein said composition is administered in an amount effective to inhibit onset of one or more symptoms of the condition involving pathological tau protein.

12. A method of treating a subject for a condition involving a pathological tau protein, said method comprising:
administering to the subject the pharmaceutical composition of claim 10, wherein said composition is administered in an amount effective to treat the condition involving pathological tau protein.

13. A method of diagnosing Alzheimer's disease and/or a tauopathy in a subject, said method comprising:
administering the antibody or binding fragment thereof according to claim 1 to the subject;
detecting, in the subject, binding of the antibody or binding fragment thereof to accumulated tau protein; and
diagnosing the subject for Alzheimer's disease and/or tauopathy based on said detecting.

14. A method of monitoring the progression of Alzheimer's disease or a tauopathy in a subject, said method comprising:
administering the antibody or binding fragment thereof according to claim 1 to the subject;
detecting, in the subject, binding of the antibody or binding fragment thereof to accumulated tau protein;
repeating said detecting periodically; and
monitoring the progression of Alzheimer's disease or tauopathy in the subject based on said repeated detecting.

15. A diagnostic kit comprising:
the antibody or binding fragment thereof of claim 1 and a detectable label.

16. An antibody or fragment thereof, said antibody or binding fragment thereof comprising a heavy chain variable region selected from the group consisting of:
(i) a heavy chain variable region comprising the CDR-H1 of SEQ ID NO: 153, the CDR-H2 of SEQ ID NO: 165, and the CDR-H3 of SEQ ID NO: 177;
(ii) a heavy chain variable region comprising the CDR-H1 of SEQ ID NO: 154, the CDR-H2 of SEQ ID NO: 166, and the CDR-H3 of SEQ ID NO: 178;
(iii) a heavy chain variable region comprising the CDR-H1 of SEQ ID NO: 155, the CDR-H2 of SEQ ID NO: 167, and the CDR-H3 of SEQ ID NO: 179;
(iv) a heavy chain variable region comprising the CDR-H1 of SEQ ID NO: 156, the CDR-H2 of SEQ ID NO: 168, and the CDR-H3 of SEQ ID NO: 180;
(v) a heavy chain variable region comprising the CDR-H1 of SEQ ID NO: 157, the CDR-H2 of SEQ ID NO: 169, and the CDR-H3 of SEQ ID NO: 181;
(vi) a heavy chain variable region comprising the CDR-H1 of SEQ ID NO: 158, the CDR-H2 of SEQ ID NO: 170, and the CDR-H3 of SEQ ID NO: 182;
(vii) a heavy chain variable region comprising the CDR-H1 of SEQ ID NO: 159, the CDR-H2 of SEQ ID NO: 171, and the CDR-H3 of SEQ ID NO: 183;
(viii) a heavy chain variable region comprising the CDR-H1 of SEQ ID NO: 160, the CDR-H2 of SEQ ID NO: 172, and the CDR-H3 of SEQ ID NO: 184;
(ix) a heavy chain variable region comprising the CDR-H1 of SEQ ID NO: 161, the CDR-H2 of SEQ ID NO: 173, and the CDR-H3 of SEQ ID NO: 185;
(x) a heavy chain variable region comprising the CDR-H1 of SEQ ID NO: 162, the CDR-H2 of SEQ ID NO: 174, and the CDR-H3 of SEQ ID NO: 186;
(xi) a heavy chain variable region comprising the CDR-H1 of SEQ ID NO: 163, the CDR-H2 of SEQ ID NO: 175, and the CDR-H3 of SEQ ID NO: 187;

(xii) a heavy chain variable region comprising the CDR-H1 of SEQ ID NO: 164, the CDR-H2 of SEQ ID NO: 176, and the CDR-H3 of SEQ ID NO: 188; and (xiii) a heavy chain variable region comprising the CDR-H1 of SEQ ID NO: 307, the CDR-H2 of SEQ ID NO: 308, and the CDR-H3 of SEQ ID NO: 309.

17. The antibody or binding fragment thereof of claim 16, wherein said antibody or binding fragment thereof binds to human tau protein.

18. The antibody or binding fragment thereof of claim 16, wherein said antibody or binding fragment thereof is a camelid antibody or binding fragment thereof.

19. The antibody or binding fragment thereof of claim 16, wherein said antibody or binding fragment thereof is a monoclonal antibody or binding fragment thereof.

20. The antibody or binding fragment thereof of claim 16, wherein said heavy chain variable region further comprises human or a humanized immunoglobulin heavy chain framework regions.

21. The antibody or binding fragment thereof of claim 20, wherein the heavy chain variable region comprises an amino acid sequence that is at least 80% identical to an amino acid sequence selected from the group consisting of SEQ ID NOs: 189-201 and 310.

22. The antibody or binding fragment thereof of claim 20, wherein the heavy chain variable region comprises an amino acid sequence selected from the group consisting of SEQ ID NOs: 189-201 and 310.

23. The antibody or binding fragment thereof of claim 16, wherein said antibody or binding fragment thereof is selected from the group consisting of: a single domain antibody (Fv), a minibody, and a bispecific antibody.

24. A polyclonal antibody composition comprising two or more antibodies or fragments thereof of claim 16.

25. A pharmaceutical composition comprising:
the antibody or binding fragment thereof of claim 16 and a pharmaceutical carrier.

26. A method of treating a subject to inhibit onset of one or more symptoms of a condition involving pathological tau protein, said method comprising:
administering to the subject the pharmaceutical composition of claim 25, wherein said composition is administered in an amount effective to inhibit onset of one or more symptoms of the condition involving pathological tau protein in the subject.

27. A method of treating a subject for a condition involving a pathological tau protein, said method comprising:
administering to the subject the pharmaceutical composition of claim 25, wherein said composition is administered in an amount effective to treat the condition involving pathological tau protein.

28. A method of diagnosing Alzheimer's disease and/or a tauopathy in a subject, said method comprising:
administering the antibody or binding fragment thereof according to claim 16 to the subject;
detecting, in the subject, binding of the antibody or binding fragment thereof to accumulated tau protein; and
diagnosing the subject for Alzheimer's disease and/or tauopathy based on said detecting.

29. A method of monitoring the progression of Alzheimer's disease or a tauopathy in a subject, said method comprising:
administering the antibody or binding fragment thereof according to claim 16 to the subject;
detecting, in the subject, binding of the antibody or binding fragment thereof to accumulated tau protein;
repeating said detecting periodically; and
monitoring the progression of Alzheimer's disease or tauopathy in the subject based on said repeated detecting.

30. A diagnostic kit comprising:
the antibody or binding fragment thereof of claim 16 and a detectable label.

31. An isolated polynucleotide encoding an antibody or binding fragment thereof comprising a heavy chain variable region selected from the group consisting of:

(i) a heavy chain variable region comprising the CDR-H1 of SEQ ID NO: 1, the CDR-H2 of SEQ ID NO: 39, and the CDR-H3 of SEQ ID NO: 77;

(ii) a heavy chain variable region comprising the CDR-H1 of SEQ ID NO: 2, the CDR-H2 of SEQ ID NO: 40, and the CDR-H3 of SEQ ID NO: 78;

(iii) a heavy chain variable region comprising the CDR-H1 of SEQ ID NO: 3, the CDR-H2 of SEQ ID NO: 41, and the CDR-H3 of SEQ ID NO: 79;

(iv) a heavy chain variable region comprising the CDR-H1 of SEQ ID NO: 4, the CDR-H2 of SEQ ID NO: 42, and the CDR-H3 of SEQ ID NO: 80;

(v) a heavy chain variable region comprising the CDR-H1 of SEQ ID NO: 5, the CDR-H2 of SEQ ID NO: 43, and the CDR-H3 of SEQ ID NO: 81;

(vi) a heavy chain variable region comprising the CDR-H1 of SEQ ID NO: 6, the CDR-H2 of SEQ ID NO: 44, and the CDR-H3 of SEQ ID NO: 82;

(vii) a heavy chain variable region comprising the CDR-H1 of SEQ ID NO: 7, the CDR-H2 of SEQ ID NO: 45, and the CDR-H3 of SEQ ID NO: 83;

(viii) a heavy chain variable region comprising the CDR-H1 of SEQ ID NO: 8, the CDR-H2 of SEQ ID NO: 46, and the CDR-H3 of SEQ ID NO: 84;

(ix) a heavy chain variable region comprising the CDR-H1 of SEQ ID NO: 9, the CDR-H2 of SEQ ID NO: 47, and the CDR-H3 of SEQ ID NO: 85;

(x) a heavy chain variable region comprising the CDR-H1 of SEQ ID NO: 10, the CDR-H2 of SEQ ID NO: 48, and the CDR-H3 of SEQ ID NO: 86;

(xi) a heavy chain variable region comprising the CDR-H1 of SEQ ID NO: 11, the CDR-H2 of SEQ ID NO: 49, and the CDR-H3 of SEQ ID NO: 87;

(xii) a heavy chain variable region comprising the CDR-H1 of SEQ ID NO: 12, the CDR-H2 of SEQ ID NO: 50, and the CDR-H3 of SEQ ID NO: 88;

(xiii) a heavy chain variable region comprising the CDR-H1 of SEQ ID NO: 13, the CDR-H2 of SEQ ID NO: 51, and the CDR-H3 of SEQ ID NO: 89;

(xiv) a heavy chain variable region comprising the CDR-H1 of SEQ ID NO: 14, the CDR-H2 of SEQ ID NO: 52, and the CDR-H3 of SEQ ID NO: 90;

(xv) a heavy chain variable region comprising the CDR-H1 of SEQ ID NO: 15, the CDR-H2 of SEQ ID NO: 53, and the CDR-H3 of SEQ ID NO: 91;

(xvi) a heavy chain variable region comprising the CDR-H1 of SEQ ID NO: 16, the CDR-H2 of SEQ ID NO: 54, and the CDR-H3 of SEQ ID NO: 92;

(xvii) a heavy chain variable region comprising the CDR-H1 of SEQ ID NO: 17, the CDR-H2 of SEQ ID NO: 55, and the CDR-H3 of SEQ ID NO: 93;

(xviii) a heavy chain variable region comprising the CDR-H1 of SEQ ID NO: 18 the CDR-H2 of SEQ ID NO: 56, and the CDR-H3 of SEQ ID NO: 94;

(xix) a heavy chain variable region comprising the CDR-H1 of SEQ ID NO: 19, the CDR-H2 of SEQ ID NO: 57, and the CDR-H3 of SEQ ID NO: 95;

(xx) a heavy chain variable region comprising the CDR-H1 of SEQ ID NO: 20, the CDR-H2 of SEQ ID NO: 58, and the CDR-H3 of SEQ ID NO: 96;
(xxi) a heavy chain variable region comprising the CDR-H1 of SEQ ID NO: 21, the CDR-H2 of SEQ ID NO: 59, and the CDR-H3 of SEQ ID NO: 97;
(xxii) a heavy chain variable region comprising the CDR-H1 of SEQ ID NO: 22, the CDR-H2 of SEQ ID NO: 60, and the CDR-H3 of SEQ ID NO: 98;
(xxiii) a heavy chain variable region comprising the CDR-H1 of SEQ ID NO: 23, the CDR-H2 of SEQ ID NO: 61, and the CDR-H3 of SEQ ID NO: 99;
(xxiv) a heavy chain variable region comprising the CDR-H1 of SEQ ID NO: 24, the CDR-H2 of SEQ ID NO: 62, and the CDR-H3 of SEQ ID NO: 100;
(xxv) a heavy chain variable region comprising the CDR-H1 of SEQ ID NO: 25, the CDR-H2 of SEQ ID NO: 63, and the CDR-H3 of SEQ ID NO: 101;
(xxvi) a heavy chain variable region comprising the CDR-H1 of SEQ ID NO: 26, the CDR-H2 of SEQ ID NO: 64, and the CDR-H3 of SEQ ID NO: 102;
(xxvii) a heavy chain variable region comprising the CDR-H1 of SEQ ID NO: 27, the CDR-H2 of SEQ ID NO: 65, and the CDR-H3 of SEQ ID NO: 103;
(xxviii) a heavy chain variable region comprising the CDR-H1 of SEQ ID NO: 28, the CDR-H2 of SEQ ID NO: 66, and the CDR-H3 of SEQ ID NO: 104;
(xxix) a heavy chain variable region comprising the CDR-H1 of SEQ ID NO: 29, the CDR-H2 of SEQ ID NO: 67, and the CDR-H3 of SEQ ID NO: 105;
(xxx) a heavy chain variable region comprising the CDR-H1 of SEQ ID NO: 30, the CDR-H2 of SEQ ID NO: 68, and the CDR-H3 of SEQ ID NO: 106;
(xxxi) a heavy chain variable region comprising the CDR-H1 of SEQ ID NO: 31, the CDR-H2 of SEQ ID NO: 69, and the CDR-H3 of SEQ ID NO: 107;
(xxxii) a heavy chain variable region comprising the CDR-H1 of SEQ ID NO: 32, the CDR-H2 of SEQ ID NO: 70, and the CDR-H3 of SEQ ID NO: 108;
(xxxiii) a heavy chain variable region comprising the CDR-H1 of SEQ ID NO: 33, the CDR-H2 of SEQ ID NO: 71, and the CDR-H3 of SEQ ID NO: 109;
(xxxiv) a heavy chain variable region comprising the CDR-H1 of SEQ ID NO: 34 the CDR-H2 of SEQ ID NO: 72, and the CDR-H3 of SEQ ID NO: 110;
(xxxv) a heavy chain variable region comprising the CDR-H1 of SEQ ID NO: 35, the CDR-H2 of SEQ ID NO: 73, and the CDR-H3 of SEQ ID NO: 111;
(xxxvi) a heavy chain variable region comprising the CDR-H1 of SEQ ID NO: 36, the CDR-H2 of SEQ ID NO: 74, and the CDR-H3 of SEQ ID NO: 112;
(xxxvii) a heavy chain variable region comprising the CDR-H1 of SEQ ID NO: 37, the CDR-H2 of SEQ ID NO: 75, and the CDR-H3 of SEQ ID NO: 113;
(xxxviii) a heavy chain variable region comprising the CDR-H1 of SEQ ID NO: 38, the CDR-H2 of SEQ ID NO: 76, and the CDR-H3 of SEQ ID NO: 114;
(xxxix) a heavy chain variable region comprising the CDR-H1 of SEQ ID NO: 202, the CDR-H2 of SEQ ID NO: 203, and the CDR-H3 of SEQ ID NO: 204;
(xl) a heavy chain variable region comprising the CDR-H1 of SEQ ID NO: 206, the CDR-H2 of SEQ ID NO: 207, and the CDR-H3 of SEQ ID NO: 208;
(xli) a heavy chain variable region comprising the CDR-H1 of SEQ ID NO: 210, the CDR-H2 of SEQ ID NO: 211, and the CDR-H3 of SEQ ID NO: 212;
(xlii) a heavy chain variable region comprising the CDR-H1 of SEQ ID NO: 214, the CDR-H2 of SEQ ID NO: 215, and the CDR-H3 of SEQ ID NO: 216;
(xliii) a heavy chain variable region comprising the CDR-H1 of SEQ ID NO: 153, the CDR-H2 of SEQ ID NO: 165, and the CDR-H3 of SEQ ID NO: 177;
(xliv) a heavy chain variable region comprising the CDR-H1 of SEQ ID NO: 154, the CDR-H2 of SEQ ID NO: 166, and the CDR-H3 of SEQ ID NO: 178;
(xlv) a heavy chain variable region comprising the CDR-H1 of SEQ ID NO: 155, the CDR-H2 of SEQ ID NO: 167, and the CDR-H3 of SEQ ID NO: 179;
(xlvi) a heavy chain variable region comprising the CDR-H1 of SEQ ID NO: 156, the CDR-H2 of SEQ ID NO: 168, and the CDR-H3 of SEQ ID NO: 180;
(xlvii) a heavy chain variable region comprising the CDR-H1 of SEQ ID NO: 157, the CDR-H2 of SEQ ID NO: 169, and the CDR-H3 of SEQ ID NO: 181;
(xlviii) a heavy chain variable region comprising the CDR-H1 of SEQ ID NO: 158, the CDR-H2 of SEQ ID NO: 170, and the CDR-H3 of SEQ ID NO: 182;
(xlix) a heavy chain variable region comprising the CDR-H1 of SEQ ID NO: 159, the CDR-H2 of SEQ ID NO: 171, and the CDR-H3 of SEQ ID NO: 183;
(l) a heavy chain variable region comprising the CDR-H1 of SEQ ID NO: 160, the CDR-H2 of SEQ ID NO: 172, and the CDR-H3 of SEQ ID NO: 184;
(li) a heavy chain variable region comprising the CDR-H1 of SEQ ID NO: 161, the CDR-H2 of SEQ ID NO: 173, and the CDR-H3 of SEQ ID NO: 185;
(lii) a heavy chain variable region comprising the CDR-H1 of SEQ ID NO: 162, the CDR-H2 of SEQ ID NO: 174, and the CDR-H3 of SEQ ID NO: 186;
(liii) a heavy chain variable region comprising the CDR-H1 of SEQ ID NO: 163, the CDR-H2 of SEQ ID NO: 175, and the CDR-H3 of SEQ ID NO: 187;
(liv) a heavy chain variable region comprising the CDR-H1 of SEQ ID NO: 164, the CDR-H2 of SEQ ID NO: 176, and the CDR-H3 of SEQ ID NO: 188; and
(lv) a heavy chain variable region comprising the CDR-H1 of SEQ ID NO: 307, the CDR-H2 of SEQ ID NO: 308, and the CDR-H3 of SEQ ID NO: 309.

32. A vector comprising the isolated polynucleotide of claim 31.

33. The vector of claim 32, wherein said vector is an adeno-associated viral vector.

34. A host cell comprising the vector of claim 33.

* * * * *

SEQUENCE LISTING

<160> NUMBER OF SEQ ID NOS: 309

<210> SEQ ID NO 1
<211> LENGTH: 12
<212> TYPE: PRT
<213> ORGANISM: Artificial Sequence
<220> FEATURE:
<223> OTHER INFORMATION: antibody sequence

<400> SEQUENCE: 1

Thr Ala Ser Gly Arg Thr Phe Arg Ala Tyr Ala Met
1               5                   10

<210> SEQ ID NO 2
<211> LENGTH: 12
<212> TYPE: PRT
<213> ORGANISM: Artificial Sequence
<220> FEATURE:
<223> OTHER INFORMATION: antibody sequence

<400> SEQUENCE: 2

Ala Ala Ser Gly Arg Ile Phe Ser Ile Trp Thr Met
1               5                   10

<210> SEQ ID NO 3
<211> LENGTH: 12
<212> TYPE: PRT
<213> ORGANISM: Artificial Sequence
<220> FEATURE:
<223> OTHER INFORMATION: antibody sequence

<400> SEQUENCE: 3

Ala Ala Ser Gly Ser Ile Phe Arg Ile Asn Asn Met
1               5                   10

<210> SEQ ID NO 4
<211> LENGTH: 12
<212> TYPE: PRT
<213> ORGANISM: Artificial Sequence
<220> FEATURE:
<223> OTHER INFORMATION: antibody sequence

<400> SEQUENCE: 4

Ala Ala Ser Gly Ser Ile Phe Arg Ile Asn Asn Met
1               5                   10

<210> SEQ ID NO 5
<211> LENGTH: 12
<212> TYPE: PRT
<213> ORGANISM: Artificial Sequence
<220> FEATURE:
<223> OTHER INFORMATION: antibody sequence

<400> SEQUENCE: 5

Ala Ala Ser Gly Arg Thr Phe Ser Asn Tyr Ala Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: antibody sequence

<400> SEQUENCE: 6

Ala Ala Ser Gly Ser Ile Phe Arg Ile Asn Ala Met
1               5                   10

<210> SEQ ID NO 7
<211> LENGTH: 12
<212> TYPE: PRT
<213> ORGANISM: Artificial Sequence
<220> FEATURE:
<223> OTHER INFORMATION: antibody sequence

<400> SEQUENCE: 7

Ala Ala Ser Gly Arg Thr Phe Ser Thr Tyr Arg Met
1               5                   10

<210> SEQ ID NO 8
<211> LENGTH: 12
<212> TYPE: PRT
<213> ORGANISM: Artificial Sequence
<220> FEATURE:
<223> OTHER INFORMATION: antibody sequence

<400> SEQUENCE: 8

Ala Ala Ser Gly Arg Thr Phe Ser Arg Tyr Ala Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: antibody sequence

<400> SEQUENCE: 9

Val Ala Ser Gly Ser Ile Phe Arg Phe Asn Ala Ile
1               5                   10

<210> SEQ ID NO 10
<211> LENGTH: 12
<212> TYPE: PRT
<213> ORGANISM: Artificial Sequence
<220> FEATURE:
<223> OTHER INFORMATION: antibody sequence

<400> SEQUENCE: 10

Ala Ala Ser Gly Ser Ile Phe Arg Ile Asn Gly Met
1               5                   10

<210> SEQ ID NO 11
<211> LENGTH: 11
<212> TYPE: PRT
<213> ORGANISM: Artificial Sequence
<220> FEATURE:
<223> OTHER INFORMATION: antibody sequence

<400> SEQUENCE: 11

Ala Ala Ser Gly Arg Ile Leu Ile Ser Ser Met
1               5                   10

<210> SEQ ID NO 12
<211> LENGTH: 12
<212> TYPE: PRT
<213> ORGANISM: Artificial Sequence
<220> FEATURE:
<223> OTHER INFORMATION: antibody sequence

<400> SEQUENCE: 12

Thr Val Ser Gly Arg Thr Phe Arg Ile Asn Gly Ile
1               5                   10

```
<210> SEQ ID NO 13
<211> LENGTH: 10
<212> TYPE: PRT
<213> ORGANISM: Artificial Sequence
<220> FEATURE:
<223> OTHER INFORMATION: antibody sequence

<400> SEQUENCE: 13

Ala Ala Ser Arg Tyr Ile Phe Gly Thr Met
1               5                   10

<210> SEQ ID NO 14
<211> LENGTH: 12
<212> TYPE: PRT
<213> ORGANISM: Artificial Sequence
<220> FEATURE:
<223> OTHER INFORMATION: antibody sequence

<400> SEQUENCE: 14

Val Ala Ser Gly Ser Arg Phe Ser Ile Asn Thr Met
1               5                   10

<210> SEQ ID NO 15
<211> LENGTH: 12
<212> TYPE: PRT
<213> ORGANISM: Artificial Sequence
<220> FEATURE:
<223> OTHER INFORMATION: antibody sequence

<400> SEQUENCE: 15

Ala Ala Ser Gly Arg Thr Phe Ser Arg Tyr Ala Met
1               5                   10

<210> SEQ ID NO 16
<211> LENGTH: 12
<212> TYPE: PRT
<213> ORGANISM: Artificial Sequence
<220> FEATURE:
<223> OTHER INFORMATION: antibody sequence

<400> SEQUENCE: 16

Ala Ala Ser Gly Arg Thr Leu Ser Ser Tyr Arg Met
1               5                   10

<210> SEQ ID NO 17
<211> LENGTH: 12
<212> TYPE: PRT
<213> ORGANISM: Artificial Sequence
<220> FEATURE:
<223> OTHER INFORMATION: antibody sequence

<400> SEQUENCE: 17

Ala Ala Ser Gly Arg Thr Phe Ser Ser Tyr Ala Met
1               5                   10

<210> SEQ ID NO 18
<211> LENGTH: 12
<212> TYPE: PRT
<213> ORGANISM: Artificial Sequence
<220> FEATURE:
<223> OTHER INFORMATION: antibody sequence

<400> SEQUENCE: 18

Ala Ala Ser Gly Arg Thr Phe Gly Leu Tyr Thr Met
1               5                   10
```

```
<210> SEQ ID NO 19
<211> LENGTH: 12
<212> TYPE: PRT
<213> ORGANISM: Artificial Sequence
<220> FEATURE:
<223> OTHER INFORMATION: antibody sequence

<400> SEQUENCE: 19

Glu Ala Ser Ala Arg Thr Phe Ser Ser Tyr Ala Val
1               5                   10

<210> SEQ ID NO 20
<211> LENGTH: 12
<212> TYPE: PRT
<213> ORGANISM: Artificial Sequence
<220> FEATURE:
<223> OTHER INFORMATION: antibody sequence

<400> SEQUENCE: 20

Ala Ala Ser Gly Arg Ile Phe Ser Ile Trp Thr Met
1               5                   10

<210> SEQ ID NO 21
<211> LENGTH: 12
<212> TYPE: PRT
<213> ORGANISM: Artificial Sequence
<220> FEATURE:
<223> OTHER INFORMATION: antibody sequence

<400> SEQUENCE: 21

Ala Ala Ser Gly Arg Thr Phe Ser Arg Tyr Ala Met
1               5                   10

<210> SEQ ID NO 22
<211> LENGTH: 12
<212> TYPE: PRT
<213> ORGANISM: Artificial Sequence
<220> FEATURE:
<223> OTHER INFORMATION: antibody sequence

<400> SEQUENCE: 22

Ala Ala Ser Gly Arg Ser Phe Ser Trp Leu Thr Met
1               5                   10

<210> SEQ ID NO 23
<211> LENGTH: 12
<212> TYPE: PRT
<213> ORGANISM: Artificial Sequence
<220> FEATURE:
<223> OTHER INFORMATION: antibody sequence

<400> SEQUENCE: 23

Val Ala Ser Gly Ser Ile Phe Arg Phe Asn Ala Ile
1               5                   10

<210> SEQ ID NO 24
<211> LENGTH: 10
<212> TYPE: PRT
<213> ORGANISM: Artificial Sequence
<220> FEATURE:
<223> OTHER INFORMATION: antibody sequence

<400> SEQUENCE: 24

Ala Ala Ser Arg Tyr Ile Phe Gly Thr Met
1               5                   10

<210> SEQ ID NO 25
```

```
<211> LENGTH: 12
<212> TYPE: PRT
<213> ORGANISM: Artificial Sequence
<220> FEATURE:
<223> OTHER INFORMATION: antibody sequence

<400> SEQUENCE: 25

Ala Ala Ser Gly Arg Thr Phe Arg Leu Tyr Ser Met
1               5                   10

<210> SEQ ID NO 26
<211> LENGTH: 12
<212> TYPE: PRT
<213> ORGANISM: Artificial Sequence
<220> FEATURE:
<223> OTHER INFORMATION: antibody sequence

<400> SEQUENCE: 26

Ala Ala Ser Gly Ser Ile Gly Ser Phe Lys Thr Met
1               5                   10

<210> SEQ ID NO 27
<211> LENGTH: 12
<212> TYPE: PRT
<213> ORGANISM: Artificial Sequence
<220> FEATURE:
<223> OTHER INFORMATION: antibody sequence

<400> SEQUENCE: 27

Val Ala Ser Gly Arg Thr Phe Ser Arg Tyr Gly Met
1               5                   10

<210> SEQ ID NO 28
<211> LENGTH: 10
<212> TYPE: PRT
<213> ORGANISM: Artificial Sequence
<220> FEATURE:
<223> OTHER INFORMATION: antibody sequence

<400> SEQUENCE: 28

Ala Ala Ser Arg Tyr Ile Phe Gly Thr Met
1               5                   10

<210> SEQ ID NO 29
<211> LENGTH: 12
<212> TYPE: PRT
<213> ORGANISM: Artificial Sequence
<220> FEATURE:
<223> OTHER INFORMATION: antibody sequence

<400> SEQUENCE: 29

Ala Ala Ser Gly Thr Ile Phe Thr Met Lys Asn Met
1               5                   10

<210> SEQ ID NO 30
<211> LENGTH: 12
<212> TYPE: PRT
<213> ORGANISM: Artificial Sequence
<220> FEATURE:
<223> OTHER INFORMATION: antibody sequence

<400> SEQUENCE: 30

Ala Ala Ser Gly Arg Thr Phe Ser Ser Tyr Ala Met
1               5                   10

<210> SEQ ID NO 31
<211> LENGTH: 12
```

```
<212> TYPE: PRT
<213> ORGANISM: Artificial Sequence
<220> FEATURE:
<223> OTHER INFORMATION: antibody sequence

<400> SEQUENCE: 31

Ala Phe Ser Gly Arg Thr Phe Gly Leu Arg Thr Met
1               5                   10

<210> SEQ ID NO 32
<211> LENGTH: 12
<212> TYPE: PRT
<213> ORGANISM: Artificial Sequence
<220> FEATURE:
<223> OTHER INFORMATION: antibody sequence

<400> SEQUENCE: 32

Ala Ala Ser Trp Arg Ile Phe Ser Pro Asn Ala Met
1               5                   10

<210> SEQ ID NO 33
<211> LENGTH: 10
<212> TYPE: PRT
<213> ORGANISM: Artificial Sequence
<220> FEATURE:
<223> OTHER INFORMATION: antibody sequence

<400> SEQUENCE: 33

Ala Ala Ser Arg Tyr Ile Phe Gly Thr Met
1               5                   10

<210> SEQ ID NO 34
<211> LENGTH: 12
<212> TYPE: PRT
<213> ORGANISM: Artificial Sequence
<220> FEATURE:
<223> OTHER INFORMATION: antibody sequence

<400> SEQUENCE: 34

Ala Ala Ser Gly Arg Phe Phe Arg Ile Asn Ala Met
1               5                   10

<210> SEQ ID NO 35
<211> LENGTH: 12
<212> TYPE: PRT
<213> ORGANISM: Artificial Sequence
<220> FEATURE:
<223> OTHER INFORMATION: antibody sequence

<400> SEQUENCE: 35

Ala Ala Ser Gly Ser Phe Phe Arg Ile Asn Thr Met
1               5                   10

<210> SEQ ID NO 36
<211> LENGTH: 12
<212> TYPE: PRT
<213> ORGANISM: Artificial Sequence
<220> FEATURE:
<223> OTHER INFORMATION: antibody sequence

<400> SEQUENCE: 36

Ala Ala Ser Gly Arg Thr Phe Ser Arg Tyr Pro Met
1               5                   10

<210> SEQ ID NO 37
<211> LENGTH: 12
<212> TYPE: PRT
```

```
<213> ORGANISM: Artificial Sequence
<220> FEATURE:
<223> OTHER INFORMATION: antibody sequence

<400> SEQUENCE: 37

Ala Ala Ser Gly Arg Thr Phe Ser Trp Tyr Ala Met
1               5                   10

<210> SEQ ID NO 38
<211> LENGTH: 12
<212> TYPE: PRT
<213> ORGANISM: Artificial Sequence
<220> FEATURE:
<223> OTHER INFORMATION: antibody sequence

<400> SEQUENCE: 38

Val Val Ser Gly Arg Thr Phe Ser Thr Ser Gln Met
1               5                   10

<210> SEQ ID NO 39
<211> LENGTH: 11
<212> TYPE: PRT
<213> ORGANISM: Artificial Sequence
<220> FEATURE:
<223> OTHER INFORMATION: antibody sequence

<400> SEQUENCE: 39

Ala Ile Ser Arg Thr Gly Gly Val Thr Thr Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: antibody sequence

<400> SEQUENCE: 40

Ala Ile Thr Ser Val Gly Asn Thr Asp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: antibody sequence

<400> SEQUENCE: 41

Thr Ile Thr Arg Gly Gly Asn Thr Asn Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: antibody sequence

<400> SEQUENCE: 42

Thr Ile Thr Arg Gly Gly Asn Thr Asn Tyr
1               5                   10

<210> SEQ ID NO 43
<211> LENGTH: 11
<212> TYPE: PRT
<213> ORGANISM: Artificial Sequence
```

```
<220> FEATURE:
<223> OTHER INFORMATION: antibody sequence

<400> SEQUENCE: 43

Ser Ile Ser Trp Ser Gly Gly Val Leu Tyr Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: antibody sequence

<400> SEQUENCE: 44

Arg Ile Asn Thr Gly Gly Asn Thr Asn Tyr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: antibody sequence

<400> SEQUENCE: 45

Ala Ile Arg Trp Ser Thr Ser Tyr
1               5

<210> SEQ ID NO 46
<211> LENGTH: 9
<212> TYPE: PRT
<213> ORGANISM: Artificial Sequence
<220> FEATURE:
<223> OTHER INFORMATION: antibody sequence

<400> SEQUENCE: 46

Gly Ile Ser Trp Ser Gly Thr Ser Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: antibody sequence

<400> SEQUENCE: 47

Arg Ile Arg Arg Leu Gly Ser Thr Ser Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: antibody sequence

<400> SEQUENCE: 48

Thr Ile Thr Arg Gly Gly Ser Thr Asn Tyr
1               5                   10

<210> SEQ ID NO 49
<211> LENGTH: 10
<212> TYPE: PRT
<213> ORGANISM: Artificial Sequence
<220> FEATURE:
```

<223> OTHER INFORMATION: antibody sequence

<400> SEQUENCE: 49

Thr Ile Thr Arg Gly Gly Thr Thr Asn Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: antibody sequence

<400> SEQUENCE: 50

Gly Ile Ser Ser Thr Gly Ser Thr Asn Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: antibody sequence

<400> SEQUENCE: 51

Ser Ile Ser Arg Gly Gly Ser Thr Asn Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: antibody sequence

<400> SEQUENCE: 52

Gly Ile Thr Arg Gly Gly Ser Thr Asn Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: antibody sequence

<400> SEQUENCE: 53

Arg Ile Ser Trp Ser Gly Gly Trp Thr Tyr Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: antibody sequence

<400> SEQUENCE: 54

Ala Ile Asn Trp Arg Gly Ser Trp Thr Tyr Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: antibody sequence

<400> SEQUENCE: 55

Ala Ile Ser Arg Ser Gly Gly Ile Thr Ser Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: antibody sequence

<400> SEQUENCE: 56

Ala Ile Ser Trp Arg Gly Leu Ser Ile Met Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: antibody sequence

<400> SEQUENCE: 57

Ala Ile Asn Trp Ser Gly Arg Arg Thr Asn Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: antibody sequence

<400> SEQUENCE: 58

Ala Ile Thr Ser Gly Gly Ser Thr Asn Tyr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: antibody sequence

<400> SEQUENCE: 59

Ala Ile Thr Trp Ser Gly Gly Ile Ile Tyr Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: antibody sequence

<400> SEQUENCE: 60

Arg Ile Thr Trp Arg Gly Thr Pro Tyr Tyr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: antibody sequence

<400> SEQUENCE: 61

Arg Ile Arg Arg Leu Gly Ser Thr Ser Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: antibody sequence

<400> SEQUENCE: 62

Ser Ile Ser Arg Gly Gly Ser Thr Asn Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: antibody sequence

<400> SEQUENCE: 63

Ser Ile Arg Trp Asn Gly Gly Asn Ile Tyr Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: antibody sequence

<400> SEQUENCE: 64

Thr Ile Thr Arg Trp Gly Phe Thr Asn Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: antibody sequence

<400> SEQUENCE: 65

Ala Ile Ser Arg Ser Gly Ala Ile Ser Tyr Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: antibody sequence

<400> SEQUENCE: 66

Ser Ile Ser Arg Gly Gly Ser Thr Asn Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: antibody sequence

<400> SEQUENCE: 67

```
Ala Ile Ser Thr Ser Gly Gly Val Thr Trp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: antibody sequence

<400> SEQUENCE: 68

Ala Ile Asn Trp Ser Gly His Ser Thr Tyr Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: antibody sequence

<400> SEQUENCE: 69

Ser Leu Thr Trp Arg Asp Asn Asn Ala Tyr Tyr
1               5                   10

<210> SEQ ID NO 70
<211> LENGTH: 10
<212> TYPE: PRT
<213> ORGANISM: Artificial Sequence
<220> FEATURE:
<223> OTHER INFORMATION: antibody sequence

<400> SEQUENCE: 70

Arg Ile Thr Trp Ala Gly Ile Thr Asn Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: antibody sequence

<400> SEQUENCE: 71

Ser Ile Ser Arg Gly Gly Ser Thr Asn Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: antibody sequence

<400> SEQUENCE: 72

Thr Ile Thr Arg Ala Gly Thr Thr Thr Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: antibody sequence

<400> SEQUENCE: 73
```

```
Ser Ile Thr Arg Gly Gly Ser Thr Asn Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: antibody sequence

<400> SEQUENCE: 74

Arg Phe Gly Trp Ser Gly Leu Ser Thr Tyr Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: antibody sequence

<400> SEQUENCE: 75

Ala Ile Arg Arg Ser Gly Gly Ile Thr Ile Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: antibody sequence

<400> SEQUENCE: 76

Arg Ile Ser Trp Arg Gly Lys Gln His Tyr
1               5                   10

<210> SEQ ID NO 77
<211> LENGTH: 9
<212> TYPE: PRT
<213> ORGANISM: Artificial Sequence
<220> FEATURE:
<223> OTHER INFORMATION: antibody sequence

<400> SEQUENCE: 77

Ala Tyr Phe Arg Trp Gly Thr Arg Tyr
1               5

<210> SEQ ID NO 78
<211> LENGTH: 16
<212> TYPE: PRT
<213> ORGANISM: Artificial Sequence
<220> FEATURE:
<223> OTHER INFORMATION: antibody sequence

<400> SEQUENCE: 78

Val Glu Ser Arg Arg Gly Ile Gly Phe Leu Arg Lys Thr Tyr Ser Tyr
1               5                   10                  15

<210> SEQ ID NO 79
<211> LENGTH: 8
<212> TYPE: PRT
<213> ORGANISM: Artificial Sequence
<220> FEATURE:
<223> OTHER INFORMATION: antibody sequence

<400> SEQUENCE: 79

Ala Asn Tyr Leu Ile Arg Ser Tyr
```

```
1               5
```

<210> SEQ ID NO 80
<211> LENGTH: 11
<212> TYPE: PRT
<213> ORGANISM: Artificial Sequence
<220> FEATURE:
<223> OTHER INFORMATION: antibody sequence

<400> SEQUENCE: 80

```
Val Lys Lys His Phe Gly Ile Arg Tyr Asp Tyr
1               5                   10
```

<210> SEQ ID NO 81
<211> LENGTH: 18
<212> TYPE: PRT
<213> ORGANISM: Artificial Sequence
<220> FEATURE:
<223> OTHER INFORMATION: antibody sequence

<400> SEQUENCE: 81

```
Ala Asn Ala Gly Leu Ser Leu Leu Arg Asn Trp Arg Thr Asn Glu Tyr
1               5                   10                  15

Ala Tyr
```

<210> SEQ ID NO 82
<211> LENGTH: 8
<212> TYPE: PRT
<213> ORGANISM: Artificial Sequence
<220> FEATURE:
<223> OTHER INFORMATION: antibody sequence

<400> SEQUENCE: 82

```
Val Gln Arg Phe Ile Thr Thr Tyr
1               5
```

<210> SEQ ID NO 83
<211> LENGTH: 14
<212> TYPE: PRT
<213> ORGANISM: Artificial Sequence
<220> FEATURE:
<223> OTHER INFORMATION: antibody sequence

<400> SEQUENCE: 83

```
Thr Gly Arg Ala Trp Ser Thr Leu Ala Thr Thr Tyr Val Tyr
1               5                   10
```

<210> SEQ ID NO 84
<211> LENGTH: 13
<212> TYPE: PRT
<213> ORGANISM: Artificial Sequence
<220> FEATURE:
<223> OTHER INFORMATION: antibody sequence

<400> SEQUENCE: 84

```
Asn Phe Lys Tyr Arg Tyr Gly Leu Gly Pro Arg Asp Tyr
1               5                   10
```

<210> SEQ ID NO 85
<211> LENGTH: 10
<212> TYPE: PRT
<213> ORGANISM: Artificial Sequence
<220> FEATURE:
<223> OTHER INFORMATION: antibody sequence

<400> SEQUENCE: 85

Ala Asp Thr His Phe Ser Thr Arg Asn Tyr
1               5                   10

<210> SEQ ID NO 86
<211> LENGTH: 16
<212> TYPE: PRT
<213> ORGANISM: Artificial Sequence
<220> FEATURE:
<223> OTHER INFORMATION: antibody sequence

<400> SEQUENCE: 86

Ala Asp Pro Arg Trp Arg Leu Pro Phe Pro Gly Tyr Gly Met Asp Tyr
1               5                   10                  15

<210> SEQ ID NO 87
<211> LENGTH: 13
<212> TYPE: PRT
<213> ORGANISM: Artificial Sequence
<220> FEATURE:
<223> OTHER INFORMATION: antibody sequence

<400> SEQUENCE: 87

Arg Val Tyr Gly Arg Val Trp Ser Arg Pro Tyr Asp Tyr
1               5                   10

<210> SEQ ID NO 88
<211> LENGTH: 17
<212> TYPE: PRT
<213> ORGANISM: Artificial Sequence
<220> FEATURE:
<223> OTHER INFORMATION: antibody sequence

<400> SEQUENCE: 88

Ala Ser Arg Gly Leu Ser Gly Ser Trp Tyr Leu Arg Ser Ser Tyr Pro
1               5                   10                  15

Tyr

<210> SEQ ID NO 89
<211> LENGTH: 15
<212> TYPE: PRT
<213> ORGANISM: Artificial Sequence
<220> FEATURE:
<223> OTHER INFORMATION: antibody sequence

<400> SEQUENCE: 89

Ala Val Pro Tyr Arg Trp Gly Ser Ser Trp Tyr Ala Gly Arg Tyr
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: antibody sequence

<400> SEQUENCE: 90

Ala Thr Leu Arg Ala Trp Ala Leu Thr Phe Ala Thr Ser Tyr Ala Tyr
1               5                   10                  15

<210> SEQ ID NO 91
<211> LENGTH: 13
<212> TYPE: PRT
<213> ORGANISM: Artificial Sequence
<220> FEATURE:
<223> OTHER INFORMATION: antibody sequence

<400> SEQUENCE: 91

```
Ala Gly Ser Arg Ala Val Leu Phe Gly Thr Tyr Asp Tyr
1               5                   10

<210> SEQ ID NO 92
<211> LENGTH: 16
<212> TYPE: PRT
<213> ORGANISM: Artificial Sequence
<220> FEATURE:
<223> OTHER INFORMATION: antibody sequence

<400> SEQUENCE: 92

Arg Pro Thr Ala Arg Trp Asp Leu Phe Arg Glu Lys Tyr Asp Phe Arg
1               5                   10                  15

<210> SEQ ID NO 93
<211> LENGTH: 8
<212> TYPE: PRT
<213> ORGANISM: Artificial Sequence
<220> FEATURE:
<223> OTHER INFORMATION: antibody sequence

<400> SEQUENCE: 93

Val Gln Arg Phe Ile Thr Thr Tyr
1               5

<210> SEQ ID NO 94
<211> LENGTH: 18
<212> TYPE: PRT
<213> ORGANISM: Artificial Sequence
<220> FEATURE:
<223> OTHER INFORMATION: antibody sequence

<400> SEQUENCE: 94

Ala Asn Ala Gly Leu Ser Leu Leu Arg Asn Trp Arg Thr Asn Glu Tyr
1               5                   10                  15

Ala Tyr

<210> SEQ ID NO 95
<211> LENGTH: 18
<212> TYPE: PRT
<213> ORGANISM: Artificial Sequence
<220> FEATURE:
<223> OTHER INFORMATION: antibody sequence

<400> SEQUENCE: 95

Ala Arg Ser Ser Leu Leu Glu Phe Trp Leu Gly Ser Arg Arg Gly Tyr
1               5                   10                  15

Asp Tyr

<210> SEQ ID NO 96
<211> LENGTH: 14
<212> TYPE: PRT
<213> ORGANISM: Artificial Sequence
<220> FEATURE:
<223> OTHER INFORMATION: antibody sequence

<400> SEQUENCE: 96

Ala Asp Ile Arg Pro Arg Ile Ile Ser Phe Phe Lys Asp Tyr
1               5                   10

<210> SEQ ID NO 97
<211> LENGTH: 9
<212> TYPE: PRT
<213> ORGANISM: Artificial Sequence
<220> FEATURE:
```

<223> OTHER INFORMATION: antibody sequence

<400> SEQUENCE: 97

Ala Tyr Phe Arg Trp Gly Thr Arg Tyr
1               5

<210> SEQ ID NO 98
<211> LENGTH: 14
<212> TYPE: PRT
<213> ORGANISM: Artificial Sequence
<220> FEATURE:
<223> OTHER INFORMATION: antibody sequence

<400> SEQUENCE: 98

Ala Ala Lys Gln Ile Leu Ile Arg Pro Asp Ala Tyr Val Tyr
1               5                   10

<210> SEQ ID NO 99
<211> LENGTH: 14
<212> TYPE: PRT
<213> ORGANISM: Artificial Sequence
<220> FEATURE:
<223> OTHER INFORMATION: antibody sequence

<400> SEQUENCE: 99

Ala Gly Arg His Pro His Phe Ser Met Asp Tyr Pro Asp Leu
1               5                   10

<210> SEQ ID NO 100
<211> LENGTH: 18
<212> TYPE: PRT
<213> ORGANISM: Artificial Sequence
<220> FEATURE:
<223> OTHER INFORMATION: antibody sequence

<400> SEQUENCE: 100

Leu Ala Leu Gly Phe Phe Thr Asn Tyr Tyr Val Arg Glu Ser Ser Tyr
1               5                   10                  15

Arg Tyr

<210> SEQ ID NO 101
<211> LENGTH: 14
<212> TYPE: PRT
<213> ORGANISM: Artificial Sequence
<220> FEATURE:
<223> OTHER INFORMATION: antibody sequence

<400> SEQUENCE: 101

Ala Gly Pro Arg Ile Ala Val Trp Arg Tyr Glu Tyr Asn Tyr
1               5                   10

<210> SEQ ID NO 102
<211> LENGTH: 16
<212> TYPE: PRT
<213> ORGANISM: Artificial Sequence
<220> FEATURE:
<223> OTHER INFORMATION: antibody sequence

<400> SEQUENCE: 102

Ala Ala Gln Gly Gly Phe Met Lys Pro Arg Ala Asn Trp Tyr Asn Ser
1               5                   10                  15

<210> SEQ ID NO 103
<211> LENGTH: 15
<212> TYPE: PRT
<213> ORGANISM: Artificial Sequence

```
<220> FEATURE:
<223> OTHER INFORMATION: antibody sequence

<400> SEQUENCE: 103

Ala Ser Ser Arg Arg Leu Leu Gly Gly Pro Phe Ala Tyr Asp Tyr
1               5                   10                  15

<210> SEQ ID NO 104
<211> LENGTH: 8
<212> TYPE: PRT
<213> ORGANISM: Artificial Sequence
<220> FEATURE:
<223> OTHER INFORMATION: antibody sequence

<400> SEQUENCE: 104

Ala Asn Arg Arg Gly Trp Asn Tyr
1               5

<210> SEQ ID NO 105
<211> LENGTH: 15
<212> TYPE: PRT
<213> ORGANISM: Artificial Sequence
<220> FEATURE:
<223> OTHER INFORMATION: antibody sequence

<400> SEQUENCE: 105

Val Arg Ser Gly Pro Arg Ile Ile Pro Gln Leu Arg Arg Glu Tyr
1               5                   10                  15

<210> SEQ ID NO 106
<211> LENGTH: 8
<212> TYPE: PRT
<213> ORGANISM: Artificial Sequence
<220> FEATURE:
<223> OTHER INFORMATION: antibody sequence

<400> SEQUENCE: 106

Leu Thr Arg Leu Leu Asn Thr Tyr
1               5

<210> SEQ ID NO 107
<211> LENGTH: 10
<212> TYPE: PRT
<213> ORGANISM: Artificial Sequence
<220> FEATURE:
<223> OTHER INFORMATION: antibody sequence

<400> SEQUENCE: 107

Val His Leu Val Phe Thr Asn Arg Asp Tyr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: antibody sequence

<400> SEQUENCE: 108

Ala Asp Arg Arg Ser Ser Tyr Leu Gly Pro Arg Phe Asp Tyr
1               5                   10

<210> SEQ ID NO 109
<211> LENGTH: 18
<212> TYPE: PRT
<213> ORGANISM: Artificial Sequence
<220> FEATURE:
```

<223> OTHER INFORMATION: antibody sequence

<400> SEQUENCE: 109

```
Ala Arg Ser Ser Leu Leu Glu Phe Trp Leu Gly Ser Arg Arg Gly Tyr
1               5                   10                  15

Asp Tyr
```

<210> SEQ ID NO 110
<211> LENGTH: 14
<212> TYPE: PRT
<213> ORGANISM: Artificial Sequence
<220> FEATURE:
<223> OTHER INFORMATION: antibody sequence

<400> SEQUENCE: 110

```
Lys Tyr Pro Thr Ile Thr Trp Tyr Gly Arg His Asp Tyr Arg
1               5                   10
```

<210> SEQ ID NO 111
<211> LENGTH: 16
<212> TYPE: PRT
<213> ORGANISM: Artificial Sequence
<220> FEATURE:
<223> OTHER INFORMATION: antibody sequence

<400> SEQUENCE: 111

```
Ala Ser Arg Phe Gly Ile Asn Tyr Tyr Thr Ala Arg Gln Tyr Gly Tyr
1               5                   10                  15
```

<210> SEQ ID NO 112
<211> LENGTH: 10
<212> TYPE: PRT
<213> ORGANISM: Artificial Sequence
<220> FEATURE:
<223> OTHER INFORMATION: antibody sequence

<400> SEQUENCE: 112

```
Ala Gly Arg Phe Met Gly Ser Tyr Asp Tyr
1               5                   10
```

<210> SEQ ID NO 113
<211> LENGTH: 17
<212> TYPE: PRT
<213> ORGANISM: Artificial Sequence
<220> FEATURE:
<223> OTHER INFORMATION: antibody sequence

<400> SEQUENCE: 113

```
Ala Asn Leu Phe Gln Trp Arg Leu Asn Asp Asn Gly Asn Gln Tyr Gly
1               5                   10                  15

Ser
```

<210> SEQ ID NO 114
<211> LENGTH: 13
<212> TYPE: PRT
<213> ORGANISM: Artificial Sequence
<220> FEATURE:
<223> OTHER INFORMATION: antibody sequence

<400> SEQUENCE: 114

```
Ala Gly Pro Arg Ala Val Leu Phe Gly Thr Tyr Asp Tyr
1               5                   10
```

<210> SEQ ID NO 115
<211> LENGTH: 117

```
<212> TYPE: PRT
<213> ORGANISM: Artificial Sequence
<220> FEATURE:
<223> OTHER INFORMATION: antibody sequence

<400> SEQUENCE: 115
```

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Phe Arg Ala Tyr
            20                  25                  30

Ala Met Gly Trp Phe Arg Gln Ala Pro Gly Lys Glu Arg Glu Leu Val
        35                  40                  45

Ala Ala Ile Ser Arg Thr Gly Val Thr Thr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Thr Glu Asp Thr Ala Val Tyr Tyr Cys
                85                  90                  95

Asn Ala Tyr Phe Arg Trp Gly Thr Arg Tyr Trp Gly Gln Gly Thr Gln
            100                 105                 110

Val Thr Val Ser Ser
        115

```
<210> SEQ ID NO 116
<211> LENGTH: 123
<212> TYPE: PRT
<213> ORGANISM: Artificial Sequence
<220> FEATURE:
<223> OTHER INFORMATION: antibody sequence

<400> SEQUENCE: 116
```

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Ile Trp
            20                  25                  30

Thr Met Gly Trp Tyr Arg Gln Ala Pro Gly Lys Gln Arg Glu Leu Val
        35                  40                  45

Ala Ala Ile Thr Ser Val Gly Asn Thr Asp Tyr Ala Asp Ser Val Lys
    50                  55                  60

Gly Arg Phe Thr Ile Ser Arg Glu Thr Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Val Glu Ser Arg Arg Gly Ile Gly Phe Leu Arg Lys Thr Tyr Ser Tyr
            100                 105                 110

Trp Gly Gln Gly Thr Gln Val Thr Val Ser Ser
        115                 120

```
<210> SEQ ID NO 117
<211> LENGTH: 115
<212> TYPE: PRT
<213> ORGANISM: Artificial Sequence
<220> FEATURE:
<223> OTHER INFORMATION: antibody sequence

<400> SEQUENCE: 117
```

Gln Val Gln Leu Gln Glu Ser Gly Gly Gly Leu Val Gln Pro Gly Gly
1               5                   10                  15

Ser Leu Thr Leu Ser Cys Ala Ala Ser Gly Ser Ile Phe Arg Ile Asn

```
            20                  25                  30
Asn Met Gly Trp Phe Arg Gln Ala Pro Gly Lys Gln Arg Glu Leu Val
            35                  40                  45

Ala Thr Ile Thr Arg Gly Gly Asn Thr Asn Tyr Ala Asp Ser Val Lys
        50                  55                  60

Gly Arg Phe Thr Ile Ser Arg Asp Asn Ala Lys Thr Leu Tyr Leu
65                  70                  75                  80

Gln Met Asn Ser Leu Lys Pro Glu Asp Thr Ala Val Tyr Tyr Cys Asn
                85                  90                  95

Ala Asn Tyr Leu Ile Arg Ser Tyr Trp Gly Gln Gly Thr Gln Val Thr
                100                 105                 110

Val Ser Ser
        115

<210> SEQ ID NO 118
<211> LENGTH: 118
<212> TYPE: PRT
<213> ORGANISM: Artificial Sequence
<220> FEATURE:
<223> OTHER INFORMATION: antibody sequence

<400> SEQUENCE: 118

Gln Val Gln Leu Gln Glu Ser Gly Gly Gly Leu Val Gln Pro Gly Gly
1               5                   10                  15

Ser Leu Thr Leu Ser Cys Ala Ala Ser Gly Ser Ile Phe Arg Ile Asn
            20                  25                  30

Asn Met Gly Trp Phe Arg Gln Ala Pro Gly Lys Gln Arg Glu Leu Val
            35                  40                  45

Ala Thr Ile Thr Arg Gly Gly Asn Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Ala Val Tyr Tyr Cys Asn
                85                  90                  95

Val Lys Lys His Phe Gly Ile Arg Tyr Asp Tyr Trp Gly Gln Gly Thr
                100                 105                 110

Gln Val Thr Val Ser Ser
        115

<210> SEQ ID NO 119
<211> LENGTH: 126
<212> TYPE: PRT
<213> ORGANISM: Artificial Sequence
<220> FEATURE:
<223> OTHER INFORMATION: antibody sequence

<400> SEQUENCE: 119

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Leu Ala Trp Phe Arg Gln Ala Pro Gly Leu Glu Arg Glu Phe Val
            35                  40                  45

Ser Ser Ile Ser Trp Ser Gly Gly Val Leu Tyr Tyr Ala Asp Ser Val
        50                  55                  60

Lys Gly Arg Phe Thr Met Ser Arg Asp Asn Gly Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Asn Ala Gly Leu Ser Leu Leu Arg Asn Trp Arg Thr Asn Glu
            100                 105                 110

Tyr Ala Tyr Trp Gly Gln Gly Thr Gln Val Thr Val Ser Ser
        115                 120                 125

<210> SEQ ID NO 120
<211> LENGTH: 115
<212> TYPE: PRT
<213> ORGANISM: Artificial Sequence
<220> FEATURE:
<223> OTHER INFORMATION: antibody sequence

<400> SEQUENCE: 120

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Ala Met Ala Trp Tyr Arg Gln Ala Pro Gly Lys Gln Arg Glu Leu Val
            35                  40                  45

Ala Arg Ile Asn Thr Gly Gly Asn Thr Asn Tyr Ala Gly Ser Val Lys
        50                  55                  60

Gly Arg Phe Thr Ile Ser Arg Asp Asn Gly Lys Asn Thr Val Tyr Leu
65                  70                  75                  80

Gln Met Asn Ser Leu Lys Pro Glu Asp Thr Gly Val Tyr Tyr Cys Asn
                85                  90                  95

Val Gln Arg Phe Ile Thr Thr Tyr Trp Gly Gln Gly Thr Gln Val Thr
            100                 105                 110

Val Ser Ser
        115

<210> SEQ ID NO 121
<211> LENGTH: 119
<212> TYPE: PRT
<213> ORGANISM: Artificial Sequence
<220> FEATURE:
<223> OTHER INFORMATION: antibody sequence

<400> SEQUENCE: 121

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Arg Met Gly Trp Phe Arg Gln Ala Pro Gly Lys Glu Arg Glu Phe Val
            35                  40                  45

Ala Ala Ile Arg Trp Ser Thr Ser Tyr Ala Asp Ser Val Lys Gly Arg
        50                  55                  60

Phe Ile Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Thr Gly
                85                  90                  95

Arg Ala Trp Ser Thr Leu Ala Thr Thr Tyr Val Tyr Trp Gly Gln Gly
            100                 105                 110

Thr Gln Val Thr Val Ser Ser
        115

<210> SEQ ID NO 122
```

```
<211> LENGTH: 119
<212> TYPE: PRT
<213> ORGANISM: Artificial Sequence
<220> FEATURE:
<223> OTHER INFORMATION: antibody sequence

<400> SEQUENCE: 122

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ala Thr Ala Trp Phe Arg Gln Ala Pro Gly Lys Glu Arg Glu Phe Val
        35                  40                  45

Ala Gly Ile Ser Trp Ser Gly Thr Ser Tyr Ala Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Ser Leu Lys Ser Glu Asp Thr Ala Val Tyr Tyr Cys Ala Asn
                85                  90                  95

Phe Lys Tyr Arg Tyr Gly Leu Gly Pro Arg Asp Tyr Trp Gly Gln Gly
            100                 105                 110

Thr Leu Val Thr Val Ser Ser
        115

<210> SEQ ID NO 123
<211> LENGTH: 117
<212> TYPE: PRT
<213> ORGANISM: Artificial Sequence
<220> FEATURE:
<223> OTHER INFORMATION: antibody sequence

<400> SEQUENCE: 123

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Ile Phe Arg Phe Asn
            20                  25                  30

Ala Ile Gly Trp Tyr Arg Gln Ala Pro Gly Lys Glu Arg Glu Leu Val
        35                  40                  45

Ala Arg Ile Arg Arg Leu Gly Ser Thr Ser Tyr Ala Asp Ser Val Lys
    50                  55                  60

Gly Arg Phe Ser Ile Ser Arg Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Thr His Phe Ser Thr Arg Asn Tyr Trp Gly Gln Gly Thr Gln
            100                 105                 110

Val Thr Val Ser Ser
        115

<210> SEQ ID NO 124
<211> LENGTH: 123
<212> TYPE: PRT
<213> ORGANISM: Artificial Sequence
<220> FEATURE:
<223> OTHER INFORMATION: antibody sequence

<400> SEQUENCE: 124

Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Ser Ile Phe Arg Ile Asn
                20                  25                  30

Gly Met Gly Trp His Arg Gln Ala Pro Gly Lys Glu Arg Glu Leu Val
            35                  40                  45

Ala Thr Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                85                  90                  95

Ala Asp Pro Arg Trp Arg Leu Pro Phe Pro Gly Tyr Gly Met Asp Tyr
            100                 105                 110

Trp Gly Lys Gly Thr Gln Val Thr Val Ser Ser
            115                 120

<210> SEQ ID NO 125
<211> LENGTH: 119
<212> TYPE: PRT
<213> ORGANISM: Artificial Sequence
<220> FEATURE:
<223> OTHER INFORMATION: antibody sequence

<400> SEQUENCE: 125

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Arg Ile Leu Ile Ser Ser
                20                  25                  30

Met Gly Trp Tyr Arg Gln Ala Gln Gly Glu Gln Arg Glu Leu Val Ala
            35                  40                  45

Thr Ile Thr Arg Gly Gly Thr Thr Asn Tyr Ala Asp Ser Val Lys Gly
 50                  55                  60

Arg Phe Thr Ile Ser Arg Asp Asn Ala Lys Asn Met Val Tyr Leu Gln
 65                  70                  75                  80

Met Asn Lys Leu Lys Ser Glu Asp Thr Ala Val Tyr Tyr Cys Ala Arg
                85                  90                  95

Val Tyr Gly Arg Val Trp Ser Arg Pro Tyr Asp Tyr Trp Gly Gln Gly
            100                 105                 110

Thr Gln Val Thr Val Ser Ser
            115

<210> SEQ ID NO 126
<211> LENGTH: 124
<212> TYPE: PRT
<213> ORGANISM: Artificial Sequence
<220> FEATURE:
<223> OTHER INFORMATION: antibody sequence

<400> SEQUENCE: 126

Gln Val Gln Leu Gln Glu Ser Gly Gly Gly Phe Val Gln Ala Gly Gly
 1               5                  10                  15

Ser Leu Arg Leu Ser Cys Thr Val Ser Gly Arg Thr Phe Arg Ile Asn
                20                  25                  30

Gly Ile Asp Trp Tyr Arg Gln Ala Pro Gly Lys Gln Arg Glu Leu Val
            35                  40                  45

Ala Gly Ile Ser Ser Thr Gly Ser Thr Asn Tyr Ala Asp Ser Val Lys
 50                  55                  60

Gly Arg Phe Thr Ile Ser Arg Asp Asn Ala Gly Asn Ala Val Tyr Leu
 65                  70                  75                  80

Gln Met Asn Asn Leu Lys Pro Glu Asp Thr Gly Arg Tyr Tyr Cys Ala
                85                  90                  95

Ala Ser Arg Gly Leu Ser Gly Ser Trp Tyr Leu Arg Ser Ser Tyr Pro
            100                 105                 110

Tyr Trp Gly Gln Gly Thr Gln Val Thr Val Ser Ser
            115                 120

<210> SEQ ID NO 127
<211> LENGTH: 120
<212> TYPE: PRT
<213> ORGANISM: Artificial Sequence
<220> FEATURE:
<223> OTHER INFORMATION: antibody sequence

<400> SEQUENCE: 127

Gln Val Gln Leu Gln Glu Ser Gly Gly Gly Leu Val Gln Pro Gly Gly
1               5                   10                  15

Ser Leu Arg Leu Ser Cys Ala Ala Ser Arg Tyr Ile Phe Gly Thr Met
            20                  25                  30

Gly Trp Tyr Arg Gln Ala Pro Gly Leu Gln Arg Glu Leu Val Ala Ser
            35                  40                  45

Ile Ser Arg Gly Gly Ser Thr Asn Tyr Ala Asp Ser Val Lys Gly Arg
50                  55                  60

Phe Ala Ile Ser Arg Asp Asn Ala Lys Lys Thr Val Tyr Leu Gln Met
65                  70                  75                  80

Asn Ser Leu Lys Pro Glu Asp Thr Ala Val Tyr Tyr Cys Asn Ala Val
                85                  90                  95

Pro Tyr Arg Trp Gly Ser Ser Trp Tyr Ala Gly Arg Tyr Trp Gly Gln
            100                 105                 110

Gly Thr Leu Val Thr Val Ser Ser
            115                 120

<210> SEQ ID NO 128
<211> LENGTH: 123
<212> TYPE: PRT
<213> ORGANISM: Artificial Sequence
<220> FEATURE:
<223> OTHER INFORMATION: antibody sequence

<400> SEQUENCE: 128

Gln Val Gln Leu Gln Gln Ser Gly Gly Gly Leu Val Gln Ala Gly Gly
1               5                   10                  15

Ser Leu Thr Leu Ser Cys Val Ala Ser Gly Ser Arg Phe Ser Ile Asn
            20                  25                  30

Thr Met Gly Trp Tyr Arg Gln Ala Pro Gly Lys Gln Arg Glu Leu Val
            35                  40                  45

Ala Gly Ile Thr Arg Gly Gly Ser Thr Asn Tyr Ala Asp Ser Val Lys
50                  55                  60

Gly Arg Phe Thr Ile Ser Arg Glu Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Thr Leu Arg Ala Trp Ala Leu Thr Phe Ala Thr Ser Tyr Ala Tyr
            100                 105                 110

Trp Gly Gln Gly Thr Gln Val Thr Val Ser Ser
            115                 120

```
<210> SEQ ID NO 129
<211> LENGTH: 121
<212> TYPE: PRT
<213> ORGANISM: Artificial Sequence
<220> FEATURE:
<223> OTHER INFORMATION: antibody sequence

<400> SEQUENCE: 129
```

Gln Val Gln Leu Gln Ala Ser Gly Gly Gly Leu Val Gln Pro Gly Gly
1               5                   10                  15

Ser Leu Thr Leu Ser Cys Ala Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Arg Ile Ser Trp Ser Gly Gly Trp Thr Tyr Tyr Ala Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser Arg Ala Val Leu Phe Gly Thr Tyr Asp Tyr Trp Gly
            100                 105                 110

Gln Gly Thr Gln Val Thr Val Ser Ser
        115                 120

```
<210> SEQ ID NO 130
<211> LENGTH: 123
<212> TYPE: PRT
<213> ORGANISM: Artificial Sequence
<220> FEATURE:
<223> OTHER INFORMATION: antibody sequence

<400> SEQUENCE: 130
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Leu Ser Ser Tyr
            20                  25                  30

Arg Met Gly Trp Phe Arg Gln Val Pro Gly Lys Glu Arg Glu Leu Val
        35                  40                  45

Ala Ala Ile Asn Trp Arg Gly Ser Trp Thr Tyr Tyr Ala Asp Ser Val
    50                  55                  60

Lys Gly Arg Val Thr Ile Ser Arg Asp Asn Ala Lys Asn Thr Val Tyr
65                  70                  75                  80

Leu Gln Met Asn Ser Leu Gln Pro Glu Asp Thr Ala Leu Tyr Tyr Cys
                85                  90                  95

Ala Arg Pro Thr Ala Arg Trp Asp Leu Phe Arg Glu Lys Tyr Asp Phe
            100                 105                 110

Arg Gly Gln Gly Thr Gln Val Thr Val Ser Ser
        115                 120

```
<210> SEQ ID NO 131
<211> LENGTH: 116
<212> TYPE: PRT
<213> ORGANISM: Artificial Sequence
<220> FEATURE:
<223> OTHER INFORMATION: antibody sequence

<400> SEQUENCE: 131
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Arg Ser Gly Gly Ile Thr Ser Tyr Ala Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Asn Val Gln Arg Phe Ile Thr Thr Tyr Trp Gly Gln Gly Thr Leu Val
            100                 105                 110

Thr Val Ser Ser
        115

<210> SEQ ID NO 132
<211> LENGTH: 126
<212> TYPE: PRT
<213> ORGANISM: Artificial Sequence
<220> FEATURE:
<223> OTHER INFORMATION: antibody sequence

<400> SEQUENCE: 132

Gln Val Gln Leu Gln Ala Ser Gly Gly Gly Leu Val Gln Ala Gly Gly
1               5                   10                  15

Ser Leu Ser Leu Ser Cys Ala Ala Ser Gly Arg Thr Phe Gly Leu Tyr
            20                  25                  30

Thr Met Gly Trp Phe Arg Gln Ala Pro Glu Lys Glu Arg Glu Phe Val
            35                  40                  45

Ala Ala Ile Ser Trp Arg Gly Leu Ser Ile Met Tyr Ala Asp Ser Val
    50                  55                  60

Lys Gly Arg Phe Thr Ile Ser Arg Asp Asn Val Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Ala Gly Leu Ser Leu Leu Arg Asn Trp Arg Thr Asn Glu
            100                 105                 110

Tyr Ala Tyr Trp Gly Gln Gly Thr Gln Val Thr Val Ser Ser
            115                 120                 125

<210> SEQ ID NO 133
<211> LENGTH: 126
<212> TYPE: PRT
<213> ORGANISM: Artificial Sequence
<220> FEATURE:
<223> OTHER INFORMATION: antibody sequence

<400> SEQUENCE: 133

Gln Val Gln Leu Gln Glu Ser Gly Gly Gly Leu Val Gln Ala Gly Gly
1               5                   10                  15

Ser Leu Arg Leu Ser Cys Glu Ala Ser Ala Arg Thr Phe Ser Ser Tyr
            20                  25                  30

Ala Val Gly Trp Phe Arg Gln Ala Pro Gly Lys Glu Arg Glu Phe Val
            35                  40                  45

Ala Ala Ile Asn Trp Ser Gly Arg Arg Thr Asn Tyr Ala Asp Ser Val
    50                  55                  60

Lys Gly Arg Phe Ser Ile Ser Arg Asp Asn Ala Lys Asn Thr Met Tyr

```
                    65                  70                  75                  80
Leu Gln Met Asn Ser Leu Lys Pro Glu Asp Thr Ala Val Tyr Tyr Cys
                    85                  90                  95

Ala Ala Arg Ser Ser Leu Leu Glu Phe Trp Leu Gly Ser Arg Arg Gly
                100                 105                 110

Tyr Asp Tyr Trp Gly Gln Gly Thr Gln Val Thr Val Ser Ser
            115                 120                 125

<210> SEQ ID NO 134
<211> LENGTH: 121
<212> TYPE: PRT
<213> ORGANISM: Artificial Sequence
<220> FEATURE:
<223> OTHER INFORMATION: antibody sequence

<400> SEQUENCE: 134

Gln Val Gln Leu Gln Gln Phe Gly Gly Gly Leu Val Gln Pro Gly Gly
1               5                   10                  15

Ser Leu Arg Leu Ser Cys Ala Ala Ser Gly Arg Ile Phe Ser Ile Trp
            20                  25                  30

Thr Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Glu Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ile Arg Pro Arg Ile Ile Ser Phe Phe Lys Asp Tyr Trp Gly
                100                 105                 110

Gln Gly Thr Gln Val Thr Val Ser Ser
            115                 120

<210> SEQ ID NO 135
<211> LENGTH: 117
<212> TYPE: PRT
<213> ORGANISM: Artificial Sequence
<220> FEATURE:
<223> OTHER INFORMATION: antibody sequence

<400> SEQUENCE: 135

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Ile Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Thr Glu Asp Thr Ala Val Tyr Tyr Cys
                85                  90                  95

Asn Ala Tyr Phe Arg Trp Gly Thr Arg Tyr Trp Gly Gln Gly Thr Leu
                100                 105                 110

Val Thr Val Ser Ser
            115
```

```
<210> SEQ ID NO 136
<211> LENGTH: 121
<212> TYPE: PRT
<213> ORGANISM: Artificial Sequence
<220> FEATURE:
<223> OTHER INFORMATION: antibody sequence

<400> SEQUENCE: 136

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Phe Ser Trp Leu
            20                  25                  30

Thr Met Ala Trp Phe Arg Gln Ala Pro Gly Lys Glu Arg Glu Ile Val
        35                  40                  45

Ala Arg Ile Thr Trp Arg Gly Thr Pro Tyr Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Ala
                85                  90                  95

Ala Ala Lys Gln Ile Leu Ile Arg Pro Asp Ala Tyr Tyr Trp Gly
            100                 105                 110

Gln Gly Thr Gln Val Thr Val Ser Ser
        115                 120

<210> SEQ ID NO 137
<211> LENGTH: 120
<212> TYPE: PRT
<213> ORGANISM: Artificial Sequence
<220> FEATURE:
<223> OTHER INFORMATION: antibody sequence

<400> SEQUENCE: 137

Gln Val Gln Leu Gln Ala Ser Gly Gly Gly Leu Val Gln Ala Gly Gly
1               5                   10                  15

Ser Leu Arg Leu Ser Cys Val Ala Ser Gly Ser Ile Phe Arg Phe Asn
            20                  25                  30

Ala Ile Gly Trp Tyr Arg Gln Ala Pro Gly Lys Glu Arg Glu Leu Val
        35                  40                  45

Ala Arg Ile Arg Arg Leu Gly Ser Thr Ser Tyr Ala Asp Ser Val Lys
    50                  55                  60

Gly Arg Phe Ser Ile Ser Arg Asp Ser Ala Lys Asn Thr Val Tyr Leu
65                  70                  75                  80

Gln Met Asp Asn Leu Lys Pro Glu Asp Thr Ala Val Tyr Tyr Cys Lys
                85                  90                  95

Ala Gly Arg His Pro His Phe Ser Met Asp Tyr Pro Asp Leu Gly Gln
            100                 105                 110

Gly Thr Gln Val Thr Val Ser Ser
        115                 120

<210> SEQ ID NO 138
<211> LENGTH: 123
<212> TYPE: PRT
<213> ORGANISM: Artificial Sequence
<220> FEATURE:
<223> OTHER INFORMATION: antibody sequence

<400> SEQUENCE: 138

Gln Val Gln Leu Gln Glu Ser Gly Gly Gly Leu Val Gln Pro Gly Gly
```

```
1               5                   10                  15
Ser Leu Arg Leu Ser Cys Ala Ala Ser Arg Tyr Ile Phe Gly Thr Met
            20                  25                  30

Gly Trp Tyr Arg Gln Ala Pro Gly Leu Gln Arg Glu Leu Val Ala Ser
            35                  40                  45

Ile Ser Arg Gly Gly Ser Thr Asn Tyr Ala Asp Ser Val Lys Gly Arg
    50                  55                  60

Phe Ala Ile Ser Arg Asp Asn Ala Lys Asn Thr Val Tyr Leu Gln Met
65                  70                  75                  80

Asn Asn Leu Lys Pro Glu Asp Thr Ala Val Tyr Tyr Cys Ala Leu Ala
                85                  90                  95

Leu Gly Phe Phe Thr Asn Tyr Tyr Val Arg Glu Ser Ser Tyr Arg Tyr
                100                 105                 110

Trp Gly Gln Gly Thr Gln Val Thr Val Ser Ser
            115                 120
```

<210> SEQ ID NO 139
<211> LENGTH: 122
<212> TYPE: PRT
<213> ORGANISM: Artificial Sequence
<220> FEATURE:
<223> OTHER INFORMATION: antibody sequence

<400> SEQUENCE: 139

```
Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Thr Phe Arg Leu Tyr
            20                  25                  30

Ser Met Ala Trp Phe Arg Gln Ala Pro Gly Lys Glu Arg Glu Phe Leu
            35                  40                  45

Gly Ser Ile Arg Trp Asn Gly Gly Asn Ile Tyr Tyr Thr Asp Ser Val
        50                  55                  60

Lys Gly Arg Phe Thr Ile Ser Arg Asp Asn Ala Lys Asn Thr Ala Tyr
65                  70                  75                  80

Leu Gln Met Asn Ser Leu Thr Pro Glu Asp Thr Ala Val Tyr Tyr Cys
                85                  90                  95

Ala Ala Gly Pro Arg Ile Ala Val Trp Arg Tyr Glu Tyr Asn Tyr Trp
                100                 105                 110

Gly Gln Gly Thr Gln Val Thr Val Ser Ser
            115                 120
```

<210> SEQ ID NO 140
<211> LENGTH: 123
<212> TYPE: PRT
<213> ORGANISM: Artificial Sequence
<220> FEATURE:
<223> OTHER INFORMATION: antibody sequence

<400> SEQUENCE: 140

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Gly Ser Phe Lys
            20                  25                  30

Thr Met Gly Trp Tyr Arg Gln Ala Pro Gly Lys Gln Arg Glu Leu Val
            35                  40                  45

Ala Thr Ile Thr Arg Trp Gly Phe Thr Asn Tyr Ala Asp Ser Val Lys
        50                  55                  60
```

```
Gly Arg Phe Thr Ile Ala Arg Asp Asn Ala Lys Ser Thr Leu Tyr Leu
 65                  70                  75                  80

Gln Met Asn Ser Leu Lys Pro Glu Asp Thr Ala Ile Tyr Tyr Cys Ala
                 85                  90                  95

Ala Ala Gln Gly Gly Phe Met Lys Pro Arg Ala Asn Trp Tyr Asn Ser
            100                 105                 110

Trp Gly Gln Gly Thr Leu Val Thr Val Ser Ser
            115                 120
```

<210> SEQ ID NO 141
<211> LENGTH: 123
<212> TYPE: PRT
<213> ORGANISM: Artificial Sequence
<220> FEATURE:
<223> OTHER INFORMATION: antibody sequence

<400> SEQUENCE: 141

```
Gln Val Gln Leu Gln Glu Ser Gly Gly Gly Leu Val Gln Ala Gly Ala
 1               5                  10                  15

Ser Leu Arg Leu Ser Cys Val Ala Ser Gly Arg Thr Phe Ser Arg Tyr
                 20                  25                  30

Gly Met Gly Trp Phe Arg Gln Ala Pro Gly Lys Glu Arg Glu Phe Val
             35                  40                  45

Ala Ala Ile Ser Arg Ser Gly Ala Ile Ser Tyr Tyr Ala Asp Ser Val
 50                  55                  60

Lys Gly Arg Phe Thr Ile Ser Arg Gly Asp Ala Thr Asn Thr Val Val
 65                  70                  75                  80

Leu Gln Met Ser Ser Leu Lys Pro Gly Asp Thr Ala Val Tyr Tyr Cys
                 85                  90                  95

Ala Ala Ser Ser Arg Arg Leu Leu Gly Gly Pro Phe Ala Tyr Asp Tyr
            100                 105                 110

Trp Gly Gln Gly Thr Leu Val Thr Val Ser Ser
            115                 120
```

<210> SEQ ID NO 142
<211> LENGTH: 113
<212> TYPE: PRT
<213> ORGANISM: Artificial Sequence
<220> FEATURE:
<223> OTHER INFORMATION: antibody sequence

<400> SEQUENCE: 142

```
Gln Val Gln Leu Gln Glu Ser Gly Gly Gly Leu Val Gln Pro Gly Gly
 1               5                  10                  15

Ser Leu Arg Leu Ser Cys Ala Ala Ser Arg Tyr Ile Phe Gly Thr Met
                 20                  25                  30

Gly Trp Tyr Arg Gln Ala Pro Gly Leu Gln Arg Glu Leu Val Ala Ser
             35                  40                  45

Ile Ser Arg Gly Gly Ser Thr Asn Tyr Ala Asp Ser Val Lys Gly Arg
 50                  55                  60

Phe Ala Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Ala Asn
                 85                  90                  95

Arg Arg Gly Trp Asn Tyr Trp Gly Gln Gly Thr Gln Val Thr Val Ser
            100                 105                 110

Ser
```

-continued

<210> SEQ ID NO 143
<211> LENGTH: 124
<212> TYPE: PRT
<213> ORGANISM: Artificial Sequence
<220> FEATURE:
<223> OTHER INFORMATION: antibody sequence

<400> SEQUENCE: 143

Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Ile Phe Thr Met Lys
            20                  25                  30

Asn Met Ala Trp Tyr Arg Gln Ala Pro Gly Lys Glu Arg Glu Phe Val
        35                  40                  45

Ala Ala Ile Ser Thr Ser Gly Gly Val Thr Trp Tyr Ala Asp Ser Ser
    50                  55                  60

Val Lys Gly Arg Phe Thr Ile Ser Arg Asp Asn Ala Lys Asn Thr Leu
65                  70                  75                  80

Tyr Leu Gln Met Asp Ser Leu Lys Pro Glu Asp Thr Ala Val Tyr Tyr
                85                  90                  95

Cys Lys Val Arg Ser Gly Pro Arg Ile Ile Pro Gln Leu Arg Arg Glu
            100                 105                 110

Tyr Trp Gly Gln Gly Thr Gln Val Thr Val Ser Ser
        115                 120

<210> SEQ ID NO 144
<211> LENGTH: 116
<212> TYPE: PRT
<213> ORGANISM: Artificial Sequence
<220> FEATURE:
<223> OTHER INFORMATION: antibody sequence

<400> SEQUENCE: 144

Gln Val Gln Leu Gln Glu Ser Gly Gly Gly Leu Val Gln Pro Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly His Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Met Leu Lys Pro Glu Asp Thr Ala Val Tyr Tyr Cys
                85                  90                  95

Lys Leu Thr Arg Leu Leu Asn Thr Tyr Trp Gly Gln Gly Thr Leu Val
            100                 105                 110

Thr Val Ser Ser
        115

<210> SEQ ID NO 145
<211> LENGTH: 118
<212> TYPE: PRT
<213> ORGANISM: Artificial Sequence
<220> FEATURE:
<223> OTHER INFORMATION: antibody sequence

<400> SEQUENCE: 145

Gln Val Gln Leu Gln Glu Ser Gly Gly Gly Leu Val Gln Ala Gly Asp

```
                1               5                  10                 15
            Ser Leu Arg Leu Ser Cys Ala Phe Ser Gly Arg Thr Phe Gly Leu Arg
                        20                  25                 30

Thr Met Gly Trp Phe Arg Gln Ala Pro Gly Lys Glu Arg Glu Phe Val
                        35                  40                 45

Ser Ser Leu Thr Trp Arg Asp Asn Ala Tyr Tyr Ala Asp Ser Val
                        50                  55                 60

Lys Gly Arg Phe Thr Ile Ser Arg Asp Asn Ala Lys Lys Thr Leu Tyr
             65                     70                  75                 80

Leu Gln Met Asn Ser Leu Lys Pro Glu Asp Thr Ala Val Tyr Phe Cys
                                85                  90                 95

Asn Val His Leu Val Phe Thr Asn Arg Asp Tyr Trp Gly Gln Gly Thr
                        100                 105                110

Gln Val Thr Val Ser Ser
                        115
```

<210> SEQ ID NO 146
<211> LENGTH: 121
<212> TYPE: PRT
<213> ORGANISM: Artificial Sequence
<220> FEATURE:
<223> OTHER INFORMATION: antibody sequence

<400> SEQUENCE: 146

```
            Gln Val Gln Leu Gln Ser Gly Gly Gly Leu Val Gln Pro Gly Gly
             1               5                  10                 15

Ser Leu Arg Leu Ser Cys Ala Ala Ser Trp Arg Ile Phe Ser Pro Asn
                        20                  25                 30

Ala Met Ala Trp Tyr Arg Gln Ala Pro Gly Lys Gln Arg Glu Leu Val
                        35                  40                 45

Ala Arg Ile Thr Trp Ala Gly Ile Thr Asn Tyr Ala Asp Ser Val Lys
                        50                  55                 60

Gly Arg Phe Thr Ile Ser Arg Asp Asn Ala Lys Asn Thr Val Tyr Leu
             65                     70                  75                 80

Gln Met His Ser Leu Lys Pro Glu Asp Thr Ala Ile Tyr Tyr Cys Val
                                85                  90                 95

Ala Asp Arg Arg Ser Ser Tyr Leu Gly Pro Arg Phe Asp Tyr Trp Gly
                        100                 105                110

Gln Gly Thr Gln Val Thr Val Ser Ser
                        115                 120
```

<210> SEQ ID NO 147
<211> LENGTH: 123
<212> TYPE: PRT
<213> ORGANISM: Artificial Sequence
<220> FEATURE:
<223> OTHER INFORMATION: antibody sequence

<400> SEQUENCE: 147

```
            Gln Val Gln Leu Gln Glu Ser Gly Gly Gly Leu Val Gln Pro Gly Gly
             1               5                  10                 15

Ser Leu Arg Leu Ser Cys Ala Ala Ser Arg Tyr Ile Phe Gly Thr Met
                        20                  25                 30

Gly Trp Tyr Arg Gln Ala Pro Gly Leu Gln Arg Glu Leu Val Ala Ser
                        35                  40                 45

Ile Ser Arg Gly Gly Ser Thr Asn Tyr Ala Asp Ser Val Lys Gly Arg
                        50                  55                 60
```

```
Phe Ala Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Ala Ala Arg
                 85                  90                  95

Ser Ser Leu Leu Glu Phe Trp Leu Gly Ser Arg Arg Gly Tyr Asp Tyr
            100                 105                 110

Trp Gly Gln Gly Thr Gln Val Thr Val Ser Ser
            115                 120

<210> SEQ ID NO 148
<211> LENGTH: 120
<212> TYPE: PRT
<213> ORGANISM: Artificial Sequence
<220> FEATURE:
<223> OTHER INFORMATION: antibody sequence

<400> SEQUENCE: 148

Gln Val Gln Leu Gln Gln Ser Gly Gly Gly Leu Val Gln Pro Gly Gly
 1               5                   10                  15

Ser Leu Arg Leu Ala Cys Ala Ala Ser Gly Arg Phe Phe Arg Ile Asn
            20                  25                  30

Ala Met Ala Trp Tyr Arg Gln Ala Pro Gly Lys Gln Arg Glu Leu Val
        35                  40                  45

Ala Thr Ile Thr Arg Ala Gly Thr Thr Thr Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Ile Ser Leu Lys Pro Glu Asp Thr Ala Val Tyr Tyr Cys Ala
                 85                  90                  95

Lys Tyr Pro Thr Ile Thr Trp Tyr Gly Arg His Asp Tyr Arg Gly Gln
            100                 105                 110

Gly Thr Gln Val Thr Val Ser Ser
            115                 120

<210> SEQ ID NO 149
<211> LENGTH: 123
<212> TYPE: PRT
<213> ORGANISM: Artificial Sequence
<220> FEATURE:
<223> OTHER INFORMATION: antibody sequence

<400> SEQUENCE: 149

Gln Val Gln Leu Gln Glu Ser Gly Gly Gly Leu Val Gln His Gly Gly
 1               5                   10                  15

Ser Leu Arg Leu Ser Cys Ala Ala Ser Gly Ser Phe Phe Arg Ile Asn
            20                  25                  30

Thr Met Ala Trp His Arg Gln Ala Pro Gly Lys Gln Arg Glu Leu Val
        35                  40                  45

Ala Ser Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Ser Glu Asp Thr Ala Val Tyr Tyr Cys Ala
                 85                  90                  95

Ala Ser Arg Phe Gly Ile Asn Tyr Tyr Thr Ala Arg Gln Tyr Gly Tyr
            100                 105                 110

Trp Gly Gln Gly Thr Gln Val Thr Val Ser Ser
            115                 120
```

<210> SEQ ID NO 150
<211> LENGTH: 118
<212> TYPE: PRT
<213> ORGANISM: Artificial Sequence
<220> FEATURE:
<223> OTHER INFORMATION: antibody sequence

<400> SEQUENCE: 150

Gln Val Gln Leu Gln Ala Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Pro Met Gly Trp Phe Arg Gln Ala Pro Gly Lys Glu Arg Glu Phe Val
        35                  40                  45

Ala Arg Phe Gly Trp Ser Gly Leu Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Arg Phe Met Gly Ser Tyr Asp Tyr Trp Gly Gln Gly Thr
            100                 105                 110

Gln Val Thr Val Ser Ser
        115

<210> SEQ ID NO 151
<211> LENGTH: 125
<212> TYPE: PRT
<213> ORGANISM: Artificial Sequence
<220> FEATURE:
<223> OTHER INFORMATION: antibody sequence

<400> SEQUENCE: 151

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Trp Tyr
            20                  25                  30

Ala Met Gly Trp Phe Arg Gln Ala Pro Gly Arg Glu Arg Glu Phe Val
        35                  40                  45

Ala Ala Ile Arg Arg Ser Gly Gly Ile Thr Ile Tyr Ala Asp Ser Val
    50                  55                  60

Lys Gly Arg Phe Ala Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Leu Phe Gln Trp Arg Leu Asn Asp Asn Gly Asn Gln Tyr
            100                 105                 110

Gly Ser Trp Gly Gln Gly Thr Leu Val Thr Val Ser Ser
        115                 120                 125

<210> SEQ ID NO 152
<211> LENGTH: 120
<212> TYPE: PRT
<213> ORGANISM: Artificial Sequence
<220> FEATURE:
<223> OTHER INFORMATION: antibody sequence

<400> SEQUENCE: 152

```
Gln Val Gln Leu Gln Glu Gly Gly Gly Leu Val Gln Ala Gly Gly
1               5                   10                  15

Ser Leu Arg Leu Ser Cys Val Val Ser Gly Arg Thr Phe Ser Thr Ser
            20                  25                  30

Gln Met Gly Trp Phe Arg Gln Pro Pro Gly Lys Glu Arg Glu Leu Val
        35                  40                  45

Ala Arg Ile Ser Trp Arg Gly Lys Gln His Tyr Ala Asp Ser Val Lys
    50                  55                  60

Gly Arg Phe Thr Ile Ser Arg Asp Tyr Ala Lys Asn Thr Val Tyr Leu
65                  70                  75                  80

Gln Met Asn Gly Leu Lys Ser Glu Asp Thr Ala Val Tyr Tyr Cys Ala
                85                  90                  95

Ala Gly Pro Arg Ala Val Leu Phe Gly Thr Tyr Asp Tyr Trp Gly Gln
            100                 105                 110

Gly Thr Gln Val Thr Val Ser Ser
        115                 120
```

<210> SEQ ID NO 153
<211> LENGTH: 10
<212> TYPE: PRT
<213> ORGANISM: Artificial Sequence
<220> FEATURE:
<223> OTHER INFORMATION: antibody sequence

<400> SEQUENCE: 153

```
Ser Gly Arg Ile Phe Ser Asn Asn Val Met
1               5                   10
```

<210> SEQ ID NO 154
<211> LENGTH: 10
<212> TYPE: PRT
<213> ORGANISM: Artificial Sequence
<220> FEATURE:
<223> OTHER INFORMATION: antibody sequence

<400> SEQUENCE: 154

```
Ser Ser Gly Pro Phe Ser Arg Tyr Ala Met
1               5                   10
```

<210> SEQ ID NO 155
<211> LENGTH: 10
<212> TYPE: PRT
<213> ORGANISM: Artificial Sequence
<220> FEATURE:
<223> OTHER INFORMATION: antibody sequence

<400> SEQUENCE: 155

```
Ser Gly Phe Asn Phe Gly Ser Phe Ala Ile
1               5                   10
```

<210> SEQ ID NO 156
<211> LENGTH: 10
<212> TYPE: PRT
<213> ORGANISM: Artificial Sequence
<220> FEATURE:
<223> OTHER INFORMATION: antibody sequence

<400> SEQUENCE: 156

```
Ser Gly Ser Ile Ser Ser Ile Asn Ala Ile
1               5                   10
```

<210> SEQ ID NO 157
<211> LENGTH: 10

```
<212> TYPE: PRT
<213> ORGANISM: Artificial Sequence
<220> FEATURE:
<223> OTHER INFORMATION: antibody sequence

<400> SEQUENCE: 157

Ser Gly Arg Thr Phe Ser Thr Tyr Thr Met
1               5                   10

<210> SEQ ID NO 158
<211> LENGTH: 10
<212> TYPE: PRT
<213> ORGANISM: Artificial Sequence
<220> FEATURE:
<223> OTHER INFORMATION: antibody sequence

<400> SEQUENCE: 158

Ser Gly Arg Thr Phe Ser Asn Tyr Ala Met
1               5                   10

<210> SEQ ID NO 159
<211> LENGTH: 10
<212> TYPE: PRT
<213> ORGANISM: Artificial Sequence
<220> FEATURE:
<223> OTHER INFORMATION: antibody sequence

<400> SEQUENCE: 159

Ser Gly Ser Thr Phe Ser Gly Tyr Val Ile
1               5                   10

<210> SEQ ID NO 160
<211> LENGTH: 10
<212> TYPE: PRT
<213> ORGANISM: Artificial Sequence
<220> FEATURE:
<223> OTHER INFORMATION: antibody sequence

<400> SEQUENCE: 160

Ser Gly Phe Thr Phe Ser Ser Tyr Trp Met
1               5                   10

<210> SEQ ID NO 161
<211> LENGTH: 10
<212> TYPE: PRT
<213> ORGANISM: Artificial Sequence
<220> FEATURE:
<223> OTHER INFORMATION: antibody sequence

<400> SEQUENCE: 161

Ser Gly Phe Pro Phe Asp Asp Tyr Pro Met
1               5                   10

<210> SEQ ID NO 162
<211> LENGTH: 10
<212> TYPE: PRT
<213> ORGANISM: Artificial Sequence
<220> FEATURE:
<223> OTHER INFORMATION: antibody sequence

<400> SEQUENCE: 162

Ser Ile Ser Ile Val Ser Ile Asn Thr Met
1               5                   10

<210> SEQ ID NO 163
<211> LENGTH: 10
<212> TYPE: PRT
```

```
<213> ORGANISM: Artificial Sequence
<220> FEATURE:
<223> OTHER INFORMATION: antibody sequence

<400> SEQUENCE: 163

Ser Met Thr Thr Leu Gly Phe Lys Thr Met
1               5                   10

<210> SEQ ID NO 164
<211> LENGTH: 11
<212> TYPE: PRT
<213> ORGANISM: Artificial Sequence
<220> FEATURE:
<223> OTHER INFORMATION: antibody sequence

<400> SEQUENCE: 164

Gly Gly Lys Ser Thr Ala Ala Val Asn Gly Val
1               5                   10

<210> SEQ ID NO 165
<211> LENGTH: 12
<212> TYPE: PRT
<213> ORGANISM: Artificial Sequence
<220> FEATURE:
<223> OTHER INFORMATION: antibody sequence

<400> SEQUENCE: 165

Ala Ile Ser Arg Ser Gly Gly Thr Thr Leu Tyr Ala
1               5                   10

<210> SEQ ID NO 166
<211> LENGTH: 12
<212> TYPE: PRT
<213> ORGANISM: Artificial Sequence
<220> FEATURE:
<223> OTHER INFORMATION: antibody sequence

<400> SEQUENCE: 166

Thr Ile Ser Arg Ser Gly Ser Ser Thr Thr Tyr Gly
1               5                   10

<210> SEQ ID NO 167
<211> LENGTH: 12
<212> TYPE: PRT
<213> ORGANISM: Artificial Sequence
<220> FEATURE:
<223> OTHER INFORMATION: antibody sequence

<400> SEQUENCE: 167

Cys Ile Ser Ser Thr Asp Asp Thr Ser Val Tyr Ser
1               5                   10

<210> SEQ ID NO 168
<211> LENGTH: 11
<212> TYPE: PRT
<213> ORGANISM: Artificial Sequence
<220> FEATURE:
<223> OTHER INFORMATION: antibody sequence

<400> SEQUENCE: 168

Lys Ile Thr Lys Gly Gly Thr Thr Ile Tyr Thr
1               5                   10

<210> SEQ ID NO 169
<211> LENGTH: 12
<212> TYPE: PRT
<213> ORGANISM: Artificial Sequence
```

```
<220> FEATURE:
<223> OTHER INFORMATION: antibody sequence

<400> SEQUENCE: 169

Ala Ile Ser Trp Ser Ser Gly Thr Ala Asn Tyr Ala
1               5                   10

<210> SEQ ID NO 170
<211> LENGTH: 12
<212> TYPE: PRT
<213> ORGANISM: Artificial Sequence
<220> FEATURE:
<223> OTHER INFORMATION: antibody sequence

<400> SEQUENCE: 170

Ala Ile Ser Trp Ser Gly Ala Tyr Thr Phe Tyr Gly
1               5                   10

<210> SEQ ID NO 171
<211> LENGTH: 11
<212> TYPE: PRT
<213> ORGANISM: Artificial Sequence
<220> FEATURE:
<223> OTHER INFORMATION: antibody sequence

<400> SEQUENCE: 171

Ile Ile Ser Ser Ser Gly Ser Thr Asn Tyr Ala
1               5                   10

<210> SEQ ID NO 172
<211> LENGTH: 12
<212> TYPE: PRT
<213> ORGANISM: Artificial Sequence
<220> FEATURE:
<223> OTHER INFORMATION: antibody sequence

<400> SEQUENCE: 172

Thr Ile Ser Pro Ser Gly Gly Thr Thr Tyr Tyr Thr
1               5                   10

<210> SEQ ID NO 173
<211> LENGTH: 12
<212> TYPE: PRT
<213> ORGANISM: Artificial Sequence
<220> FEATURE:
<223> OTHER INFORMATION: antibody sequence

<400> SEQUENCE: 173

Ser Val Ser Pro Asn Gly Gly Ser Thr Phe Tyr Ala
1               5                   10

<210> SEQ ID NO 174
<211> LENGTH: 11
<212> TYPE: PRT
<213> ORGANISM: Artificial Sequence
<220> FEATURE:
<223> OTHER INFORMATION: antibody sequence

<400> SEQUENCE: 174

Gly Ile Thr Ser Gly Gly Ser Thr Asn Tyr Ala
1               5                   10

<210> SEQ ID NO 175
<211> LENGTH: 11
<212> TYPE: PRT
<213> ORGANISM: Artificial Sequence
<220> FEATURE:
```

<223> OTHER INFORMATION: antibody sequence

<400> SEQUENCE: 175

Arg Ile Ser Ser Gly Gly Gln Thr Asn Tyr Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: antibody sequence

<400> SEQUENCE: 176

Ala Ile Arg Pro Gly Gly Arg Arg Asp Tyr Leu
1               5                   10

<210> SEQ ID NO 177
<211> LENGTH: 15
<212> TYPE: PRT
<213> ORGANISM: Artificial Sequence
<220> FEATURE:
<223> OTHER INFORMATION: antibody sequence

<400> SEQUENCE: 177

Gly Lys Val Asp Glu Ile Arg Pro Thr Val Ser Ala Ser Tyr Asp
1               5                   10                  15

<210> SEQ ID NO 178
<211> LENGTH: 18
<212> TYPE: PRT
<213> ORGANISM: Artificial Sequence
<220> FEATURE:
<223> OTHER INFORMATION: antibody sequence

<400> SEQUENCE: 178

Ala Val Ser Arg Tyr Tyr Thr Ala Gly Ala Ser Ala Asp Thr Lys Thr
1               5                   10                  15

Tyr Asp

<210> SEQ ID NO 179
<211> LENGTH: 22
<212> TYPE: PRT
<213> ORGANISM: Artificial Sequence
<220> FEATURE:
<223> OTHER INFORMATION: antibody sequence

<400> SEQUENCE: 179

Ala Thr Val Gly Gln Ser Cys Asp Leu Trp Asp His Pro Gln Val Pro
1               5                   10                  15

Val Arg Tyr Arg Gly Arg
            20

<210> SEQ ID NO 180
<211> LENGTH: 13
<212> TYPE: PRT
<213> ORGANISM: Artificial Sequence
<220> FEATURE:
<223> OTHER INFORMATION: antibody sequence

<400> SEQUENCE: 180

Gly Ala Asp Val Asn Tyr Gly Ser Pro Asp Tyr Ile Asp
1               5                   10

<210> SEQ ID NO 181

```
<211> LENGTH: 9
<212> TYPE: PRT
<213> ORGANISM: Artificial Sequence
<220> FEATURE:
<223> OTHER INFORMATION: antibody sequence

<400> SEQUENCE: 181

Asn Ala Trp Ser Pro Val Gly His Asp
1               5

<210> SEQ ID NO 182
<211> LENGTH: 13
<212> TYPE: PRT
<213> ORGANISM: Artificial Sequence
<220> FEATURE:
<223> OTHER INFORMATION: antibody sequence

<400> SEQUENCE: 182

Ala Ala Ala Arg Gly Gly Arg Trp Tyr Ser Thr Tyr Asp
1               5                   10

<210> SEQ ID NO 183
<211> LENGTH: 8
<212> TYPE: PRT
<213> ORGANISM: Artificial Sequence
<220> FEATURE:
<223> OTHER INFORMATION: antibody sequence

<400> SEQUENCE: 183

Asn Ala Arg Leu Trp Leu Asn Asn
1               5

<210> SEQ ID NO 184
<211> LENGTH: 11
<212> TYPE: PRT
<213> ORGANISM: Artificial Sequence
<220> FEATURE:
<223> OTHER INFORMATION: antibody sequence

<400> SEQUENCE: 184

Ala Ala Arg Arg Ser Gly Arg Tyr Glu Tyr Asp
1               5                   10

<210> SEQ ID NO 185
<211> LENGTH: 18
<212> TYPE: PRT
<213> ORGANISM: Artificial Sequence
<220> FEATURE:
<223> OTHER INFORMATION: antibody sequence

<400> SEQUENCE: 185

Ala Lys Val Leu Asp Tyr Tyr Cys Ser Gly Tyr Gly Cys Tyr Ala Ser
1               5                   10                  15

Tyr Asp

<210> SEQ ID NO 186
<211> LENGTH: 13
<212> TYPE: PRT
<213> ORGANISM: Artificial Sequence
<220> FEATURE:
<223> OTHER INFORMATION: antibody sequence

<400> SEQUENCE: 186

Asn Ala Gly Arg Tyr Val Pro Gly Ala Ile Val Thr Asn
1               5                   10
```

```
<210> SEQ ID NO 187
<211> LENGTH: 14
<212> TYPE: PRT
<213> ORGANISM: Artificial Sequence
<220> FEATURE:
<223> OTHER INFORMATION: antibody sequence

<400> SEQUENCE: 187

Asn Ala Arg Arg Tyr Tyr Ser Leu Ala Arg Tyr Asp Tyr Asn
1               5                   10

<210> SEQ ID NO 188
<211> LENGTH: 10
<212> TYPE: PRT
<213> ORGANISM: Artificial Sequence
<220> FEATURE:
<223> OTHER INFORMATION: antibody sequence

<400> SEQUENCE: 188

Tyr Ala Glu Gly Leu Leu Leu Pro Ser Thr
1               5                   10

<210> SEQ ID NO 189
<211> LENGTH: 123
<212> TYPE: PRT
<213> ORGANISM: Artificial Sequence
<220> FEATURE:
<223> OTHER INFORMATION: antibody sequence

<400> SEQUENCE: 189

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Asn Asn
            20                  25                  30

Val Met Gly Trp Phe Arg Gln Ala Pro Gly Lys Glu Arg Glu Phe Val
        35                  40                  45

Ala Ala Ile Ser Arg Ser Gly Gly Thr Thr Leu Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Gly Lys Val Asp Glu Ile Arg Pro Thr Val Ser Ala Ser Tyr Asp Leu
            100                 105                 110

Trp Gly Gln Gly Thr Leu Val Thr Val Ser Ser
        115                 120

<210> SEQ ID NO 190
<211> LENGTH: 126
<212> TYPE: PRT
<213> ORGANISM: Artificial Sequence
<220> FEATURE:
<223> OTHER INFORMATION: antibody sequence

<400> SEQUENCE: 190

Gln Val Gln Leu Gln Glu Ser Gly Gly Gly Leu Val Gln Ala Gly Asp
1               5                   10                  15

Ser Leu Arg Leu Ser Cys Ala Ala Ser Ser Gly Pro Phe Ser Arg Tyr
            20                  25                  30

Ala Met Gly Trp Phe Arg Gln Ala Pro Gly Lys Glu Arg Glu Phe Val
        35                  40                  45

Ala Thr Ile Ser Arg Ser Gly Ser Ser Thr Thr Tyr Gly Asp Ser Val
```

```
            50                  55                  60
Lys Gly Arg Phe Thr Ile Ser Arg Asp Asn Ala Lys Asn Thr Leu Tyr
 65                  70                  75                  80

Leu Glu Met Asn Ser Leu Thr Pro Glu Asp Thr Ala Val Tyr Tyr Cys
                 85                  90                  95

Ala Val Ser Arg Tyr Tyr Thr Ala Gly Ala Ser Ala Asp Thr Lys Thr
                100                 105                 110

Tyr Asp Tyr Trp Gly Gln Gly Thr Leu Val Thr Val Ser Ser
            115                 120                 125

<210> SEQ ID NO 191
<211> LENGTH: 126
<212> TYPE: PRT
<213> ORGANISM: Artificial Sequence
<220> FEATURE:
<223> OTHER INFORMATION: antibody sequence

<400> SEQUENCE: 191

Gln Val Gln Leu Gln Ala Ser Gly Gly Gly Leu Val Gln Pro Gly Gly
 1                5                  10                  15

Ser Leu Lys Leu Ser Cys Gln Ala Ser Gly Phe Asn Phe Gly Ser Phe
                 20                  25                  30

Ala Ile Ala Trp Phe Arg Gln Ala Pro Gly Lys Gly Arg Glu Gly Ile
                 35                  40                  45

Ser Cys Ile Ser Ser Thr Asp Asp Thr Ser Val Tyr Ser Asp Ala Val
                 50                  55                  60

Lys Gly Arg Phe Ala Ile Ser Arg Asp Asn Ala Lys Arg Ala Ala Tyr
 65                  70                  75                  80

Leu Gln Met Asn Ser Leu Ile Pro Glu Asp Thr Ala Asn Tyr Tyr Cys
                 85                  90                  95

Ala Thr Val Gly Gln Ser Cys Asp Leu Trp Asp His Pro Gln Val Pro
                100                 105                 110

Val Arg Tyr Arg Gly Arg Gly Thr Leu Val Thr Val Ser Ser
            115                 120                 125

<210> SEQ ID NO 192
<211> LENGTH: 126
<212> TYPE: PRT
<213> ORGANISM: Artificial Sequence
<220> FEATURE:
<223> OTHER INFORMATION: antibody sequence

<400> SEQUENCE: 192

Gln Val Gln Leu Gln Ala Ser Gly Gly Gly Leu Val Gln Pro Gly Gly
 1                5                  10                  15

Ser Leu Lys Leu Ser Cys Gln Ala Ser Gly Phe Asn Phe Gly Ser Phe
                 20                  25                  30

Ala Ile Ala Trp Phe Arg Gln Ala Pro Gly Lys Gly Arg Glu Gly Ile
                 35                  40                  45

Ser Cys Ile Ser Ser Thr Asp Asp Thr Ser Val Tyr Ser Asp Ala Val
                 50                  55                  60

Lys Gly Arg Phe Ala Ile Ser Arg Asp Asn Ala Lys Arg Ala Ala Tyr
 65                  70                  75                  80

Leu Gln Met Asn Ser Leu Ile Pro Glu Asp Thr Ala Asn Tyr Tyr Cys
                 85                  90                  95

Ala Thr Val Gly Gln Ser Cys Asp Leu Trp Asp His Pro Gln Val Pro
                100                 105                 110
```

```
Val Arg Tyr Arg Gly Arg Gly Thr Gln Val Thr Val Ser Ser
        115                 120                 125

<210> SEQ ID NO 193
<211> LENGTH: 120
<212> TYPE: PRT
<213> ORGANISM: Artificial Sequence
<220> FEATURE:
<223> OTHER INFORMATION: antibody sequence

<400> SEQUENCE: 193

Gln Val Gln Leu Gln Glu Ser Gly Gly Gly Phe Val Gln Ala Gly Thr
1               5                   10                  15

Ser Leu Arg Leu Ser Cys Ala Ala Ser Gly Ser Ile Ser Ile Asn
            20                  25                  30

Ala Ile Ala Trp Tyr Arg Gln Gly Arg Gly Asn Gln Arg Glu Leu Leu
            35                  40                  45

Ala Lys Ile Thr Lys Gly Gly Thr Thr Ile Tyr Thr Asn Ser Val Lys
        50                  55                  60

Gly Arg Phe Thr Ile Ser Arg Asp Asn Asn Lys Asn Thr Val Tyr Leu
65                  70                  75                  80

Gln Met Asp Ser Leu Lys Pro Asp Thr Ala Val Tyr Tyr Cys Gly
            85                  90                  95

Ala Asp Val Asn Tyr Gly Ser Pro Asp Tyr Ile Asp Tyr Trp Gly Gln
            100                 105                 110

Gly Thr Gln Val Thr Val Ser Ser
        115                 120

<210> SEQ ID NO 194
<211> LENGTH: 117
<212> TYPE: PRT
<213> ORGANISM: Artificial Sequence
<220> FEATURE:
<223> OTHER INFORMATION: antibody sequence

<400> SEQUENCE: 194

Gln Val Gln Leu Gln Glu Ser Gly Gly Gly Leu Val Gln Ser Gly Gly
1               5                   10                  15

Ser Leu Arg Leu Ser Cys Ala Ala Ser Gly Arg Thr Phe Ser Thr Tyr
            20                  25                  30

Thr Met Gly Trp Phe Arg Gln Ala Pro Gly Lys Glu Arg Glu Phe Val
            35                  40                  45

Ala Ala Ile Ser Trp Ser Ser Gly Thr Ala Asn Tyr Ala Asp Ser Val
        50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
            85                  90                  95

Asn Ala Trp Ser Pro Val Gly His Asp Tyr Trp Gly Gln Gly Thr Gln
            100                 105                 110

Val Thr Val Ser Ser
115

<210> SEQ ID NO 195
<211> LENGTH: 121
<212> TYPE: PRT
<213> ORGANISM: Artificial Sequence
<220> FEATURE:
<223> OTHER INFORMATION: antibody sequence
```

```
<400> SEQUENCE: 195

Gln Val Gln Leu Gln Gln Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ala Tyr Thr Tyr Tyr Gly Asn Ser Val
    50                  55                  60

Arg Gly Arg Phe Thr Ile Ser Arg Asp Asn Pro Asn Thr Val Tyr
65                  70                  75                  80

Leu Gln Met Asn Ser Leu Lys Pro Glu Asp Thr Ala Thr Tyr Tyr Cys
                85                  90                  95

Ala Ala Ala Arg Gly Gly Arg Trp Tyr Ser Thr Tyr Asp Tyr Trp Gly
            100                 105                 110

Gln Gly Thr Gln Val Thr Val Ser Ser
        115                 120

<210> SEQ ID NO 196
<211> LENGTH: 117
<212> TYPE: PRT
<213> ORGANISM: Artificial Sequence
<220> FEATURE:
<223> OTHER INFORMATION: antibody sequence

<400> SEQUENCE: 196

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Gly Tyr
            20                  25                  30

Val Ile Gly Trp Tyr Arg Gln Ala Pro Gly Lys Gln Arg Glu Glu Val
        35                  40                  45

Ala Ile Ile Ser Ser Ser Gly Ser Thr Asn Tyr Ala Asp Ser Val Lys
    50                  55                  60

Gly Arg Phe Thr Ile Ser Arg Asp Asn Ala Asn Ala Lys Thr Thr Phe
65                  70                  75                  80

Tyr Leu Gln Met Asn Ser Leu Lys Pro Glu Asp Thr Ala Val Tyr Tyr
                85                  90                  95

Cys Asn Ala Arg Leu Trp Leu Asn Asn Tyr Trp Gly Gln Gly Thr Leu
            100                 105                 110

Val Thr Val Ser Ser
        115

<210> SEQ ID NO 197
<211> LENGTH: 119
<212> TYPE: PRT
<213> ORGANISM: Artificial Sequence
<220> FEATURE:
<223> OTHER INFORMATION: antibody sequence

<400> SEQUENCE: 197

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45
```

```
Ser Thr Ile Ser Pro Ser Gly Gly Thr Thr Tyr Tyr Thr Asn Ser Ala
    50                  55                  60

Lys Gly Arg Phe Thr Ile Ser Arg Asp Asn Ala Lys Asn Thr Val Tyr
 65                  70                  75                  80

Leu Gln Val Asn Asn Leu Lys Pro Glu Asp Thr Ala Val Tyr Tyr Cys
                 85                  90                  95

Ala Ala Arg Arg Ser Gly Arg Tyr Glu Tyr Asp Tyr Trp Gly Gln Gly
             100                 105                 110

Thr Gln Val Thr Val Ser Ser
            115
```

<210> SEQ ID NO 198
<211> LENGTH: 126
<212> TYPE: PRT
<213> ORGANISM: Artificial Sequence
<220> FEATURE:
<223> OTHER INFORMATION: antibody sequence

<400> SEQUENCE: 198

```
Gln Val Gln Leu Gln Glu Ser Gly Gly Asp Leu Val Gln Pro Gly Gly
 1               5                  10                  15

Ser Leu Arg Leu Ser Cys Val Ala Ser Gly Phe Pro Phe Asp Asp Tyr
            20                  25                  30

Pro Met Ser Trp Val Arg Gln Ala Pro Gly Lys Gly Leu Glu Trp Val
        35                  40                  45

Ser Ser Val Ser Pro Asn Gly Gly Ser Thr Phe Tyr Ala Asp Ser Leu
    50                  55                  60

Lys Gly Arg Phe Thr Ile Ser Arg Asp Asn Ala Lys Asn Thr Leu Tyr
 65                  70                  75                  80

Leu Gln Ile Asn Ser Leu Lys Ser Asp Asp Thr Ala Val Tyr His Cys
                 85                  90                  95

Ala Lys Val Leu Asp Tyr Tyr Cys Ser Gly Tyr Gly Cys Tyr Ala Ser
             100                 105                 110

Tyr Asp Leu Trp Gly Gln Gly Thr Gln Val Thr Val Ser Ser
         115                 120                 125
```

<210> SEQ ID NO 199
<211> LENGTH: 120
<212> TYPE: PRT
<213> ORGANISM: Artificial Sequence
<220> FEATURE:
<223> OTHER INFORMATION: antibody sequence

<400> SEQUENCE: 199

```
Gln Val Gln Leu Gln Glu Ser Gly Gly Gly Leu Val Gln Pro Gly Gly
 1               5                  10                  15

Ser Leu Arg Leu Ser Cys Ala Ala Ser Ile Ser Ile Val Ser Ile Asn
            20                  25                  30

Thr Met Ala Trp Tyr Arg Gln Ala Pro Gly Lys Gln Arg Glu Leu Val
        35                  40                  45

Ala Gly Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Ser Leu
 65                  70                  75                  80

Gln Met Asn Ser Leu Lys Pro Glu Asp Thr Ala Val Tyr Tyr Cys Asn
                 85                  90                  95

Ala Gly Arg Tyr Val Pro Gly Ala Ile Val Thr Asn Tyr Trp Gly Gln
             100                 105                 110
```

Gly Thr Gln Val Thr Val Ser Ser
        115                 120

<210> SEQ ID NO 200
<211> LENGTH: 121
<212> TYPE: PRT
<213> ORGANISM: Artificial Sequence
<220> FEATURE:
<223> OTHER INFORMATION: antibody sequence

<400> SEQUENCE: 200

Gln Val Gln Leu Gln Glu Phe Gly Gly Leu Val Gln Ala Gly Gly
1               5                   10                  15

Ser Leu Arg Leu Ser Cys Leu Ala Ser Met Thr Thr Leu Gly Phe Lys
            20                  25                  30

Thr Met Gly Trp Tyr Arg Gln Ala Pro Gly Lys Gln Arg Glu Leu Val
            35                  40                  45

Ala Arg Ile Ser Ser Gly Gly Gln Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Ile Ser Leu Lys Pro Glu Asp Thr Ala Val Tyr Tyr Cys Asn
                85                  90                  95

Ala Arg Arg Tyr Tyr Ser Leu Ala Arg Tyr Asp Tyr Asn Tyr Trp Gly
            100                 105                 110

Gln Gly Thr Gln Val Thr Val Ser Ser
        115                 120

<210> SEQ ID NO 201
<211> LENGTH: 116
<212> TYPE: PRT
<213> ORGANISM: Artificial Sequence
<220> FEATURE:
<223> OTHER INFORMATION: antibody sequence

<400> SEQUENCE: 201

Gln Val Gln Leu Gln Ala Phe Gly Gly Ala Ala Ala Gln Ala Gly Asp
1               5                   10                  15

Ser Leu Arg Leu Ser Cys Val Val Gly Gly Lys Ser Thr Ala Ala Val
            20                  25                  30

Asn Gly Val Gly Trp Tyr Arg Gln Ala Pro Gly Arg Gln Arg Glu Phe
            35                  40                  45

Val Ala Ala Ile Arg Pro Gly Arg Arg Asp Tyr Leu Asp Ser Val
        50                  55                  60

Lys Gly Arg Phe Ser Val Phe Arg Asn Lys Thr Thr Val Tyr Leu Arg
65                  70                  75                  80

Met Asn Asp Leu Arg Ile Glu Asp Thr Ala Val Tyr Tyr Cys Tyr Ala
                85                  90                  95

Glu Gly Leu Leu Leu Pro Ser Thr Tyr Trp Gly Gln Gly Thr Leu Val
            100                 105                 110

Thr Val Ser Ser
        115

<210> SEQ ID NO 202
<211> LENGTH: 10
<212> TYPE: PRT
<213> ORGANISM: Artificial Sequence
<220> FEATURE:
<223> OTHER INFORMATION: antibody sequence

<400> SEQUENCE: 202

Val Ser Gly Arg Thr Phe Ser Thr Ser Gln
1               5                   10

<210> SEQ ID NO 203
<211> LENGTH: 10
<212> TYPE: PRT
<213> ORGANISM: Artificial Sequence
<220> FEATURE:
<223> OTHER INFORMATION: antibody sequence

<400> SEQUENCE: 203

Ala Arg Ile Ser Trp Arg Gly Lys Gln His
1               5                   10

<210> SEQ ID NO 204
<211> LENGTH: 14
<212> TYPE: PRT
<213> ORGANISM: Artificial Sequence
<220> FEATURE:
<223> OTHER INFORMATION: antibody sequence

<400> SEQUENCE: 204

Ala Ala Asp Arg Arg Arg Thr Tyr Leu Gly Gln Gln His Asp
1               5                   10

<210> SEQ ID NO 205
<211> LENGTH: 121
<212> TYPE: PRT
<213> ORGANISM: Artificial Sequence
<220> FEATURE:
<223> OTHER INFORMATION: antibody sequence

<400> SEQUENCE: 205

Gln Val Gln Leu Ala Glu Ser Gly Gly Gly Leu Val Gln Ala Gly Gly
1               5                   10                  15

Ser Leu Arg Leu Ser Cys Val Val Ser Gly Arg Thr Phe Ser Thr Ser
            20                  25                  30

Gln Met Gly Trp Phe Arg Gln Pro Pro Gly Lys Glu Arg Glu Leu Val
        35                  40                  45

Ala Arg Ile Ser Trp Arg Gly Lys Gln His Tyr Ala Asp Ser Val Lys
    50                  55                  60

Gly Arg Phe Thr Ile Ser Arg Asp Tyr Ala Lys Asn Thr Val Tyr Leu
65                  70                  75                  80

Gln Met Asn Gly Leu Lys Ser Glu Asp Thr Ala Val Tyr Tyr Cys Ala
                85                  90                  95

Ala Asp Arg Arg Arg Thr Tyr Leu Gly Gln Gln His Asp Tyr Trp Gly
            100                 105                 110

Gln Gly Thr Leu Val Thr Val Ser Ser
        115                 120

<210> SEQ ID NO 206
<211> LENGTH: 10
<212> TYPE: PRT
<213> ORGANISM: Artificial Sequence
<220> FEATURE:
<223> OTHER INFORMATION: antibody sequence

<400> SEQUENCE: 206

Ala Ser Gly Ser Ile Phe Arg Ile Asn Gly
1               5                   10

<210> SEQ ID NO 207
<211> LENGTH: 10
<212> TYPE: PRT
<213> ORGANISM: Artificial Sequence
<220> FEATURE:
<223> OTHER INFORMATION: antibody sequence

<400> SEQUENCE: 207

```
Ala Thr Ile Thr Arg Gly Gly Ser Ile Ser
1               5                   10
```

<210> SEQ ID NO 208
<211> LENGTH: 21
<212> TYPE: PRT
<213> ORGANISM: Artificial Sequence
<220> FEATURE:
<223> OTHER INFORMATION: antibody sequence

<400> SEQUENCE: 208

```
Ala Lys Tyr Arg Arg Pro Leu Phe Tyr Ser Gly Ser Asn Tyr Arg Glu
1               5                   10                  15

Gly Asp Phe Ala Ser
            20
```

<210> SEQ ID NO 209
<211> LENGTH: 127
<212> TYPE: PRT
<213> ORGANISM: Artificial Sequence
<220> FEATURE:
<223> OTHER INFORMATION: antibody sequence

<400> SEQUENCE: 209

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
            20                  25                  30

Gly Met Gly Trp His Arg Gln Ala Pro Gly Lys Glu Arg Glu Leu Val
        35                  40                  45

Ala Thr Ile Thr Arg Gly Gly Ser Ile Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Asn Leu Lys Pro Glu Asp Thr Ala Val Tyr Tyr Cys Ala
                85                  90                  95

Lys Tyr Arg Arg Pro Leu Phe Tyr Ser Gly Ser Asn Tyr Arg Glu Gly
            100                 105                 110

Asp Phe Ala Ser Trp Gly Gln Gly Thr Gln Val Thr Val Ser Ser
        115                 120                 125
```

<210> SEQ ID NO 210
<211> LENGTH: 10
<212> TYPE: PRT
<213> ORGANISM: Artificial Sequence
<220> FEATURE:
<223> OTHER INFORMATION: antibody sequence

<400> SEQUENCE: 210

```
Ala Ser Gly Arg Thr Phe Gly Ser Tyr Thr
1               5                   10
```

<210> SEQ ID NO 211
<211> LENGTH: 11

```
<212> TYPE: PRT
<213> ORGANISM: Artificial Sequence
<220> FEATURE:
<223> OTHER INFORMATION: antibody sequence

<400> SEQUENCE: 211

Ala Ala Ile Ser Arg Ser Gly Gly Ser Thr Tyr
1               5                   10

<210> SEQ ID NO 212
<211> LENGTH: 15
<212> TYPE: PRT
<213> ORGANISM: Artificial Sequence
<220> FEATURE:
<223> OTHER INFORMATION: antibody sequence

<400> SEQUENCE: 212

Asn Val Arg Gly Arg Pro Phe Ile Leu Ser Lys Pro Phe Asp Ser
1               5                   10                  15

<210> SEQ ID NO 213
<211> LENGTH: 122
<212> TYPE: PRT
<213> ORGANISM: Artificial Sequence
<220> FEATURE:
<223> OTHER INFORMATION: antibody sequence

<400> SEQUENCE: 213

Gln Val Gln Leu Gln Ala Ser Gly Gly Gly Leu Val Gln Ala Gly Gly
1               5                   10                  15

Ser Leu Arg Leu Ser Cys Ala Ala Ser Gly Arg Thr Phe Gly Ser Tyr
            20                  25                  30

Thr Met Gly Trp Phe Arg Gln Ala Pro Gly Lys Glu Arg Glu Phe Val
        35                  40                  45

Ala Ala Ile Ser Arg Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Val Arg Gly Arg Pro Phe Ile Leu Ser Lys Pro Phe Asp Ser Trp
            100                 105                 110

Gly Gln Gly Thr Leu Val Thr Val Ser Ser
        115                 120

<210> SEQ ID NO 214
<211> LENGTH: 10
<212> TYPE: PRT
<213> ORGANISM: Artificial Sequence
<220> FEATURE:
<223> OTHER INFORMATION: antibody sequence

<400> SEQUENCE: 214

Ala Ser Gly Arg Thr Phe Ser Asn Tyr Ala
1               5                   10

<210> SEQ ID NO 215
<211> LENGTH: 11
<212> TYPE: PRT
<213> ORGANISM: Artificial Sequence
<220> FEATURE:
<223> OTHER INFORMATION: antibody sequence

<400> SEQUENCE: 215
```

Ala Ala Ile Thr Arg Asn Gly Gly Ile Thr Tyr
1               5                   10

<210> SEQ ID NO 216
<211> LENGTH: 15
<212> TYPE: PRT
<213> ORGANISM: Artificial Sequence
<220> FEATURE:
<223> OTHER INFORMATION: antibody sequence

<400> SEQUENCE: 216

Asn Ile Lys Ala Arg Arg Gly Ser Phe Phe Asn Pro Val Asn Asn
1               5                   10                  15

<210> SEQ ID NO 217
<211> LENGTH: 123
<212> TYPE: PRT
<213> ORGANISM: Artificial Sequence
<220> FEATURE:
<223> OTHER INFORMATION: antibody sequence

<400> SEQUENCE: 217

Gln Val Gln Leu Gln Glu Ser Gly Gly Gly Leu Val Gln Ala Gly Asn
1               5                   10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Lys Glu Arg Glu Phe Val
            35                  40                  45

Ala Ala Ile Thr Arg Asn Gly Gly Ile Thr Tyr Tyr Ala Glu Ser Val
        50                  55                  60

Lys Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Asn Ile Lys Ala Arg Arg Gly Ser Phe Phe Asn Pro Val Asn Asn Tyr
            100                 105                 110

Trp Gly Gln Gly Thr Gln Val Thr Val Ser Ser
        115                 120

<210> SEQ ID NO 218
<211> LENGTH: 498
<212> TYPE: DNA
<213> ORGANISM: Artificial Sequence
<220> FEATURE:
<223> OTHER INFORMATION: antibody sequence

<400> SEQUENCE: 218
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtacagcctc tggacgcacc ttccgtgcct atgccatggg gtggttccgc     180
caggctccag ggaaggagcg tgagttggta gcagctatta ccgcactgg tggtgtcaca      240 acctatgcag actccgtgaa gggccgattc accatctcca gagacaacgc caagaatacg     300
gtgtatctgc aaatgaacaa cctgaagact gaggacacgg ccgtctatta ttgtaatgca     360
tacttccgtt ggggtactcg ctactgggc caggggaccc aggtcaccgt ctcctcaact      420
agtggcccgg gaggccaaca ccatcaccac catcatggcg cagaacaaaa actcatctca     480
gaagaggatc tgtcttag                                                   498

<210> SEQ ID NO 219
<211> LENGTH: 516
<212> TYPE: DNA
<213> ORGANISM: Artificial Sequence
<220> FEATURE:
<223> OTHER INFORMATION: antibody sequence

<400> SEQUENCE: 219

```
atgaaatacc tattgcctac ggcggccgct ggattgttat tactcgcggc ccagccggcc      60
atggcgcagg tgcagctgca ggagtctggg ggaggcttgg tgcagcctgg ggggtctctg     120
agactctcct gtgcagcctc tggaaggatc ttcagtattt ggaccatggg ctggtaccgc     180
caggctccag ggaagcagcg cgagttggtc gcggctatta ctagtgttgg taacacagac     240
tatgcagact ccgtgaaggg ccgattcacc atctccagag agactgccaa gaagacggtg     300
tatctgcaaa tgaacagcct gaaacctgag gacacggccg tctattactg taatgtagaa     360
tctcggcgtg gtataggctt cctacgtaaa acgtatagct actggggcca ggggacccag     420
gtcaccgtct cctcaactag tggcccggga ggccaacacc atcaccacca tcatggcgca     480
gaacaaaaac tcatctcaga agaggatctg tcttag                                516
```

<210> SEQ ID NO 220
<211> LENGTH: 492
<212> TYPE: DNA
<213> ORGANISM: Artificial Sequence
<220> FEATURE:
<223> OTHER INFORMATION: antibody sequence

<400> SEQUENCE: 220

```
atgaaatacc tattgcctac ggcggccgct ggattgttat tactcgcggc ccagccggcc      60
atggcgcagg tgcagctgca ggagtctggg ggaggcttgg tgcagcctgg ggggtctctg     120
acactctcct gtgcagcctc tggaagcatc ttcagaatca ataacatggg ctggttccgc     180
caggctccag ggaagcagcg cgagttggtc gcaactatta ctcgtggtgg taacacaaac     240
tatgcagact ccgtgaaggg ccgattcacc atctccagag acaacgccaa gaaaacgctg     300
tatctgcaaa tgaacagcct gaaacctgag gacacggccg tctattactg taatgcaaat     360
tatcttattc gatcatactg gggccagggg acccaggtca ccgtctcctc aactagtggc     420
ccgggaggcc aacaccatca ccaccatcat ggcgcagaac aaaaactcat ctcagaagag     480
gatctgtctt ag                                                          492
```

<210> SEQ ID NO 221
<211> LENGTH: 501
<212> TYPE: DNA
<213> ORGANISM: Artificial Sequence
<220> FEATURE:
<223> OTHER INFORMATION: antibody sequence

<400> SEQUENCE: 221

```
atgaaatacc tattgcctac ggcggccgct ggattgttat tactcgcggc ccagccggcc      60
atggcgcagg tgcagttgca ggagtctggg ggaggcttgg tgcagcctgg ggggtctctg     120
acactctcct gtgcagcctc tggaagcatc ttcagaatca ataacatggg ctggttccgc     180
caggctccag ggaagcagcg cgagttggtc gcaactatta ctcgtggtgg taacacaaac     240
tatgcagact ccgtgaaggg ccgattcacc atctccagag acaacgccaa gaacacggtg     300
tatctgcaaa tggacagcct gaaacctgag gacacggccg tctattactg taatgtaaaa     360
aagcatttcg gcattcgata tgactactgg ggccagggga cccaggtcac cgtctcctca     420
```
actagtggcc cgggaggcca acaccatcac caccatcatg gcgcagaaca aaaactcatc    480
tcagaagagg atctgtctta g                                              501

<210> SEQ ID NO 222
<211> LENGTH: 525
<212> TYPE: DNA
<213> ORGANISM: Artificial Sequence
<220> FEATURE:
<223> OTHER INFORMATION: antibody sequence

<400> SEQUENCE: 222
atgaaatacc tattgcctac ggcggccgct ggattgttat tactcgcggc ccagccggcc    60
atggcgcagg tgcagctgca ggagtctggg ggaggcttgg tgcaggctgg gggctctctg    120
agactctcct gcgcagcctc tggacgcacc ttcagcaact atgccttggc ctggttccgc    180
caggctccag ggttggagcg tgagtttgtg tcaagtatta gctggagtgg tggtgtacta    240
tactatgcag actccgtgaa gggccgattc accatgtcca gagacaacgg caagaacacg    300
gtgtacctgc aaatgaacag cctgaaacct gaggacacgg ccgtttatta ctgtgcagcg    360
aacgccgggt tgagtttatt aaggaattgg aggactaatg agtatgccta ctggggccag    420
ggaacccagg tcaccgtctc ctcaactagt ggcccgggag ccaacacca tcaccaccat    480 catggcgcag aacaaaaact catctcagaa gaggatctgt cttag                    525

<210> SEQ ID NO 223
<211> LENGTH: 492
<212> TYPE: DNA
<213> ORGANISM: Artificial Sequence
<220> FEATURE:
<223> OTHER INFORMATION: antibody sequence

<400> SEQUENCE: 223
atgaaatacc tattgcctac ggcggccgct ggattgttat tactcgcggc ccagccggcc    60
atggcgcagg tgcagttgca ggagtctggg ggaggcttgg tgcaggctgg gggctctctg    120
agactctcct gtgcagcctc tggaagcatc ttccgtatca atgccatggc ctggtaccgc    180
caggctccag ggaagcagcg cgagttggtc gctagaatta atactggtgg taacacaaac    240
tatgcaggct ccgtgaaggg ccgattcacc atctccagag acaacggcaa gaacacggtg    300
tatctgcaaa tgaacagcct gaaacctgag gacacgggcg tctattactg taatgtacag    360
agattcatca ctacctattg gggccagggg acccaggtca ccgtctcctc aactagtggc    420
ccgggaggcc aacaccatca ccaccatcat ggcgcagaac aaaaactcat ctcagaagag    480
gatctgtctt ag                                                        492

<210> SEQ ID NO 224
<211> LENGTH: 504
<212> TYPE: DNA
<213> ORGANISM: Artificial Sequence
<220> FEATURE:
<223> OTHER INFORMATION: antibody sequence

<400> SEQUENCE: 224
atgaaatacc tattgcctac ggcggccgct ggattgttat tactcgcggc ccagccggcc    60
atggcgcagg tgcagttgca ggagtctggg ggaggattgg tgcaggctgg gggctctctg    120
agactctcct gtgcagcctc tggacgcacc ttcagtacct ataggatggg ctggttccgc    180
caggctccag ggaaggagcg tgagtttgta gcagctatta ggtggagtac aagttatgca    240

| | |
|---|---|
| gattccgtga agggccgatt catcatctcc agagacaacg ccaagaacac ggtgtatctg | 300 |
| caaatgaaca gcctgaaacc tgaggacacg gccgtttatt actgtgcaac agggagggcc | 360 |
| tggagtacac tggccacgac atatgtttac tggggccagg ggacccaggt caccgtctcc | 420 |
| tcaactagtg gcccgggagg ccaacaccat caccaccatc atggcgcaga acaaaaactc | 480 |
| atctcagaag aggatctgtc ttag | 504 |

<210> SEQ ID NO 225
<211> LENGTH: 504
<212> TYPE: DNA
<213> ORGANISM: Artificial Sequence
<220> FEATURE:
<223> OTHER INFORMATION: antibody sequence

<400> SEQUENCE: 225

| | |
|---|---|
| atgaaatacc tattgcctac ggcggccgct ggattgttat tactcgcggc ccagccggcc | 60 |
| atggcgcagg tgcagctgca ggagtctggg ggaggattgg tgcaggccgg gggctctctg | 120 |
| agactctcct gtgcagcctc tggacgcacc ttcagtagat atgccacggc ctggttccgc | 180 |
| caggctccag ggaaggagcg tgagtttgta gcaggtatta gctggagtgg aacatcgtat | 240 |
| gcagactccg tgaagggccg attcaccatc tccagagaca cgccaagaa cacgctgtat | 300 |
| ctgcaaatga acagtctgaa atctgaggac acggccgtgt attactgtgc aaactttaaa | 360 |
| taccggtacg ggttggggcc ccgcgactac tggggccagg gaccctggt caccgtttcc | 420 |
| tcaactagtg gcccgggagg ccaacaccat caccaccatc atggcgcaga acaaaaactc | 480 |
| atctcagaag aggatctgtc ttag | 504 |

<210> SEQ ID NO 226
<211> LENGTH: 498
<212> TYPE: DNA
<213> ORGANISM: Artificial Sequence
<220> FEATURE:
<223> OTHER INFORMATION: antibody sequence

<400> SEQUENCE: 226

| | |
|---|---|
| atgaaatacc tattgcctac ggcggccgct ggattgttat tactcgcggc ccagccggcc | 60 |
| atggcgcagg tgcagctgca ggagtctggg ggaggcctgg tgcaggctgg ggggtctctg | 120 |
| agactctcct gtgtagcctc tggaagcatc ttcaggttca atgccatcgg ctggtaccgc | 180 |
| caggctccag ggaaggagcg cgagttggtc gcacgtatta ggcgtcttgg aagcacgtcc | 240 |
| tatgcagact ccgtgaaggg ccgattctcc atctccagag acagcgccaa gaacacggtg | 300 |
| tatctgcaga tgaacagcct gaaacctgag gacacggccg tctattactg taatgccgac | 360 |
| actcactttt cgacgcgcaa ctattggggc caggggaccc aggtcaccgt ctcctcaact | 420 |
| agtggcccgg gaggccaaca ccatcaccac catcatggcg cagaacaaaa actcatctca | 480 |
| gaagaggatc tgtcttag | 498 |

<210> SEQ ID NO 227
<211> LENGTH: 516
<212> TYPE: DNA
<213> ORGANISM: Artificial Sequence
<220> FEATURE:
<223> OTHER INFORMATION: antibody sequence

<400> SEQUENCE: 227

| | |
|---|---|
| atgaaatacc tattgcctac ggcggccgct ggattgttat tactcgcggc ccagccggcc | 60 |
| atggcgcagg tgcagttgca ggagtctggg ggaggcttgg tgcaggctgg gggctctctg | 120 |

```
agactctcct gtgcagcctc tggaagcatc ttccgtatca atggcatggg ctggcatcgc    180
caggctccag ggaaggagcg cgagttggtc gcaactatta ctcgtggtgg gagcacaaac    240
tatgcagact ccgtgaaggg ccgattcacc atctccagag acaacgccaa gaacacggtg    300
tatctgcaaa tgaacagcct gaaacctgag gacacggccg tttattactg tgcagcagac    360
ccgcggtggc gactcccttt tcccgggtac ggcatggact actggggcaa agggacccag    420
gtcaccgttt cctcaactag tggcccggga ggccaacacc atcaccacca tcatggcgca    480
gaacaaaaac tcatctcaga agaggatctg tcttag                              516
```

<210> SEQ ID NO 228
<211> LENGTH: 504
<212> TYPE: DNA
<213> ORGANISM: Artificial Sequence
<220> FEATURE:
<223> OTHER INFORMATION: antibody sequence

<400> SEQUENCE: 228

```
atgaaatacc tattgcctac ggcggccgct ggattgttat tactcgcggc ccagccggcc     60
atggcgcagg tgcagctgca ggagtctggg ggaggcttgg tgcagcctgg ggggtcgctg    120
agactctcct gtgcagcctc tggacgtatc cttatcagtt ccatgggctg gtaccgccag    180
gctcaaggag agcagcgcga gttggtcgct actatcacta gaggcggtac cacaaactat    240
gcagattccg tgaagggccg attcaccatc tccagagaca cgccaagaa catggtgtat    300 ctgcaaatga caaactgaa atctgaggac acggccgtgt attactgtgc aagggtgtac    360
ggtcgtgtct ggtcccgccc ttatgactac tggggccagg gacccaggt caccgtctcc    420 tcaactagtg gcccgggagg ccaacaccat caccaccatc atggcgcaga acaaaaactc    480
atctcagaag aggatctgtc ttag                                           504
```

<210> SEQ ID NO 229
<211> LENGTH: 504
<212> TYPE: DNA
<213> ORGANISM: Artificial Sequence
<220> FEATURE:
<223> OTHER INFORMATION: antibody sequence

<400> SEQUENCE: 229

```
atgaaatacc tattgcctac ggcggccgct ggattgttat tactcgcggc ccagccggcc     60
atggcgcagg tgcagctgca ggagtctggg ggaggcttgg tgcagcctgg ggggtcgctg    120
agactctcct gtgcagcctc tggacgtatc cttatcagtt ccatgggctg gtaccgccag    180
gctcaaggag agcagcgcga gttggtcgct actatcacta gaggcggtac cacaaactat    240
gcagattccg tgaagggccg attcaccatc tccagagaca cgccaagaa catggtgtat    300 ctgcaaatga caaactgaa atctgaggac acggccgtgt attactgtgc aagggtgtac    360
ggtcgtgtct ggtcccgccc ttatgactac tggggccagg gacccaggt caccgtttcc    420 tcaactagtg gcccgggagg ccaacaccat caccaccatc atggcgcaga acaaaaactc    480
atctcagaag aggatctgtc ttag                                           504
```

<210> SEQ ID NO 230
<211> LENGTH: 519
<212> TYPE: DNA
<213> ORGANISM: Artificial Sequence
<220> FEATURE:
<223> OTHER INFORMATION: antibody sequence

<400> SEQUENCE: 230

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtctggg | ggaggcttcg | tgcaggctgg | ggggtctctg | 120 |
| agactctcct | gtacagtctc | tggaaggacc | ttcaggatca | atggcatcga | ctggtaccgc | 180 |
| caggctccag | ggaagcagcg | cgagttggtc | gcagggatta | gtagtactgg | tagcacaaac | 240 |
| tatgcagact | ccgtgaaggg | ccgattcacc | atctccagag | acaacgcagg | gaatgcggtc | 300 |
| tatctgcaaa | tgaacaacct | gaaacctgag | gacacgggcc | gatattactg | tgcagcctcg | 360 |
| cgtggtttga | gtggtagctg | gtatctccgg | tcgtcgtatc | cttattgggg | ccaggggacc | 420 |
| caggtcaccg | tctcctcaac | tagtggcccg | ggaggccaac | accatcacca | ccatcatggc | 480 |
| gcagaacaaa | aactcatctc | agaagaggat | ctgtcttag | | | 519 |

<210> SEQ ID NO 231
<211> LENGTH: 507
<212> TYPE: DNA
<213> ORGANISM: Artificial Sequence
<220> FEATURE:
<223> OTHER INFORMATION: antibody sequence

<400> SEQUENCE: 231

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggcttgg | tgcagcctgg | ggggtctctg | 120 |
| agactctcct | gtgcagcctc | cgctacatc | ttcggtacca | tgggctggta | ccgccaggct | 180 |
| ccagggctgc | agcgcgagtt | ggtcgcatca | atttctcgtg | gtggtagtac | aaactatgca | 240 |
| gactccgtga | agggccgatt | cgccatctcc | agagacaacg | ccagaaaac | ggtgtatctg | 300 |
| caaatgaaca | gcctgaaacc | tgaggacacg | gccgtctatt | actgtaatgc | agtaccatac | 360 |
| cgttggggta | gtagctggta | cgctggtcgc | tactggggcc | aggggaccct | ggtcaccgtc | 420 |
| tcctcaacta | gtggcccggg | aggccaacac | catcaccacc | atcatggcgc | agaacaaaaa | 480 |
| ctcatctcag | aagaggatct | gtcttag | | | | 507 |

<210> SEQ ID NO 232
<211> LENGTH: 516
<212> TYPE: DNA
<213> ORGANISM: Artificial Sequence
<220> FEATURE:
<223> OTHER INFORMATION: antibody sequence

<400> SEQUENCE: 232

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | gcagtctggg | ggaggcttgg | tccaggctgg | ggggtctctg | 120 |
| acgctctcct | gtgtagcctc | tggaagccgc | ttcagtatca | ataccatggg | ctggtaccgc | 180 |
| caggctccag | ggaagcagcg | cgagttggtc | gcaggtatta | ctcgtggtgg | gagcacaaac | 240 |
| tatgcagact | ccgtgaaggg | ccgattcacc | atctctagag | agaacgccaa | gaacacggtg | 300 |
| tatctgcaaa | tgaatagcct | gaaacctgag | gacacggccg | tttattactg | tgcagccaca | 360 |
| ctccgtgcgt | gggccttac | tttcgcgact | tcgtatgcct | actggggcca | ggggaccag | 420 |
| gtcaccgtct | cctcaactag | tggcccggga | ggccaacacc | atcaccacca | tcatggcgca | 480 |
| gaacaaaaac | tcatctcaga | agaggatctg | tcttag | | | 516 |

<210> SEQ ID NO 233
<211> LENGTH: 510

<212> TYPE: DNA
<213> ORGANISM: Artificial Sequence
<220> FEATURE:
<223> OTHER INFORMATION: antibody sequence

<400> SEQUENCE: 233

```
atgaaatacc tattgcctac ggcggccgct ggattgttat tactcgcggc ccagccggcc    60
atggcgcagg tgcagctgca ggcgtctggg ggaggcttgg tgcagcctgg gggctctctg   120
acactctcct gtgcagcctc tggacgcacc ttcagtcgct atgccatggg ctggttccgc   180
caggctccag ggaaggagcg tgagtttgta gcacgtatta gctggagtgg tggttggaca   240
tactatgcag actccgtgaa gggccgattc gccatctcca gagacaacgc caagaacacg   300
gtgtatctgc aaatgaacag cctgaaacct gaggacacgg ccgtttatta ctgtgcagca   360
ggttcccgcg cggtactatt tggtacctat gactactggg gccaggggac ccaggtcacc   420
gtctcctcaa ctagtggccc gggaggccaa caccatcacc accatcatgg cgcagaacaa   480
aaactcatct cagaagagga tctgtcttag                                     510
```

<210> SEQ ID NO 234
<211> LENGTH: 516
<212> TYPE: DNA
<213> ORGANISM: Artificial Sequence
<220> FEATURE:
<223> OTHER INFORMATION: antibody sequence

<400> SEQUENCE: 234

```
atgaaatacc tattgcctac ggcggccgct ggattgttat tactcgcggc ccagccggcc    60
atggcgcagg tgcagttgca ggagtctggg ggaggattgg tgcaggctgg gggctctctg   120
agactctcct gtgcagcctc tggacgcacc ttgagcagct atcgcatggg ctggttccgc   180
caggttccag ggaaggagcg tgagcttgta gcagctatta ctggagagg tagttggaca   240
tactatgcag actccgtgaa gggccgggtc accatctcca gagacaacgc caagaacacg   300
gtgtatctgc aaatgaacag cctacaacct gaggacacgg ccctgtatta ctgtgcaagg   360
ccgactgcgc gttgggacct gttcagggaa aagtatgact ccggggcca ggggacccag   420
gtcaccgtct cctcaactag tggcccggga ggccaacacc atcaccacca tcatggcgca   480
gaacaaaaac tcatctcaga agaggatctg tcttag                             516
```

<210> SEQ ID NO 235
<211> LENGTH: 495
<212> TYPE: DNA
<213> ORGANISM: Artificial Sequence
<220> FEATURE:
<223> OTHER INFORMATION: antibody sequence

<400> SEQUENCE: 235

```
atgaaatacc tattgcctac ggcggccgct ggattgttat tactcgcggc ccagccggcc    60
atggcgcagg tgcagttgca ggagtctggg ggaggattgg tgcaggctgg gggctctctg   120
agactctcct gtgcagcctc tggacgcacc ttcagtagtt atgccatggg ctggttccgc   180
caggctccag ggaaggagcg tgagtttgta gcagctatta gcaggagtgg tggtattaca   240
tcatatgcag actccgtgaa gggccgattc gccatctcca gagacaatgc caagaacacg   300
gtgtatctgc aaatgaacag cctgaaacct gaggacacgg cgtctatta ctgtaatgta   360
cagagattca tcactaccta ttggggccag gggaccctgg tcaccgtttc ctcaactagt   420
ggcccgggag ccaacacca tcaccaccat catggcgcag aacaaaaact catctcagaa   480
```

```
gaggatctgt cttag                                                        495
```

<210> SEQ ID NO 236
<211> LENGTH: 525
<212> TYPE: DNA
<213> ORGANISM: Artificial Sequence
<220> FEATURE:
<223> OTHER INFORMATION: antibody sequence

<400> SEQUENCE: 236

```
atgaaatacc tattgcctac ggcggccgct ggattgttat tactcgcggc ccagccggcc        60
atggcgcagg tgcagttgca ggcgtctggg ggaggattgg tgcaggctgg gggctctctg       120
agcctctcct gtgcagcctc tggacgcacc ttcggtctgt ataccatggg ctggttccgc       180
caggctccag agaaggagcg tgagtttgta gcagctatta gttggagagg tcttagtata       240
atgtatgcag actccgtgaa gggccgattc accatctcca gagacaacgt caagaacacg       300
gtgtatctgc aaatgaacag cctgaaacct gaggacacgg ccgtttatta ctgtgcagcg       360
aacgccgggt tgagtttatt aaggaattgg aggactaatg agtatgccta ctggggccag       420
gggacccagg tcaccgtctc ctcaactagt ggcccgggag gccaacacca tcaccaccat       480
catggcgcag aacaaaaact catctcagaa gaggatctgt cttag                       525
```

<210> SEQ ID NO 237
<211> LENGTH: 525
<212> TYPE: DNA
<213> ORGANISM: Artificial Sequence
<220> FEATURE:
<223> OTHER INFORMATION: antibody sequence

<400> SEQUENCE: 237

```
atgaaatacc tattgcctac ggcggccgct ggattgttat tactcgcggc ccagccggcc        60
atggcgcagg tgcagctgca ggagtctggg ggaggattgg tgcaggctgg gggctctctg       120
agactctcct gtgaagcctc tgcgcgtact ttcagtagtt atgccgtggg ctggttccgc       180
caggctccgg ggaaggagcg tgagtttgta gcagctatta ctggagtggg cgtcgcaca        240
aactatgcag actccgtgaa gggccgattc tccatctcca gagacaacgc caagaacacg       300
atgtatctgc aaatgaacag cctgaaacct gaggacacgg ccgtttatta ctgtgcagca       360
aggtcgtctc ttctagagtt ctggttgggg tcccgaagag ggtatgacta ctggggccag       420
gggacccagg tcaccgtctc ctcaactagt ggcccgggag gccaacacca tcaccaccat       480
catggcgcag aacaaaaact catctcagaa gaggatctgt cttag                       525
```

<210> SEQ ID NO 238
<211> LENGTH: 510
<212> TYPE: DNA
<213> ORGANISM: Artificial Sequence
<220> FEATURE:
<223> OTHER INFORMATION: antibody sequence

<400> SEQUENCE: 238

```
atgaaatacc tattgcctac ggcggccgct ggattgttat tactcgcggc ccagccggcc        60
atggcgcagg tgcagctgca gcagtttggg ggaggcttgg tgcagcctgg ggggtctctg       120
agactctcct gtgcagcctc tggaaggatc ttcagtattt ggaccatggg ctggtaccgc       180
caggctccag ggaagcagcg cgagttggtc gcggctatta ctagtggtgg tagcacaaac       240
tatgcagact ccgtgaaggg ccgattcacc atctccagac aacgccga aaacacggtg        300
tatctgcaaa tgaacagcct gaaacctgag gacacggccg tctattactg taatgctgat       360
```
atacgccccc gtattatctc gttctttaag gattactggg gccaggggac ccaggtcacc     420
gtctcctcaa ctagtggccc gggaggccaa caccatcacc accatcatgg cgcagaacaa     480
aaactcatct cagaagagga tctgtcttag                                      510

<210> SEQ ID NO 239
<211> LENGTH: 498
<212> TYPE: DNA
<213> ORGANISM: Artificial Sequence
<220> FEATURE:
<223> OTHER INFORMATION: antibody sequence

<400> SEQUENCE: 239
atgaaatacc tattgcctac ggcggccgct ggattgttat tactcgcggc ccagccggcc      60
atggcgcagg tgcagctgca ggagtctggg ggaggattgg tgcagcctgg gggctctctg     120
agactctcct gtgcagcctc tggacgcacc ttcagtcgct atgctatggg ctggttccgc     180
caggctccag gaaggagcg tgagtttgta gcagctatta cctggagtgg tggtatcata     240
tattatgcag actccgtgaa gggccgattc accatctcca gagacaacgc caagaacacg     300
gtgtatctgc aaatgaacaa cctgaagact gaggacacgg ccgtctatta ttgtaatgca     360
tacttccgtt ggggtactcg ctactggggc caggggaccc tggtcaccgt ctcctcaact     420
agtggcccgg gaggccaaca ccatcaccac catcatggcg cagaacaaaa actcatctca     480
gaagaggatc tgtcttag                                                   498

<210> SEQ ID NO 240
<211> LENGTH: 510
<212> TYPE: DNA
<213> ORGANISM: Artificial Sequence
<220> FEATURE:
<223> OTHER INFORMATION: antibody sequence

<400> SEQUENCE: 240
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactttcct gtgcagcctc tggacgctcc ttcagttggt tgaccatggc atggttccgc     180
caggctccag gaaggagcg tgaaattgtg gctcgtatta cgtggcgtgg taccccatac     240
tatgcagact ctgtgaaggg ccggttcgcc atctccagag acaacgccaa gaacacggtg     300
tatctgcaaa tgaacagcct gaaacctgag gacacggcca tttattactg tgcagccgca     360
aaacagatac tgattagacc ggatgcatat gtctactggg gccaggggac ccaggtcacc     420
gtttcctcaa ctagtggccc gggaggccaa caccatcacc accatcatgg cgcagaacaa     480
aaactcatct cagaagagga tctgtcttag                                      510

<210> SEQ ID NO 241
<211> LENGTH: 510
<212> TYPE: DNA
<213> ORGANISM: Artificial Sequence
<220> FEATURE:
<223> OTHER INFORMATION: antibody sequence

<400> SEQUENCE: 241
atgaaatacc tattgcctac ggcggccgct ggattgttat tactcgcggc ccagccggcc      60
atggcgcagg tgcagctgca ggcgtctggg ggaggcctgg tgcaggctgg ggggtctctg     120
agactctcct gtgtagcctc tggaagcatc ttcaggttca atgccatcgg ctggtaccgc     180

```
caggctccag ggaaggagcg cgagttggtc gcacgtatta ggcgtcttgg aagcacgtcc    240
tatgcagact ccgtgaaggg ccgattctcc atctccagag acagcgccaa gaacacggtg    300
tatctgcaaa tggacaacct gaaacctgag gacacggccg tttattactg taaagcaggc    360
aggcatcccc attttagtat ggattagtac cctgacttag gccaggggac ccaggtcacc    420
gtctcctcaa ctagtggccc gggaggccaa caccatcacc accatcatgg cgcagaacaa    480
aaactcatct cagaagagga tctgtcttag                                     510
```

<210> SEQ ID NO 242
<211> LENGTH: 516
<212> TYPE: DNA
<213> ORGANISM: Artificial Sequence
<220> FEATURE:
<223> OTHER INFORMATION: antibody sequence

<400> SEQUENCE: 242

```
atgaaatacc tattgcctac ggcggccgct ggattgttat tactcgcggc ccagccggcc     60
atggcgcagg tgcagttgca ggagtctggg ggaggcttgg tgcagcctgg ggggtctctg    120
agactctcct gtgcagcctc ccgctacatc ttcggtacca tgggctggta ccgccaggct    180
ccagggctgc agcgcgagtt ggtcgcatca atttctcgtg gtggtagtac aaactatgca    240
gactccgtga agggccgatt cgccatctcc agagacaacg ccaagaacac ggtgtatctg    300
caaatgaaca acctgaaacc tgaggacacg gccgtctatt actgtgccct ggctctaggt    360
ttctttacta attactacgt ccgcgagtca agctatcgct actggggcca ggggacccag    420
gtcaccgtct cctcaactag tggcccggga ggccaacacc atcaccacca tcatggcgca    480
gaacaaaaac tcatctcaga agaggatctg tcttag                              516
```

<210> SEQ ID NO 243
<211> LENGTH: 513
<212> TYPE: DNA
<213> ORGANISM: Artificial Sequence
<220> FEATURE:
<223> OTHER INFORMATION: antibody sequence

<400> SEQUENCE: 243

```
atgaaatacc tattgcctac ggcggccgct ggattgttat tactcgcggc ccagccggcc     60
atggcgcagg tgcagctgca ggagtctggg ggaggattgg tacagactgg gggctctctg    120
agactctcct gtgcagcctc tggacgcacc ttccgtcttt attccatggc ctggtttcgc    180
caggcgccag gaaggagcg cgagttttta ggatcgatta ggtggaatgg tgcaacata    240 tactatacag actccgtgaa gggccgattc accatctcca gagacaacgc caagaacacg    300
gcgtatctgc aaatgaacag cctgacacct gaggacacgg ccgttatta ctgtgcagca    360 ggtcctcgga tagcggtatg cgctatgag tataactact ggggccaggg gacccaggtc    420
accgtctcct caactagtgg cccgggaggc caacaccatc accaccatca tggcgcagaa    480
caaaaactca tctcagaaga ggatctgtct tag                                 513
```

<210> SEQ ID NO 244
<211> LENGTH: 516
<212> TYPE: DNA
<213> ORGANISM: Artificial Sequence
<220> FEATURE:
<223> OTHER INFORMATION: antibody sequence

<400> SEQUENCE: 244

```
atgaaatacc tattgcctac ggcggccgct ggattgttat tactcgcggc ccagccggcc     60
```

```
atggcgcagg tgcagctgca ggagtctggg ggaggcttgg tgcagcctgg ggggtctctg    120
agactctcct gtgcagcctc tggaagcatc ggcagtttca agaccatggg ctggtaccgc    180
caggctccag ggaagcagcg cgagttggtc gcaactatta ctcgttgggg ttttacaaac    240
tatgcagact ccgtgaaggg ccgattcacc atcgccagag acaacgccaa gagcacgctg    300
tatctgcaaa tgaacagcct gaaacctgag gacacggcca tttattactg tgcagcagcg    360 caggggggt ttatgaaacc gcgcgccaat tggtataact cgtggggcca ggggaccctg     420
gtcaccgtct cctcaactag tggcccggga ggccaacacc atcaccacca tcatggcgca    480
gaacaaaaac tcatctcaga agaggatctg tcttag                              516
```

<210> SEQ ID NO 245
<211> LENGTH: 516
<212> TYPE: DNA
<213> ORGANISM: Artificial Sequence
<220> FEATURE:
<223> OTHER INFORMATION: antibody sequence

<400> SEQUENCE: 245

```
atgaaatacc tattgcctac ggcggccgct ggattgttat tactcgcggc ccagccggcc     60
atggcgcagg tgcagttgca ggagtctggg ggcggattgg tgcaggctgg ggcctctctg    120
agactctcct gtgtagcctc tggacgcacc ttcagccgct atggtatggg ctggttccgc    180
caggctccag ggaaggagcg tgagtttgta gcagccatta gccggagtgg tgcaatctca    240
tactatgcag actccgtgaa gggccgattc accatctcca gaggcgacgc cacgaacacg    300
gtcgtcctgc aaatgagcag cctgaaacct ggggacacgg ccgtttatta ctgtgcagct    360
tcaagcagac gtctgcttgg tggtccattt gcgtacgact actggggcca ggggaccctg    420
gtcaccgtct cctcaactag tggcccggga ggccaacacc atcaccacca tcatggcgca    480
gaacaaaaac tcatctcaga agaggatctg tcttag                              516
```

<210> SEQ ID NO 246
<211> LENGTH: 486
<212> TYPE: DNA
<213> ORGANISM: Artificial Sequence
<220> FEATURE:
<223> OTHER INFORMATION: antibody sequence

<400> SEQUENCE: 246

```
atgaaatacc tattgcctac ggcggccgct ggattgttat tactcgcggc ccagccggcc     60
atggcgcagg tgcagctgca ggagtctggg ggaggcttgg tgcagcctgg ggggtctctg    120
agactctcct gtgcagcctc ccgctacatc ttcggtacca tgggctggta ccgccaggct    180
ccagggctgc agcgcgagtt ggtcgcatca atttctcgtg gtggtagtac aaactatgca    240
gactccgtga agggccgatt cgccatctcc agagacaacg ccaagaacac ggtttatctg    300
caaatgaaca gccttaaacc tgaggacacg gccgtctatt actgtaatgc aaaccgtcgc    360
gggtggaact actggggcca ggggacccag gtcaccgttt cctcaactag tggcccggga    420
ggccaacacc atcaccacca tcatggcgca gaacaaaaac tcatctcaga agaggatctg    480
tcttag                                                               486
```

<210> SEQ ID NO 247
<211> LENGTH: 519
<212> TYPE: DNA
<213> ORGANISM: Artificial Sequence
<220> FEATURE:

<223> OTHER INFORMATION: antibody sequence

<400> SEQUENCE: 247

| | |
|---|---|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaaccatc ttcactatga agaacatggc ttggtaccgc | 180 |
| caggctccag ggaaggagcg tgagtttgta gcagctatta gcacgagtgg tggtgtgaca | 240 |
| tggtatgcag actcctccgt gaagggccga ttcaccatct cccgagacaa cgccaagaac | 300 |
| acgctgtatc tgcaaatgga cagcctgaaa cctgaggaca cggccgtcta ttactgtaaa | 360 |
| gtcagatcgg ccccccgaat tatacccccaa ttgcgccgtg agtactgggg ccaggggacc | 420 |
| caggtcaccg tctcctcaac tagtggcccg ggaggccaac accatcacca ccatcatggc | 480 |
| gcagaacaaa aactcatctc agaagaggat ctgtcttag | 519 |

<210> SEQ ID NO 248
<211> LENGTH: 495
<212> TYPE: DNA
<213> ORGANISM: Artificial Sequence
<220> FEATURE:
<223> OTHER INFORMATION: antibody sequence

<400> SEQUENCE: 248

| | |
|---|---|
| atgaaatacc tattgcctac ggcggccgct ggattgttat tactcgcggc ccagccggcc | 60 |
| atggcgcagg tgcagttgca ggagtctggg ggaggcttgg tgcagcctgg ggactctctg | 120 |
| agactctcct gtgcagcctc tggacgcacc ttcagtagct atgccatggg ctggttccgc | 180 |
| caggctccag ggaaggagcg tgagtttgtg gcggctatta actggagtgg tcatagcaca | 240 |
| tactatgcag actccgtgaa gggccgattc accatctcca gagacaacgc caagaacacg | 300 |
| gtgtatctgc aaatgaacat gctgaaacct gaggacacgg ccgtctacta ttgtaaactt | 360 |
| actcgtttgc taaatacgta ctggggccag gggaccctgg tcaccgtctc ctcaactagt | 420 |
| ggcccgggag gccaacacca tcaccaccat catggcgcag aacaaaaact catctcagaa | 480 |
| gaggatctgt cttag | 495 |

<210> SEQ ID NO 249
<211> LENGTH: 501
<212> TYPE: DNA
<213> ORGANISM: Artificial Sequence
<220> FEATURE:
<223> OTHER INFORMATION: antibody sequence

<400> SEQUENCE: 249

| | |
|---|---|
| atgaaatacc tattgcctac ggcggccgct ggattgttat tactcgcggc ccagccggcc | 60 |
| atggcgcagg tgcagctgca ggagtctggg ggaggattgg ttcaggctgg ggactctctg | 120 |
| agactctcct gtgcattctc tggacgcacc ttcggccttc gcaccatggg ctggttccgc | 180 |
| caggctccag ggaaggagcg tgagtttgta tcaagtctta catggcgtga ataatgca | 240 |
| tactatgcag actccgtgaa gggccgattc accatctcca gagacaacgc caagaaaacg | 300 |
| ctgtatctgc aaatgaacag cctgaaacct gaggacacgg ccgtctattt ctgtaatgta | 360 |
| catctagtct ttaccaaccg agattactgg ggccagggga cccaggtcac cgtctcctca | 420 |
| actagtggcc cggggaggcca acaccatcac caccatcatg gcgcagaaca aaaactcatc | 480 |
| tcagaagagg atctgtctta g | 501 |

<210> SEQ ID NO 250
<211> LENGTH: 510
<212> TYPE: DNA
<213> ORGANISM: Artificial Sequence
<220> FEATURE:
<223> OTHER INFORMATION: antibody sequence

<400> SEQUENCE: 250

```
atgaaatacc tattgcctac ggcggccgct ggattgttat tactcgcggc ccagccggcc    60
atggcgcagg tgcagttgca gcagtctggg ggaggcttgg tgcagcctgg ggggtctctg   120
agactctcct gtgcagcctc ttggcgcatc ttcagtccca atgccatggc ctggtaccgc   180
caggctccag ggaagcagcg cgagttggtc gcacgaatta cgtgggctgg tatcacaaac   240
tatgcagact ccgtgaaggg ccgattcacc atctccagag acaacgccaa aaacacggtg   300
tatctgcaaa tgcacagcct gaaacctgag gatacggcca tttattactg tgtcgcagat   360
cgtcgaagca gctacctagg ccacggtttt gactactggg gccaggggac ccaggtcacc   420
gtctcctcaa ctagtggccc gggaggccaa caccatcacc accatcatgg cgcagaacaa   480
aaactcatct cagaagagga tctgtcttag                                    510
```

<210> SEQ ID NO 251
<211> LENGTH: 516
<212> TYPE: DNA
<213> ORGANISM: Artificial Sequence
<220> FEATURE:
<223> OTHER INFORMATION: antibody sequence

<400> SEQUENCE: 251

```
atgaaatacc tattgcctac ggcggccgct ggattgttat tactcgcggc ccagccggcc    60
atggcgcagg tgcagctgca ggagtctggg ggaggcttgg tgcagcctgg ggggtctctg   120
agactctcct gtgcagcctc ccgctacatc ttcggtacca tgggctggta ccgccaggct   180
ccagggctgc agcgcgagtt ggtcgcatca atttctcgtg gtggtagtac aaactatgca   240
gactccgtga agggccgatt cgccatctcc agagacaacg ccaagaacac ggtgtatctg   300
caaatgaaca gcctgaaacc tgaggacacg gccgtttatt actgtgcagc aaggtcgtct   360
cttctagagt tctggttggg gtcccgaaga gggtatgact actggggcca ggggacccag   420
gtcaccgtct cctcaactag tggcccggga ggccaacacc atcaccacca tcatggcgca   480
gaacaaaaac tcatctcaga agaggatctg tcttag                             516
```

<210> SEQ ID NO 252
<211> LENGTH: 507
<212> TYPE: DNA
<213> ORGANISM: Artificial Sequence
<220> FEATURE:
<223> OTHER INFORMATION: antibody sequence

<400> SEQUENCE: 252

```
atgaaatacc tattgcctac ggcggccgct ggattgttat tactcgcggc ccagccggcc    60
atggcgcagg tgcagttgca gcagtctggg ggaggcttgg tgcagcctgg ggggtctctg   120
agactcgcct gtgcagcctc cggaaggttc ttcaggatca atgccatggc ctggtaccgc   180
caggctccag ggaagcagcg cgaattggtc gcaactatta cgcgtgctgg tactacaacc   240
tatgcagact ccgtgaaggg ccgattcacc atctccagag acaacgccaa gaacacggtg   300
tatctgcaaa tgatcagcct gaaacctgag gacacgccg tgtattactg tgcaaaatac   360
cctactatta cgtggtatgg ccggcatgac taccggggtc aggggaccca ggtcaccgtc   420
```

```
tcctcaacta gtggcccggg aggccaacac catcaccacc atcatggcgc agaacaaaaa    480
ctcatctcag aagaggatct gtcttag                                       507
```

<210> SEQ ID NO 253
<211> LENGTH: 516
<212> TYPE: DNA
<213> ORGANISM: Artificial Sequence
<220> FEATURE:
<223> OTHER INFORMATION: antibody sequence

<400> SEQUENCE: 253

```
atgaaatacc tattgcctac ggcggccgct ggattgttat tactcgcggc ccagccggcc    60
atggcgcagg tgcagttgca ggagtctggg ggaggcttgg tgcagcatgg ggggtctctg   120
agactctcct gtgcagcctc tggaagcttc ttcagaatca ataccatggc ctggcaccgc   180
caggctccag gaagcagcg cgagttggtc gcatcgatca ctcgtggtgg tagcacaaac   240
tatgcagact ccgtgaaggg ccgattcacc atctccagag acaacgccaa gaacacggtg   300
tatctgcaaa tgaacagcct gaaatctgag gacacagccg tctattactg tgcagcaagc   360
cggtttggta ttaactacta caccgcccga cagtatggtt attggggcca ggggacccag   420
gtcaccgtct cctcaactag tggcccggga ggccaacacc atcaccacca tcatggcgca   480
gaacaaaaac tcatctcaga agaggatctg tcttag                            516
```

<210> SEQ ID NO 254
<211> LENGTH: 501
<212> TYPE: DNA
<213> ORGANISM: Artificial Sequence
<220> FEATURE:
<223> OTHER INFORMATION: antibody sequence

<400> SEQUENCE: 254

```
atgaaatacc tattgcctac ggcggccgct ggattgttat tactcgcggc ccagccggcc    60
atggcgcagg tgcagttgca ggcgtctggg ggaggattgg tgcaggctgg gggctctctg   120
agactctcct gtgcagcctc tggacgcacc ttcagtcgct atccatgggc tggttccgc   180 caggctccag ggaaggagcg tgagtttgta gcacgttttg ggtggagtgg tcttagcacc   240
tactatgccg actccgtgaa gggccgattc accatctcca gagacaacgc caagaatacg   300
gtgtatctgc aaatgaacag cctgaaacct gaggacacgg ccgttttatta ctgtgcagcc   360 gggcgcttca tgggttcgta tgactactgg ggccagggga cccaggtcac cgtctcctca   420
actagtggcc cggaggcca acaccatcac caccatcatg gcgcagaaca aaaactcatc   480
tcagaagagg atctgtctta g                                           501
```

<210> SEQ ID NO 255
<211> LENGTH: 522
<212> TYPE: DNA
<213> ORGANISM: Artificial Sequence
<220> FEATURE:
<223> OTHER INFORMATION: antibody sequence

<400> SEQUENCE: 255

```
atgaaatacc tattgcctac ggcggccgct ggattgttat tactcgcggc ccagccggcc    60
atggcgcagg tgcagctgca ggagtctggg ggaggattgg tgcaggctgg gggctctctg   120
agactctcct gtgcagcctc tggacgcacc ttcagttggt atgccatggg ctggttccgc   180
caggctccag ggagggagcg tgagtttgta gcagctatta gcggagtgg tggtatcaca   240 atctatgcag actccgtgaa gggccgattc gccgtctcca gagacaacgc caagaacacg   300
```

```
gtgtatctgc aaatgaatag cctgaaacct gaggacacgg ccgtttatta ctgtgcagca    360
aacttatttc agtggcgact aaacgacaac ggcaaccagt atggctcctg gggccagggg    420
accctggtca ccgtctcctc aactagtggc ccgggaggcc aacaccatca ccaccatcat    480
ggcgcagaac aaaaactcat ctcagaagag gatctgtctt ag                       522
```

<210> SEQ ID NO 256
<211> LENGTH: 507
<212> TYPE: DNA
<213> ORGANISM: Artificial Sequence
<220> FEATURE:
<223> OTHER INFORMATION: antibody sequence

<400> SEQUENCE: 256

```
atgaaatacc tattgcctac ggcggccgct ggattgttat tactcgcggc ccagccggcc    60
atggcgcagg tgcagctgca ggagtctggg ggaggattgg tgcaggctgg gggctctctg    120
agactctcct gtgtagtttc tggacgcacc ttcagtactt ctcagatggg ctggttccgc    180
cagcctccag ggaaggagcg tgagttggta gcacgtatta gttggcgtgg taagcaacac    240
tatgcagatt ccgtgaaggg ccgcttcacc atttccagag actacgccaa gaacacggtg    300
tacctgcaaa tgaatggcct gaaatctgag gacacggccg tttattactg tgcagcaggt    360
ccccgtgcgg tacttttttgg cacctatgac tactggggcc aggggaccca ggtcaccgtc    420
tcctcaacta gtggcccggg aggccaacac catcaccacc atcatggcgc agaacaaaaa    480
ctcatctcag aagaggatct gtcttag                                        507
```

<210> SEQ ID NO 257
<211> LENGTH: 510
<212> TYPE: DNA
<213> ORGANISM: Artificial Sequence
<220> FEATURE:
<223> OTHER INFORMATION: antibody sequence

<400> SEQUENCE: 257

```
atgaaatacc tattgcctac ggcggccgct ggattgttat tactcgcggc ccagccggcc    60
atggcgcagg tgcagctggc agagtctggg ggaggattgg tgcaggctgg gggctctctg    120
agactctcct gtgtagtttc tggacgcacc ttcagtactt ctcagatggg ctggttccgc    180
cagcctccag ggaaggagcg tgagttggta gcacgtatta gttggcgtgg taagcaacac    240
tatgcagatt ccgtgaaggg ccgcttcacc atttccagag actacgccaa gaacacggtg    300
tacctgcaaa tgaatggcct gaaatctgag gacacggccg tgtattactg tgcagcagat    360
cgtcggagga cctacttggg gcaacaacat gactactggg gccagggga cctggtcacc    420 gtctcctcaa ctagtggccc gggaggccaa caccatcacc accatcatgg cgcagaacaa    480
aaactcatct cagaagagga tctgtcttag                                     510
```

<210> SEQ ID NO 258
<211> LENGTH: 528
<212> TYPE: DNA
<213> ORGANISM: Artificial Sequence
<220> FEATURE:
<223> OTHER INFORMATION: antibody sequence

<400> SEQUENCE: 258

```
atgaaatacc tattgcctac ggcggccgct ggattgttat tactcgcggc ccagccggcc    60
atggcgcagg tgcagttgca ggagtctggg ggaggcttgg tgcaggctgg gggctctctg    120
```

| | |
|---|---:|
| agactctcct gtgcagcctc tggaagcatc ttccgtatca atggcatggg ctggcatcgc | 180 |
| caggctccag ggaaggagcg cgagttggtc gcaactatta ctcgtggtgg tagcataagc | 240 |
| tatgcagact ccgtgaaggg ccgattcacc atctccagag acaacgccaa gaacacgctg | 300 |
| tatctgcaaa tgaacaacct gaaacctgag gacacggccg tgtattactg tgcaaaatac | 360 |
| cgaagaccgt tattttatag tggtagtaac taccgtgaag gtgactttgc ttcctggggc | 420 |
| caggggaccc aggtcaccgt ctcctcaact agtggcccgg gaggccaaca ccatcaccac | 480 |
| catcatggcg cagaacaaaa actcatctca gaagaggatc tgtcttag | 528 |

<210> SEQ ID NO 259
<211> LENGTH: 387
<212> TYPE: DNA
<213> ORGANISM: Artificial Sequence
<220> FEATURE:
<223> OTHER INFORMATION: antibody sequence

<400> SEQUENCE: 259

| | |
|---|---:|
| caggtgcagt tgcaggcgtc tgggggagga ttggtgcagg ctggggggctc tctgagactc | 60 |
| tcctgtgcag cctctggacg cacgttcggt agctatacca tgggctggtt ccgccaggct | 120 |
| ccagggaagg agcgtgagtt tgtagcagct attagtagga cgtggtag cacatactat | 180 |
| gcagactccg tgaagggccg attcaccatc tcccgagaca acgccaagaa cacggtgtat | 240 |
| ctgcaaatga acagcctgaa acctgaggac acggccgtct attactgtaa tgtacgaggg | 300 |
| agaccgttta tattgagcaa accgtttgat tcctggggcc aggggaccct ggtcaccgtc | 360 |
| tcctcaacta gtggcccggg aggccaa | 387 |

<210> SEQ ID NO 260
<211> LENGTH: 390
<212> TYPE: DNA
<213> ORGANISM: Artificial Sequence
<220> FEATURE:
<223> OTHER INFORMATION: antibody sequence

<400> SEQUENCE: 260

| | |
|---|---:|
| caggtgcagc tgcaggagtc tgggggagga ttggtgcagg ctggggaactc tctgagactc | 60 |
| tcctgtgcag cctctggacg caccttcagt aattatgcca tgggctggtt ccgccaggct | 120 |
| ccagggaagg agcgtgagtt tgtagcagct attaccagga atggtggtat tacatactat | 180 |
| gcagagtccg tgaagggccg attcaccatc tccagagaca acgccaagaa catggtgtat | 240 |
| ctgcaaatga acagcctgaa acctgaggac acggccgtct attactgtaa tattaaggca | 300 |
| agacgcggta gtttcttcaa tcccgtaaat aactactggg gccaggggac ccaggtcacc | 360 |
| gtctcctcaa ctagtggccc gggaggccaa | 390 |

<210> SEQ ID NO 261
<211> LENGTH: 516
<212> TYPE: DNA
<213> ORGANISM: Artificial Sequence
<220> FEATURE:
<223> OTHER INFORMATION: antibody sequence

<400> SEQUENCE: 261

| | |
|---|---:|
| atgaaatacc tattgcctac ggcggccgct ggattgttat tactcgcggc ccagccggcc | 60 |
| atggcgcagg tgcagctgca ggagtctggg ggaggattgg tgcaggctgg gggctctctg | 120 |
| agactctcct gtgcagcctc tggacgcatc ttcagtaaca atgtgatggg ctggttccgc | 180 |
| caggctccag ggaaggagcg tgaatttgta gcagctatta gccggagcgg tggtaccaca | 240 |

```
ttgtatgcag aatccatgaa gggccgattc accatctcca gagacaacgc caagaacacg    300
ctgtatctgc aaatgaacag tctgaaatct gaagacacgg ccatgtatta ctgtgggaaa    360
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggatctg tcttag                              516
```

<210> SEQ ID NO 262
<211> LENGTH: 516
<212> TYPE: DNA
<213> ORGANISM: Artificial Sequence
<220> FEATURE:
<223> OTHER INFORMATION: antibody sequence

<400> SEQUENCE: 262

```
atgaaatacc tattgcctac ggcggccgct ggattgttat tactcgcggc ccagccggcc    60
atggcgcagg tgcagctgca ggagtctggg ggaggattgg tgcaggctgg gggctctctg    120
agactctcct gtgcagcctc tggacgcatc ttcagtaaca atgtgatggg ctggttccgc    180
caggctccag ggaaggagcg tgaatttgta gcagctatta gccggagcgg tggtaccaca    240
ttgtatgcag aatccatgaa gggccgattc accatctcca gagacaacgc caagaacacg    300
ctgtatctgc aaatgaacag tctgaaatct gaagacacgg ccatgtatta ctgtgggaaa    360
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggatctg tcttag                              516
```

<210> SEQ ID NO 263
<211> LENGTH: 516
<212> TYPE: DNA
<213> ORGANISM: Artificial Sequence
<220> FEATURE:
<223> OTHER INFORMATION: antibody sequence

<400> SEQUENCE: 263

```
atgaaatacc tattgcctac ggcggccgct ggattgttat tactcgcggc ccagccggcc    60
atggcgcagg tgcagctgca ggagtctggg ggaggattgg tgcaggctgg gggctctctg    120
agactctcct gtgcagcctc tggacgcatc ttcagtaaca atgtgatggg ctggttccgc    180
caggctccag ggaaggagcg tgaatttgta gcagctatta gccggagcgg tggtaccaca    240
ttgtatgcag aatccatgaa gggccgattc accatctcca gagacaacgc caagaacacg    300
ctgtatctgc aaatgaacag tctgaaatct gaagacacgg ccatgtatta ctgtgggaaa    360
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggatctg tcttag                              516
```

<210> SEQ ID NO 264
<211> LENGTH: 516
<212> TYPE: DNA
<213> ORGANISM: Artificial Sequence
<220> FEATURE:
<223> OTHER INFORMATION: antibody sequence

<400> SEQUENCE: 264

```
atgaaatacc tattgcctac ggcggccgct ggattgttat tactcgcggc ccagccggcc    60
```

| | |
|---|---|
| atggcgcagg tgcagctgca ggagtctggg ggaggattgg tgcaggctgg gggctctctg | 120 |
| agactctcct gtgcagcctc tggacgcatc ttcagtaaca atgtgatggg ctggttccgc | 180 |
| caggctccag ggaaggagcg tgaatttgta gcagctatta gccggagcgg tggtaccaca | 240 |
| ttgtatgcag aatccatgaa gggccgattc accatctcca gagacaacgc caagaacacg | 300 |
| ctgtatctgc aaatgaacag tctgaaatct gaagacacgg ccatgtatta ctgtgggaaa | 360 |
| gttgatgaga tccggccaac cgtctctgct tcgtatgacc tctggggcca ggggaccctg | 420 |
| gtcaccgtct cctcaactag tggcccggga ggccaacacc atcaccacca tcatggcgca | 480 |
| gaacaaaaac tcatctcaga agaggatctg tcttag | 516 |

<210> SEQ ID NO 265
<211> LENGTH: 516
<212> TYPE: DNA
<213> ORGANISM: Artificial Sequence
<220> FEATURE:
<223> OTHER INFORMATION: antibody sequence

<400> SEQUENCE: 265

| | |
|---|---|
| atgaaatacc tattgcctac ggcggccgct ggattgttat tactcgcggc ccagccggcc | 60 |
| atggcgcagg tgcagctgca ggagtctggg ggaggattgg tgcaggctgg gggctctctg | 120 |
| agactctcct gtgcagcctc tggacgcatc ttcagtaaca atgtgatggg ctggttccgc | 180 |
| caggctccag ggaaggagcg tgaatttgta gcagctatta gccggagcgg tggtaccaca | 240 |
| ttgtatgcag aatccatgaa gggccgattc accatctcca gagacaacgc caagaacacg | 300 |
| ctgtatctgc aaatgaacag tctgaaatct gaagacacgg ccatgtatta ctgtgggaaa | 360 |
| gttgatgaga tccggccaac cgtctctgct tcgtatgacc tctggggcca ggggaccctg | 420 |
| gtcaccgtct cctcaactag tggcccggga ggccaacacc atcaccacca tcatggcgca | 480 |
| gaacaaaaac tcatctcaga agaggatctg tcttag | 516 |

<210> SEQ ID NO 266
<211> LENGTH: 516
<212> TYPE: DNA
<213> ORGANISM: Artificial Sequence
<220> FEATURE:
<223> OTHER INFORMATION: antibody sequence

<400> SEQUENCE: 266

| | |
|---|---|
| atgaaatacc tattgcctac ggcggccgct ggattgttat tactcgcggc ccagccggcc | 60 |
| atggcgcagg tgcagctgca ggagtctggg ggaggattgg tgcaggctgg gggctctctg | 120 |
| agactctcct gtgcagcctc tggacgcatc ttcagtaaca atgtgatggg ctggttccgc | 180 |
| caggctccag ggaaggagcg tgaatttgta gcagctatta gccggagcgg tggtaccaca | 240 |
| ttgtatgcag aatccatgaa gggccgattc accatctcca gagacaacgc caagaacacg | 300 |
| ctgtatctgc aaatgaacag tctgaaatct gaagacacgg ccatgtatta ctgtgggaaa | 360 |
| gttgatgaga tccggccaac cgtctctgct tcgtatgacc tctggggcca ggggaccctg | 420 |
| gtcaccgtct cctcaactag tggcccggga ggccaacacc atcaccacca tcatggcgca | 480 |
| gaacaaaaac tcatctcaga agaggatctg tcttag | 516 |

<210> SEQ ID NO 267
<211> LENGTH: 516
<212> TYPE: DNA
<213> ORGANISM: Artificial Sequence
<220> FEATURE:
<223> OTHER INFORMATION: antibody sequence

```
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 267
atgaaatacc tattncntnc ggcgnncgct ggattgttat tactcgcggc ccanccgncc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                              516

<210> SEQ ID NO 268
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (468)..(468)
<223> OTHER INFORMATION: n is a, c, g, or t

<400> SEQUENCE: 268
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccanca tcatggcgca     480
gaacaaaaac tcatctcaga agaggatctg tcttag                              516

<210> SEQ ID NO 269
```

<211> LENGTH: 516
<212> TYPE: DNA
<213> ORGANISM: Artificial Sequence
<220> FEATURE:
<223> OTHER INFORMATION: antibody sequence

<400> SEQUENCE: 269

```
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                               516
```

<210> SEQ ID NO 270
<211> LENGTH: 516
<212> TYPE: DNA
<213> ORGANISM: Artificial Sequence
<220> FEATURE:
<223> OTHER INFORMATION: antibody sequence

<400> SEQUENCE: 270

```
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                               516
```

<210> SEQ ID NO 271
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature

```
<222> LOCATION: (25)..(25)
<223> OTHER INFORMATION: n is a, c, g, or t

<400> SEQUENCE: 271
atnaaatncn tattgcntac ggcgnccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                              516

<210> SEQ ID NO 272
<211> LENGTH: 516
<212> TYPE: DNA
<213> ORGANISM: Artificial Sequence
<220> FEATURE:
<223> OTHER INFORMATION: antibody sequence

<400> SEQUENCE: 272
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                              516

<210> SEQ ID NO 273
<211> LENGTH: 516
<212> TYPE: DNA
<213> ORGANISM: Artificial Sequence
<220> FEATURE:
<223> OTHER INFORMATION: antibody sequence

<400> SEQUENCE: 273
atgaaatacc tattgcctac ggcggccgct ggattgttat tactcgcggc ccagccggcc      60
atggcgcagg tgcagctgca ggagtctggg ggaggattgg tgcaggctgg gggctctctg     120
agactctcct gtgcagcctc tggacgcatc ttcagtaaca atgtgatggg ctggttccgc     180
caggctccag ggaaggagcg tgaatttgta gcagctatta gccggagcgg tggtaccaca     240
ttgtatgcag aatccatgaa gggccgattc accatctcca gagacaacgc caagaacacg     300
ctgtatctgc aaatgaacag tctgaaatct gaagacacgg ccatgtatta ctgtgggaaa     360
gttgatgaga tccggccaac cgtctctgct tcgtatgacc tctggggcca ggggaccctg     420
gtcaccgtct cctcaactag tggcccggga ggccaacacc atcaccacca tcatggcgca     480
gaacaaaaac tcatctcaga agaggatctg tcttag                              516
```

<210> SEQ ID NO 274
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (506)..(506)
<223> OTHER INFORMATION: n is a, c, g, or t

<400> SEQUENCE: 274

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggattgg | tgcaggctgg | gggctctctg | 120 |
| agactctcct | gtgcagcctc | tggacgcatc | ttcagtaaca | atgtgatggg | ctggttccgc | 180 |
| caggctccag | ggaaggagcg | tgaatttgta | gcagctatta | gccggagcgg | tggtaccaca | 240 |
| ttgtatgcag | aatccatgaa | gggccgattc | accatctcca | gagacaacgc | caagaacacg | 300 |
| ctgtatctgc | aaatgaacag | tctgaaatct | gaagacacgg | ccatgtatta | ctgtgggaaa | 360 |
| gttgatgaga | tccggccaac | cgtctctgct | tcgtatgacc | tctggggcca | ggggaccctg | 420 |
| gtcaccgtct | cctcaactag | tggcccggga | ggccaacacc | atcaccacca | tcatggcgca | 480 |
| gaacaaaaac | tcatctcaga | agaggntctg | tcttag | | | 516 |

<210> SEQ ID NO 275
<211> LENGTH: 516
<212> TYPE: DNA
<213> ORGANISM: Artificial Sequence
<220> FEATURE:
<223> OTHER INFORMATION: antibody sequence

<400> SEQUENCE: 275

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggattgg | tgcaggctgg | gggctctctg | 120 |
| agactctcct | gtgcagcctc | tggacgcatc | ttcagtaaca | atgtgatggg | ctggttccgc | 180 |
| caggctccag | ggaaggagcg | tgaatttgta | gcagctatta | gccggagcgg | tggtaccaca | 240 |
| ttgtatgcag | aatccatgaa | gggccgattc | accatctcca | gagacaacgc | caagaacacg | 300 |
| ctgtatctgc | aaatgaacag | tctgaaatct | gaagacacgg | ccatgtatta | ctgtgggaaa | 360 |
| gttgatgaga | tccggccaac | cgtctctgct | tcgtatgacc | tctggggcca | ggggaccctg | 420 |
| gtcaccgtct | cctcaactag | tggcccggga | ggccaacacc | atcaccacca | tcatggcgca | 480 |
| gaacaaaaac | tcatctcaga | agaggatctg | tcttag | | | 516 |

<210> SEQ ID NO 276
<211> LENGTH: 516
<212> TYPE: DNA
<213> ORGANISM: Artificial Sequence
<220> FEATURE:
<223> OTHER INFORMATION: antibody sequence

<400> SEQUENCE: 276

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggattgg | tgcaggctgg | gggctctctg | 120 |
| agactctcct | gtgcagcctc | tggacgcatc | ttcagtaaca | atgtgatggg | ctggttccgc | 180 |
| caggctccag | ggaaggagcg | tgaatttgta | gcagctatta | gccggagcgg | tggtaccaca | 240 |
| ttgtatgcag | aatccatgaa | gggccgattc | accatctcca | gagacaacgc | caagaacacg | 300 | ctgtatctgc aaatgaacag tctgaaatct gaagacacgg ccatgtatta ctgtgggaaa      360 gttgatgaga tccggccaac cgtctctgct tcgtatgacc tctggggcca ggggaccctg      420 gtcaccgtct cctcaactag tggcccggga ggccaacacc atcaccacca tcatggcgca      480 gaacaaaaac tcatctcaga agaggatctg tcttag                                516

<210> SEQ ID NO 277
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (506)..(506)
<223> OTHER INFORMATION: n is a, c, g, or t

<400> SEQUENCE: 277
atgaaatacc tattgcctac ggcggccgct ggattgttat tactcgcggc ccagccggcc      60
atggcgcagg tgcagctgca ggagtctggg ggaggattgg tgcaggctgg gggctctctg      120
agactctcct gtgcagcctc tggacgcatc ttcagtaaca atgtgatggg ctggttccgc      180
caggctccag ggaaggagcg tgaatttgta gcagctatta gccggagcgg tggtaccaca      240
ttgtatgcag aatccatgaa gggccgattc accatctcca gagacaacgc caagaacacg      300
ctgtatctgc aaatgaacag tctgaaatct gaagacacgg ccatgtatta ctgtgggaaa      360
gttgatgaga tccggccaac cgtctctgct tcgtatgacc tctggggcca ggggaccctg      420
gtcaccgtct cctcaactag tggcccggga ggccaacacc atcaccacca tcatggcgca      480
gaacaaaaac tcatctcaga agaggntctg tcttag                                516

<210> SEQ ID NO 278
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t

<400> SEQUENCE: 278
atgaaatacc tattgcctac ggcggccgct ggattgttat tactcgcggc ccagccggcc      60
atggcgcagg tgcagctgca ggagtctggg ggaggattgg tgcaggctgg gggctctctg      120
agactctcct gtgcagcctc tggacgcatc ttcagtaaca atgtgatggg ctggttccgc      180
caggctccag ggaaggagcg tgaatttgta gcagctatta gccggagcgg tggtaccaca      240
ttgtatgcag aatccatgaa gggccgattc accatctcca gagacaacgc caagaacacg      300
ctgtatctgc aaatgaacag tctgaaatct gaagacacgg ccatgtatta ctgtgggaaa      360
gttgatgaga tccggccaac cgtctctgct tcgtatgacc tctggggcca ggggaccctg      420
gtcaccgtct cctcaactag tggcccggga ggccaacacc atcaccacca tcatggcgca      480
gaacaaaaac tcntctcaga agaggntctg tcttag                                516

<210> SEQ ID NO 279

<211> LENGTH: 516
<212> TYPE: DNA
<213> ORGANISM: Artificial Sequence
<220> FEATURE:
<223> OTHER INFORMATION: antibody sequence

<400> SEQUENCE: 279

```
atgaaatacc tattgcctac ggcggccgct ggattgttat tactcgcggc ccagccggcc    60
atggcgcagg tgcagctgca ggagtctggg ggaggattgg tgcaggctgg gggctctctg   120
agactctcct gtgcagcctc tggacgcatc ttcagtaaca atgtgatggg ctggttccgc   180
caggctccag ggaaggagcg tgaatttgta gcagctatta gccggagcgg tggtaccaca   240
ttgtatgcag aatccatgaa gggccgattc accatctcca gagacaacgc caagaacacg   300
ctgtatctgc aaatgaacag tctgaaatct gaagacacgg ccatgtatta ctgtgggaaa   360
gttgatgaga tccggccaac cgtctctgct tcgtatgacc tctggggcca ggggaccctg   420
gtcaccgtct cctcaactag tggcccggga ggccaacacc atcaccacca tcatggcgca   480
gaacaaaaac tcatctcaga agaggatctg tcttag                              516
```

<210> SEQ ID NO 280
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (493)..(493)
<223> OTHER INFORMATION: n is a, c, g, or t

<400> SEQUENCE: 280

```
atgaaatacc tattgcctac ggcggccgct ggattgttat tactcgcggc ccagccggcc    60
atggcgcagg tgcagctgca ggagtctggg ggaggattgg tgcaggctgg gggctctctg   120
agactctcct gtgcagcctc tggacgcatc ttcagtaaca atgtgatggg ctggttccgc   180
caggctccag ggaaggagcg tgaatttgta gcagctatta gccggagcgg tggtaccaca   240
ttgtatgcag aatccatgaa gggccgattc accatctcca gagacaacgc caagaacacg   300
ctgtatctgc aaatgaacag tctgaaatct gaagacacgg ccatgtatta ctgtgggaaa   360
gttgatgaga tccggccaac cgtctctgct tcgtatgacc tctggggcca ggggaccctg   420
gtcaccgtct cctcaactag tggcccggga ggccaacacc atcaccacca tcatggcgca   480
gaacaaaaac tcntctcaga agaggatctg tcttag                              516
```

<210> SEQ ID NO 281
<211> LENGTH: 516
<212> TYPE: DNA
<213> ORGANISM: Artificial Sequence
<220> FEATURE:
<223> OTHER INFORMATION: antibody sequence

<400> SEQUENCE: 281

```
atgaaatacc tattgcctac ggcggccgct ggattgttat tactcgcggc ccagccggcc    60
atggcgcagg tgcagctgca ggagtctggg ggaggattgg tgcaggctgg gggctctctg   120
agactctcct gtgcagcctc tggacgcatc ttcagtaaca atgtgatggg ctggttccgc   180
caggctccag ggaaggagcg tgaatttgta gcagctatta gccggagcgg tggtaccaca   240
ttgtatgcag aatccatgaa gggccgattc accatctcca gagacaacgc caagaacacg   300
ctgtatctgc aaatgaacag tctgaaatct gaagacacgg ccatgtatta ctgtgggaaa   360
```

```
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggatctg tcttag                              516
```

```
<210> SEQ ID NO 282
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (506)..(506)
<223> OTHER INFORMATION: n is a, c, g, or t

<400> SEQUENCE: 282
```

```
atgaaatacc tattgcctac ggcggccgct ggattgttat tactcgcggc ccagccggcc     60
atggcgcagg tgcagctgca ggagtctggg ggaggattgg tgcaggctgg gggctctctg    120
agactctcct gtgcagcctc tggacgcatc ttcagtaaca atgtgatggg ctggttccgc    180
caggctccag ggaaggagcg tgaatttgta gcagctatta gccggagcgg tggtaccaca    240
ttgtatgcag aatccatgaa gggccgattc accatctcca gagacaacgc caagaacacg    300
ctgtatctgc aaatgaacag tctgaaatct gaagacacgg ccatgtatta ctgtgggaaa    360
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggntctg tcttag                              516
```

```
<210> SEQ ID NO 283
<211> LENGTH: 516
<212> TYPE: DNA
<213> ORGANISM: Artificial Sequence
<220> FEATURE:
<223> OTHER INFORMATION: antibody sequence

<400> SEQUENCE: 283
```

```
atgaaatacc tattgcctac ggcggccgct ggattgttat tactcgcggc ccagccggcc     60
atggcgcagg tgcagctgca ggagtctggg ggaggattgg tgcaggctgg gggctctctg    120
agactctcct gtgcagcctc tggacgcatc ttcagtaaca atgtgatggg ctggttccgc    180
caggctccag ggaaggagcg tgaatttgta gcagctatta gccggagcgg tggtaccaca    240
ttgtatgcag aatccatgaa gggccgattc accatctcca gagacaacgc caagaacacg    300
ctgtatctgc aaatgaacag tctgaaatct gaagacacgg ccatgtatta ctgtgggaaa    360
gttgatgaga tccggccaac cgtctctgct tcgtatgacc tctggggcca ggggaccctg    420
gtcaccgtct cctcaactag tggcccggga ggccaacacc atcaccacca tcatggcgca    480
gaacaaaaac tcatctcaga agaggatctg tcttag                              516
```

```
<210> SEQ ID NO 284
<211> LENGTH: 516
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (484)..(484)
<223> OTHER INFORMATION: n is a, c, g, or t
```

<400> SEQUENCE: 284

```
atgaaatacc tattgcctac ggcggccgct ggattgttat tactcgcggc ccagccggcc    60
atggcgcagg tgcagctgca ggagtctggg ggaggattgg tgcaggctgg gggctctctg   120
agactctcct gtgcagcctc tggacgcatc ttcagtaaca atgtgatggg ctggttccgc   180
caggctccag ggaaggagcg tgaatttgta gcagctatta gccggagcgg tggtaccaca   240
ttgtatgcag atccatgaa gggccgattc accatctcca gagacaacgc caagaacacg   300
ctgtatctgc aaatgaacag tctgaaatct gaagacacgg ccatgtatta ctgtgggaaa   360
gttgatgaga tccggccaac cgtctctgct cgtatgacc tctggggcca ggggaccctg   420
gtcaccgtct cctcaactag tggcccggga ggccaacacc atcaccacca tcatggcgca   480
gaanaaaaac tcatctcaga agaggatctg tcttag                             516
```

<210> SEQ ID NO 285
<211> LENGTH: 525
<212> TYPE: DNA
<213> ORGANISM: Artificial Sequence
<220> FEATURE:
<223> OTHER INFORMATION: antibody sequence

<400> SEQUENCE: 285

```
atgaaatacc tattgcctac ggcggccgct ggattgttat tactcgcggc ccagccggcc    60
atggcgcagg tgcagctgca ggagtctggg ggaggattgg tgcaggctgg ggactctctg   120
agactctcct gtgcagcctc tagcggcccc ttcagtagat atgccatggg ctggttccgc   180
caggctccag ggaaggagcg tgagtttgta gcaactatta gccggagtgg tagtagtaca   240
acttatggag actccgtgaa gggccgattc accatctcca gagacaacgc caagaacaca   300
ctatatctcg aaatgaacag cctgacgcct gaggacacgg ccgttttatta ctgtgcagtc   360
tcgaggtact atacagcagg tgctagtgct gatacaaaaa catatgacta ctggggccag   420
gggaccctgg tcaccgtctc ctcaactagt ggcccgggag ccaacacca tcaccaccat   480
catggcgcag aacaaaaact catctcagaa gaggatctgt cttag                   525
```

<210> SEQ ID NO 286
<211> LENGTH: 525
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (515)..(515)
<223> OTHER INFORMATION: n is a, c, g, or t

<400> SEQUENCE: 286

```
atgaaatacc tattgcctac ggcggccgct ggattgttat tactcgcggc ccagccggcc    60
atggcgcagg tgcagttgca ggcgtctggg ggaggcttgg tgcagcctgg ggggtcgctg   120
aaactctcct gtcaagcctc tggattcaat tttggcagtt ttgccatagc ctggttccgc   180
caggccccag ggaagggccg cgaggggatc tcatgtatca gtagtacaga cgatacatca   240
gtctattcag acgccgtcaa gggccgattc gccatttcca gagacaatgc caagagagcg   300
gcgtacttgc agatgaacag tctgattcct gaggacacgg ccaattatta ctgcgcaacc   360
gtgggccagt cctgtgattt gtgggaccac ccccaggttc cagtgcgcta ccggggccgc   420
gggaccctgg tcaccgtctc ctcaactagt ggcccgggag ccaacacca tcaccaccat   480
catggcgcag aacaaaaact catctcagaa gaggntctgt cttag                   525
```

<210> SEQ ID NO 287
<211> LENGTH: 525
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (515)..(515)
<223> OTHER INFORMATION: n is a, c, g, or t

<400> SEQUENCE: 287

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggcgtctggg | ggaggcttgg | tgcagcctgg | ggggtcgctg | 120 |
| aaactctcct | gtcaagcctc | tggattcaat | tttggcagtt | ttgccatagc | ctggttccgc | 180 |
| caggccccag | ggaagggccg | cgaggggatc | tcatgtatca | gtagtacaga | cgatacatca | 240 |
| gtctattcag | acgccgtcaa | gggccgattc | gccatttcca | gagacaatgc | caagagagcg | 300 |
| gcgtacttgc | agatgaacag | tctgattcct | gaggacacgg | ccaattatta | ctgcgcaacc | 360 |
| gtgggccagt | cctgtgattt | gtgggaccac | ccccaggttc | cagtgcgcta | ccggggccgc | 420 |
| gggacccagg | tcaccgtttc | ctcaactagt | ggcccgggag | gccaacacca | tcaccaccat | 480 |
| catggcgcag | aacaaaaact | catctcagaa | gaggntctgt | cttag | | 525 |

<210> SEQ ID NO 288
<211> LENGTH: 525
<212> TYPE: DNA
<213> ORGANISM: Artificial Sequence
<220> FEATURE:
<223> OTHER INFORMATION: antibody sequence

<400> SEQUENCE: 288

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggcgtctggg | ggaggcttgg | tgcagcctgg | ggggtcgctg | 120 |
| aaactctcct | gtcaagcctc | tggattcaat | tttggcagtt | ttgccatagc | ctggttccgc | 180 |
| caggccccag | ggaagggccg | cgaggggatc | tcatgtatca | gtagtacaga | cgatacatca | 240 |
| gtctattcag | acgccgtcaa | gggccgattc | gccatttcca | gagacaatgc | caagagagcg | 300 |
| gcgtacttgc | agatgaacag | tctgattcct | gaggacacgg | ccaattatta | ctgcgcaacc | 360 |
| gtgggccagt | cctgtgattt | gtgggaccac | ccccaggttc | cagtgcgcta | ccggggccgc | 420 |
| gggacccagg | tcaccgtttc | ctcaactagt | ggcccgggag | gccaacacca | tcaccaccat | 480 |
| catggcgcag | aacaaaaact | catctcagaa | gaggatctgt | cttag | | 525 |

<210> SEQ ID NO 289
<211> LENGTH: 525
<212> TYPE: DNA
<213> ORGANISM: Artificial Sequence
<220> FEATURE:
<223> OTHER INFORMATION: antibody sequence

<400> SEQUENCE: 289

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggcgtctggg | ggaggcttgg | tgcagcctgg | ggggtcgctg | 120 |
| aaactctcct | gtcaagcctc | tggattcaat | tttggcagtt | ttgccatagc | ctggttccgc | 180 |
| caggccccag | ggaagggccg | cgaggggatc | tcatgtatca | gtagtacaga | cgatacatca | 240 |

```
gtctattcag acgccgtcaa gggccgattc gccatttcca gagacaatgc caagagagcg    300
gcgtacttgc agatgaacag tctgattcct gaggacacgg ccaattatta ctgcgcaacc    360
gtgggccagt cctgtgattt gtgggaccac ccccaggttc cagtgcgcta ccggggccgc    420
gggacccagg tcaccgtttc ctcaactagt ggcccgggag ccaacacca tcaccaccat      480 catggcgcag aacaaaaact catctcagaa gaggatctgt cttag                    525
```

<210> SEQ ID NO 290
<211> LENGTH: 525
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t

<400> SEQUENCE: 290

```
atgaaatacc tattgcctac ggcggccgct ggattgttat tactcgcggc ccagccggcc     60
atggcgcagg tgcagctgca ggcgtctggg ggaggcttgg tgcagcctgg ggggtcgctg    120
aaactctcct gtcaagcctc tggattcaat tttggcagtt ttgccatagc ctggttccgc    180
caggccccag ggaagggccg cgaggggatc tcatgtatca gtagtacaga cgatacatca    240
gtctattcag acgccgtcaa gggccgattc gccatttcca gagacaatgc caagagagcg    300
gcgtacttgc agatgaacag tctgattcct gaggacacgg ccaattatta ctgcgcaacc    360
gtgggccagt cctgtgattt gtgggaccac ccccaggttc cagtgcgcta ccggggccgc    420
gggacccagg tcaccgtttc ctcaactagt ggcccgggag ccaacacca tcaccaccat      480 catggcgcag aacaaaaact cntctcagaa gaggntctgt cttag                    525
```

<210> SEQ ID NO 291
<211> LENGTH: 525
<212> TYPE: DNA
<213> ORGANISM: Artificial Sequence
<220> FEATURE:
<223> OTHER INFORMATION: antibody sequence

<400> SEQUENCE: 291

```
atgaaatacc tattgcctac ggcggccgct ggattgttat tactcgcggc ccagccggcc     60
atggcgcagg tgcagctgca ggcgtctggg ggaggcttgg tgcagcctgg ggggtcgctg    120
aaactctcct gtcaagcctc tggattcaat tttggcagtt ttgccatagc ctggttccgc    180
caggccccag ggaagggccg cgaggggatc tcatgtatca gtagtacaga cgatacatca    240
gtctattcag acgccgtcaa gggccgattc gccatttcca gagacaatgc caagagagcg    300
gcgtacttgc agatgaacag tctgattcct gaggacacgg ccaattatta ctgcgcaacc    360
gtgggccagt cctgtgattt gtgggaccac ccccaggttc cagtgcgcta ccggggccgc    420
gggacccagg tcaccgtctc ctcaactagt ggcccgggag ccaacacca tcaccaccat      480 catggcgcag aacaaaaact catctcagaa gaggatctgt cttag                    525
```

<210> SEQ ID NO 292
<211> LENGTH: 127
<212> TYPE: PRT
<213> ORGANISM: Artificial Sequence
<220> FEATURE:
<223> OTHER INFORMATION: antibody sequence

<400> SEQUENCE: 292

Gln Val Gln Leu Gln Glu Phe Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Ser Met Gly Trp Phe Arg Gln Ala Pro Gly Lys Glu Arg Glu Phe Val
        35                  40                  45

Gly Gly Ile Ser Arg Ser Gly Gly Trp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Val Ser Arg Ile Asn Asp Tyr Ala Pro Ala Leu Ser Arg
            100                 105                 110

Ala Tyr Asp Tyr Trp Gly Gln Gly Thr Gln Val Thr Val Ser Ser
        115                 120                 125

<210> SEQ ID NO 293
<211> LENGTH: 525
<212> TYPE: DNA
<213> ORGANISM: Artificial Sequence
<220> FEATURE:
<223> OTHER INFORMATION: antibody sequence

<400> SEQUENCE: 293
atgaaatacc tattgcctac ggcggccgct ggattgttat tactcgcggc ccagccggcc     60
atggcgcagg tgcagctgca ggcgtctggg ggaggcttgg tgcagcctgg ggggtcgctg    120
aaactctcct gtcaagcctc tggattcaat tttggcagtt ttgccatagc ctggttccgc    180
caggccccag gaagggccg cgaggggatc tcatgtatca gtagtacaga cgatacatca    240
gtctattcag acgccgtcaa gggccgattc gccatttcca gagacaatgc aagagagcg    300
gcgtacttgc agatgaacag tctgattcct gaggacacgg ccaattatta ctgcgcaacc    360
gtgggccagt cctgtgattt gtgggaccac cccaggttc cagtgcgcta ccggggccgc    420
gggacccagg tcaccgtttc ctcaactagt ggcccgggag ccaacacca tcaccaccat    480
catggcgcag aacaaaaact catctcagaa aggatctgt cttag                    525

<210> SEQ ID NO 294
<211> LENGTH: 507
<212> TYPE: DNA
<213> ORGANISM: Artificial Sequence
<220> FEATURE:
<223> OTHER INFORMATION: antibody sequence

<400> SEQUENCE: 294
atgaaatacc tattgcctac ggcggccgct ggattgttat tactcgcggc ccagccggcc     60
atggcgcagg tgcagttgca ggagtcaggg ggaggcttcg tgcaggctgg gacttctctg    120
agactgtcct gtcagcctc tggaagtatc tcgagtatca atgccatcgc ctggtaccgc    180
cagggtcgcg ggaaccagcg cgagttgctc gcgaaaatta ctaaaggtgg tactacaata    240
tatacaaact ccgtgaaggg ccgattcacc atctctagag acaacaacaa gaacacggtg    300
tatctacaaa tggacagcct gaaacctgac gacacagctg tctattattg tgagcagat    360

```
gtgaactacg gaagccctga ttacatagac tactggggcc aagggaccca ggtcaccgtc    420
tcctcaacta gtggcccggg aggccaacac catcaccacc atcatggcgc agaacaaaaa    480
ctcatctcag aagaggatct gtcttag                                        507
```

<210> SEQ ID NO 295
<211> LENGTH: 498
<212> TYPE: DNA
<213> ORGANISM: Artificial Sequence
<220> FEATURE:
<223> OTHER INFORMATION: antibody sequence

<400> SEQUENCE: 295

```
atgaaatacc tattgcctac ggcggccgct ggattgttat tactcgcggc ccagccggcc     60
atggcgcagg tgcagctgca ggagtctggg ggaggattgg tgcagtctgg gggctctctg    120
agactctcct gtgcagcctc tggacgcacc ttcagtacct ataccatggg ctggttccgc    180
caggctccag ggaaggagcg tgagtttgta gcagctatta gctggagttc tggtaccgct    240
aactatgcag actccgtgaa gggccgattc accatctcca gagacagcgc caagaacacg    300
gtgtatctgc aaatgaacag cctgaaacct gaggatacgg ccgtctatta ctgtaatgcg    360
tggagtccgg ttggtcatga ctactggggt caggggaccc aggtcaccgt ctcctcaact    420
agtggcccgg gaggccaaca ccatcaccac catcatggcg cagaacaaaa actcatctca    480
gaagaggatc tgtcttag                                                  498
```

<210> SEQ ID NO 296
<211> LENGTH: 498
<212> TYPE: DNA
<213> ORGANISM: Artificial Sequence
<220> FEATURE:
<223> OTHER INFORMATION: antibody sequence

<400> SEQUENCE: 296

```
atgaaatacc tattgcctac ggcggccgct ggattgttat tactcgcggc ccagccggcc     60
atggcgcagg tgcagctgca ggagtctggg ggaggattgg tgcagtctgg gggctctctg    120
agactctcct gtgcagcctc tggacgcacc ttcagtacct ataccatggg ctggttccgc    180
caggctccag ggaaggagcg tgagtttgta gcagctatta gctggagttc tggtaccgct    240
aactatgcag actccgtgaa gggccgattc accatctcca gagacagcgc caagaacacg    300
gtgtatctgc aaatgaacag cctgaaacct gaggatacgg ccgtctatta ctgtaatgcg    360
tggagtccgg ttggtcatga ctactggggt caggggaccc aggtcaccgt ctcctcaact    420
agtggcccgg gaggccaaca ccatcaccac catcatggcg cagaacaaaa actcatctca    480
gaagaggatc tgtcttag                                                  498
```

<210> SEQ ID NO 297
<211> LENGTH: 510
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature

```
<222> LOCATION: (500)..(500)
<223> OTHER INFORMATION: n is a, c, g, or t

<400> SEQUENCE: 297
atgaaatncn tattgcctac ggcggccgct ggattgttat tactcgcggc ccagccggcc      60
atggcgcagg tgcagctgca gcagtctggg ggaggattgg tgcaggctgg gggctctctg     120
agactctcct gtgcagcctc tgggcgcacc ttcagtaact acgccatggg ctggttccgc     180
caggctccag ggaaggagcg tgaattcgta gcagctatta gttggagtgg tgcttacaca     240
tttatggaa actccgtgag gggccgattc accatctcca gagacaaccc caacaacacg      300
gtgtatctgc aaatgaacag cctgaaacct gaggacacgg ccacttatta ctgcgcagca     360
gcccgaggag gtagatggta cagtacctat gactactggg gccaggggac ccaggtcacc     420
gtctcctcaa ctagtggccc gggaggccaa caccatcacc accatcatgg cgcagaacaa     480
aaactcatct cagaagaggn tctgtcttag                                      510

<210> SEQ ID NO 298
<211> LENGTH: 498
<212> TYPE: DNA
<213> ORGANISM: Artificial Sequence
<220> FEATURE:
<223> OTHER INFORMATION: antibody sequence

<400> SEQUENCE: 298
atgaaatacc tattgcctac ggcggccgct ggattgttat tactcgcggc ccagccggcc      60
atggcgcagg tgcagctgca ggagtctggg ggaggcttgg tgcaggctgg ggggtctctg     120
agactctcct gtgcagcctc tggaagcacc ttcagcggct atgtcatcgg ctggtaccgg     180
caggctccag ggaagcagcg cgaggaggtc gcaattatta gtagtagtgg tagcacaaac     240
tatgcagact ccgtgaaggg ccgattcacc atctccagag acaacgccaa cgccaagacc     300
acgtttatc tgcaaatgaa cagcctgaaa cctgaggaca cggccgtcta ttactgtaat     360
gcgagacttt ggctaaataa ctactggggc caggggaccc tggtcaccgt ctcctcaact    420
agtggcccgg gaggccaaca ccatcaccac catcatggcg cagaacaaaa actcatctca    480
gaagaggatc tgtcttag                                                   498

<210> SEQ ID NO 299
<211> LENGTH: 504
<212> TYPE: DNA
<213> ORGANISM: Artificial Sequence
<220> FEATURE:
<223> OTHER INFORMATION: antibody sequence

<400> SEQUENCE: 299
atgaaatacc tattgcctac ggcggccgct ggattgttat tactcgcggc ccagccggcc      60
atggcgcagg tgcagctgca ggagtctggg ggaggcttgg tgcagcctgg ggggtctctg     120
agactctcct gtgcagcctc tggattcacc ttcagtagct actggatgta ttgggtccgt     180
caggctccag ggaagggggct cgaatgggtc tcaactatta gtcctagtgg tggtacaaca    240
tactatacaa actccgcgaa gggccgattc accatctcca gagacaacgc caagaacacg    300
gtgtatctgc aagtgaacaa cctgaaacct gaggacacgg ccgtttatta ctgtgcagcc    360
cgacgaagtg gtagatatga gtatgactac tggggccagg gacccaggt caccgtctcc    420
tcaactagtg gcccgggagg ccaacaccat caccaccatc atggcgcaga acaaaaactc    480
atctcagaag aggatctgtc ttag                                           504
```

<210> SEQ ID NO 300
<211> LENGTH: 525
<212> TYPE: DNA
<213> ORGANISM: Artificial Sequence
<220> FEATURE:
<223> OTHER INFORMATION: antibody sequence

<400> SEQUENCE: 300

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtctggg | ggagacttgg | tgcagcctgg | ggggtctctg | 120 |
| agactctcct | gtgtagcctc | tggattccct | tttgatgatt | atcccatgag | ctgggtccga | 180 |
| caggctccag | ggaaggggct | ggagtgggtc | tcgtctgtta | gcccgaatgg | tggtagcaca | 240 |
| ttctatgcag | actccctgaa | gggccgattc | accatctcca | gagacaacgc | caagaacacg | 300 |
| ctgtatctgc | aaataaacag | tctgaaatca | gacgacacgg | ccgtgtatca | ctgtgcaaag | 360 |
| gttctcgact | actactgctc | aggctatggg | tgttatgcct | catatgacct | ttggggccag | 420 |
| gggacccagg | tcaccgtctc | ctcaactagt | ggcccgggag | gccaacacca | tcaccaccat | 480 |
| catggcgcag | aacaaaaact | catctcagaa | gaggatctgt | cttag | | 525 |

<210> SEQ ID NO 301
<211> LENGTH: 525
<212> TYPE: DNA
<213> ORGANISM: Artificial Sequence
<220> FEATURE:
<223> OTHER INFORMATION: antibody sequence

<400> SEQUENCE: 301

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtctggg | ggagacttgg | tgcagcctgg | ggggtctctg | 120 |
| agactctcct | gtgtagcctc | tggattccct | tttgatgatt | atcccatgag | ctgggtccga | 180 |
| caggctccag | ggaaggggct | ggagtgggtc | tcgtctgtta | gcccgaatgg | tggtagcaca | 240 |
| ttctatgcag | actccctgaa | gggccgattc | accatctcca | gagacaacgc | caagaacacg | 300 |
| ctgtatctgc | aaataaacag | tctgaaatca | gacgacacgg | ccgtgtatca | ctgtgcaaag | 360 |
| gttctcgact | actactgctc | aggctatggg | tgttatgcct | catatgacct | ttggggccag | 420 |
| gggacccagg | tcaccgtctc | ctcaactagt | ggcccgggag | gccaacacca | tcaccaccat | 480 |
| catggcgcag | aacaaaaact | catctcagaa | gaggatctgt | cttag | | 525 |

<210> SEQ ID NO 302
<211> LENGTH: 507
<212> TYPE: DNA
<213> ORGANISM: Artificial Sequence
<220> FEATURE:
<223> OTHER INFORMATION: antibody sequence

<400> SEQUENCE: 302

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggcttgg | tgcagcctgg | ggggtctctg | 120 |
| agactctcct | gtgcagcctc | tataagcatc | gtcagtatca | ataccatggc | ctggtaccgc | 180 |
| caggctccag | ggaagcagcg | cgagttggtc | gcaggtatta | ctagtggtgg | tagcacaaac | 240 |
| tatgcagact | ccgtgaaggg | ccgattcacc | atttccagag | acaacgccaa | gaacacggtg | 300 |
| tcgctgcaaa | tgaacagcct | gaaacctgag | gacacggccg | tctattactg | taatgcaggc | 360 |
| cgctacgtcc | ctggtgcgat | tgttactaac | tactggggcc | aggggaccca | ggtcaccgtc | 420 |

-continued

| tcctcaacta gtggcccggg aggccaacac catcaccacc atcatggcgc agaacaaaaa | 480 |
| ctcatctcag aagaggatct gtcttag | 507 |

<210> SEQ ID NO 303
<211> LENGTH: 510
<212> TYPE: DNA
<213> ORGANISM: Artificial Sequence
<220> FEATURE:
<223> OTHER INFORMATION: antibody sequence

<400> SEQUENCE: 303

| atgaaatacc tattgcctac ggcggccgct ggattgttat tactcgcggc ccagccggcc | 60 |
| atggcgcagg tgcagttgca ggagtttggg ggaggcttgg tgcaggctgg ggggtctctg | 120 |
| agactctcct gtttagcctc tatgactacc ctcgggttca agaccatggg ctggtaccgc | 180 |
| caggctccag ggaagcagcg cgagttggtc gcacgtatta gtagtggtgg tcagacaaac | 240 |
| tatgcagact ccgtgaaggg ccgattcacc atctccagag acaacgccaa gaacacagtg | 300 |
| tatctgcaaa tgatcagtct gaaacctgag gatacggccg tctattattg taatgcgcgg | 360 |
| cgttactata gtctagcgcg ctacgactat aactactggg gccaggggac ccaggtcacc | 420 |
| gtctcctcaa ctagtggccc gggaggccaa caccatcacc accatcatgg cgcagaacaa | 480 |
| aaactcatct cagaagagga tctgtcttag | 510 |

<210> SEQ ID NO 304
<211> LENGTH: 495
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (485)..(485)
<223> OTHER INFORMATION: n is a, c, g, or t

<400> SEQUENCE: 304

| atgaaatacc tattgcctac ggcggccgct ggattgttat tactcgcggc ccagccggcc | 60 |
| atggcgcagg tgcagctgca ggcgtttggg ggagccgcgg cacaggctgg agactctttg | 120 |
| agactttcct gtgtcgttgg tggaaagagc accgccgccg tcaatggcgt ggggtggtac | 180 |
| cgccaggctc cgggtcgtca gcgcgaattt gtcgcggcta ttagacctgg cggtagacga | 240 |
| gactatctgg attccgtgaa aggccgtttc tcggtattta ggaataagac cacagtttac | 300 |
| ttgcgaatga cgatctgagg attgaagaca cggccgtct actactgtta tgcagagggt | 360 |
| cttctattac cgtcgacgta ctggggccag gggaccctgg tcaccgtctc ctcaactagt | 420 |
| ggcccgggag gccaacacca tcaccaccat catggcgcag aacaaaaact catctcagaa | 480 |
| gaggntctgt cttag | 495 |

<210> SEQ ID NO 305
<211> LENGTH: 525
<212> TYPE: DNA
<213> ORGANISM: Artificial Sequence
<220> FEATURE:
<223> OTHER INFORMATION: antibody sequence

<400> SEQUENCE: 305

| atgaaatacc tattgcctac ggcggccgct ggattgttat tactcgcggc ccagccggcc | 60 |
| atggcgcagg tgcagttgca ggcgtctggg ggaggcttgg tgcagcctgg ggggtcgctg | 120 |

```
aaactctcct gtcaagcctc tggattcaat tttggcagtt ttgccatagc ctggttccgc    180 caggcccccag ggaagggccg cgaggggatc tcatgtatca gtagtacaga cgatacatca   240
gtctattcag acgccgtcaa gggccgattc gccatttcca gagacaatgc caagagagcg   300
gcgtacttgc agatgaacag tctgattcct gaggacacgg ccaattatta ctgcgcaacc   360
gtgggccagt cctgtgattt gtgggaccac ccccaggttc cagtgcgcta ccggggccgc   420
gggaccctgg tcaccgtctc ctcaactagt ggcccgggag ccaacaccca tcaccaccat   480
catggcgcag aacaaaaact catctcagaa gaggatctgt cttag                   525

<210> SEQ ID NO 306
<211> LENGTH: 528
<212> TYPE: DNA
<213> ORGANISM: Artificial Sequence
<220> FEATURE:
<223> OTHER INFORMATION: antibody sequence

<400> SEQUENCE: 306
atgaaatacc tattgcctac ggcggccgct ggattgttat tactcgcggc ccagccggcc    60
atggcgcagg tgcagctgca ggagtttggg ggaggattgg tgcaggctgg gggctctctg   120
agactctcct gtgcagcctc tggacgcacc ttcagtggct attccatggg ctggttccgc   180
caggctccag ggaaggagcg tgagtttgta ggaggtatta gccggagtgg tgggtggaca   240
tactatgcag actccgtgaa gggccgattc accatctcca gagacaacgc caagaacaca   300
gtgtatctgc aaatgaacag cctgaaacct gaggacacgg ccgtttatta ctgtgcagca   360 gcagttttccc gtattaacga ctatgcgccg gccttaagca gggcgtatga ctactggggc   420
caggggaccc aggtcaccgt ctcctcaact agtggcccgg gaggccaaca ccatcaccac   480
catcatggcg cagaacaaaa actcatctca gaagaggatc tgtcttag                528

<210> SEQ ID NO 307
<211> LENGTH: 9
<212> TYPE: PRT
<213> ORGANISM: Artificial Sequence
<220> FEATURE:
<223> OTHER INFORMATION: antibody sequence

<400> SEQUENCE: 307

Ser Gly Arg Thr Phe Ser Gly Tyr Ser
1               5

<210> SEQ ID NO 308
<211> LENGTH: 11
<212> TYPE: PRT
<213> ORGANISM: Artificial Sequence
<220> FEATURE:
<223> OTHER INFORMATION: antibody sequence

<400> SEQUENCE: 308

Val Gly Gly Ile Ser Arg Ser Gly Gly Trp Thr
1               5                   10
```

```
<210> SEQ ID NO 309
<211> LENGTH: 19
<212> TYPE: PRT
<213> ORGANISM: Artificial Sequence
<220> FEATURE:
<223> OTHER INFORMATION: antibody sequence

<400> SEQUENCE: 309

Ala Ala Ala Val Ser Arg Ile Asn Asp Tyr Ala Pro Ala Leu Ser Arg
1               5                   10                  15

Ala Tyr Asp
```